(12) United States Patent
Xu et al.

(10) Patent No.: US 11,612,602 B2
(45) Date of Patent: *Mar. 28, 2023

(54) HETEROCYCLIC COMPOUNDS AND USES AS ANTICANCER AGENTS

(71) Applicant: ACEA Therapeutics, Inc., San Diego, CA (US)

(72) Inventors: Xiao Xu, San Diego, CA (US); Xiaobo Wang, San Diego, CA (US); Long Mao, San Diego, CA (US); Li Zhao, San Diego, CA (US); Biao Xi, San Diego, CA (US)

(73) Assignee: ACEA Therapeutics, Inc., San Diego, CA (US)

( * ) Notice: Subject to any disclaimer, the term of this patent is extended or adjusted under 35 U.S.C. 154(b) by 121 days.

This patent is subject to a terminal disclaimer.

(21) Appl. No.: 17/001,147

(22) Filed: Aug. 24, 2020

(65) Prior Publication Data

US 2021/0100802 A1 Apr. 8, 2021

Related U.S. Application Data

(63) Continuation of application No. 13/740,182, filed on Jan. 12, 2013, now Pat. No. 10,799,504.

(60) Provisional application No. 61/586,718, filed on Jan. 13, 2012.

(51) Int. Cl.
| | | |
|---|---|---|
| A61K 31/519 | (2006.01) | |
| C07D 403/12 | (2006.01) | |
| A61P 35/00 | (2006.01) | |
| A61K 31/52 | (2006.01) | |
| C07D 473/32 | (2006.01) | |
| A61K 31/506 | (2006.01) | |
| C07D 487/04 | (2006.01) | |
| C07D 401/14 | (2006.01) | |
| C07D 473/34 | (2006.01) | |
| A61K 45/06 | (2006.01) | |
| C07D 239/48 | (2006.01) | |
| C07D 473/24 | (2006.01) | |
| C07D 239/46 | (2006.01) | |
| C07D 473/40 | (2006.01) | |
| C07D 239/42 | (2006.01) | |
| C07D 487/02 | (2006.01) | |
| C07D 473/16 | (2006.01) | |
| C07D 239/47 | (2006.01) | |
| C07D 401/12 | (2006.01) | |

(52) U.S. Cl.
CPC .......... *A61K 31/519* (2013.01); *A61K 31/506* (2013.01); *A61K 31/52* (2013.01); *A61K 45/06* (2013.01); *A61P 35/00* (2018.01); *C07D 239/42* (2013.01); *C07D 239/46* (2013.01); *C07D 239/47* (2013.01); *C07D 239/48* (2013.01); *C07D 401/12* (2013.01); *C07D 401/14* (2013.01); *C07D 403/12* (2013.01); *C07D 473/16* (2013.01); *C07D 473/24* (2013.01); *C07D 473/32* (2013.01); *C07D 473/34* (2013.01); *C07D 473/40* (2013.01); *C07D 487/02* (2013.01); *C07D 487/04* (2013.01)

(58) Field of Classification Search
CPC .......................... C07D 403/10; C07D 403/12
See application file for complete search history.

(56) References Cited

U.S. PATENT DOCUMENTS

| | | |
|---|---|---|
| 7,192,752 B2 | 3/2007 | Xu et al. |
| 7,459,303 B2 | 12/2008 | Wang et al. |
| 7,468,255 B2 | 12/2008 | Xu et al. |
| 7,470,533 B2 | 12/2008 | Xu et al. |
| 7,560,269 B2 | 7/2009 | Wang et al. |
| 7,732,127 B2 | 6/2010 | Wang et al. |
| 8,685,988 B2 | 4/2014 | Xu et al. |
| 8,975,249 B2 | 3/2015 | Lee et al. |
| 9,034,885 B2 | 5/2015 | Xu et al. |
| 9,464,089 B2 | 10/2016 | Xu et al. |
| 9,586,965 B2 | 3/2017 | Xu et al. |
| 9,763,949 B2 | 9/2017 | Xu et al. |
| 9,920,074 B2 | 3/2018 | Xu et al. |
| 10,449,196 B2 | 10/2019 | Xu et al. |
| 10,533,011 B2 * | 1/2020 | Mao ............ C07D 487/04 |
| 10,562,918 B2 | 2/2020 | Xu et al. |
| 10,596,174 B2 | 3/2020 | Xu et al. |
| 10,799,504 B2 | 10/2020 | Xu et al. |
| 11,007,197 B2 | 5/2021 | Xu et al. |
| 2004/0116422 A1 | 6/2004 | Kitano et al. |
| 2008/0318950 A1 | 12/2008 | Ahn et al. |

(Continued)

FOREIGN PATENT DOCUMENTS

| | | |
|---|---|---|
| CN | 102083800 A | 6/2011 |
| CN | 103748096 A | 4/2014 |

(Continued)

OTHER PUBLICATIONS

Second Office Action for CN 201380001359.4, dated Jul. 11, 2016, 11 pages.
Second Office Action for CN 201380013279.0, dated Dec. 3, 2015, 10 pages.
Shan et al., "Prodrug strategies based on intramolecular cyclization reactions," J. Pharm. Sci. (1997) 86(7):765-767.
Slichenmeyer et al., "CI-1033, a pan-erbB tyrosine kinase inhibitor," Semin. Oncol. (2001) 28(5 Suppl. 16):80-85.
Smaill et al., "Tyrosine Kinase Inhibitors. 17. Irreversible Inhibitors of the Epidermal Growth Factor Receptor: 4-(Phenylamino)quinazoline- and 4-(Phenylamino)pyrido[3,2-d]pyrimidine-6-acrylamides Bearing Additional Solubilizing Functions," J. Med. Chem. (2000) 43:1380-1397.

(Continued)

*Primary Examiner* — James D. Anderson
(74) *Attorney, Agent, or Firm* — McNeill Baur PLLC

(57) ABSTRACT

The present disclosure provides pharmaceutical compounds, compositions and methods, especially as they are related to compositions and methods for the treatment of tumors and related diseases related to the dysregulation of kinase (such as EGFR (including HER), Alk, PDGFR, but not limited to) pathways.

20 Claims, 16 Drawing Sheets
(16 of 16 Drawing Sheet(s) Filed in Color)

(56) References Cited

U.S. PATENT DOCUMENTS

| | | | |
|---|---|---|---|
| 2009/0076037 | A1 | 3/2009 | Connolly et al. |
| 2010/0016296 | A1 | 1/2010 | Singh et al. |
| 2010/0029610 | A1 | 2/2010 | Singh et al. |
| 2010/0239631 | A1 | 9/2010 | Bourke et al. |
| 2010/0249092 | A1 | 9/2010 | Singh et al. |
| 2011/0207736 | A1 | 8/2011 | Gray et al. |
| 2012/0094999 | A1 | 4/2012 | Gray et al. |
| 2013/0190320 | A1 | 7/2013 | Xu et al. |
| 2015/0133457 | A1 | 5/2015 | Xu et al. |

FOREIGN PATENT DOCUMENTS

| | | | |
|---|---|---|---|
| CN | 104306348 A | | 1/2015 |
| WO | 0132632 | A2 | 5/2001 |
| WO | 02083653 | A1 | 10/2002 |
| WO | 03026664 | A1 | 4/2003 |
| WO | 2004021979 | A2 | 3/2004 |
| WO | 2004045624 | A1 | 6/2004 |
| WO | 2005062795 | A2 | 7/2005 |
| WO | 2005066156 | A1 | 7/2005 |
| WO | 2005084401 | A2 | 9/2005 |
| WO | 2006009755 | A2 | 1/2006 |
| WO | 2006014325 | A2 | 2/2006 |
| WO | 2007039404 | A1 | 4/2007 |
| WO | 2007042298 | A1 | 4/2007 |
| WO | 2007055514 | A1 | 5/2007 |
| WO | 2007071393 | A2 | 6/2007 |
| WO | 2007103233 | A2 | 9/2007 |
| WO | 2007126841 | A2 | 11/2007 |
| WO | 2008073687 | A2 | 6/2008 |
| WO | 2008094737 | A2 | 8/2008 |
| WO | 2008150118 | A2 | 12/2008 |
| WO | 2009017838 | A2 | 2/2009 |
| WO | 2009020990 | A1 | 2/2009 |
| WO | 2009032694 | A1 | 3/2009 |
| WO | 2009032703 | A1 | 3/2009 |
| WO | 2009051822 | A1 | 4/2009 |
| WO | 2009131687 | A2 | 10/2009 |
| WO | 2009143389 | A1 | 11/2009 |
| WO | 2009158571 | A1 | 12/2009 |
| WO | 2010045451 | A1 | 4/2010 |
| WO | 2010090764 | A1 | 8/2010 |
| WO | 2010129053 | A2 | 11/2010 |
| WO | 2011079231 | A1 | 6/2011 |
| WO | 2011090760 | A1 | 7/2011 |
| WO | 2011140338 | A1 | 11/2011 |
| WO | 2011162515 | A2 | 12/2011 |
| WO | 2012061299 | A1 | 5/2012 |
| WO | 2012061303 | A1 | 5/2012 |
| WO | 2012064706 | A1 | 5/2012 |
| WO | 2012120048 | A1 | 9/2012 |
| WO | 2012135801 | A1 | 10/2012 |
| WO | 2012156437 | A1 | 11/2012 |
| WO | 2013106792 | A1 | 7/2013 |
| WO | 2015006754 | A2 | 1/2015 |

OTHER PUBLICATIONS

The First Office Action (translation) for CN 201380013279.0, dated Apr. 29, 2015, 3 pages.
The Third Office Action (translation) for CN 201380013279.0, dated May 17, 2016, 3 pages.
Third Office Action for CN 201380001359.4, dated Jan. 25, 2017, 18 pages.
Xu et al., "AC0010, an irreversible EGFR inhibitor selectively targeting mutated EGFR and overcoming T790M-induced resistance in animal models and lung cancer patients," Molecular Cancer Therapeutics, Published Online Aug. 29, 2016, DOI: 10.1158/1535-7163. MCT-16-0281, 32 pages.
Zhou et al., "Discovery of selective irreversible inhibitors for EGFR-T790M," Bioorganic & Medicinal Chemistry Letters (2011) 21:638-643.
Zhou et al., "Novel mutant-selective EGFR kinase inhibitors against EGFR T790M," Nature (2009) 462 (24/31):1070-1074.
Abbot et al., "Synthesis of heteroaryl-fused pyrazoles as P38 kinase inhibitors," Heterocycles (2009) 78) 11):2811-2826.
Amendment after Notice of Allowance for U.S. Appl. No. 14/329,890, dated Aug. 8, 2016, 3 pages.
Andries et al., "TMC125, a novel next-generation nonnucleoside reverse transcriptase inhibitor active against nonnucleoside reverse transcriptase inhibitor-resistant human immunodeficiency virus type 1," Antimicrobial Agents and Chemotherapy (2004) 48(12):4680-4686.
Avizienyte et al.,"Comparison of the EGFR resistance mutation profiles generated by EGFR-targeted tyrosine kinase inhibitors and the impact of drug combinations," Biochem. J. (2008) 415:197-206.
Bagshawe, "Antibody-directed enzyme prodrug therapy: A review," Drug Dev. Res. (1995) 34(2):220-230.
Baselga et al., "Critical Update and Emerging Trends in Epidermal Growth Factor Receptor Targeting in Cancer," Journal of Clinical Oncology (2005) 23(11 ):2445-2459.
Bean et al., "Acquired Resistance to Epidermal Growth Factor Receptor Kinase Inhibitors Associated with a Novel T854A Mutation in a Patient with EGFR-Mutant LungAdenocarcinoma," Clin. Cancer Res. (2008) 14(22):7519-7525.
Berge et al., "Pharmaceutical Salts," J. Pharm. Sci. (1977) 66:1-19.
Bertolini et al., "A new rational hypothesis for the pharmacophore of the active metabolite of leflunomide, a potent immunosuppressive drug," J. Med Chem. (1997) 40(13):2011-2016.
Blair et al., "Structure-guided development of affinity probes for tyrosine kinases using chemical agents," Nature Chemical Biology (2007) 3(4):229-238.
Bodor, "Novel approaches to the design of safer drugs: soft drugs and site-specific chemical delivery systems," Adv. Drug. Res. (1984) 13:255-331.
Carter et al., "Inhibition of drug-resistant mutants of ABL, KIT, and EGF receptor kinases," Proc. Natl. Acad. Sci. 2005, 102(31), 11011-11016.
Chamberlain et al., "Discovery of 4,6-bis-anilino-1 H-pyrrolo[2.3-d]pyrimidines: Potent inhibitors of the IGF-1 R receptor tyrosine kinase," Bioorganic & Medicinal Chemistry Letters (2009) 19:469-473.
Chamberlain et al., "Optimization of 4,6-bis-anilino-1 H-pyrrolo[2,3-d]pyrimidine IGF-1 R tyrosine kinase inhibitors. towards JNI< selectivity," Bioorganic & Medicinal Chemistry Letters (2009) 19:360-364.
Chamberlain et al., "Optimization of a series of 4,6-bis-anilino-1 H-pyrrolo[2,3-d]pyrimidine inhibitors of IG~:-1 R: Elimination of an acid-mediated decomposition pathway," Bioorganic & Medicinal Chemistry Letters (2009) 19:373-377.
CI-1033 (Canertinib, PD183805), Selleck Chemicals, retrieved from the Internet Aug. 15, 2013, 5 pages.
Communication pursuant to Article 94(3) EPC for EP 13 701 326.4, dated Oct. 27, 2017, 5 pages.
Communication pursuant to Article 94(3) EPC for EP 13 701 326.4, dated May 24, 2016, 5 pages.
Communication pursuant to Article 94(3) EPC for EP 13 745 491.4, dated Jan. 25, 2016, 3 pages.
Communication pursuant to Article 94(3) EPC for EP 13701326.4, dated Aug. 10, 2015, 5 pages.
Communication pursuant to Article 94(3) EPC for EP 14 748 351.5, dated Dec. 20, 2017, 4 pages.
Communication pursuant to Article 94(3) EPC for EP 14 748 351.5, dated Jul. 13, 2017, 6 pages.
Communication pursuant to Article 94(3) EPC, dated Feb. 1, 2017, 5 pages.
Communication pursuant to Article 94(3) EPC, dated Apr. 3, 2017, 3 pages.
Communication pursuant to Rules 161 (1) and 162 EPC for EP 13745491.4, dated Mar. 17, 2015, 2 pages.
Communication under Rule 71 (3) EPC for EP 13 745 491.4, dated Jun. 20, 2016, 7 pages.
Corrected Notice of Allowance for U.S. Appl. No. 14/329,890, dated Jun. 20, 2016, 4 pages.
Decision of Rejection for CN 201380013279.0, dated Dec. 2, 2016, 9 pages.

(56) References Cited

OTHER PUBLICATIONS

Decision on grant of patent for invention for RU 2015107831, dated Nov. 24, 2017, 37 pages (including English translation).
Decision to Grant for EP 13745491.4, dated Nov. 10, 2016, 2 pages.
European Search Report for EP 16202341.0, dated Feb. 22, 2017, 7 pages.
Examination Report for AU 2013300106, dated Oct. 27, 2017, 3 pages.
Examination Report No. 2 for AU 2013207712, dated Apr. 3, 2017, 6 pages.
Examination Report No. 3 for AU 2013207712, dated Jun. 19, 2017, 11 pages.
Examination Report No. 1 for AU 2014287016, dated Nov. 15, 2017, 6 pages.
Final Office Action for U.S. Appl. No. 13/740,182, dated Jun. 30, 2015, 28 pages.
Final Office Action for U.S. Appl. No. 14/329,890, dated Mar. 3, 2016, 5 pages.
Final Office Action for U.S. Appl. No. 14/420,341, dated Sep. 22, 2016, 8 pages.
Final Office Action for U.S. Appl. No. 14/712,794, dated Jul. 22, 2016, 6 pages.
First Examination Report for NZ 629807, dated Aug. 26, 2015, 2 pages.
First Office Action (translation) for CN 201380001359.4, dated Jan. 13, 2016, 7 pages.
First Office Action for CN 2017121302212480, dated Dec. 18, 2017, 10 pages (Including English translation).
Frenkel et al., "Concentration and pH Dependent Aggregation of Hydrophobic Drug Molecules and Relevance to Oral Bioavailability," J. Med. Chem. (2005) 48:1974-1983.
Fry et al., "Specific, irreversible inactivation of the epidermal growth factor receptor and erbB2, by a new class of tyrosine kinase inhibitor," PNAS USA (1998) 95:12022-12027.
Further Examination Report Acceptance for NZ 697824, dated Apr. 4, 2017, 2 pages.
Further Examination Report for NZ 629807, dated Dec. 13, 2016, 2 pages.
Ghosh et al., "2,4-bis(aryloxy)pyrimidines as antimierobial agents," J. Med. Chem. (1968) 11 (6):1237-1238.
Gura et al., "Systems for identifying new drugs are often faulty," Science (1997) 278:1041-1042.
Han et al., "Novel Hybrids of (Phenylsulfonyl)furoxan and Anilinopyrimidine as Potent and Selective Epidermal Growth Factor Receptor Inhibitors for Intervention of Non-Small-Cell Lung Cancer," Journal of Medicinal Chemistry (2013) 56:4738-4748.
International Preliminary Report on Patentability for PCT/US14/46442, dated Jul. 28, 2015, 5 pages.
International Preliminary Report on Patentability for PCT/US2013/021338, dated Jul. 15, 2014, 15 pages.
International Preliminary Report on Patentability for PCT/US2013/050163, dated Feb. 10, 2015, 5 pages.
International Search Report and Written Opinion for PCT Appln. No. PCT/US2013/050163, dated Sep. 4, 2013 (10 pages).
International Search Report and Written Opinion for PCT/CN2016/087857, dated Sep. 29, 2016, 10 pages.
International Search Report and Written Opinion for PCT/US2013/021338, dated Jun. 12, 2013, 25 pages.
International Search Report and Written Opinion for PCT/US2014/046442, dated Jan. 5, 2015, 22 pages.
Invitation to Pay Additional Fees for PCT/US2014/046442, dated Oct. 7, 2014, 6 pages.
Invitation to Respond to Written Opinion for SG 11201500872S, dated Aug. 1, 2016, 7 pages.
Invitation to Respond to Written Opinion for SG 11201500872S, dated Dec. 22, 2015, 9 pages.
Johnson et al., "Relationships between drug activity in NCI preclinical in vitro and in vivo models and early clinical trials," British Journal of Cancer (2001) 84:1424-1431.
Kato et al., "Ketene and its derivatives. XVII. Reaction of diketene with imidates," Chemical and Pharmaceutical Bulletin (1967) 15(9):1334-1338.
Kumar et al., "Structure and Clinical Relevance of the Epidermal Growth Factor Receptor in Human Cancer," J. Clin. Oncol. 2008, 26(10), 1742-1751 (Apr. 2008).
Li et al., "BIBW2992, an irreversible EGFR/HER2 inhibitor highly effective in preclinical lung cancer models," Oncoqene (2008) 27(34):4702-4711.
Ludovici et al., "Evolution of Anti-HIV Drug Candidates. Part 3: Diarylpyrimidine (DAPY) Analogues," Bioorganic & Medicinal Chemistry Letters 11 (2001) 2235-2239.
Mellinghoff, "Why Do Cancer Cells Become "Addicted" to Oncogenic Epidermal Growth Factor Receptor?" PLoS Medicine (2007) 4(1 0):e321 :1620-1622.
Modjtahedi et al., "Epidermal growth factor receptor inhibitors in cancer treatment: advances, challenges and opportunities," Anti-Cancer Drugs (2009) 220(10):851-855. (Abstract).
Non-Final Rejection for U.S. Appl. No. 15/271,124, dated Jan. 17, 2017, 6 pages.
Notice of acceptance for AU 2013207712, dated Aug. 22, 2017, 3 pages.
Notice of Acceptance for AU 2013300106, dated Nov. 21, 2017, 3 pages.
Notice of Allowance for JP 2015-526540, dated Sep. 4, 2017, 3 pages.
Notice of Allowance for U.S. Appl. No. 13/843,554, dated Jan. 13, 2015, 8 pages.
Notice of Allowance for U.S. Appl. No. 13/917,514, dated Nov. 14, 2013, 10 pages.
Notice of Allowance for U.S. Appl. No. 14/329,890, dated May 27, 2016, 7 pages.
Notice of Allowance for U.S. Appl. No. 14/420,341, dated Oct. 18, 2016, 16 pages.
Notice of Allowance for U.S. Appl. No. 14/712,794, dated Dec. 2, 2016, 7 pages.
Notice of Allowance for U.S. Appl. No. 14/712,794, dated Apr. 24, 2017, 4 pages.
Notice of Allowance for U.S. Appl. No. 15/271,124, dated Jul. 10, 2017, 7 pages.
Notice of Allowance for U.S. Appl. No. 15/271,124, dated Oct. 25, 2017, 7 pages.
Notice of Eligibility for Grant for SG 11201500872S, dated Feb. 1, 2017, 6 pages.
Notice of Grant for Patent for AU 20132077120, dated Dec. 18, 2017, 144 pages.
Notice of Grounds for Rejection (translation) for JP 2014-552357, dated Aug. 1, 2017, 6 pages.
Notice of Grounds of Rejection for JP 2014-552357, dated Nov. 4, 2016, 13 pages.
Notice of Reasons for Rejection for JP 2015-526540, dated Apr. 25, 2017, 5 pages.
Notice of Reasons for Rejection for JP 2015-526540, dated Oct. 17, 2016, 10 pages.
Notification of Defects in IL 237023, dated Jan. 4, 2017, 2 pages.
Notification of Defects in Patent Application IL No. 237023, dated Nov. 14, 2017, 2 pages (English translation).
Notification of Reexamination (translation) for CN 201380013279.0, dated Sep. 8, 2017,1 page.
Office Action for JP 2017-005935, dated Aug. 3, 2017, 2 pages.
Office Action for RU 2015107831, dated Apr. 5, 2017, 14 pages.
Office Action for U.S. Appl. No. 13/843,554, dated Aug. 19, 2014, 7 pages.
Office Action for U.S. Appl. No. 14/329,890, dated Sep. 23, 2015, 16 pages.
Office Action for U.S. Appl. No. 14/420,341, dated Jun. 3, 2016, 7 pages.
Office Action for U.S. Appl. No. 14/712,794, dated Mar. 8, 2016, 20 pages.
Office Action for U.S. Appl. No. 15/435,722, dated Jul. 3, 2017, 48 pages.
Official Action (translation) for RU 2015107831, dated Aug. 11, 2017, 3 pages.

(56) References Cited

OTHER PUBLICATIONS

Patani et al., "Bioisosterism: A Rational Approach in Drug Design," Chem. Rev. (1996) 96:3147-3176.
Patent Examination Report No. 1 for AU 2013207712, dated Sep. 19, 2016, 4 pages.
Patent Examination Report No. 1 for AU 2013300106, dated Nov. 23, 2016, 3 pages.
Petter et al., A novel small-molecule drug platform to silence cancer targets—Application to the pan-ErbB kinases, Poster from AACR 2009, Denver, CO—Abstr. 3746 (presented on Apr. 18-22, 2009).
Profft et al., "Uber in 2- und 6-Stellung substituierte 4-Methylpyrimidine," Archiv. der Pharmazie (1962) 295 (9):649-662.
Raymond et al., "Epidermal growth factor receptor tyrosine kinase as a target for anticancer therapy," Drugs (2000) 60(Suppl 1):15-23.
Request for Continued Examination for U.S. Appl. No. 14/329,890, filed May 3, 2016, 17 pages.
Request for Continued Examination for U.S. Appl. No. 14/712,794, filed Oct. 6, 2016, 27 pages.
Request for Continued Examination for U.S. Appl. No. 15/271,124, dated Oct. 10, 2017, 3 pages.
Request for re-examination for CN 201380013279.0, dated Mar. 15, 2017, 256 pages.
Response for Non-final Rejection for U.S. Appl. No. 15/271,124, dated Apr. 17, 2017, 15 pages.
Response to Communication pursuant to Art 94(3) for EP 13 701 326.4, dated Dec. 2, 2016, 25 pages.
Response to Communication pursuant to Art 94(3) for EP 13 701 326.4, dated Jun. 29, 2017, 21 pages.
Response to Communication pursuant to Art. 94(3) EPC for EP 13 701 326.4, filed Feb. 22, 2016, 66 pages.
Response to Communication pursuant to Article 94(3) EPC for EP 14 748 351.5, dated Nov. 14, 2017, 15 pages.
Response to Communication pursuant to Rules 161 (1) and 162 EPC for EP 13 701 326.4, filed Feb. 26, 2015, 11 pages.
Response to Communication pursuant to Rules 161 (1) and 162 EPC for EP 13 745 491.4, dated Sep. 25, 2015, 4 pages.
Response to examination report for AU 2013207712, filed Aug. 15, 2017, 28 pages.
Response to Examination Report for AU 2013300106, dated Oct. 26, 2017, 38 pages.
Response to Examination Report for AU 2013300106, dated Nov. 9, 2017, 34 pages.
Response to Examination Report for NZ 629807, dated Nov. 24, 2016, 163 pages.
Response to Examination Report for NZ 629807, dated Mar. 8, 2017, 168 pages.
Response to Examination Report No. 1 for AU 2013207712, filed Mar. 23, 2017, 35 pages.
Response to JPOA 2014552357, dated Oct. 26, 2017, 7 pages.
Response to Non-Final Office Action for U.S. Appl. No. 13/843,554, filed Dec. 19, 2014, 19 pages.
Response to Non-final Rejection for U.S. Appl. No. 15/271,124, dated Oct. 26, 2017, 41 pages.
Response to Non-Final Rejection for U.S. Appl. No. 15/435,722, dated Oct. 26, 2017, 33 pages.
Response to Notice of Reason for Rejection for JP 2015-526540, dated Jan. 17, 2017, 35 pages.
Response to Notice of Reason for Rejection for JP 2015-526540, dated Feb. 3, 2017, 20 pages.
Response to Notification of Reexamination (translation) for CN 201380013279.0, dated Oct. 20, 2017, 12 pages.
Response to Office Action for CN 201380001359.4, filed May 30, 2016, 31 pages.
Response to Office Action for CN 201380013279.0, filed Feb. 16, 2016, 26 pages.
Response to Office Action for U.S. Appl. No. 14/329,890, filed Dec. 21, 2015, 14 pages.
Response to Office Action for U.S. Appl. No. 14/420,341, filed Sep. 1, 2016, 12 pages.
Response to Office Action for U.S. Appl. No. 14/712,794, filed Jul. 8, 2016, 34 pages.
Response to Official Action for RU 2015107831, filed Nov. 13, 2017, 28 pages.
Response to Official Action for RU 2015107831, filed Jun. 30, 2017, 6 pages.
Response to Restriction Requirement for U.S. Appl. No. 13/843,554, filed Aug. 5, 2014, 3 pages.
Response to Restriction Requirement for U.S. Appl. No. 13/917,514, filed Oct. 9, 2013, 13 pages.
Response to Restriction Requirement for U.S. Appl. No. 14/329,890, filed Aug. 3, 2015, 12 pages.
Response to Restriction Requirement for U.S. Appl. No. 14/420,341, filed Apr. 22, 2016, 12 pages.
Response to Second Office Action for CN 201380001359.4, dated Nov. 25, 2016, 46 pages.
Response to the Communication pursuant to Art. 94(3) EPC for EP 13 745 491.4, filed May 16, 2016, 27 pages.
Response to the communication pursuant to Article 94(3) EPC for EP 14 748 351.5, filed Jun. 13, 2017, 13 pages.
Response to the First Office Action for CN 201380013279.0, filed Sep. 14, 2015, 30 pages.
Response to the Third Office Action for CN 201380013279.0, filed Aug. 1, 2016, 24 pages.
Response to Third Office Action for CN 201380001359.4, dated Apr. 10, 2017, 24 pages.
Response to Written Opinion for SG 11201500872s, dated Dec. 23, 2016, 25 pages.
Response to Written Opinion for SG 11201500872S, filed May 12, 2016, 22 pages.
Response to Written Opinion with Chapter II Demand and Article 34 Amendments for PCT/US2014/046442, filed May 11, 2015, 62 pages.
Restriction Requirement for U.S. Appl. No. 13/843,554, dated Jun. 30, 2014, 8 pages.
Restriction Requirement for U.S. Appl. No. 13/917,514, dated Sep. 10, 2013, 8 pages.
Restriction Requirement for U.S. Appl. No. 14/329,890, dated Jun. 3, 2015, 9 pages.
Restriction Requirement for U.S. Appl. No. 14/420,341, dated Feb. 22, 2016, 8 pages.
Rotili et al., "Diarylpyrimidine-Dihydrobenzyloxopyrimidine Hybrids: New, Wide-Spectrum Anti-HIV-1 Aqents Active at (Sub)-Nanomolar Level," J. Med. Chem. (2011) 54(8):3091-3096.
Singh et al., U.S. Appl. No. 61/076,450, filed Jun. 27, 2008.

* cited by examiner

HETEROCYCLIC COMPOUNDS AND USES AS ANTICANCER AGENTS

CROSS-REFERENCE TO RELATED APPLICATION

This application is a continuation of U.S. patent application Ser. No. 13/740,182, filed Jan. 12, 2013, now allowed, which claims priority from U.S. Provisional Patent Application No. 61/586,718, filed Jan. 13, 2012. The contents and disclosures of the above applications are incorporated herein by reference in their entireties for all purposes.

FIELD OF THE INVENTION

The field of this invention is pharmaceutical compounds, compositions and methods, especially as they are related to compositions and methods for the treatment of tumors and related diseases related to the dysregulation of kinase (such as EGFR (including HER), Alk, PDGFR, but not limited to) pathways.

BACKGROUND OF THE INVENTION

Protein kinases are a group of enzymes that regulate diverse, important biological processes including cell growth, proliferation, survival, invasion and differentiation, organ formation, tissue repair and regeneration, etc. Protein kinases exert their physiological functions through catalyzing the phsophorylation of protein and thereby modulating the cellular activities. Because protein kinases have profound effects on cells, their activities are highly regulated. Kinases are turned on or off by phosphorylation (sometimes by autophosphorylation), by binding of activator proteins or inhibitor proteins, or small molecules, or by controlling their location in the cell relative to their substrates. Dysfunctions in the activities of kinases, arising from genetic abnormalities or environmental factors, are known to be associated with many diseases. Several severe pathological states, including cancer and chronic inflammation, are associated with stimulation of intra-cellular signaling, and since kinases positively relay signaling events, their inhibition offers a powerful way to inhibit or control signal transduction cascades.

The epidermal growth factor receptor (EGFR; ErbB-1; HER1 in humans) is a member of the ErbB family of receptors, a subfamily of four closely related receptor tyrosine kinases: EGFR (ErbB-1), HER2/c-neu (ErbB-2), Her 3 (ErbB-3) and Her 4 (ErbB-4). EGFR is the cell-surface receptor for members of the epidermal growth factor family (EGF-family) of extracellular protein ligands. Mutations affecting EGFR expression or activity could result in cancer. EGFR is reported deregulated in most solid tumor types i.e. lung cancer, breast cancer and brain tumor. It is estimated that mutations, amplifications or misregulations of EGFR or family members are implicated in about 30% of all epithelial cancers. Therapeutic approaches have been developed based on the inhibition of EGFR by either antibody drug or small molecular inhibitor drug, such as gefitinib and erlotinib. In the case of non small cell lung cancer, gefitinib and erlotinib have shown benefit for 10~40% of the patients. However, acquired resistant to gefitinib or erlotinib after a period of treatment become a major clinical problem. Research has confirmed that one main reason resistance developed is due to the present of the new mutation of T790M, which is the gatekeeper of EGFR. Subsequently, inhibitors can overcome this T790M have been developed and showed advantage in the clinical trial, such as BIBW2992. However, these T790M targeted EGFR inhibitor still has relative inhibitory activity towards wild type EGFR which limit the clinical application. It is needed to further develop more efficient type of EGFR inhibitor which will target mutation only but not the wild type protein.

DISCLOSURE OF THE INVENTION

The present invention is directed to various classes of fused or unfused pyrimidine derivatives and other related/similar fused/unfused ring systems described herein, pharmaceutical compositions, and methods of using these compounds and compositions to treat cancers. In some embodiments, these compounds have been shown to possess anti-cancer activity in cell based assays as described herein using various cancer cell lines, which demonstrate very efficient EGFR inhibitory activity targeting mutation only but not the wild type protein. Accordingly, the compounds and compositions comprising the compounds of the invention are useful to treat conditions characterized by those mutated cancer cells. In particular, the compounds are useful to treat leukemia, lymphoma, lung cancer, colon cancer, CNS cancer, melanoma, ovarian cancer, renal cancer, prostate cancer, breast cancer, head and neck cancers, and pancreatic cancer.

The fused or unfused pyrimidine or similar heterocyclic moiety of the compounds described herein can be further fused with other aryl/non-aryl ring or substituted with substituted aryl amino, substituted arylthio, substituted aryloxy, substituted heterocyclic amino, substituted heterocyclic thio, and substituted heterocyclic oxy derivatives thereof. In some embodiments, the fused or unfused pyrimidine or similar heterocyclic moiety of the compounds described herein include pyrmidine, pyrrolopyrimidine, and purine. The compounds as described herein exhibit anti-tumor, anticancer, anti-inflammation, anti-infectious, and anti-proliferation activity. The present invention also relates to the methods of making and formulating the described compounds and methods to use them therapeutically and/or prophylacticly.

In one aspect, the contemplated heterocyclic compounds have a structure according to Formula I:

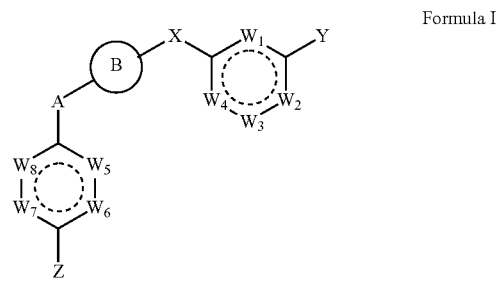

Formula I where

in a ring indicates the ring is an aromatic or heteroaromatic ring;

X is O, S, C═O, —NR, SO, SO2, C1-C6 alkyl, or C1-C6 haloalkyl;

$W_1$, $W_2$, $W_3$, $W_4$, $W_5$, $W_6$, $W_7$ and $W_8$ are each independently absent, N, NH, $NR^1$, O, S, CH, or $CR^2$;

not more than one of them is absent;

$R^1$ and $R^2$ is independently selected from H, OH, Halo, NHR, NRR, OR, SR, COOR, C(=O)R, CN, $CF_3$, $OCF_3$, $NO_2$, OC(O)R, $SO_3R$, $PO_3R_2$, and $CR(COOR)_2$;

Y is H, OH, Halo, NHR, NRR, NHC(=O)R, OR, SR, COOR, C(=O)R, CN, $CF_3$, $OCF_3$, $NO_2$, OC(O)R, $SO_3R$, $PO_3R_2$, or $CR(COOR)_2$;

Z is H, OH, Halo, NHR, NRR, OR, SR, COOR, C(=O)R, CN, $CF_3$, $OCF_3$, $NO_2$, OC(O)R, $SO_3R$, $PO_3R_2$, $CR(COOR)_2$, or

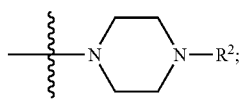

A is NH, S, SO, $SO_2$, $SO_2NH$, $SO_2NR^3$, $NHSO_2$, $NR^1$, $CR^1R^2$, $NR^1$, or O;

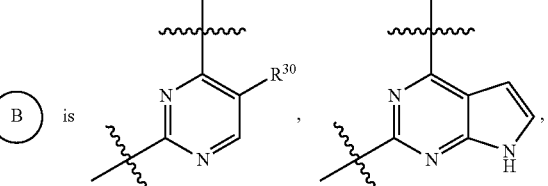

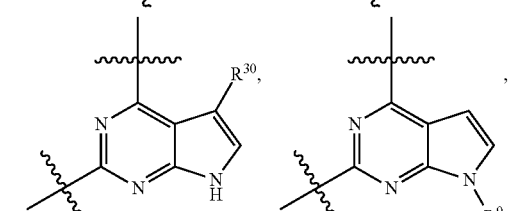

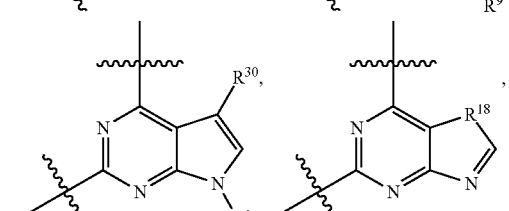

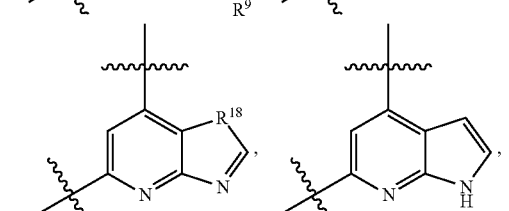

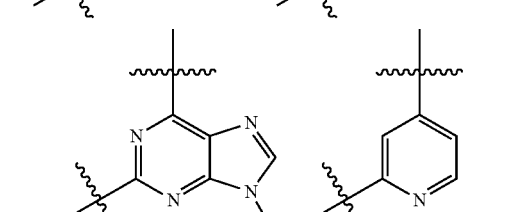

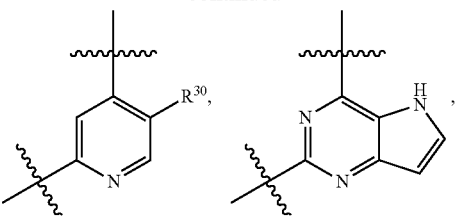

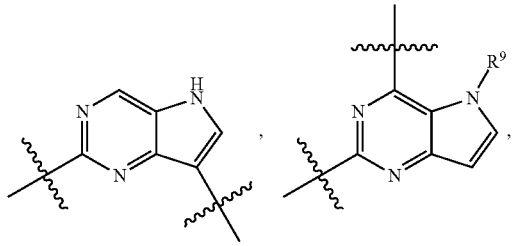

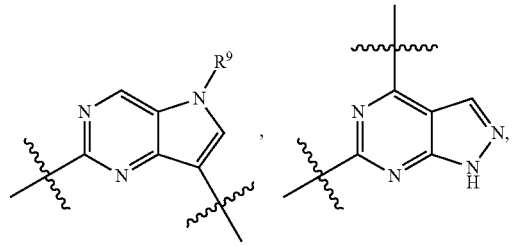

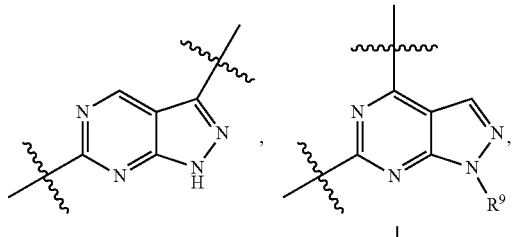

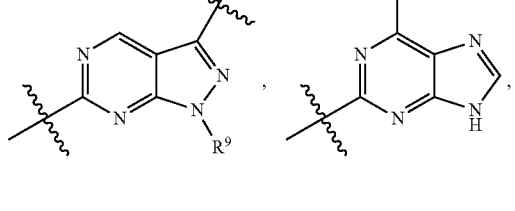

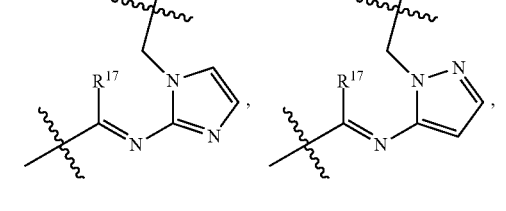

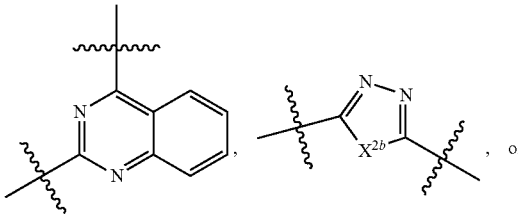, or

-continued

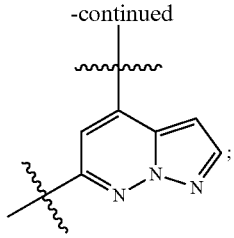

R[17] is N, CH, or CR[30];
R[18] is O or S;
R[10] is halogen or $C_1$-$C_6$ alkyl; and
each R—[11] is independently hydrogen, $C_1$-$C_3$ alkyl, $C_1$—$C_3$ alkoxy, $C_1$—$C_3$ haloalkyl, or $C_1$-$C_3$ haloalkoxy;
R[12] is $CH_2$ or C(O);
$X^{2b}$ is O, S, NH, or NR;
each R is selected from H, substituted or unsubstituted $C_{1-8}$ alkyl, $C_{2-8}$ alkenyl, $C_{2-8}$ alkynyl, aryl, fused aryl, heteroaryl, fused heterocycle, a $C_{3-8}$ carbocyclic ring or a $C_{3-8}$ heterocyclic ring, saturated or unsaturated, wherein each $C_{1-8}$ alkyl, $C_{3-8}$ cyclic alkyl, $C_{2-8}$ alkenyl, $C_{2-8}$ alkynyl can optionally contain a heteroatom selected from N, O and S in place of a carbon atom;
or a pharmaceutically acceptable salt thereof.

In another aspect of these compounds, X is C1-C6 haloalkyl.

In some embodiments of these compounds, X is $CF_2$, CHF, $CHCF_3$ or $CHCF_3$ or $C(CF_3)_2$.

The present disclosure provides a compound of Formula Ia:

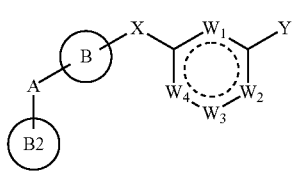

Formula Ia where

in a ring indicates the ring is an aromatic or heteroaromatic ring;

X is O, S, C=O, —NR, SO, $SO_2$, $C_1$-$C_6$ alkyl or $C_1$-$C_6$ haloalkyl;

$W_1$, $W_2$, $W_3$, $W_4$, $W_5$, $W_6$, $W_7$ and $W_8$ are each independently absent, N, NH, $NR^1$, O, S, CH, or $CR^2$;

not more than one of them is absent;

$R^1$ and $R^2$ are each independently selected from H, $C_1$-$C_6$ alkyl, OH, halogen, NHR, NRR, OR, SR, COOR, C(=O)R, CN, $CF_3$, $OCF_3$, $NO_2$, OC(O)R, $SO_3R$, $SO_2R$, $PO_3R_2$,— $POR_2$, $CR(COOR)_2$, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, —$C(O)NR_2$, sulfonyl, sulfonylamino, aminosulfonyl, acylamino, alkoxycarbonylamino, and aminocarbonylamino;

Y is H, OH, halogen, NHR, NRR, NHC(=O)R, OR, SR, COOR, C(=O)R, CN, $CF_3$, $OCF_3$, $NO_2$, OC(O)R, $SO_3R$, $PO_3R_2$, or $CR(COOR)_2$;

A is NH, S, SO, $SO_2$, $SO_2NH$, $SO_2NR^3$, $NHSO_2$, $NR^1$, $CR^1R^2$, $NR^1$, or O;

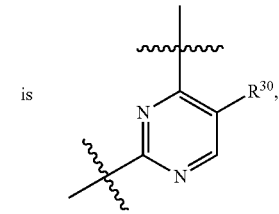

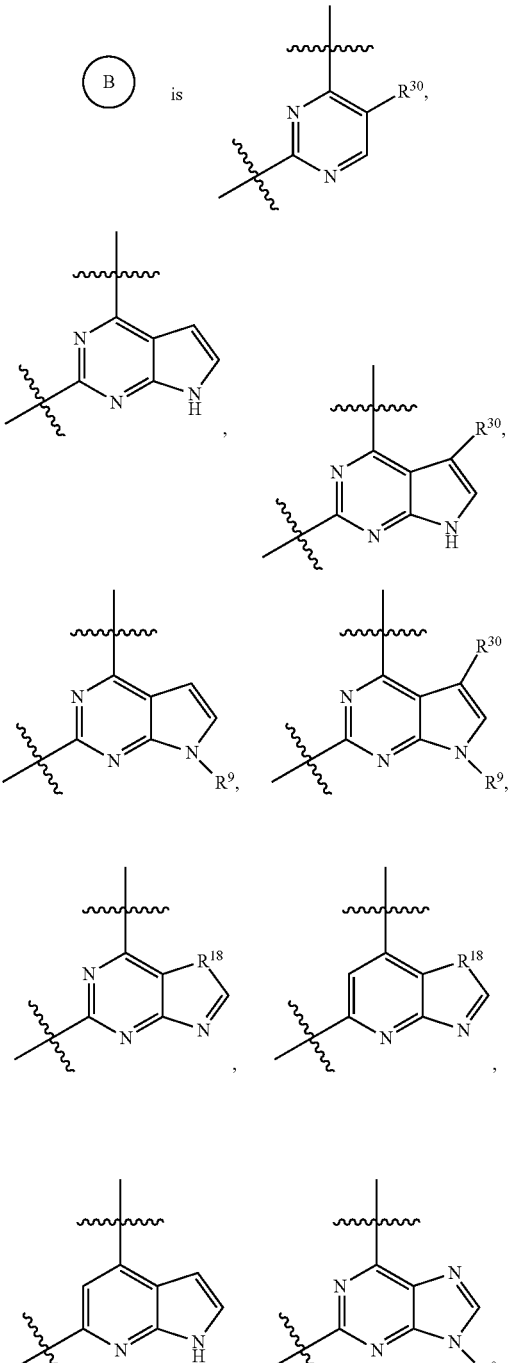

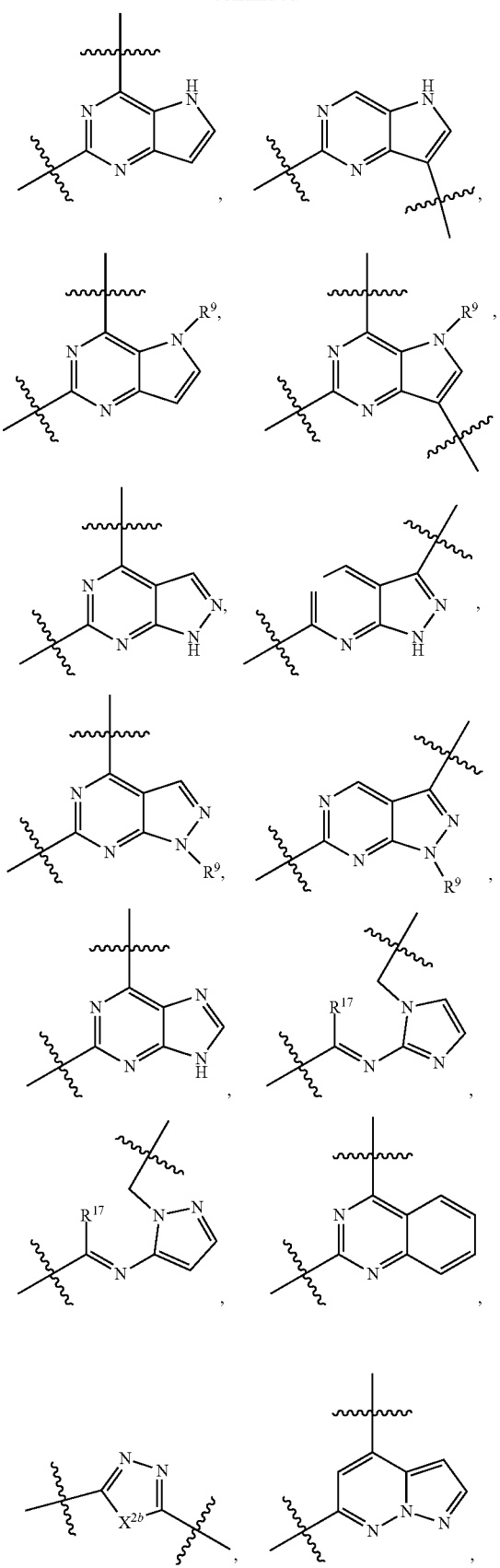

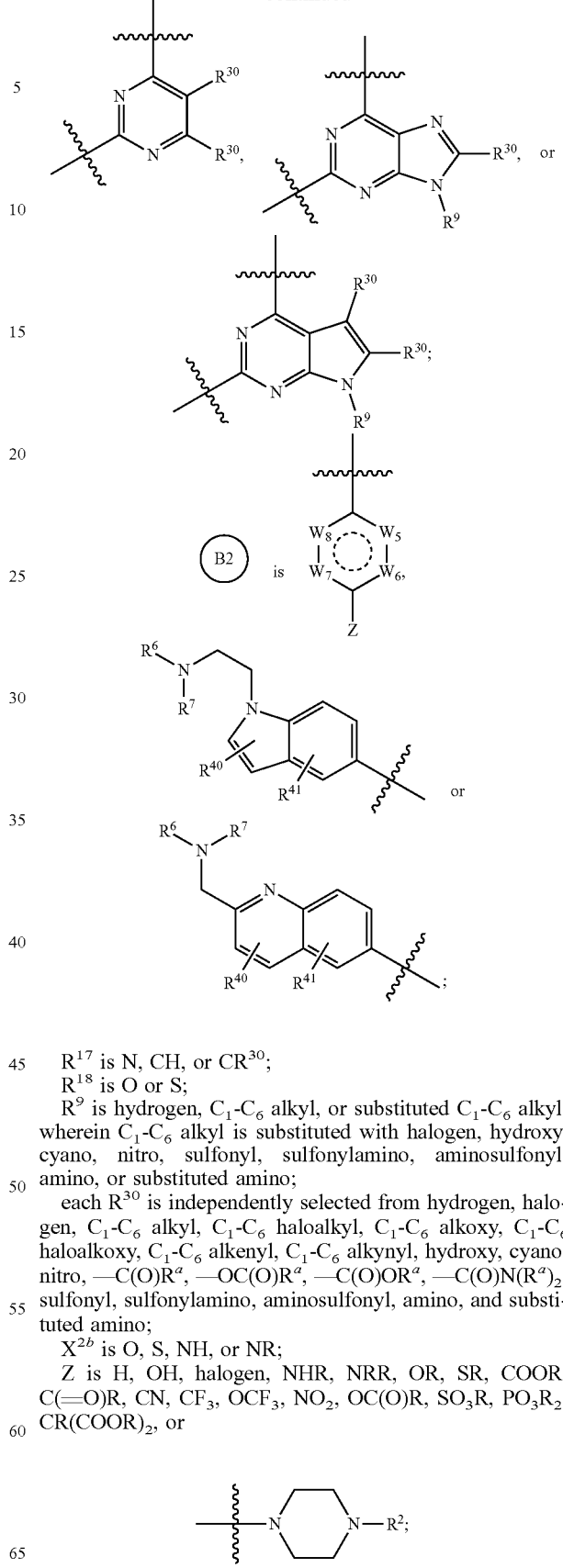

$R^{17}$ is N, CH, or $CR^{30}$;

$R^{18}$ is O or S;

$R^9$ is hydrogen, $C_1$-$C_6$ alkyl, or substituted $C_1$-$C_6$ alkyl, wherein $C_1$-$C_6$ alkyl is substituted with halogen, hydroxy, cyano, nitro, sulfonyl, sulfonylamino, aminosulfonyl, amino, or substituted amino;

each $R^{30}$ is independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, and substituted amino;

$X^{2b}$ is O, S, NH, or NR;

Z is H, OH, halogen, NHR, NRR, OR, SR, COOR, C(=O)R, CN, CF$_3$, OCF$_3$, NO$_2$, OC(O)R, SO$_3$R, PO$_3$R$_2$, CR(COOR)$_2$, or R[6] is hydrogen or $C_1$-$C_6$ alkyl;

R[7] is hydrogen or $C_1$-$C_6$ alkyl;

R[40] and R[41] are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)R[a], —OC(O)R[a], —C(O)OR[a], —C(O)N(R[a])$_2$, sulfonyl, sulfonylamino, aminosulfonyl, amino, substituted amino, acylamino, alkoxycarbonylamino, and aminocarbonylamino; and each R is selected from H, substituted or unsubstituted $C_{1-8}$ alkyl, $C_{2-20}$ alkenyl, $C_{2-8}$ alkynyl, aryl, fused aryl, heteroaryl, fused heterocycle, a $C_{3-8}$ carbocyclic ring or a $C_{3-8}$ heterocyclic ring, saturated or unsaturated, wherein each $C_{1-8}$ alkyl, $C_{3-8}$ cyclic alkyl, $C_{2-8}$ alkenyl, $C_{2-8}$ alkynyl can optionally contain a heteroatom selected from N, O and S in place of a carbon atom;

or a pharmaceutically acceptable salt thereof.

The present disclosure provides a compound of Formula Ib:

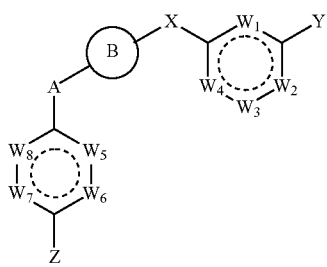

Formula Ib where

in a ring indicates the ring is an aromatic or heteroaromatic ring;

X is O, S, C=O, —NR, SO, $SO_2$, $C_1$-$C_6$ alkyl or $C_1$-$C_6$ haloalkyl; $W_1$, $W_2$, $W_3$, $W_4$, $W_5$, $W_6$, $W_7$ and $W_8$ are each independently absent, N, NH, NR[1], O, S, CH, or CR[2];

not more than one of them is absent;

R[1] and R[2] are each independently selected from H, $C_1$-$C_6$ alkyl, OH, halogen, NHR, NRR, OR, SR, COOR, C(=O)R, CN, $CF_3$, $OCF_3$, $NO_2$, OC(O)R, $SO_3R$, $SO_2R$, $PO_3R_2$,— $POR_2$, $CR(COOR)_2$, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, —C(O)NR$_2$, sulfonyl, sulfonylamino, aminosulfonyl, acylamino, alkoxycarbonylamino, and aminocarbonylamino;

Y is H, OH, halogen, NHR, NRR, NHC(=O)R, OR, SR, COOR, C(=O)R, CN, $CF_3$, $OCF_3$, $NO_2$, OC(O)R, $SO_3R$, $PO_3R_2$, or $CR(COOR)_2$;

Z is H, OH, halogen, NHR, NRR, OR, SR, COOR, C(=O)R, CN, $CF_3$, $OCF_3$, $NO_2$, OC(O)R, $SO_3R$, $PO_3R_2$, $CR(COOR)_2$, or

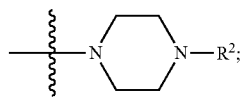

A is NH, S, SO, $SO_2$, $SO_2NH$, $SO_2NR^3$, $NHSO_2$, NR[1], $CR^1R^2$, NR[1], or O;

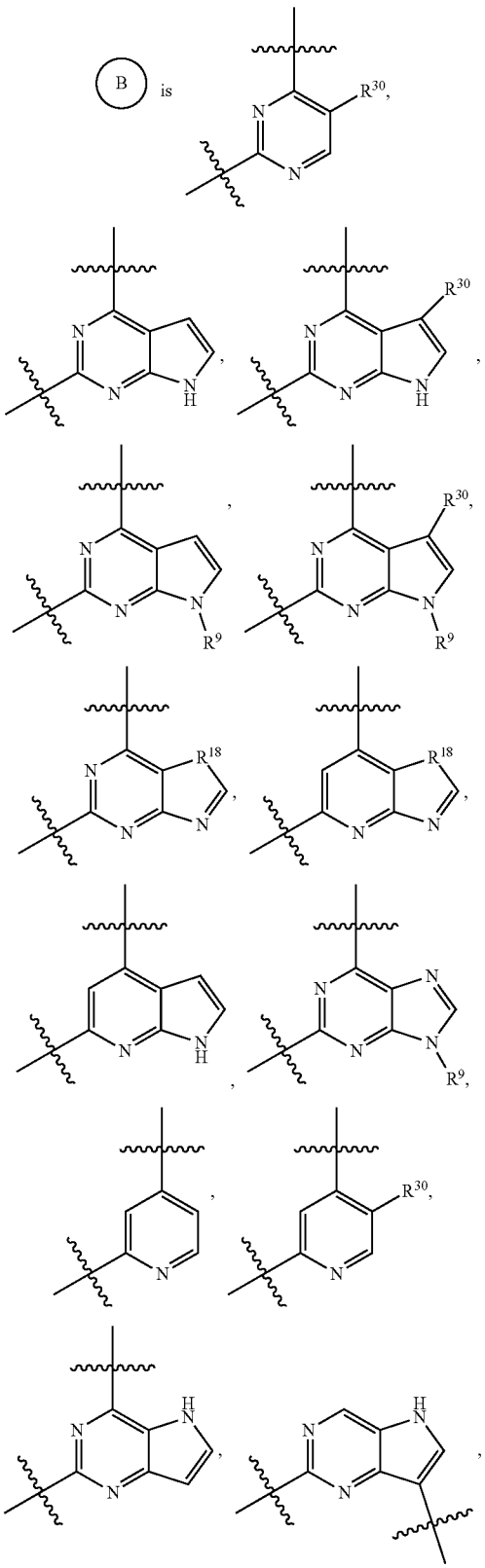

R[17] is N, CH, or CR[30];

R[18] is O or S;

R[9] is hydrogen, $C_1$-$C_6$ alkyl, or substituted $C_1$-$C_6$ alkyl, wherein $C_1$-$C_6$ alkyl is substituted with halogen, hydroxy, cyano, nitro, sulfonyl, sulfonylamino, aminosulfonyl, amino, or substituted amino;

each R[30] is independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)R$^a$, —OC(O)R$^a$, —C(O)OR$^a$, —C(O)N(R$^a$)$_2$, sulfonyl, sulfonylamino, aminosulfonyl, amino, and substituted amino; and X$^{2b}$ is O, S, NH, or NR;

each R is selected from H, substituted or unsubstituted $C_{1-8}$ alkyl, $C_{2-20}$ alkenyl, $C_{2-8}$ alkynyl, aryl, fused aryl, heteroaryl, fused heterocycle, a $C_{3-8}$ carbocyclic ring or a $C_{3-8}$ heterocyclic ring, saturated or unsaturated, wherein each $C_{1-8}$ alkyl, $C_{3-8}$ cyclic alkyl, $C_{2-8}$ alkenyl, $C_{2-8}$ alkynyl can optionally contain a heteroatom selected from N, O and S in place of a carbon atom;

or a pharmaceutically acceptable salt thereof.

In some embodiments of these compounds, X is $C_1$-$C_6$ haloalkyl.

In some embodiments of these compounds, X is selected from $CF_2$, CHF, $CHCF_3$ or $C(CF_3)_2$.

The present disclosure provides a compound of Formula Ic:

Formula Ic wherein

X is $CF_2$, O, $CH_2$ S, or NR$^b$;

R$^b$ is selected from H, substituted or unsubstituted $C_{1-8}$ alkyl, $C_{2-8}$ alkenyl, $C_{2-8}$ alkynyl, aryl, fused aryl, heteroaryl, fused heterocycle, a $C_{3-8}$ carbocyclic ring or a $C_{3-8}$ heterocyclic ring, saturated or unsaturated, wherein each $C_{1-8}$ alkyl, $C_{3-8}$ cyclic alkyl, $C_{2-8}$ alkenyl, $C_{2-8}$ alkynyl can optionally contain a heteroatom selected from N, O and S in place of a carbon atom;

R$^3$ and R$^4$ are independently hydrogen, $C_1$-$C_6$ alkyl, or —(CH$_2$)$_m$N(R$^a$)$_2$, wherein m is one to 6;

$R^5$ is hydrogen or $C_1$-$C_6$ alkyl;
$R^6$ is hydrogen or $C_1$-$C_6$ alkyl;
$R^7$ is hydrogen or $C_1$-$C_6$ alkyl;

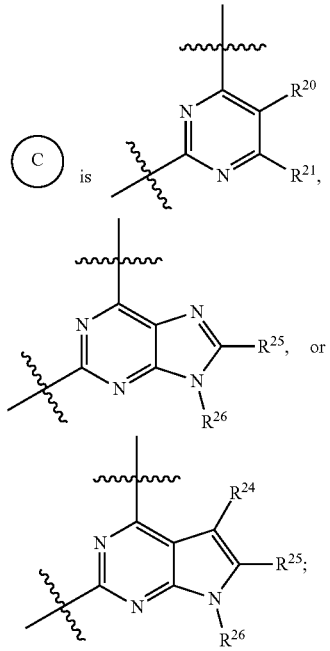

$R^{24}$ and $R^{25}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, and substituted amino;

$R^{24}$ and $R^{25}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, and substituted amino;

R26 is hydrogen, $C_1$-$C_6$ alkyl, or substituted $C_1$-$C_6$ alkyl, wherein $C_1$-$C_6$ alkyl is substituted with halogen, hydroxy, cyano, nitro, sulfonyl, sulfonylamino, aminosulfonyl, amino, or substituted amino;

$R^{22}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, thiol, —C(O)$R^a$, —OC(O)$R^a$, —C(O)O$R^a$, —C(O)N($R^a$)$_2$, sulfonyl, sulfonylamino, aminosulfonyl, amino, substituted amino, acylamino, alkoxycarbonylamino, and aminocarbonylamino;

$R^{23}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, substituted amino, acylamino, alkoxycarbonylamino, and aminocarbonylamino;

each $R^a$ is independently hydrogen or $C_1$-$C_6$ alkyl; and

Q is CH, CR$^{23}$, or N;

or a pharmaceutically acceptable salt thereof.

In another aspect, the contemplated compounds have a structure according to Formula II:

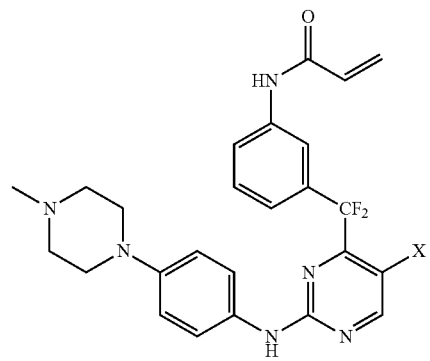

Formula II where X is halo wherein the halo is Cl, F, I, or Br.

In some embodiments of these compounds, halo is F, I, or Br.

The present disclosure provides a compound of Formula IIa:

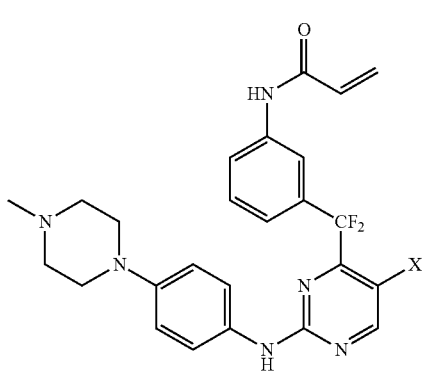

Formula IIa where X is $C_1$-$C_6$ alkyl, $C_1$-$C_6$ alkoxy, or halo, wherein the halo is Cl, F, I, or Br.

In some embodiments of these compounds, halo is F, I, or Br.

The present disclosure provides a compound of Formula III:

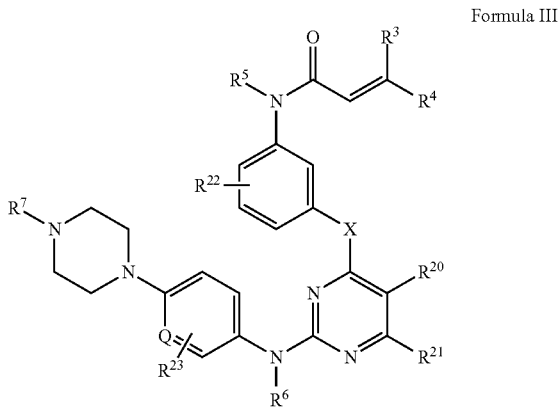

Formula III wherein

X is $CF_2$, O, $CH_2$ S, or $NR^b$;

$R^b$ is selected from H, substituted or unsubstituted $C_{1-8}$ alkyl, $C_{2-8}$ alkenyl, $C_{2-8}$ alkynyl, aryl, fused aryl, heteroaryl, fused heterocycle, a $C_{3-8}$ carbocyclic ring or a $C_{3-8}$ heterocyclic ring, saturated or unsaturated, wherein each $C_{1-8}$ alkyl, $C_{3-8}$ cyclic alkyl, $C_{2-8}$ alkenyl, $C_{2-8}$ alkynyl can optionally contain a heteroatom selected from N, O and S in place of a carbon atom;

$R^3$ and $R^4$ are independently hydrogen, $C_1$-$C_6$ alkyl, or —$(CH_2)_m N(R^a)_2$, wherein m is one to 6;

$R^5$ is hydrogen or $C_1$-$C_6$ alkyl;

$R^6$ is hydrogen or $C_1$-$C_6$ alkyl;

$R^7$ is hydrogen or $C_1$-$C_6$ alkyl;

$R^{20}$ and $R^{21}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, and substituted amino;

$R^{22}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, thiol, —$C(O)R^a$, —$OC(O)R^a$, —$C(O)OR^a$, —$C(O)N(R^a)_2$, sulfonyl, sulfonylamino, aminosulfonyl, amino, substituted amino, acylamino, alkoxycarbonylamino, and aminocarbonylamino;

$R^{23}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, substituted amino, acylamino, alkoxycarbonylamino, and aminocarbonylamino;

each $R^a$ is independently hydrogen or $C_1$-$C_6$ alkyl; and

Q is CH, $CR^{23}$, or N;

or a pharmaceutically acceptable salt thereof.

In some embodiments of these compounds, $R^{20}$ is hydrogen, halogen, $C_1$-$C_6$ alkyl, or $C_1$-$C_6$ alkoxy.

In some embodiments of these compounds, $R^2$ is hydrogen, fluoro, chloro, $C_1$-$C_6$ alkyl, or $C_1$-$C_6$ alkoxy.

In some embodiments of these compounds, $R^{20}$ is hydrogen, fluoro, iodo, bromo, $C_1$-$C_6$ alkyl, or $C_1$-$C_6$ alkoxy.

In some embodiments of these compounds, $R^{21}$ is hydrogen.

In some embodiments of these compounds, $R^{23}$ is hydrogen, halogen, or $C_1$-$C_6$ alkoxy.

In some embodiments of these compounds, $R^7$ is $C_1$-$C_3$ alkyl.

In some embodiments of these compounds, $R^3$ and $R^4$ are hydrogen.

In some embodiments of these compounds, at least one of $R^3$ and $R^4$ is $C_1$-$C_6$ alkyl.

In some embodiments of these compounds, Q is CH or $CR^{23}$.

In some embodiments of these compounds, Q is N.

The present disclosure provides a compound of Formula IV:

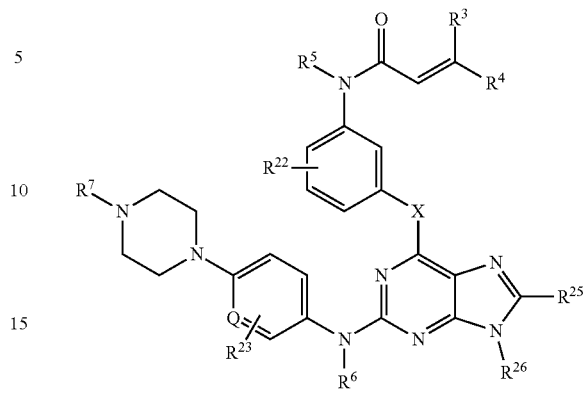

Formula IV wherein

X is $CF_2$, O, $CH_2$ S, or $NR^b$;

$R^b$ is selected from H, substituted or unsubstituted $C_{1-8}$ alkyl, $C_{2-8}$ alkenyl, $C_{2-8}$ alkynyl, aryl, fused aryl, heteroaryl, fused heterocycle, a $C_{3-8}$ carbocyclic ring or a $C_{3-8}$ heterocyclic ring, saturated or unsaturated, wherein each $C_{1-8}$ alkyl, $C_{3-8}$ cyclic alkyl, $C_{2-8}$ alkenyl, $C_{2-8}$ alkynyl can optionally contain a heteroatom selected from N, O and S in place of a carbon atom;

$R^3$ and $R^4$ are independently hydrogen, $C_1$-$C_6$ alkyl, or —$(CH_2)_m N(R^a)_2$, wherein m is one to 6;

$R^5$ is hydrogen or $C_1$-$C_6$ alkyl;

$R^6$ is hydrogen or $C_1$-$C_6$ alkyl;

$R^7$ is hydrogen or $C_1$-$C_6$ alkyl;

$R^{25}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, and substituted amino;

$R^{26}$ is hydrogen, $C_1$-$C_6$ alkyl, or substituted $C_1$-$C_6$ alkyl, wherein $C_1$-$C_6$ alkyl is substituted with halogen, hydroxy, cyano, nitro, sulfonyl, sulfonylamino, aminosulfonyl, amino, or substituted amino;

$R^{22}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, substituted amino, acylamino, alkoxycarbonylamino, and aminocarbonylamino;

$R^{23}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, substituted amino, acylamino, alkoxycarbonylamino, and aminocarbonylamino;

each $R^a$ is independently hydrogen or $C_1$-$C_6$ alkyl; and

Q is CH, $CR^{23}$, or N;

or a pharmaceutically acceptable salt thereof.

In some embodiments of these compounds, $R^{25}$ and $R^{26}$ are hydrogen.

In some embodiments of these compounds, $R^{23}$ is hydrogen, halogen, or $C_1$-$C_6$ alkoxy.

In some embodiments of these compounds, Q is CH.

In some embodiments of these compounds, $R^7$ is $C_1$-$C_3$ alkyl.

In some embodiments of these compounds, $R^3$ and $R^4$ are hydrogen.

The present disclosure provides a compound of Formula V:

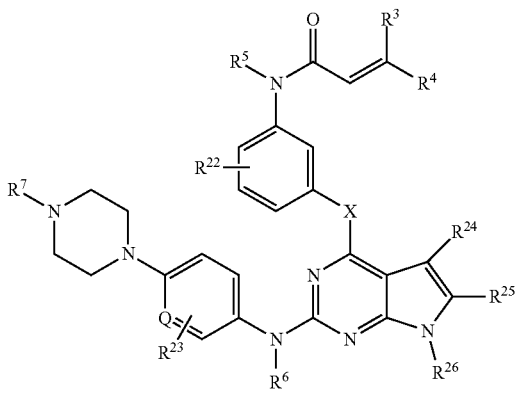

Formula V wherein
X is $CF_2$, O, $CH_2$ S, or $NR^b$;
$R^b$ is selected from H, substituted or unsubstituted $C_{1-8}$ alkyl, $C_{2-8}$ alkenyl, $C_{2-8}$ alkynyl, aryl, fused aryl, heteroaryl, fused heterocycle, a $C_{3-8}$ carbocyclic ring or a $C_{3-8}$ heterocyclic ring, saturated or unsaturated, wherein each $C_{1-8}$ alkyl, $C_{3-8}$ cyclic alkyl, $C_{2-8}$ alkenyl, $C_{2-8}$ alkynyl can optionally contain a heteroatom selected from N, O and S in place of a carbon atom;
$R^3$ and $R^4$ are independently hydrogen, $C_1$-$C_6$ alkyl, or —$(CH_2)_m N(R^a)_2$, wherein m is one to 6;
$R^5$ is hydrogen or $C_1$-$C_6$ alkyl;
$R^6$ is hydrogen or $C_1$-$C_6$ alkyl;
$R^7$ is hydrogen or $C_1$-$C_6$ alkyl;
$R^{24}$ and $R^{25}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, and substituted amino;
$R^{26}$ is hydrogen, $C_1$-$C_6$ alkyl, or substituted $C_1$-$C_6$ alkyl, wherein $C_1$-$C_6$ alkyl is substituted with halogen, hydroxy, cyano, nitro, sulfonyl, sulfonylamino, aminosulfonyl, amino, or substituted amino;
$R^{22}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, substituted amino acylamino, alkoxycarbonylamino, and aminocarbonylamino;
$R^{23}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, substituted amino acylamino, alkoxycarbonylamino, and aminocarbonylamino;
each $R^a$ is independently hydrogen or $C_1$-$C_6$ alkyl; and
Q is CH, $CR^{23}$, or N;
or a pharmaceutically acceptable salt thereof.
In some embodiments of these compounds, $R^{24}$ and $R^{25}$ are hydrogen.
In some embodiments of these compounds, $R^{26}$ is hydrogen.
In some embodiments of these compounds, $R^{26}$ is substituted $C_1$-$C_6$ alkyl, wherein $C_1$-$C_6$ alkyl is substituted with hydroxy.

In some embodiments of these compounds, $R^{24}$, $R^{25}$ and $R^{26}$ are hydrogen.
In some embodiments of these compounds, $R^{23}$ is hydrogen, halogen, or $C_1$-$C_6$ alkoxy.
In some embodiments of these compounds, Q is CH or $CR^{23}$.
In some embodiments of these compounds, Q is N.
In some embodiments of these compounds, $R^7$ is $C_1$-$C_3$ alkyl.
In some embodiments of these compounds, $R^3$ and $R^4$ are hydrogen.
In some embodiments of these compounds, at least one of $R^3$ and $R^4$ is $C_1$-$C_6$ alkyl.
The present disclosure provides a compound of Formula Id:

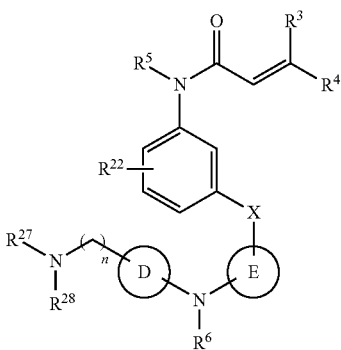

Formula Id wherein
X is $CF_2$, O, $CH_2$ S, or $NR^b$;
$R^b$ is selected from H, substituted or unsubstituted $C_{1-8}$ alkyl, $C_{2-8}$ alkenyl, $C_{2-8}$ alkynyl, aryl, fused aryl, heteroaryl, fused heterocycle, a $C_{3-8}$ carbocyclic ring or a $C_{3-8}$ heterocyclic ring, saturated or unsaturated, wherein each $C_{1-8}$ alkyl, $C_{3-8}$ cyclic alkyl, $C_{2-8}$ alkenyl, $C_{2-8}$ alkynyl can optionally contain a heteroatom selected from N, O and S in place of a carbon atom;
$R^3$ and $R^4$ are independently hydrogen, $C_1$-$C_6$ alkyl, or —$(CH_2)_m N(R^a)_2$, wherein m is one to 6;
$R^5$ is hydrogen or $C_1$-$C_6$ alkyl;
$R^6$ is hydrogen or $C_1$-$C_6$ alkyl;

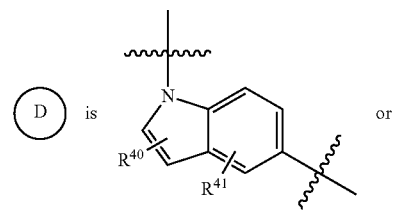

D is

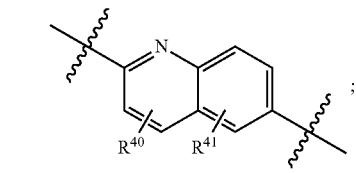

or

;

-continued

E is

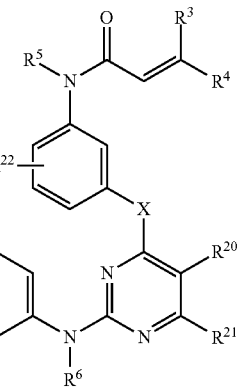

R²⁰ and R²¹ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)R$^a$, —OC(O)R$^a$, —C(O)OR$^a$, —C(O)N(R$^a$)$_2$, sulfonyl, sulfonylamino, aminosulfonyl, amino, and substituted amino;

R²⁴ and R²⁵ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)R$^a$, —OC(O)R$^a$, —C(O)OR$^a$, —C(O)N(R$^a$)$_2$, sulfonyl, sulfonylamino, aminosulfonyl, amino, and substituted amino;

R²⁶ is hydrogen, $C_1$-$C_6$ alkyl, or substituted $C_1$-$C_6$ alkyl, wherein $C_1$-$C_6$ alkyl is substituted with halogen, hydroxy, cyano, nitro, sulfonyl, sulfonylamino, aminosulfonyl, amino, or substituted amino;

R⁴⁰ and R⁴¹ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)R$^a$, —OC(O)R$^a$, —C(O)OR$^a$, —C(O)N(R$^a$)$_2$, sulfonyl, sulfonylamino, aminosulfonyl, amino, substituted amino, acylamino, alkoxycarbonylamino, and aminocarbonylamino;

R²² is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, thiol, —C(O)R$^a$, —OC(O)R$^a$, —C(O)OR$^a$, —C(O)N(R$^a$)$_2$, sulfonyl, sulfonylamino, aminosulfonyl, amino, substituted amino, acylamino, alkoxycarbonylamino, and aminocarbonylamino;

each R$^a$ is independently hydrogen or $C_1$-$C_6$ alkyl;

R²⁷ and R²⁸ are independently hydrogen or $C_1$-$C_6$ alkyl; and n is one or two;

or a pharmaceutically acceptable salt thereof.

The present disclosure provides a compound of Formula VI:

Formula VI wherein

X is CF$_2$, O, CH$_2$ S, or NR$^b$;

R$^b$ is selected from H, substituted or unsubstituted $C_{1-8}$ alkyl, $C_{2-8}$ alkenyl, $C_{2-8}$ alkynyl, aryl, fused aryl, heteroaryl, fused heterocycle, a $C_{3-8}$ carbocyclic ring or a $C_{3-8}$ heterocyclic ring, saturated or unsaturated, wherein each $C_{1-8}$ alkyl, $C_{3-8}$ cyclic alkyl, $C_{2-8}$ alkenyl, $C_{2-8}$ alkynyl can optionally contain a heteroatom selected from N, O and S in place of a carbon atom;

R³ and R⁴ are independently hydrogen, $C_1$-$C_6$ alkyl, or —(CH$_2$)$_m$N(R$^a$)$_2$, wherein m is one to 6;

R⁵ is hydrogen or $C_1$-$C_6$ alkyl;

R⁶ is hydrogen or $C_1$-$C_6$ alkyl;

R²⁰ and R²¹ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)R$^a$, —OC(O)R$^a$, —C(O)OR$^a$, —C(O)N(R$^a$)$_2$, sulfonyl, sulfonylamino, aminosulfonyl, amino, and substituted amino;

R²² is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)R$^a$, —OC(O)R$^a$, —C(O)OR$^a$, —C(O)N(R$^a$)$_2$, sulfonyl, sulfonylamino, aminosulfonyl, amino, substituted amino, acylamino, alkoxycarbonylamino, and aminocarbonylamino;

R⁴⁰ and R⁴¹ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)R$^a$, —OC(O)R$^a$, —C(O)OR$^a$, —C(O)N(R$^a$)$_2$, sulfonyl, sulfonylamino, aminosulfonyl, amino, substituted amino, acylamino, alkoxycarbonylamino, and aminocarbonylamino;

each R$^a$ is independently hydrogen or $C_1$-$C_6$ alkyl; and

R²⁷ and R²⁸ are independently hydrogen or $C_1$-$C_6$ alkyl;

or a pharmaceutically acceptable salt thereof.

The present disclosure provides a compound of Formula VII:

Formula VII

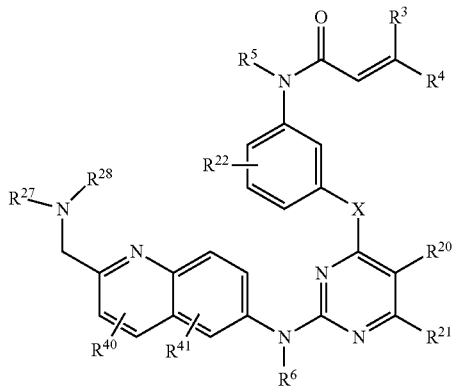

Formula VIII

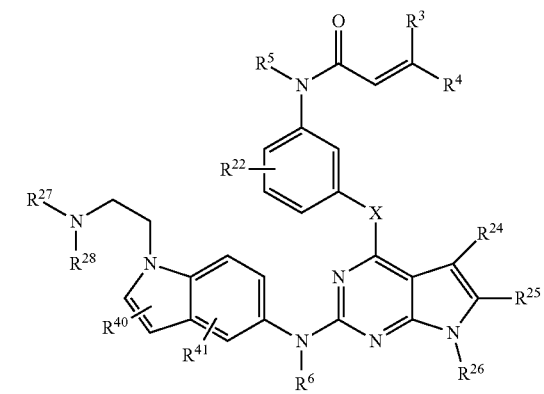

wherein

X is $CF_2$, O, $CH_2$ S, or $NR^b$;

$R^b$ is selected from H, substituted or unsubstituted $C_{1-8}$ alkyl, $C_{2-8}$ alkenyl, $C_{2-8}$ alkynyl, aryl, fused aryl, heteroaryl, fused heterocycle, a $C_{3-8}$ carbocyclic ring or a $C_{3-8}$ heterocyclic ring, saturated or unsaturated, wherein each $C_{1-8}$ alkyl, $C_{3-8}$ cyclic alkyl, $C_{2-8}$ alkenyl, $C_{2-8}$ alkynyl can optionally contain a heteroatom selected from N, O and S in place of a carbon atom;

$R^3$ and $R^4$ are independently hydrogen, $C_1$-$C_6$ alkyl, or $(CH_2)_m N(R^a)_2$, wherein m is one to 6;

$R^5$ is hydrogen or $C_1$-$C_6$ alkyl;

$R^6$ is hydrogen or $C_1$-$C_6$ alkyl;

$R^{20}$ and $R^{21}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, and substituted amino;

$R^{22}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, substituted amino, acylamino, alkoxycarbonylamino, and aminocarbonylamino;

$R^{40}$ and $R^{41}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, substituted amino, acylamino, alkoxycarbonylamino, and aminocarbonylamino;

each $R^a$ is independently hydrogen or $C_1$-$C_6$ alkyl; and $R^{27}$ and $R^{28}$ are independently hydrogen or $C_1$-$C_6$ alkyl; or a pharmaceutically acceptable salt thereof.

The present disclosure provides a compound of Formula VIII:

wherein

X is $CF_2$, O, $CH_2$ S, or $NR^b$;

$R^b$ is selected from H, substituted or unsubstituted $C_{1-8}$ alkyl, $C_{2-8}$ alkenyl, $C_{2-8}$ alkynyl, aryl, fused aryl, heteroaryl, fused heterocycle, a $C_{3-8}$ carbocyclic ring or a $C_{3-8}$ heterocyclic ring, saturated or unsaturated, wherein each $C_{1-8}$ alkyl, $C_{3-8}$ cyclic alkyl, $C_{2-8}$ alkenyl, $C_{2-8}$ alkynyl can optionally contain a heteroatom selected from N, O and S in place of a carbon atom;

$R^3$ and $R^4$ are independently hydrogen, $C_1$-$C_6$ alkyl, or $(CH_2)_m N(R^a)_2$, wherein m is one to 6;

$R^5$ is hydrogen or $C_1$-$C_6$ alkyl;

$R^6$ is hydrogen or $C_1$-$C_6$ alkyl;

$R^{24}$ and $R^{25}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, and substituted amino;

$R^{26}$ is hydrogen, $C_1$-$C_6$ alkyl, or substituted $C_1$-$C_6$ alkyl, wherein $C_1$-$C_6$ alkyl is substituted with halogen, hydroxy, cyano, nitro, sulfonyl, sulfonylamino, aminosulfonyl, amino, or substituted amino;

$R^{22}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, substituted amino, acylamino, alkoxycarbonylamino, and aminocarbonylamino;

$R^{40}$ and $R^{41}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, substituted amino, acylamino, alkoxycarbonylamino, and aminocarbonylamino;

each $R^a$ is independently hydrogen or $C_1$-$C_6$ alkyl; and $R^{27}$ and $R^{28}$ are independently hydrogen or $C_1$-$C_6$ alkyl; or a pharmaceutically acceptable salt thereof.

The present disclosure provides a compound of Formula IX:

Formula IX

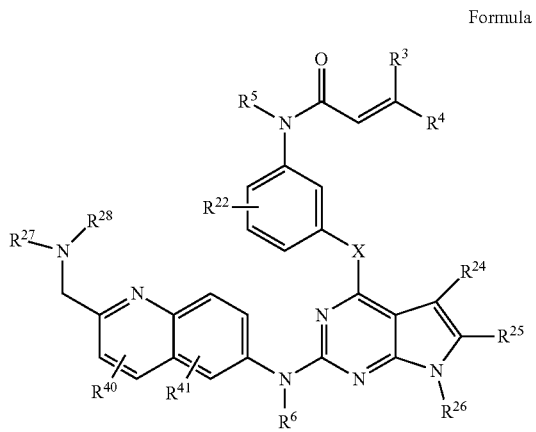

Formula X

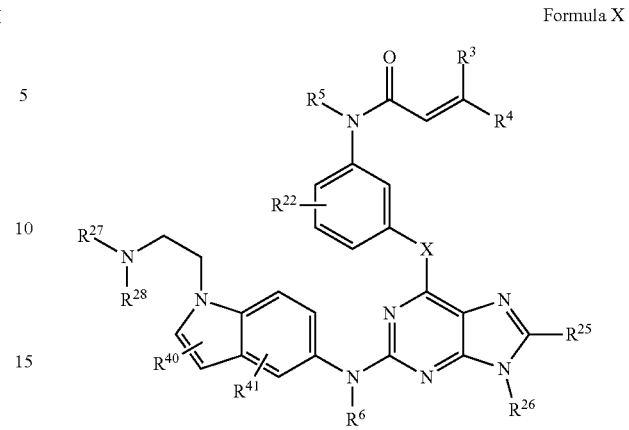

wherein

X is $CF_2$, O, $CH_2$ S, or $NR^b$;

$R^b$ is selected from H, substituted or unsubstituted $C_{1-8}$ alkyl, $C_{2-8}$ alkenyl, $C_{2-8}$ alkynyl, aryl, fused aryl, heteroaryl, fused heterocycle, a $C_{3-8}$ carbocyclic ring or a $C_{3-8}$ heterocyclic ring, saturated or unsaturated, wherein each $C_{1-8}$ alkyl, $C_{3-8}$ cyclic alkyl, $C_{2-8}$ alkenyl, $C_{2-8}$ alkynyl can optionally contain a heteroatom selected from N, O and S in place of a carbon atom;

$R^3$ and $R^4$ are independently hydrogen, $C_1$-$C_6$ alkyl, or —$(CH_2)_m N(R^a)_2$, wherein m is one to 6;

$R^5$ is hydrogen or $C_1$-$C_6$ alkyl;

$R^6$ is hydrogen or $C_1$-$C_6$ alkyl;

$R^{24}$ and $R^{25}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, and substituted amino;

$R^{26}$ is hydrogen, $C_1$-$C_6$ alkyl, or substituted $C_1$-$C_6$ alkyl, wherein $C_1$-$C_6$ alkyl is substituted with halogen, hydroxy, cyano, nitro, sulfonyl, sulfonylamino, aminosulfonyl, amino, or substituted amino;

$R^{22}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, substituted amino, acylamino, alkoxycarbonylamino, and aminocarbonylamino;

$R^{40}$ and $R^{41}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, substituted amino, acylamino, alkoxycarbonylamino, and aminocarbonylamino;

each $R^a$ is independently hydrogen or $C_1$-$C_6$ alkyl; and $R^{27}$ and $R^{28}$ are independently hydrogen or $C_1$-$C_6$ alkyl;

or a pharmaceutically acceptable salt thereof.

The present disclosure provides a compound of Formula X:

wherein

X is $CF_2$, O, $CH_2$ S, or $NR^b$;

$R^b$ is selected from H, substituted or unsubstituted $C_{1-8}$ alkyl, $C_{2-8}$ alkenyl, $C_{2-8}$ alkynyl, aryl, fused aryl, heteroaryl, fused heterocycle, a $C_{3-8}$ carbocyclic ring or a $C_{3-8}$ heterocyclic ring, saturated or unsaturated, wherein each $C_{1-8}$ alkyl, $C_{3-8}$ cyclic alkyl, $C_{2-8}$ alkenyl, $C_{2-8}$ alkynyl can optionally contain a heteroatom selected from N, O and S in place of a carbon atom;

$R^3$ and $R^4$ are independently hydrogen, $C_1$-$C_6$ alkyl, or —$(CH_2)_m N(R^a)_2$, wherein m is one to 6;

$R^5$ is hydrogen or $C_1$-$C_6$ alkyl;

$R^6$ is hydrogen or $C_1$-$C_6$ alkyl;

$R^{25}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, and substituted amino;

$R^{26}$ is hydrogen, $C_1$-$C_6$ alkyl, or substituted $C_1$-$C_6$ alkyl, wherein $C_1$-$C_6$ alkyl is substituted with halogen, hydroxy, cyano, nitro, sulfonyl, sulfonylamino, aminosulfonyl, amino, or substituted amino;

$R^{22}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, substituted amino, acylamino, alkoxycarbonylamino, and aminocarbonylamino;

$R^{40}$ and $R^{41}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, substituted amino, acylamino, alkoxycarbonylamino, and aminocarbonylamino;

each $R^a$ is independently hydrogen or $C_1$-$C_6$ alkyl; and $R^{27}$ and $R^{28}$ are independently hydrogen or $C_1$-$C_6$ alkyl;

or a pharmaceutically acceptable salt thereof.

The present disclosure provides a compound of Formula XI:

Formula XI

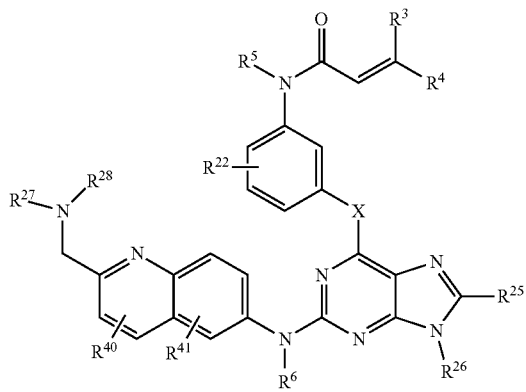

wherein

X is $CF_2$, O, $CH_2$ S, or $NR^b$;

$R^b$ is selected from H, substituted or unsubstituted $C_{1-8}$ alkyl, $C_{2-8}$ alkenyl, $C_{2-8}$ alkynyl, aryl, fused aryl, heteroaryl, fused heterocycle, a $C_{3-8}$ carbocyclic ring or a $C_{3-8}$ heterocyclic ring, saturated or unsaturated, wherein each $C_{1-8}$ alkyl, $C_{3-8}$ cyclic alkyl, $C_{2-8}$ alkenyl, $C_{2-8}$ alkynyl can optionally contain a heteroatom selected from N, O and S in place of a carbon atom;

$R^3$ and $R^4$ are independently hydrogen, $C_1$-$C_6$ alkyl, or —$(CH_2)_m N(R^a)_2$, wherein m is one to 6;

$R^5$ is hydrogen or $C_1$-$C_6$ alkyl;

$R^6$ is hydrogen or $C_1$-$C_6$ alkyl;

$R^{25}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, and substituted amino;

$R^{26}$ is hydrogen, $C_1$-$C_6$ alkyl, or substituted $C_1$-$C_6$ alkyl, wherein $C_1$-$C_6$ alkyl is substituted with halogen, hydroxy, cyano, nitro, sulfonyl, sulfonylamino, aminosulfonyl, amino, or substituted amino;

$R^{22}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, substituted amino, acylamino, alkoxycarbonylamino, and aminocarbonylamino;

$R^{40}$ and $R^{41}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, substituted amino, acylamino, alkoxycarbonylamino, and aminocarbonylamino;

each $R^a$ is independently hydrogen or $C_1$-$C_6$ alkyl; and $R^{27}$ and $R^{28}$ are independently hydrogen or $C_1$-$C_6$ alkyl;

or a pharmaceutically acceptable salt thereof.

Other aspects of the invention provide pharmaceutical compositions comprising a compound of the invention and methods of using these compounds and compositions for treating proliferative disorders such as cancers.

The present disclosure provides a pharmaceutical composition comprising a compound of Formula I-XI admixed with at least one pharmaceutically acceptable carrier or excipient. In some embodiments, the pharmaceutical composition can comprise at least one sterile pharmaceutically acceptable carrier or excipient. In some embodiments, the pharmaceutical composition can comprise at least two pharmaceutically acceptable carriers and/or excipients.

The present disclosure provides a compound of Formula I-XI for use in therapy. In some embodiments, the use in therapy is a use to treat cancer. In some embodiments, the cancer is selected from leukemia, lymphoma, lung cancer, colon cancer, CNS cancer, melanoma, ovarian cancer, renal cancer, prostate cancer, breast cancer, head and neck cancers, and pancreatic cancer.

The present disclosure provides a method to treat cancer, which comprises administering to a subject in need thereof an effective amount of a compound of Formula I-XI. In some embodiments, the cancer is selected from leukemia, lymphoma, lung cancer, colon cancer, CNS cancer, melanoma, ovarian cancer, renal cancer, prostate cancer, breast cancer, head and neck cancers, and pancreatic cancer.

The present disclosure provides a use of a compound of Formula I-XI for the manufacture of a medicament. In some embodiments, the cancer is selected from leukemia, lymphoma, lung cancer, colon cancer, CNS cancer, melanoma, ovarian cancer, renal cancer, prostate cancer, breast cancer, head and neck cancers, and pancreatic cancer.

BRIEF DESCRIPTION OF THE DRAWINGS

The patent or application file contains five drawings executed in color which are necessary to accurately and clearly depict the subject matter sought to be patented. Copies of this patent or patent application publication with color drawings will be provided by the office upon request and payment of the necessary fee.

DESCRIPTION OF SELECTED EMBODIMENTS

Figure 1:
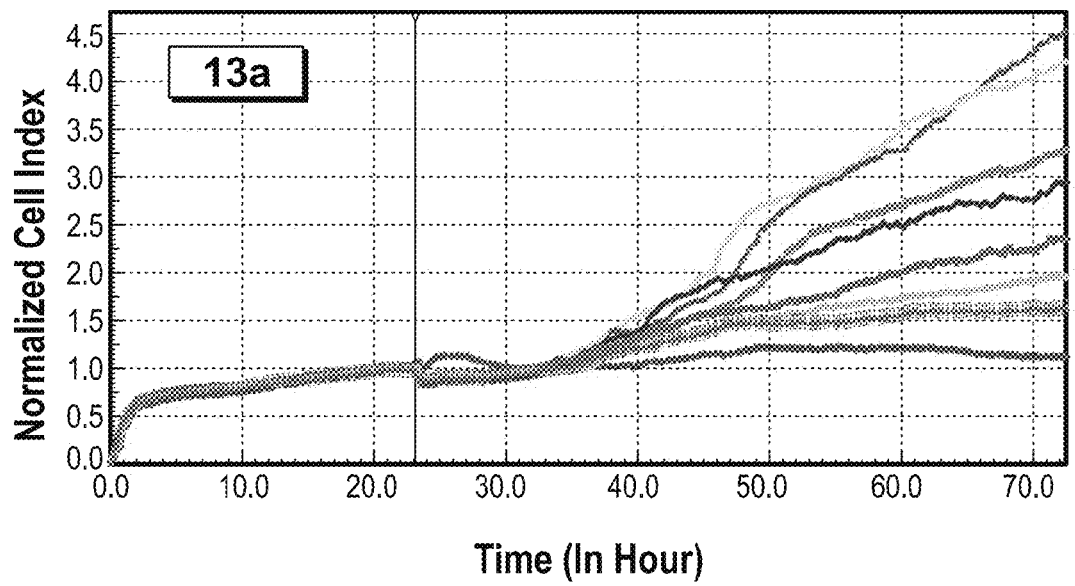
FIG. 1 shows detailed assay plots of H1975 viability assay for Compounds 13a, 13b, 19 and WZ4002.
Figure 1:
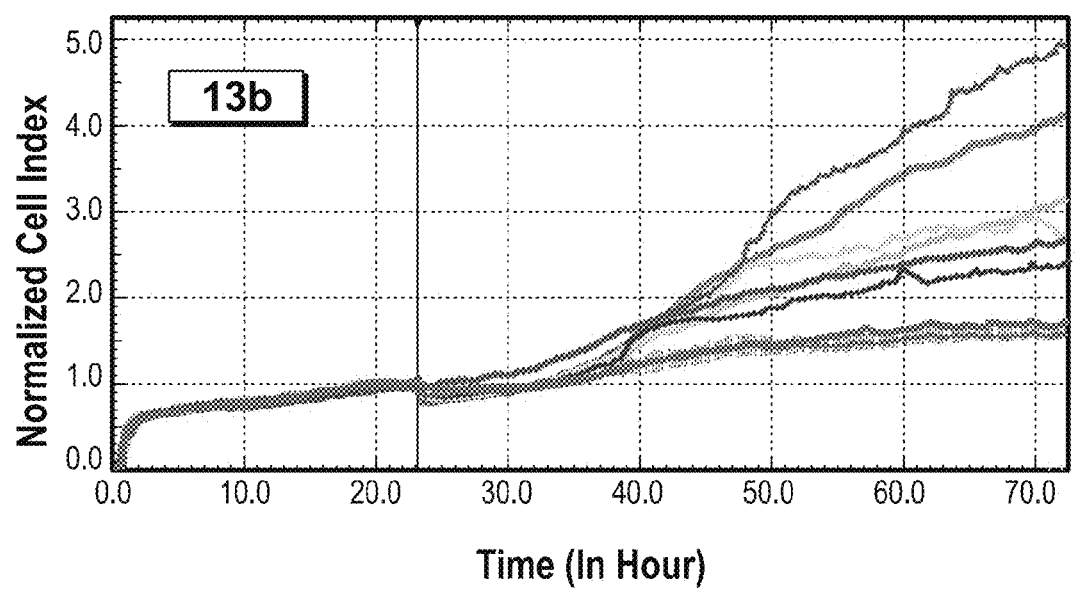
Figure 1:
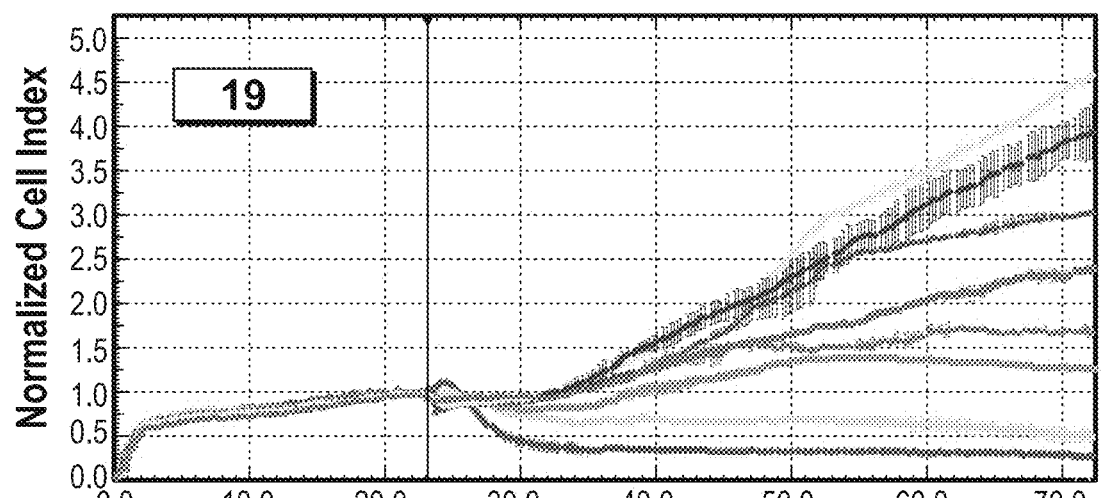
Figure 1:
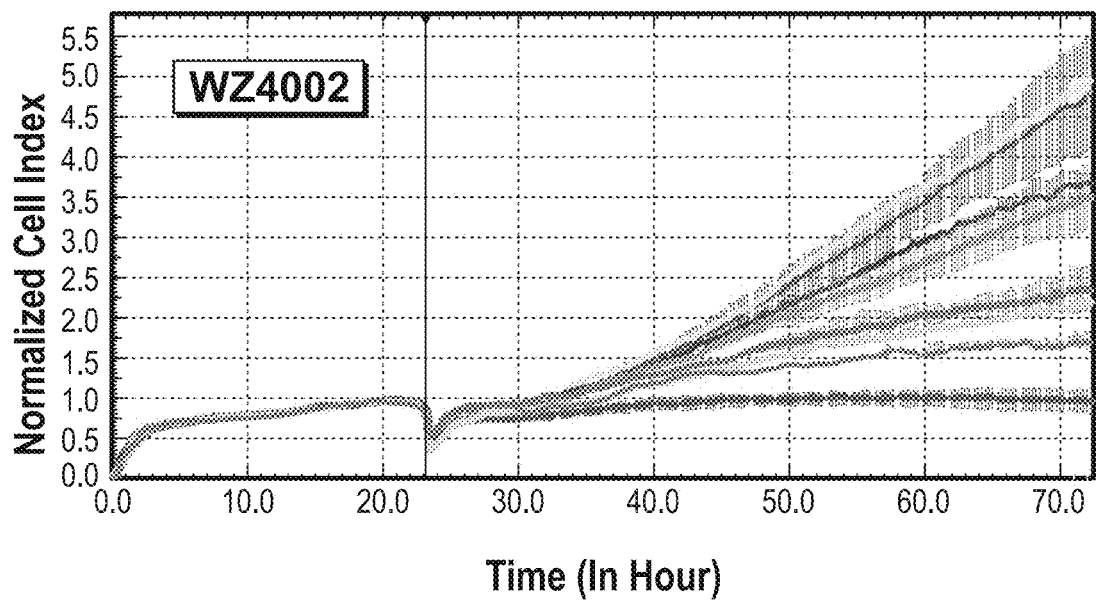
Figure 1:
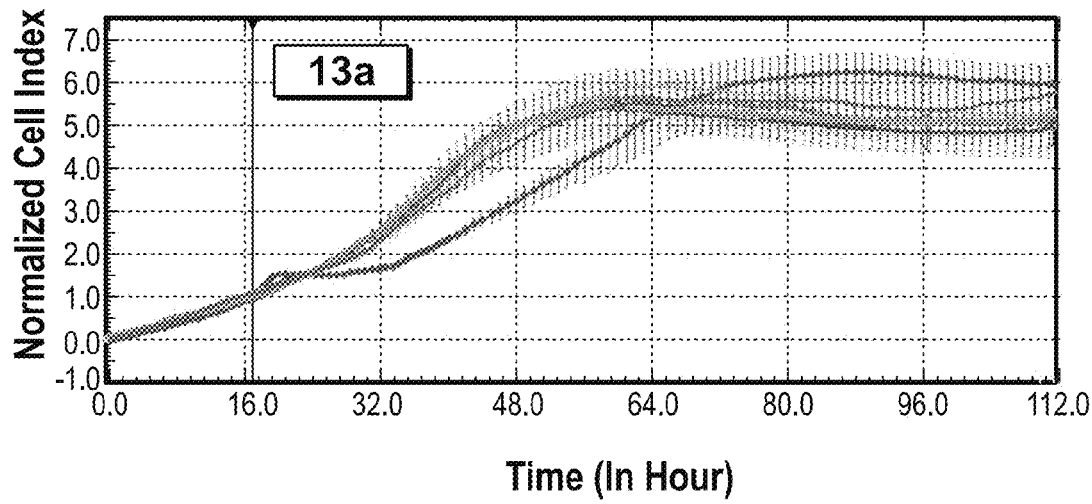
Figure 1:
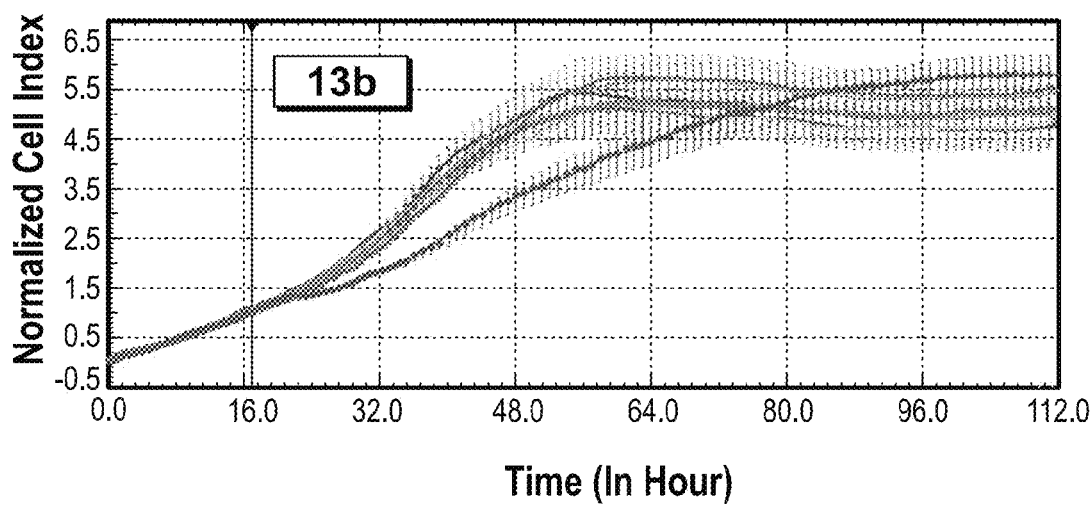
Figure 1:
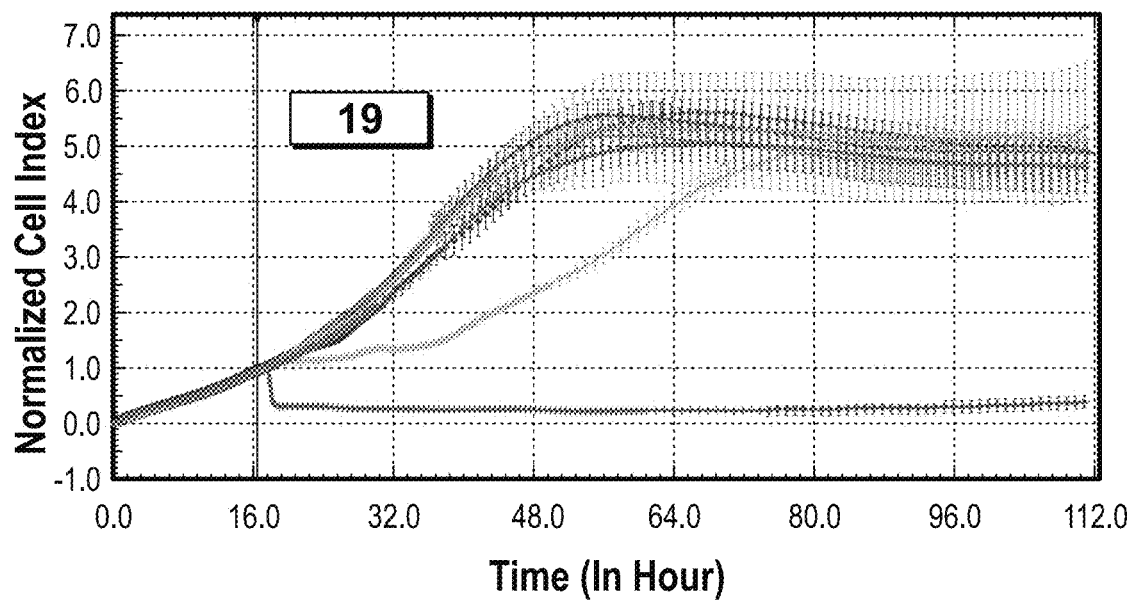
Figure 1:
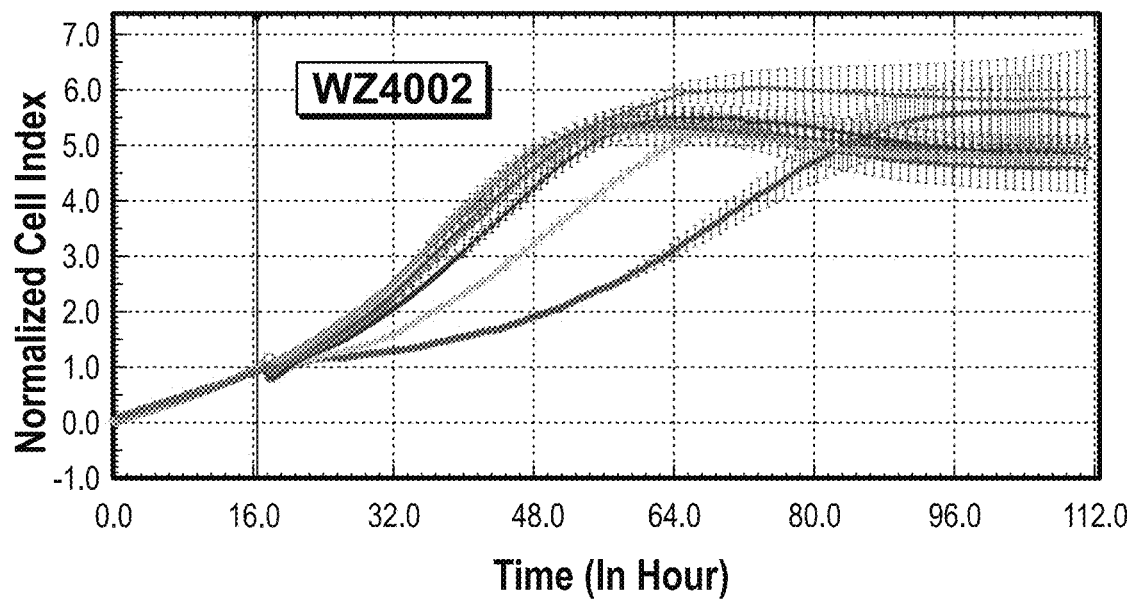

General Definitions:

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

As used herein, "a" or "an" means "at least one" or "one or more".

The term "alkyl" as used herein refers to saturated hydrocarbon groups in a straight, branched, or cyclic configuration or any combination thereof, and particularly contemplated alkyl groups include those having ten or less carbon atoms, especially 1-6 carbon atoms and lower alkyl groups having 1-4 carbon atoms. Exemplary alkyl groups are methyl, ethyl, propyl, isopropyl, butyl, sec-butyl, tertiary butyl, pentyl, isopentyl, hexyl, cyclopropylmethyl, etc.

Alkyl groups can be unsubstituted, or they can be substituted to the extent that such substitution makes sense chemically. Typical substituents include, but are not limited to, halo, =O, =N—CN, =N—$OR^a$, =$NR^a$, —$OR^a$, —$NR^a_2$, —$SR^a$, —$SO_2R^a$, —$SO_2NR^a_2$, —$NR^aSO_2R^a$, —$NR^a$-$CONR^a_2$, —$NR^aCOOR^a$, —$NR^aCOR^a$, —CN, —$COOR^a$, —$CONR^a_2$, —$OOCR^a$, —$COR^a$, and —$NO_2$, wherein each $R^a$ is independently H, C1-C8 alkyl, C2-C8 heteroalkyl, C3-C8 heterocyclyl, C4-C10 heterocyclyclalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each $R^a$ is optionally substituted with halo, =O, =N—CN, =N—$OR^b$, =$NR^b$, $OR^b$, $NR^b_2$, $SR^b$, $SO_2R^b$, $SO_2NR^b_2$, $NR^bSO_2R^b$, $NR^bCONR^b_2$, $NR^bCOOR^b$, $NR^bCOR^b$, CN, $COOR^b$, $CONR^b_2$, $OOCR^b$, $COR^b$, and $NO_2$, wherein each $R^b$ is independently H, C1-C8 alkyl, C2-C8 heteroalkyl, C3-C8 heterocyclyl, C4-C10 heterocyclyclalkyl, C1-C8 acyl, C2-C8 heteroacyl, C6-C10 aryl or C5-C10 heteroaryl. Alkyl, alkenyl and alkynyl groups can also be substituted by C1-C8 acyl, C2-C8 heteroacyl, C6-C10 aryl or C5-C10 heteroaryl, each of which can be substituted by the substituents that are appropriate for the particular group. Where a substituent group contains two $R^a$ or $R^b$ groups on the same or adjacent atoms (e.g., —$NR^b2$, or —$NR^b$—C(O) $R^b$), the two $R^a$ or $R^b$ groups can optionally be taken together with the atoms in the substituent group to which the are attached to form a ring having 5-8 ring members, which can be substituted as allowed for the $R^a$ or $R^b$ itself, and can contain an additional heteroatom (N, O or S) as a ring member.

The term "alkenyl" as used herein refers to an alkyl as defined above having at least two carbon atoms and at least one carbon-carbon double bond. Thus, particularly contemplated alkenyl groups include straight, branched, or cyclic alkenyl groups having two to ten carbon atoms (e.g., ethenyl, propenyl, butenyl, pentenyl, etc.) or 5-10 atoms for cyclic alkenyl groups. Alkenyl groups are optionally substituted by groups suitable for alkyl groups as set forth herein.

Similarly, the term "alkynyl" as used herein refers to an alkyl or alkenyl as defined above and having at least two (preferably three) carbon atoms and at least one carbon-carbon triple bond. Especially contemplated alkynyls include straight, branched, or cyclic alkynes having two to ten total carbon atoms (e.g., ethynyl, propynyl, butynyl, cyclopropylethynyl, etc.). Alkynyl groups are optionally substituted by groups suitable for alkyl groups as set forth herein.

The term "cycloalkyl" as used herein refers to a cyclic alkane (i.e., in which a chain of carbon atoms of a hydrocarbon forms a ring), preferably including three to eight carbon atoms. Thus, exemplary cycloalkanes include cyclopropyl, cyclobutyl, cyclopentyl, cyclohexyl, cycloheptyl, and cyclooctyl. Cycloalkyls also include one or two double bonds, which form the "cycloalkenyl" groups. Cycloalkyl groups are optionally substituted by groups suitable for alkyl groups as set forth herein.

The term "aryl" or "aromatic moiety" as used herein refers to an aromatic ring system, which may further include one or more non-carbon atoms. These are typically 5-6 membered isolated rings, or 8-10 membered bicyclic groups, and can be substituted. Thus, contemplated aryl groups include (e.g., phenyl, naphthyl, etc.) and pyridyl. Further contemplated aryl groups may be fused (i.e., covalently bound with 2 atoms on the first aromatic ring) with one or two 5- or 6-membered aryl or heterocyclic group, and are thus termed "fused aryl" or "fused aromatic".

Aromatic groups containing one or more heteroatoms (typically N, O or S) as ring members can be referred to as heteroaryl or heteroaromatic groups. Typical heteroaromatic groups include monocyclic C5-C6 aromatic groups such as pyridyl, pyrimidyl, pyrazinyl, thienyl, furanyl, pyrrolyl, pyrazolyl, thiazolyl, oxazolyl, isothiazolyl, isoxazolyl, and imidazolyl and the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, benzothiazolyl, benzofuranyl, pyrazolopyridyl, pyrazolopyrimidyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms.

As also used herein, the terms "heterocycle", "cycloheteroalkyl", and "heterocyclic moieties" are used interchangeably herein and refer to any compound in which a plurality of atoms form a ring via a plurality of covalent bonds, wherein the ring includes at least one atom other than a carbon atom as a ring member. Particularly contemplated heterocyclic rings include 5- and 6-membered rings with nitrogen, sulfur, or oxygen as the non-carbon atom (e.g., imidazole, pyrrole, triazole, dihydropyrimidine, indole, pyridine, thiazole, tetrazole etc.). Typically these rings contain 0-1 oxygen or sulfur atoms, at least one and typically 2-3 carbon atoms, and up to four nitrogen atoms as ring members. Further contemplated heterocycles may be fused (i.e., covalently bound with two atoms on the first heterocyclic ring) to one or two carbocyclic rings or heterocycles, and are thus termed "fused heterocycle" or "fused heterocyclic ring" or "fused heterocyclic moieties" as used herein. Where the ring is aromatic, these can be referred to herein as 'heteroaryl' or heteroaromatic groups.

Heterocyclic groups that are not aromatic can be substituted with groups suitable for alkyl group substituents, as set forth above.

Aryl and heteroaryl groups can be substituted where permitted. Suitable substituents include, but are not limited to, halo, —$OR^a$, —$NR^a_2$, —$SR^a$, —$SO_2R^a$, —$SO_2NR^a_2$, —$NR^aSO_2R^a$, —$NR^aCONR^a_2$, —$NR^aCOOR^a$, —$NR^a$-$COR^a$, —CN, —$COOR^a$, —$CONR^a_2$, —$OOCR^a$, —$COR^a$, and —$NO_2$, wherein each $R^a$ is independently H, C1-C8 alkyl, C2-C8 heteroalkyl, C3-C8 heterocyclyl, C4-C10 heterocyclyclalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each $R^a$ is optionally substituted with halo, =O, =N—CN, =N—$OR^b$, =$NR^b$, $OR^b$, $NR^b_2$, $SR^b$, $SO_2R^b$, $SO_2NR^b_2$, $NR^bSO_2R^b$, $NR^bCONR^b_2$, $NR^bCOOR^b$, $NR^bCOR^b$, CN, $COOR^b$, $CONR^b_2$, $OOCR^b$, $COR^b$, and $NO_2$, wherein each $R^b$ is independently H, C1-C8 alkyl, C2-C8 heteroalkyl, C3-C8 heterocyclyl, C4-C10 heterocyclyclalkyl, C1-C8 acyl, C2-C8 heteroacyl, C6-C10 aryl or C5-C10 heteroaryl. Alkyl, alkenyl and alkynyl groups can also be substituted by C1-C8 acyl, C2-C8 heteroacyl, C6-C10 aryl or C5-C10 heteroaryl, each of which can be substituted by the substituents that are appropriate for the particular group. Where a substituent group contains two $R^a$ or $R^b$ groups on the same or adjacent atoms (e.g., —$NR^b2$, or —$NR^b$—C(O) $R^b$), the two $R^a$ or $R^b$ groups can optionally be taken together with the atoms in the substituent group to which the are attached to form a ring having 5-8 ring members, which can be substituted as allowed for the $R^a$ or $R^b$ itself, and can contain an additional heteroatom (N, O or S) as a ring member.

As also used herein, the terms "imidazopyridine" or "imidazopyrimidine" or "thiazopyridine" or "thiazopyrimidine" herein refer to any compound in which the two designated heterocyclic rings are fused by any two adjacent atoms on the two heterocyclic rings.

The term "alkoxy" as used herein refers to a hydrocarbon group connected through an oxygen atom, e.g., —O—Hc, wherein the hydrocarbon portion Hc may have any number of carbon atoms, typically 1-10 carbon atoms, may further include a double or triple bond and may include one or two oxygen, sulfur or nitrogen atoms in the alkyl chains, and can be substituted with aryl, heteroaryl, cycloalkyl, and/or heterocyclyl groups. For example, suitable alkoxy groups include methoxy, ethoxy, propyloxy, isopropoxy, methoxyethoxy, benzyloxy, allyloxy, and the like. Similarly, the term "alkylthio" refers to alkylsulfides of the general formula —S—Hc, wherein the hydrocarbon portion Hc is as described for alkoxy groups. For example, contemplated alkylthio groups include methylthio, ethylthio, isopropylthio, methoxyethylthio, benzylthio, allylthio, and the like.

The term 'amino' as used herein refers to the group —NH$_2$. The term "alkylamino" refers to amino groups where one or both hydrogen atoms are replaced by a hydrocarbon group Hc as described above, wherein the amino nitrogen "N" can be substituted by one or two Hc groups as set forth for alkoxy groups described above. Exemplary alkylamino groups include methylamino, dimethylamino, ethylamino, diethylamino, etc. Also, the term "substituted amino" refers to amino groups where one or both hydrogen atoms are replaced by a hydrocarbon group Hc as described above, wherein the amino nitrogen "N" can be substituted by one or two Hc groups as set forth for alkoxy groups described above.

The term 'acyl' as used herein refers to a group of the formula —C(=O)—D, where D represents an alkyl, alkenyl, alkynyl, cycloalkyl, aryl, heteroaryl, or heterocycle as described above. Typical examples are groups wherein D is a C1-C10 alkyl, C2-C10 alkenyl or alkynyl, or phenyl, each of which is optionally substituted. In some embodiments, D can be H, Me, Et, isopropyl, propyl, butyl, C1-C4 alkyl substituted with —OH, —OMe, or NH$_2$, phenyl, halophenyl, alkylphenyl, and the like.

The term "aryloxy" as used herein refers to an aryl group connecting to an oxygen atom, wherein the aryl group may be further substituted. For example suitable aryloxy groups include phenyloxy, etc. Similarly, the term "arylthio" as used herein refers to an aryl group connecting to a sulfur atom, wherein the aryl group may be further substituted. For example suitable arylthio groups include phenylthio, etc.

The hydrocarbon portion of each alkoxy, alkylthio, alkylamino, and aryloxy, etc. can be substituted as appropriate for the relevant hydrocarbon moiety.

The term "halogen" as used herein refers to fluorine, chlorine, bromine and iodine. Where present as a substituent group, halogen or halo typically refers to F or Cl or Br, more typically F or Cl.

The term "haloalkyl" refers to an alkyl group as described above, wherein one or more hydrogen atoms on the alkyl group have been substituted with a halo group. Examples of such groups include, without limitation, fluoroalkyl groups, such as fluoroethyl, trifluoromethyl, difluoromethyl, trifluoroethyl and the like.

The term "haloalkoxy" refers to the group alkyl-O— wherein one or more hydrogen atoms on the alkyl group have been substituted with a halo group and include, by way of examples, groups such as trifluoromethoxy, and the like.

The term "sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cycloalkyl, SO$_2$-cycloalkenyl, SO$_2$-substituted cycloalkenyl, SO$_2$-aryl, SO$_2$-substituted aryl, SO$_2$-heteroaryl, SO$_2$-substituted heteroaryl, SO$_2$-heterocyclic, and SO$_2$-substituted heterocyclic, wherein each alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.

The term "sulfonylamino" refers to the group —NR$^{21}$SO$_2$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein The term "aminosulfonyl" refers to the group —SO$_2$NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where R$^{21}$ and R$^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

The term "acylamino" refers to the groups —NR$^{20}$C(O) alkyl, —NR$^{20}$C(O)substituted alkyl, —NR$^{20}$C(O)cycloalkyl, —NR$^{20}$C(O)substituted cycloalkyl, —NR$^{20}$C(O)cycloalkenyl, —NR$^{20}$C(O)substituted cycloalkenyl, —NR$^{20}$C(O)alkenyl, —NR$^{20}$C(O)substituted alkenyl, —NR$^{20}$C(O) alkynyl, —NR$^{20}$C(O)substituted alkynyl, —NR$^{20}$C(O)aryl, —NR$^{20}$C(O)substituted aryl, —NR$^{20}$C(O)heteroaryl, —NR$^{20}$C(O)substituted heteroaryl, —NR$^{20}$C(O)heterocyclic, and —NR20C(O)substituted heterocyclic, wherein R$^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "alkoxycarbonylamino" refers to the group —NRC(O)OR where each R is independently hydrogen, alkyl, substituted alkyl, aryl, heteroaryl, or heterocyclyl wherein alkyl, substituted alkyl, aryl, heteroaryl, and heterocyclyl are as defined herein The term "aminocarbonylamino" refers to the group —NR20C(O)NR$^{21}$R$^{22}$, wherein R$^{20}$ is hydrogen or alkyl and $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

It should further be recognized that all of the above-defined groups may further be substituted with one or more substituents, which may in turn be substituted with hydroxy, amino, cyano, C1-C4 alkyl, halo, or C1-C4 haloalkyl. For example, a hydrogen atom in an alkyl or aryl can be replaced by an amino, halo or C1-4 haloalkyl or alkyl group.

The term "substituted" as used herein refers to a replacement of a hydrogen atom of the unsubstituted group with a functional group, and particularly contemplated functional groups include nucleophilic groups (e.g., $-NH_2$, $-OH$, $-SH$, $-CN$, etc.), electrophilic groups (e.g., $C(O)OR$, $C(X)OH$, etc.), polar groups (e.g., $-OH$), non-polar groups (e.g., heterocycle, aryl, alkyl, alkenyl, alkynyl, etc.), ionic groups (e.g., $-NH_3^+$), and halogens (e.g., $-F$, $-Cl$), NHCOR, $NHCONH_2$, $OCH_2COOH$, $OCH_2CONH_2$, $OCH_2CONHR$, $NHCH_2COOH$, $NHCH_2CONH_2$, $NHSO_2R$, $OCH_2$-heterocycles, $PO_3H$, $SO_3H$, amino acids, and all chemically reasonable combinations thereof. Moreover, the term "substituted" also includes multiple degrees of substitution, and where multiple substituents are disclosed or claimed, the substituted compound can be independently substituted by one or more of the disclosed or claimed substituent moieties.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, compounds arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "pharmaceutically acceptable salt" means a salt which is acceptable for administration to a patient, such as a mammal, such as human (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

The compounds and compositions described herein can be administered to a subject in need of treatment for a cell proliferation disorder such as cancer, particularly cancers selected from leukemia, lymphoma, lung cancer, colon cancer, CNS cancer, melanoma, ovarian cancer, renal cancer, prostate cancer, breast cancer, head and neck cancers, and pancreatic cancer. The subject is typically a mammal diagnosed as being in need of treatment for one or more of such proliferative disorders, and frequently the subject is a human. The methods comprise administering an effective amount of at least one compound of the invention; optionally the compound may be administered in combination with one or more additional therapeutic agents, particularly therapeutic agents known to be useful for treating the cancer or proliferative disorder afflicting the particular subject.

Exemplary Compounds

Formula I

In one aspect, the invention provides a compound of Formula (I):

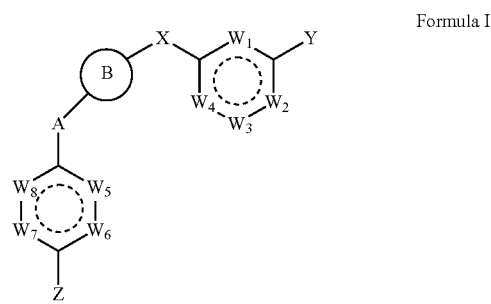

Formula I where

in a ring indicates the ring is an aromatic or heteroaromatic ring;

X is O, S, C=O, —NR, SO, SO2, C1-C6 alkyl or C1-C6 haloalkyl;

$W_1$, $W_2$, $W_3$, $W_4$, $W_5$, $W_6$, $W_7$ and $W_8$ are each independently absent, N, NH, $NR^1$, 0, S, CH, or $CR^2$;

not more than one of them is absent;

$R^1$ and $R^2$ is independently selected from H, OH, Halo, NHR, NRR, OR, SR, COOR, C(=O)R, CN, $CF_3$, $OCF_3$, $NO_2$, OC(O)R, $SO_3R$, $PO_3R_2$, and $CR(COOR)_2$;

Y is H, OH, Halo, NHR, NRR, NHC(=O)R, OR, SR, COOR, C(=O)R, CN, $CF_3$, $OCF_3$, $NO_2$, OC(O)R, $SO_3R$, $PO_3R_2$, or $CR(COOR)_2$;

Z is H, OH, Halo, NHR, NRR, OR, SR, COOR, C(=O)R, CN, $CF_3$, $OCF_3$, $NO_2$, OC(O)R, $SO_3R$, $PO_3R_2$, CR$(COOR)_2$, or

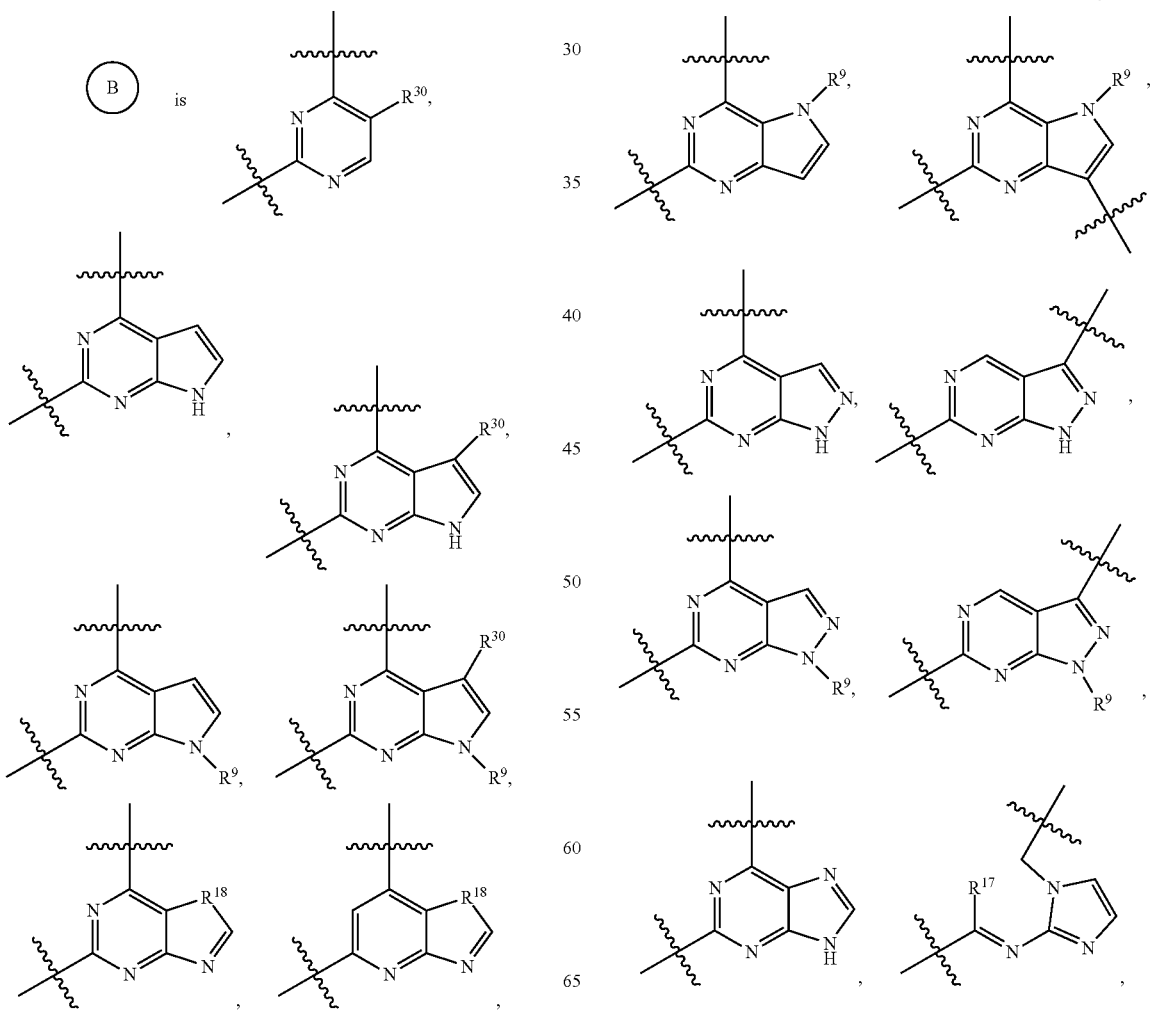

A is NH, S, SO, $SO_2$, $SO_2NH$, $SO_2NR^3$, $NHSO_2$, $NR^1$, $CR^1R^2$, $NR^1$, or O;

B is

-continued

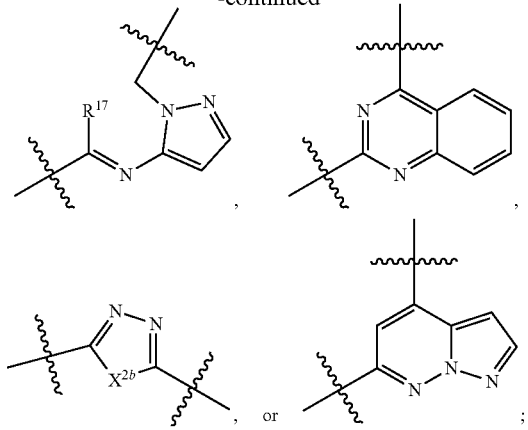

$R^{17}$ is N, CH, or $CR^{30}$;

$R^{18}$ is O or S;

$R^{10}$ is halogen or $C_1$-$C_6$ alkyl; and each $R^{-11}$ is independently hydrogen, $C_1$-$C_3$ alkyl, $C_1$-$C_3$ alkoxy, $C_1$-$C_3$ haloalkyl, or $C_1$-$C_3$ haloalkoxy;

$R^{12}$ is $CH_2$ or $C(O)$;

$X^{2b}$ is O, S, NH, or NR;

each R is selected from H, substituted or unsubstituted $C_{1-8}$ alkyl, $C_{2-8}$ alkenyl, $C_{2-8}$ alkynyl, aryl, fused aryl, heteroaryl, fused heterocycle, a $C_{3-8}$ carbocyclic ring or a $C_{3-8}$ heterocyclic ring, saturated or unsaturated, wherein each $C_{1-8}$ alkyl, $C_{3-8}$ cyclic alkyl, $C_{2-8}$ alkenyl, $C_{2-8}$ alkynyl can optionally contain a heteroatom selected from N, O and S in place of a carbon atom;

or a pharmaceutically acceptable salt thereof.

In some embodiments of these compounds, X is C1-C6 haloalkyl.

In another embodiment of these compounds, X is $CF_2$, CHF, $CHCF_3$ or $C(CF_3)_2$.

In another embodiment of these compounds Z is NRR, where the two R groups can optionally be taken together with the N atom in the substituent group to which the two R groups are attached to form a ring having 5-8 ring members, which can be substituted as allowed for the R itself, and can contain an additional heteroatom (N, O or S) as a ring member.

Formula Ia

In another embodiment, the compounds have a structure according to Formula Ia:

Formula Ia

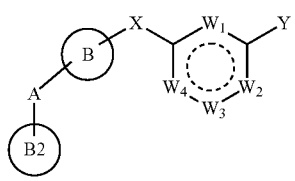

where

in a ring indicates the ring is an aromatic or heteroaromatic ring;

X is O, S, C=O, —NR, SO, $SO_2$, $C_1$-$C_6$ alkyl or $C_1$-$C_6$ haloalkyl;

$W_1$, $W_2$, $W_3$, $W_4$, $W_5$, $W_6$, $W_7$ and $W_8$ are each independently absent, N, NH, $NR^1$, O, S, CH, or $CR^2$;

not more than one of them is absent;

$R^1$ and $R^2$ are each independently selected from H, $C_1$-$C_6$ alkyl, OH, halogen, NHR, NRR, OR, SR, COOR, C(=O)R, CN, $CF_3$, $OCF_3$, $NO_2$, OC(O)R, $SO_3R$, $SO_2R$, $PO_3R_2$,—$POR_2$, $CR(COOR)_2$, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, —C(O)$NR_2$, sulfonyl, sulfonylamino, aminosulfonyl, acylamino, alkoxycarbonylamino, and aminocarbonylamino;

Y is H, OH, halogen, NHR, NRR, NHC(=O)R, OR, SR, COOR, C(=O)R, CN, $CF_3$, $OCF_3$, $NO_2$, OC(O)R, $SO_3R$, $PO_3R_2$, or $CR(COOR)_2$;

A is NH, S, SO, $SO_2$, $SO_2NH$, $SO_2NR^3$, $NHSO_2$, $NR^1$, $CR^1R^2$, $NR^1$, or O;

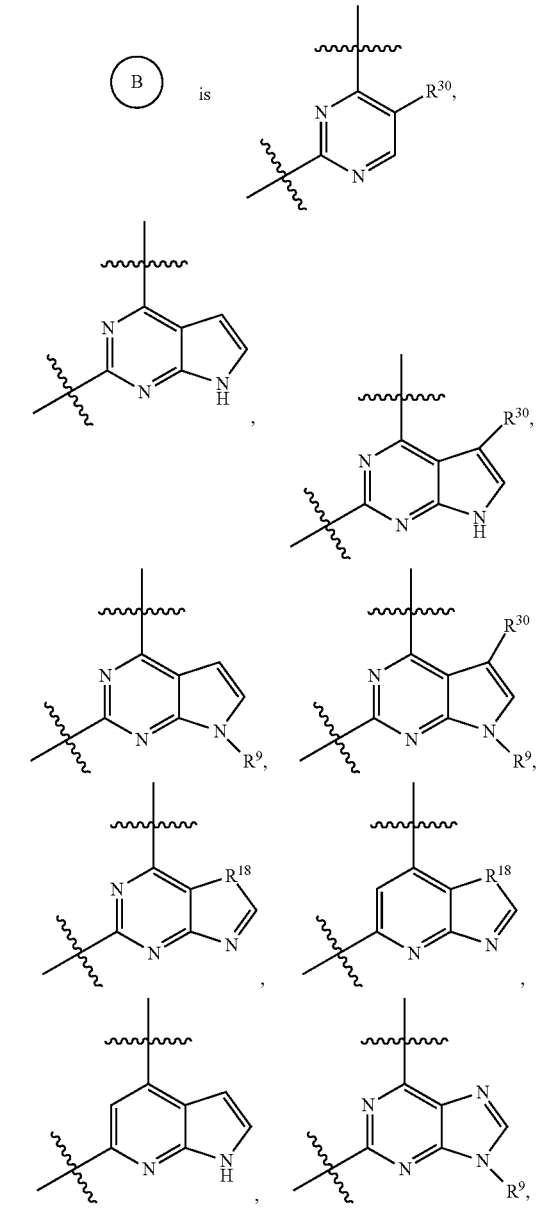

-continued

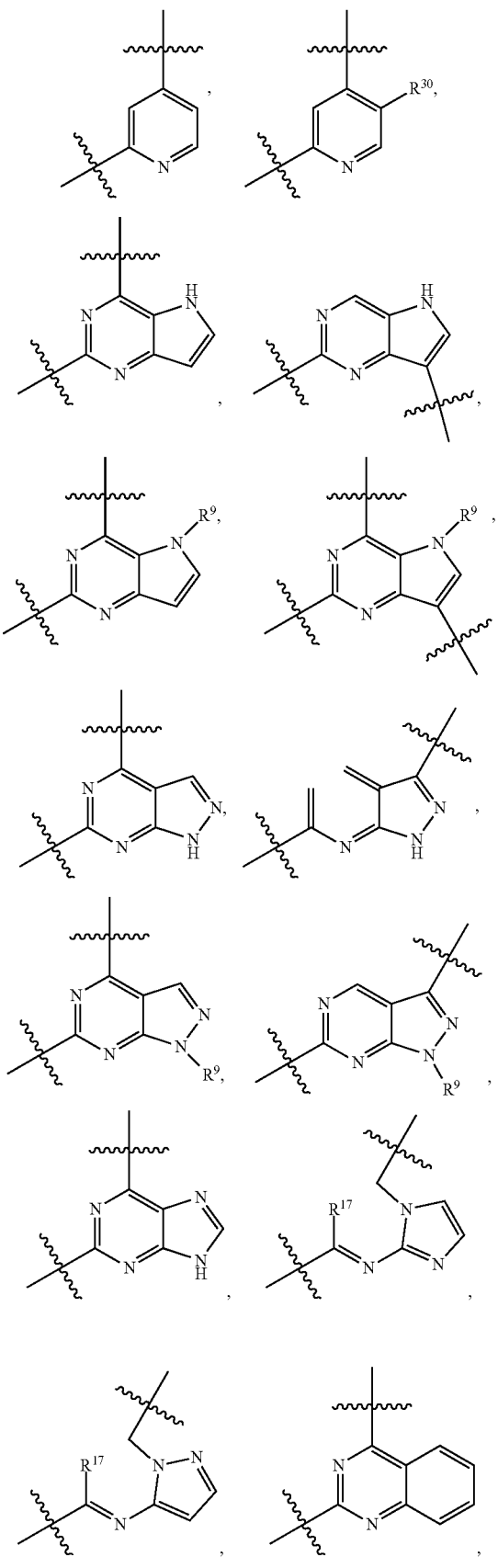

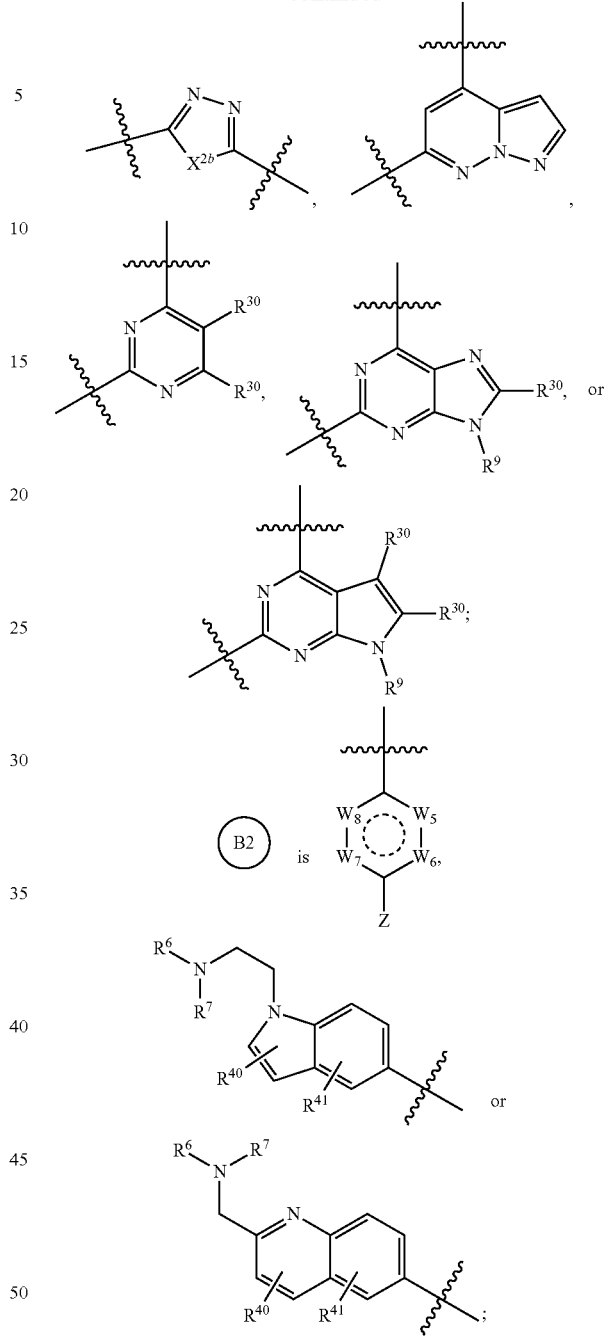

$R^{17}$ is N, CH, or $CR^{30}$;

$R^{18}$ is O or S;

$R^9$ is hydrogen, $C_1$-$C_6$ alkyl, or substituted $C_1$-$C_6$ alkyl, wherein $C_1$-$C_6$ alkyl is substituted with halogen, hydroxy, cyano, nitro, sulfonyl, sulfonylamino, aminosulfonyl, amino, or substituted amino;

each $R^{30}$ is independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, and substituted amino;

$X^{2b}$ is O, S, NH, or NR;

Z is H, OH, halogen, NHR, NRR, OR, SR, COOR, C(=O)R, CN, $CF_3$, $OCF_3$, $NO_2$, OC(O)R, $SO_3R$, $PO_3R_2$, $CR(COOR)_2$, or

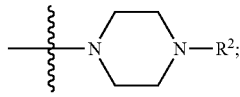

$R^6$ is hydrogen or $C_1$-$C_6$ alkyl;

$R^7$ is hydrogen or $C_1$-$C_6$ alkyl;

$R^{40}$ and $R^{41}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, substituted amino, acylamino, alkoxycarbonylamino, and aminocarbonylamino; and each R is selected from H, substituted or unsubstituted $C_{1-8}$ alkyl, $C_{2-20}$ alkenyl, $C_{2-8}$ alkynyl, aryl, fused aryl, heteroaryl, fused heterocycle, a $C_{3-8}$ carbocyclic ring or a $C_{3-8}$ heterocyclic ring, saturated or unsaturated, wherein each $C_{1-8}$ alkyl, $C_{3-8}$ cyclic alkyl, $C_{2-8}$ alkenyl, $C_{2-8}$ alkynyl can optionally contain a heteroatom selected from N, O and S in place of a carbon atom;

or a pharmaceutically acceptable salt thereof.

In some embodiments of these compounds, X is $C_1$-$C_6$ haloalkyl.

In some embodiments of these compounds, X is selected from $CF_2$, CHF, $CHCF_3$ or $C(CF_3)_2$.

In some embodiments of these compounds, R is substituted or unsubstituted $C_{2-20}$ alkenyl. In some embodiments of these compounds, R is substituted or unsubstituted $C_{2-8}$ alkenyl.

In some embodiments of these compounds, $R^9$ is $C_1$-$C_6$ alkyl.

In some embodiments of these compounds, $R^{30}$ is hydrogen, halogen, or $C_1$-$C_6$ alkyl. In some embodiments of these compounds, $R^{30}$ is halogen or $C_1$-$C_6$ alkyl.

In another embodiment of these compounds Z is NRR, where the two R groups can optionally be taken together with the N atom in the substituent group to which the two R groups are attached to form a ring having 5-8 ring members, which can be substituted as allowed for the R itself, and can contain an additional heteroatom (N, O or S) as a ring member.

Formula Ib

In another embodiment, the compounds have a structure according to Formula Ib:

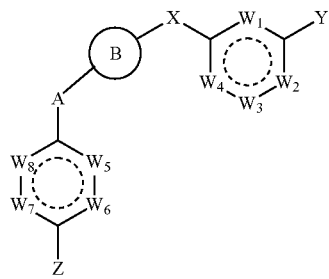

Formula Ib where

in a ring indicates the ring is an aromatic or heteroaromatic ring; X is O, S, C=O, —NR, SO, $SO_2$, $C_1$-$C_6$ alkyl or $C_1$-$C_6$ haloalkyl;

$W_1$, $W_2$, $W_3$, $W_4$, $W_5$, $W_6$, $W_7$ and $W_8$ are each independently absent, N, NH, $NR^1$, O, S, CH, or $CR^2$;

not more than one of them is absent;

$R^1$ and $R^2$ are each independently selected from H, $C_1$-$C_6$ alkyl, OH, halogen, NHR, NRR, OR, SR, COOR, C(=O)R, CN, $CF_3$, $OCF_3$, $NO_2$, OC(O)R, $SO_3R$, $SO_2R$, $PO_3R_2$,—$POR_2$, $CR(COOR)_2$, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, —C(O)$NR_2$, sulfonyl, sulfonylamino, aminosulfonyl, acylamino, alkoxycarbonylamino, and aminocarbonylamino;

Y is H, OH, halogen, NHR, NRR, NHC(=O)R, OR, SR, COOR, C(=O)R, CN, $CF_3$, $OCF_3$, $NO_2$, OC(O)R, $SO_3R$, $PO_3R_2$, or $CR(COOR)_2$;

Z is H, OH, halogen, NHR, NRR, OR, SR, COOR, C(=O)R, CN, $CF_3$, $OCF_3$, $NO_2$, OC(O)R, $SO_3R$, $PO_3R_2$, $CR(COOR)_2$, or

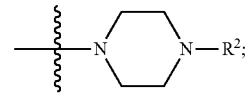

A is NH, S, SO, $SO_2$, $SO_2NH$, $SO_2NR^3$, $NHSO_2$, $NR^1$, $CR^1R^2$, $NR^1$, or O;

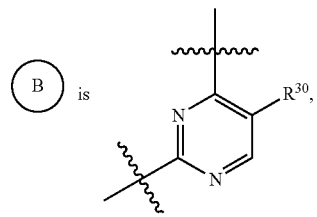

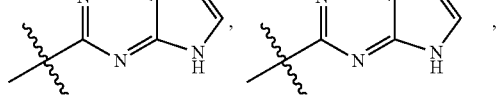

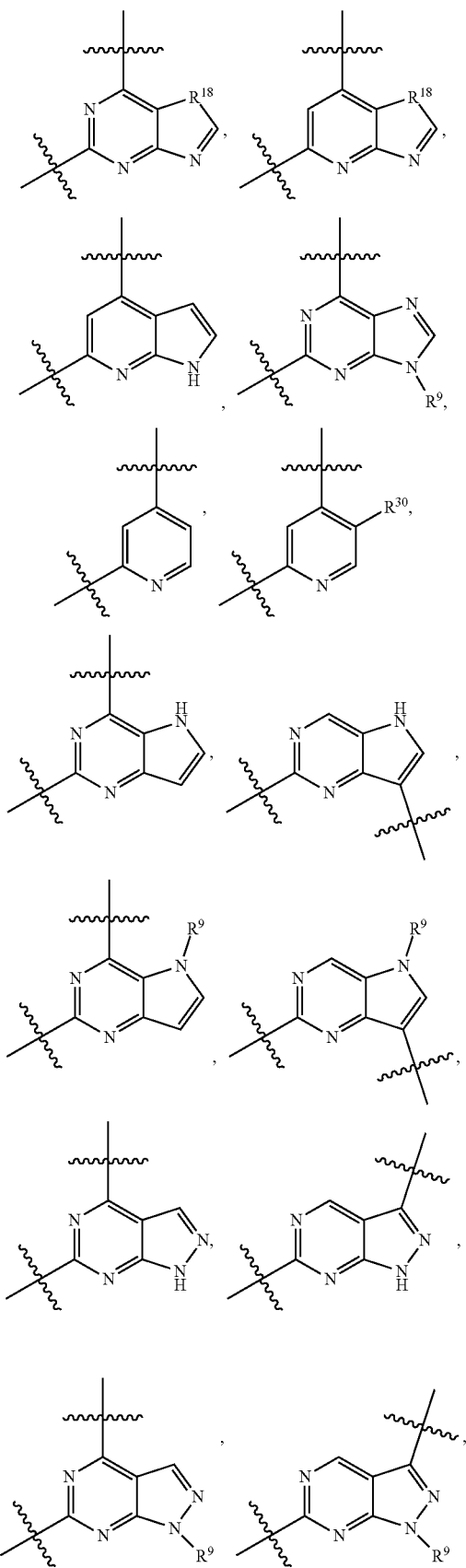
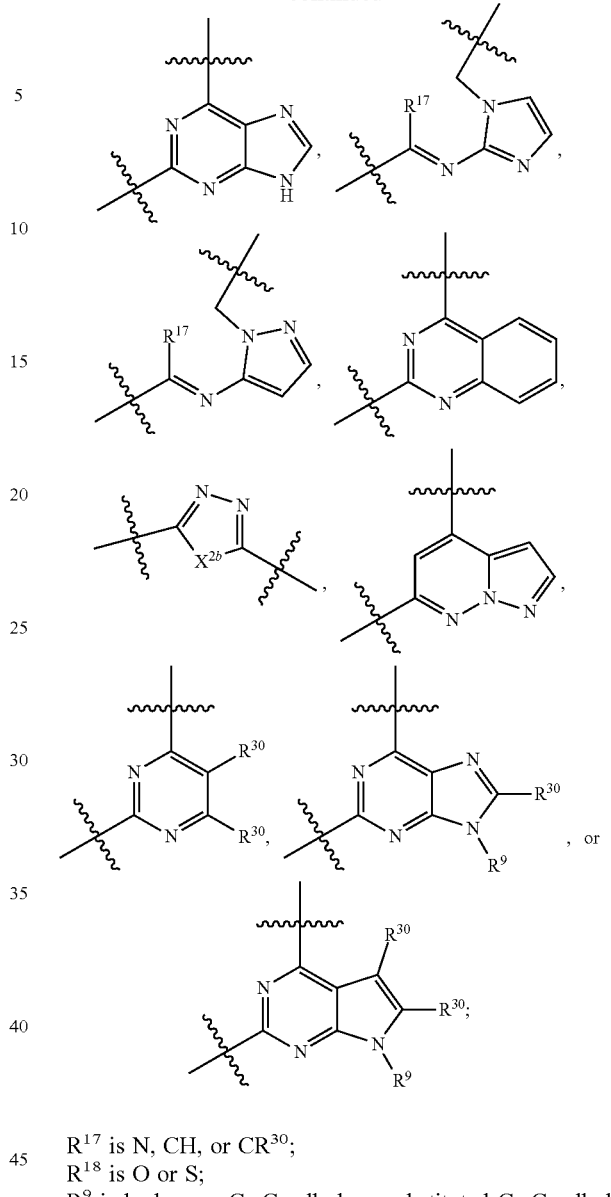

$R^{17}$ is N, CH, or $CR^{30}$;

$R^{18}$ is O or S;

$R^9$ is hydrogen, $C_1$-$C_6$ alkyl, or substituted $C_1$-$C_6$ alkyl, wherein $C_1$-$C_6$ alkyl is substituted with halogen, hydroxy, cyano, nitro, sulfonyl, sulfonylamino, aminosulfonyl, amino, or substituted amino;

each $R^{30}$ is independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, and substituted amino; and $X^{2b}$ is O, S, NH, or NR;

each R is selected from H, substituted or unsubstituted $C_{1-8}$ alkyl, $C_{2-20}$ alkenyl, $C_{2-8}$ alkynyl, aryl, fused aryl, heteroaryl, fused heterocycle, a $C_{3-8}$ carbocyclic ring or a $C_{3-8}$ heterocyclic ring, saturated or unsaturated, wherein each $C_{1-8}$ alkyl, $C_{3-8}$ cyclic alkyl, $C_{2-8}$ alkenyl, $C_{2-8}$ alkynyl can optionally contain a heteroatom selected from N, O and S in place of a carbon atom;

or a pharmaceutically acceptable salt thereof.

In some embodiments of these compounds, X is $C_1$-$C_6$ haloalkyl.

In some embodiments of these compounds, X is selected from $CF_2$, CHF, $CHCF_3$ or $C(CF_3)_2$.

In some embodiments of these compounds, R is substituted or unsubstituted $C_{2-20}$ alkenyl. In some embodiments of these compounds, R is substituted or unsubstituted $C_{2-8}$ alkenyl.

In some embodiments of these compounds, $R^9$ is $C_1$-$C_6$ alkyl.

In some embodiments of these compounds, $R^{30}$ is hydrogen, halogen, or $C_1$-$C_6$ alkyl. In some embodiments of these compounds, $R^{30}$ is halogen or $C_1$-$C_6$ alkyl.

In another embodiment of these compounds Z is NRR, where the two R groups can optionally be taken together with the N atom in the substituent group to which the two R groups are attached to form a ring having 5-8 ring members, which can be substituted as allowed for the R itself, and can contain an additional heteroatom (N, O or S) as a ring member.

Formula Ic

In another embodiment, the compounds have a structure according to Formula Ic:

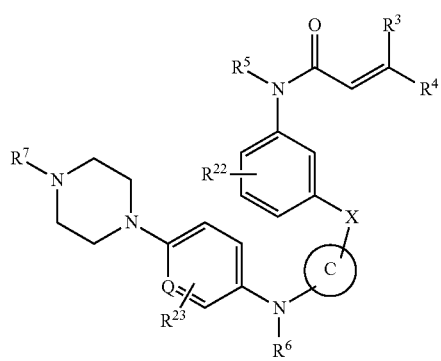

Formula Ic wherein

X is $CF_2$, O, $CH_2$ S, or $NR^b$;

$R^b$ is selected from H, substituted or unsubstituted $C_{1-8}$ alkyl, $C_{2-8}$ alkenyl, $C_{2-8}$ alkynyl, aryl, fused aryl, heteroaryl, fused heterocycle, a $C_{3-8}$ carbocyclic ring or a $C_{3-8}$ heterocyclic ring, saturated or unsaturated, wherein each $C_{1-8}$ alkyl, $C_{3-8}$ cyclic alkyl, $C_{2-8}$ alkenyl, $C_{2-8}$ alkynyl can optionally contain a heteroatom selected from N, O and S in place of a carbon atom;

$R^3$ and $R^4$ are independently hydrogen, $C_1$-$C_6$ alkyl, or —$(CH_2)_m N(R^a)_2$, wherein m is one to 6;

$R^5$ is hydrogen or $C_1$-$C_6$ alkyl;

$R^6$ is hydrogen or $C_1$-$C_6$ alkyl;

$R^7$ is hydrogen or $C_1$-$C_6$ alkyl;

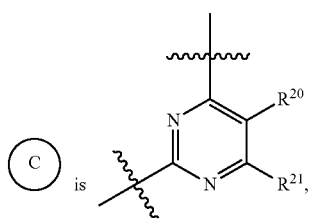

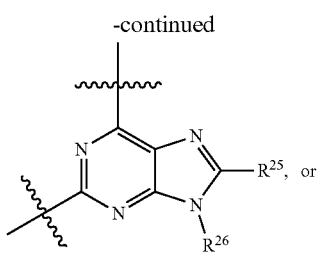

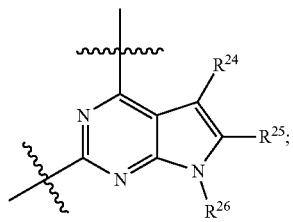

$R^{20}$ and $R^{21}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, and substituted amino;

$R^{24}$ and $R^{25}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, and substituted amino;

$R^{26}$ is hydrogen, $C_1$-$C_6$ alkyl, or substituted $C_1$-$C_6$ alkyl, wherein $C_1$-$C_6$ alkyl is substituted with halogen, hydroxy, cyano, nitro, sulfonyl, sulfonylamino, aminosulfonyl, amino, or substituted amino;

$R^{22}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, thiol, —C(O)$R^a$, —OC(O)$R^a$, —C(O)O$R^a$, —C(O)N($R^a$)$_2$, sulfonyl, sulfonylamino, aminosulfonyl, amino, substituted amino, acylamino, alkoxycarbonylamino, and aminocarbonylamino;

$R^{23}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, substituted amino, acylamino, alkoxycarbonylamino, and aminocarbonylamino;

each $R^a$ is independently hydrogen or $C_1$-$C_6$ alkyl; and

Q is CH, $CR^{23}$, or N;

or a pharmaceutically acceptable salt thereof.

Formula Id

In another embodiment, the compounds have a structure according to Formula Id:

Formula Id

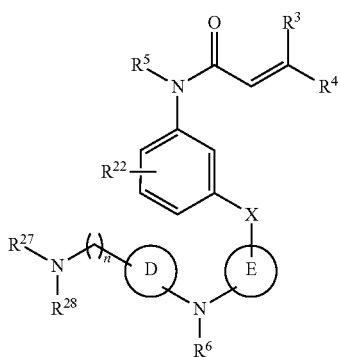

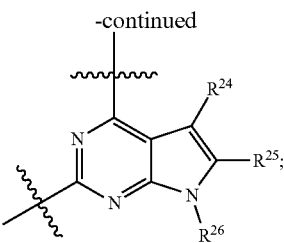

wherein

X is $CF_2$, O, $CH_2$ S, or $NR^b$;

$R^b$ is selected from H, substituted or unsubstituted $C_{1-8}$ alkyl, $C_{2-8}$ alkenyl, $C_{2-8}$ alkynyl, aryl, fused aryl, heteroaryl, fused heterocycle, a $C_{3-8}$ carbocyclic ring or a $C_{3-8}$ heterocyclic ring, saturated or unsaturated, wherein each $C_{1-8}$ alkyl, $C_{3-8}$ cyclic alkyl, $C_{2-8}$ alkenyl, $C_{2-8}$ alkynyl can optionally contain a heteroatom selected from N, O and S in place of a carbon atom;

$R^3$ and $R^4$ are independently hydrogen, $C_1$-$C_6$ alkyl, or —$(CH_2)_m N(R^a)_2$, wherein m is one to 6;

$R^5$ is hydrogen or $C_1$-$C_6$ alkyl;

$R^6$ is hydrogen or $C_1$-$C_6$ alkyl;

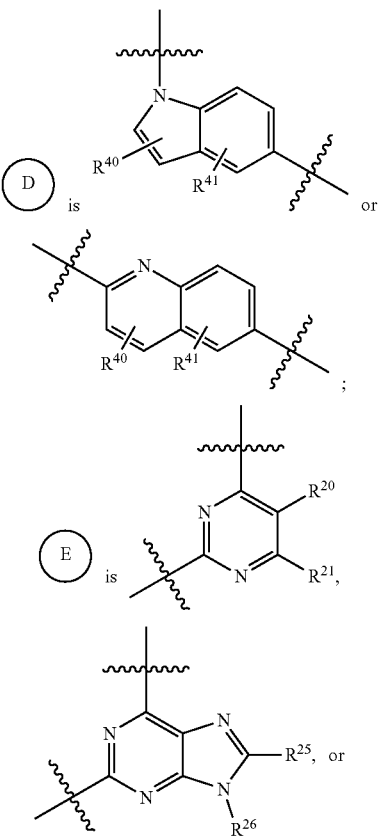

$R^{20}$ and $R^{21}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, and substituted amino;

$R^{24}$ and $R^{25}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, and substituted amino;

$R^{26}$ is hydrogen, $C_1$-$C_6$ alkyl, or substituted $C_1$-$C_6$ alkyl, wherein $C_1$-$C_6$ alkyl is substituted with halogen, hydroxy, cyano, nitro, sulfonyl, sulfonylamino, aminosulfonyl, amino, or substituted amino;

$R^{40}$ and $R^{41}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, substituted amino, acylamino, alkoxycarbonylamino, and aminocarbonylamino;

$R^{22}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, thiol, —$C(O)R^a$, —$OC(O)R^a$, —$C(O)OR^a$, —$C(O)N(R^a)_2$, sulfonyl, sulfonylamino, aminosulfonyl, amino, substituted amino, acylamino, alkoxycarbonylamino, and aminocarbonylamino;

each $R^a$ is independently hydrogen or $C_1$-$C_6$ alkyl;

$R^{27}$ and $R^{28}$ are independently hydrogen or $C_1$-$C_6$ alkyl; and n is one or two;

or a pharmaceutically acceptable salt thereof.

Formula II

In another embodiment, the compounds have a structure according to Formula II:

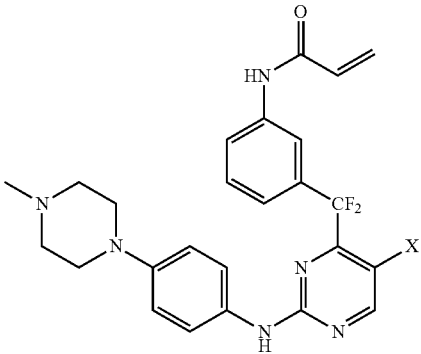

where X is halo wherein the halo is Cl, F, I, or Br.

In some embodiments of these compounds, halo is F, I, or Br. In some embodiments of these compounds, halo is F.

Formula IIa

The present disclosure provides a compound of Formula II:

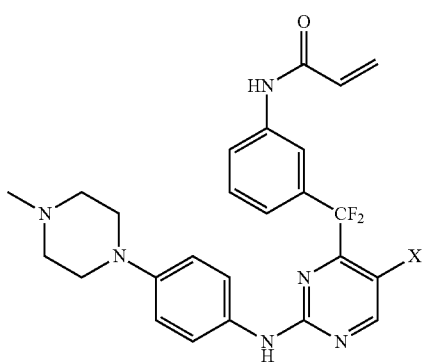

Formula IIa where X is $C_1$-$C_6$ alkyl, $C_1$-$C_6$ alkoxy, or halo, wherein the halo is Cl, F, I, or Br.

In some embodiments of these compounds, halo is F, I, or Br. In some embodiments of these compounds, X is $C_1$-$C_3$ alkyl. In some embodiments of these compounds, X is methyl. In some embodiments of these compounds, X is $C_1$-$C_3$ alkoxy. In some embodiments of these compounds, X is methoxy.

Formula III

In another embodiment, the compounds have a structure according to Formula III:

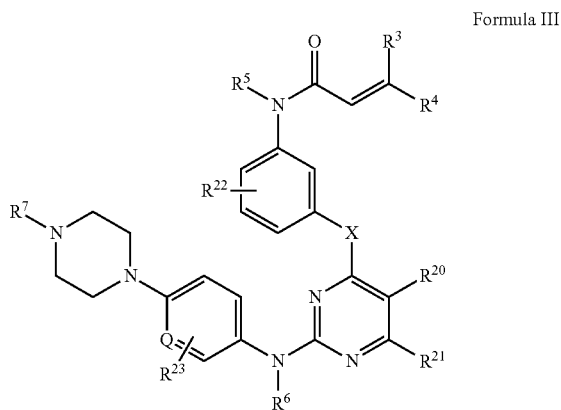

Formula III wherein

X is $CF_2$, O, $CH_2$ S, or $NR^b$;

$R^b$ is selected from H, substituted or unsubstituted $C_{1-8}$ alkyl, $C_{2-8}$ alkenyl, $C_{2-8}$ alkynyl, aryl, fused aryl, heteroaryl, fused heterocycle, a $C_{3-8}$ carbocyclic ring or a $C_{3-8}$ heterocyclic ring, saturated or unsaturated, wherein each $C_{1-8}$ alkyl, $C_{3-8}$ cyclic alkyl, $C_{2-8}$ alkenyl, $C_{2-8}$ alkynyl can optionally contain a heteroatom selected from N, O and S in place of a carbon atom;

$R^3$ and $R^4$ are independently hydrogen, $C_1$-$C_6$ alkyl, or $(CH_2)_m N(R^a)_2$, wherein m is one to 6;

$R^5$ is hydrogen or $C_1$-$C_6$ alkyl;

$R^6$ is hydrogen or $C_1$-$C_6$ alkyl;

$R^7$ is hydrogen or $C_1$-$C_6$ alkyl;

$R^{20}$ and $R^{21}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, and substituted amino;

$R^{22}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, thiol, —C(O)$R^a$, —OC(O)$R^a$, —C(O)O$R^a$, —C(O)N($R^a$)$_2$, sulfonyl, sulfonylamino, aminosulfonyl, amino, substituted amino, acylamino, alkoxycarbonylamino, and aminocarbonylamino;

$R^{23}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, substituted amino, acylamino, alkoxycarbonylamino, and aminocarbonylamino;

each $R^a$ is independently hydrogen or $C_1$-$C_6$ alkyl; and

Q is CH, $CR^{23}$, or N;

or a pharmaceutically acceptable salt thereof.

In some embodiments of compounds, X is $CF_2$. In some embodiments of compounds, X is O. In some embodiments, X is $CH_2$. In some embodiments of compounds, X is S. In some embodiments, X is $NR^b$. In some embodiments, X is $NR^b$, wherein $R^b$ is hydrogen or $C_1$-$C_6$ alkyl.

In some embodiments of these compounds, $R^{20}$ is hydrogen, halogen, $C_1$-$C_6$ alkyl, or $C_1$-$C_6$ alkoxy. In some embodiments of these compounds, $R^{20}$ is hydrogen, fluoro, chloro, $C_1$-$C_6$ alkyl, or $C_1$-$C_6$ alkoxy. In some embodiments of these compounds, $R^{20}$ is hydrogen, fluoro, iodo, bromo, $C_1$-$C_6$ alkyl, or $C_1$-$C_6$ alkoxy. In some embodiments of compounds, $R^{20}$ is not Cl. In some embodiments of compounds, when X is O, $R^{20}$ is not Cl.

In some embodiments, $R^{20}$ is methoxy, fluoro, chloro, or methyl. In some embodiments, $R^{20}$ is methoxy, ethoxy, propoxy, or isopropoxy. In some embodiments, $R^{20}$ is methoxy. In some embodiments, $R^{20}$ is fluoro or chloro. In some embodiments, $R^{20}$ is fluoro. In some embodiments, $R^{20}$ is chloro. In some embodiments, $R^{20}$ is methyl, ethyl, propyl, isopropyl, or butyl. In some embodiments, $R^{20}$ is methyl.

In some embodiments of these compounds, $R^{21}$ is hydrogen.

In some embodiments of these compounds, $R^{23}$ is hydrogen, halogen, or $C_1$-$C_6$ alkoxy.

In some embodiments, $R^{23}$ is situated ortho to $NR^6$. In some embodiments, $R^{23}$ is situated meta to $NR^6$.

In some embodiments, $R^{23}$ is hydrogen. In some embodiments, $R^{23}$ is methoxy, ethoxy, propoxy, or isopropoxy. In some embodiments, $R^{23}$ is methoxy. In some embodiments, $R^{23}$ is fluoro. In some embodiments, $R^{23}$ is methoxy or fluoro.

In some embodiments of these compounds, $R^7$ is $C_1$-$C_3$ alkyl.

In some embodiments, $R^7$ is methyl, ethyl, propyl, isopropyl, or butyl. In some embodiments, $R^7$ is methyl or ethyl. In some embodiments, $R^7$ is methyl. In some embodiments, $R^7$ is ethyl.

In some embodiments of these compounds, $R^3$ and $R^4$ are hydrogen. In some embodiments of these compounds, at least one of $R^3$ and $R^4$ is $C_1$-$C_6$ alkyl. In some embodiments, at least one of $R^3$ and $R^4$ is $C_1$-$C_3$ alkyl. In some embodiments, at least one of $R^3$ and $R^4$ is methyl. In some embodiments of these compounds, at least one of $R^3$ and $R^4$ is —(CH$_2$)$_m$N(R$^a$)$_2$, wherein m is one to 6. In some embodiments of these compounds, at least one of R$^3$ and R$^4$ is —CH$_2$N(CH$_3$)$_2$.

In some embodiments of these compounds, Q is CH or CR$^{23}$. In some embodiments of these compounds, Q is N.

In some embodiments, Q is CH. In some embodiments, Q is CR$^{23}$, where R$^{23}$ is halogen, C$_1$-C$_6$ alkyl, C$_1$-C$_6$ haloalkyl, C$_1$-C$_6$ alkoxy, or C$_1$-C$_6$ haloalkoxy. In some embodiments, Q is CR$^{23}$, where R$^{23}$ is halogen. In some embodiments, Q is CR$^{23}$, where R$^{23}$ is fluoro. In some embodiments, Q is CR$^{23}$, where R$^{23}$ is chloro.

In some embodiments, R$^5$ is hydrogen. In some embodiments, R$^5$ is methyl.

In some embodiments, R$^6$ is hydrogen. In some embodiments, R$^6$ is methyl.

In some embodiments, R$^{22}$ is hydrogen.

Formula IV

In another embodiment, the compounds have a structure according to Formula IV:

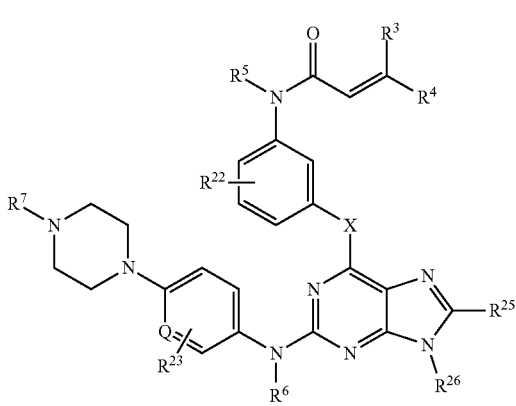

Formula IV wherein

X is CF$_2$, O, CH$_2$ S, or NR$^b$;

R$^b$ is selected from H, substituted or unsubstituted C$_{1-8}$ alkyl, C$_{2-8}$ alkenyl, C$_{2-8}$ alkynyl, aryl, fused aryl, heteroaryl, fused heterocycle, a C$_{3-8}$ carbocyclic ring or a C$_{3-8}$ heterocyclic ring, saturated or unsaturated, wherein each C$_{1-8}$ alkyl, C$_{3-8}$ cyclic alkyl, C$_{2-8}$ alkenyl, C$_{2-8}$ alkynyl can optionally contain a heteroatom selected from N, O and S in place of a carbon atom;

R$^3$ and R$^4$ are independently hydrogen, C$_1$-C$_6$ alkyl, or —(CH$_2$)$_m$N(R$^a$)$_2$, wherein m is one to 6;

R$^5$ is hydrogen or C$_1$-C$_6$ alkyl;

R$^6$ is hydrogen or C$_1$-C$_6$ alkyl;

R$^7$ is hydrogen or C$_1$-C$_6$ alkyl;

R$^{25}$ is selected from hydrogen, halogen, C$_1$-C$_6$ alkyl, C$_1$-C$_6$ haloalkyl, C$_1$-C$_6$ alkoxy, C$_1$-C$_6$ haloalkoxy, C$_1$-C$_6$ alkenyl, C$_1$-C$_6$ alkynyl, hydroxy, cyano, nitro, —C(O)R$^a$, —OC(O)R$^a$, —C(O)OR$^a$, —C(O)N(R$^a$)$_2$, sulfonyl, sulfonylamino, aminosulfonyl, amino, and substituted amino;

R$^{26}$ is hydrogen, C$_1$-C$_6$ alkyl, or substituted C$_1$-C$_6$ alkyl, wherein C$_1$-C$_6$ alkyl is substituted with halogen, hydroxy, cyano, nitro, sulfonyl, sulfonylamino, aminosulfonyl, amino, or substituted amino;

R$^{22}$ is selected from hydrogen, halogen, C$_1$-C$_6$ alkyl, C$_1$-C$_6$ haloalkyl, C$_1$-C$_6$ alkoxy, C$_1$-C$_6$ haloalkoxy, C$_1$-C$_6$ alkenyl, C$_1$-C$_6$ alkynyl, hydroxy, cyano, nitro, —C(O)R$^a$, —OC(O)R$^a$, —C(O)OR$^a$, —C(O)N(R$^a$)$_2$, sulfonyl, sulfonylamino, aminosulfonyl, amino, substituted amino, acylamino, alkoxycarbonylamino, and aminocarbonylamino;

R$^{23}$ is selected from hydrogen, halogen, C$_1$-C$_6$ alkyl, C$_1$-C$_6$ haloalkyl, C$_1$-C$_6$ alkoxy, C$_1$-C$_6$ haloalkoxy, C$_1$-C$_6$ alkenyl, C$_1$-C$_6$ alkynyl, hydroxy, cyano, nitro, —C(O)R$^a$, —OC(O)R$^a$, —C(O)OR$^a$, —C(O)N(R$^a$)$_2$, sulfonyl, sulfonylamino, aminosulfonyl, amino, substituted amino, acylamino, alkoxycarbonylamino, and aminocarbonylamino;

each R$^a$ is independently hydrogen or C$_1$-C$_6$ alkyl; and

Q is CH, CR$^{23}$, or N;

or a pharmaceutically acceptable salt thereof.

In some embodiments of compounds, X is CF$_2$. In some embodiments of compounds, X is O. In some embodiments, X is CH$_2$. In some embodiments of compounds, X is S. In some embodiments, X is NR$^b$. In some embodiments, X is NR$^b$, wherein R$^b$ is hydrogen or C$_1$-C$_6$ alkyl.

In some embodiments of these compounds, R$^{25}$ and R$^{26}$ are hydrogen.

In some embodiments, R$^{25}$ is hydrogen. In some embodiments, R$^{26}$ is hydrogen.

In some embodiments of these compounds, R$^{23}$ is hydrogen, halogen, or C$_1$-C$_6$ alkoxy.

In some embodiments, R$^{23}$ is situated ortho to NR$^6$. In some embodiments, R$^{23}$ is situated meta to NR$^6$.

In some embodiments, R$^{23}$ is hydrogen. In some embodiments, R$^{23}$ is methoxy, ethoxy, propoxy, or isopropoxy. In some embodiments, R$^{23}$ is methoxy. In some embodiments, R$^{23}$ is fluoro. In some embodiments, R$^{23}$ is methoxy or fluoro.

In some embodiments of these compounds, Q is CH.

In some embodiments of these compounds, R$^7$ is C$_1$-C$_3$ alkyl.

In some embodiments, R$^7$ is methyl, ethyl, propyl, isopropyl, or butyl. In some embodiments, R$^7$ is methyl or ethyl. In some embodiments, R$^7$ is methyl. In some embodiments, R$^7$ is ethyl.

In some embodiments of these compounds, R$^3$ and R$^4$ are hydrogen. In some embodiments of these compounds, at least one of R$^3$ and R$^4$ is C$_1$-C$_6$ alkyl. In some embodiments, at least one of R$^3$ and R$^4$ is C$_1$-C$_3$ alkyl. In some embodiments, at least one of R$^3$ and R$^4$ is methyl. In some embodiments of these compounds, at least one of R$^3$ and R$^4$ is —(CH$_2$)$_m$N(R$^a$)$_2$, wherein m is one to 6. In some embodiments of these compounds, at least one of R$^3$ and R$^4$ is —CH$_2$N(CH$_3$)$_2$.

In some embodiments, R$^5$ is hydrogen. In some embodiments, R$^5$ is methyl.

In some embodiments, R$^6$ is hydrogen. In some embodiments, R$^6$ is methyl.

In some embodiments, R$^{22}$ is hydrogen.

Formula V

In another embodiment, the compounds have a structure according to Formula V:

Formula V

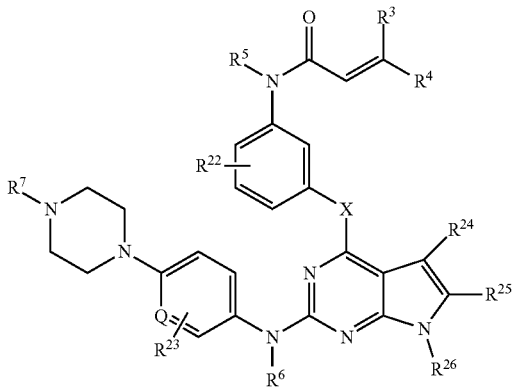

wherein

X is $CF_2$, O, $CH_2$ S, or $NR^b$;

$R^b$ is selected from H, substituted or unsubstituted $C_{1-8}$ alkyl, $C_{2-8}$ alkenyl, $C_{2-8}$ alkynyl, aryl, fused aryl, heteroaryl, fused heterocycle, a $C_{3-8}$ carbocyclic ring or a $C_{3-8}$ heterocyclic ring, saturated or unsaturated, wherein each $C_{1-8}$ alkyl, $C_{3-8}$ cyclic alkyl, $C_{2-8}$ alkenyl, $C_{2-8}$ alkynyl can optionally contain a heteroatom selected from N, O and S in place of a carbon atom;

$R^3$ and $R^4$ are independently hydrogen, $C_1$-$C_6$ alkyl, or —$(CH_2)_m N(R^a)_2$, wherein m is one to 6;

$R^5$ is hydrogen or $C_1$-$C_6$ alkyl;

$R^6$ is hydrogen or $C_1$-$C_6$ alkyl;

$R^7$ is hydrogen or $C_1$-$C_6$ alkyl;

$R^{24}$ and $R^{25}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, and substituted amino;

$R^{26}$ is hydrogen, $C_1$-$C_6$ alkyl, or substituted $C_1$-$C_6$ alkyl, wherein $C_1$-$C_6$ alkyl is substituted with halogen, hydroxy, cyano, nitro, sulfonyl, sulfonylamino, aminosulfonyl, amino, or substituted amino;

$R^{22}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, substituted amino acylamino, alkoxycarbonylamino, and aminocarbonylamino;

$R^{23}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, substituted amino acylamino, alkoxycarbonylamino, and aminocarbonylamino;

each $R^a$ is independently hydrogen or $C_1$-$C_6$ alkyl; and

Q is CH, $CR^{23}$, or N;

or a pharmaceutically acceptable salt thereof.

In some embodiments of compounds, X is $CF_2$. In some embodiments of compounds, X is O. In some embodiments, X is $CH_2$. In some embodiments of compounds, X is S. In some embodiments, X is $NR^b$. In some embodiments, X is $NR^b$, wherein $R^b$ is hydrogen or $C_1$-$C_6$ alkyl.

In some embodiments of these compounds, $R^{24}$ and $R^{25}$ are hydrogen.

In some embodiments, $R^{24}$ is hydrogen. In some embodiments, $R^{25}$ is hydrogen.

In some embodiments of these compounds, $R^{26}$ is hydrogen. In some embodiments of these compounds, $R^{26}$ is substituted $C_1$-$C_6$ alkyl, wherein $C_1$-$C_6$ alkyl is substituted with hydroxy.

In some embodiments of these compounds, $R^{24}$, $R^{25}$ and $R^{26}$ are hydrogen.

In some embodiments of these compounds, $R^{23}$ is hydrogen, halogen, or $C_1$-$C_6$ alkoxy.

In some embodiments, $R^{23}$ is situated ortho to $NR^6$. In some embodiments, $R^{23}$ is situated meta to $NR^6$.

In some embodiments, $R^{23}$ is hydrogen. In some embodiments, $R^{23}$ is methoxy, ethoxy, propoxy, or isopropoxy. In some embodiments, $R^{23}$ is methoxy. In some embodiments, $R^{23}$ is fluoro. In some embodiments, $R^{23}$ is methoxy or fluoro.

In some embodiments of these compounds, Q is CH or $CR^{23}$.

In some embodiments of these compounds, Q is N.

In some embodiments, Q is CH. In some embodiments, Q is $CR^{23}$, where $R^{23}$ is halogen, $C_1$-$C_6$ alkyl, $C_1$-$C_6$ haloalkyl, $C_1$-$C_6$ alkoxy, or $C_1$-$C_6$ haloalkoxy. In some embodiments, Q is $CR^{23}$, where $R^{23}$ is halogen. In some embodiments, Q is $CR^{23}$, where $R^{23}$ is fluoro. In some embodiments, Q is $CR^{23}$, where $R^{23}$ is chloro.

In some embodiments of these compounds, $R^7$ is $C_1$-$C_3$ alkyl.

In some embodiments, $R^7$ is methyl, ethyl, propyl, isopropyl, or butyl. In some embodiments, $R^7$ is methyl or ethyl. In some embodiments, $R^7$ is methyl. In some embodiments, $R^7$ is ethyl.

In some embodiments of these compounds, $R^3$ and $R^4$ are hydrogen. In some embodiments of these compounds, at least one of $R^3$ and $R^4$ is $C_1$-$C_6$ alkyl. In some embodiments, at least one of $R^3$ and $R^4$ is $C_1$-$C_3$ alkyl. In some embodiments, at least one of $R^3$ and $R^4$ is methyl. In some embodiments of these compounds, at least one of $R^3$ and $R^4$ is —$(CH_2)_m N(R^a)_2$, wherein m is one to 6. In some embodiments of these compounds, at least one of $R^3$ and $R^4$ is —$CH_2N(CH_3)_2$.

In some embodiments, $R^5$ is hydrogen. In some embodiments, $R^5$ is methyl.

In some embodiments, $R^6$ is hydrogen. In some embodiments, $R^6$ is methyl.

In some embodiments, $R^{22}$ is hydrogen.

Formula VI

In another embodiment, the compounds have a structure according to Formula VI:

Formula VI

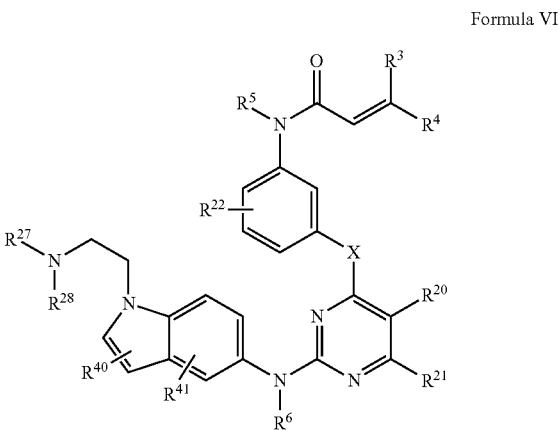

wherein

X is $CF_2$, O, $CH_2$ S, or $NR^b$;

$R^b$ is selected from H, substituted or unsubstituted $C_{1-8}$ alkyl, $C_{2-8}$ alkenyl, $C_{2-8}$ alkynyl, aryl, fused aryl, heteroaryl, fused heterocycle, a $C_{3-8}$ carbocyclic ring or a $C_{3-8}$ heterocyclic ring, saturated or unsaturated, wherein each $C_{1-8}$ alkyl, $C_{3-8}$ cyclic alkyl, $C_{2-8}$ alkenyl, $C_{2-8}$ alkynyl can optionally contain a heteroatom selected from N, O and S in place of a carbon atom;

$R^3$ and $R^4$ are independently hydrogen, $C_1$-$C_6$ alkyl, or —$(CH_2)_m N(R^a)_2$, wherein m is one to 6;

$R^5$ is hydrogen or $C_1$-$C_6$ alkyl;

$R^6$ is hydrogen or $C_1$-$C_6$ alkyl;

$R^{20}$ and $R^{21}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, and substituted amino;

$R^{22}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, substituted amino, acylamino, alkoxycarbonylamino, and aminocarbonylamino;

$R^{40}$ and $R^{41}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, substituted amino, acylamino, alkoxycarbonylamino, and aminocarbonylamino;

each $R^a$ is independently hydrogen or $C_1$-$C_6$ alkyl; and $R^{27}$ and $R^{28}$ are independently hydrogen or $C_1$-$C_6$ alkyl; or a pharmaceutically acceptable salt thereof.

Formula VII

In another embodiment, the compounds have a structure according to Formula VII:

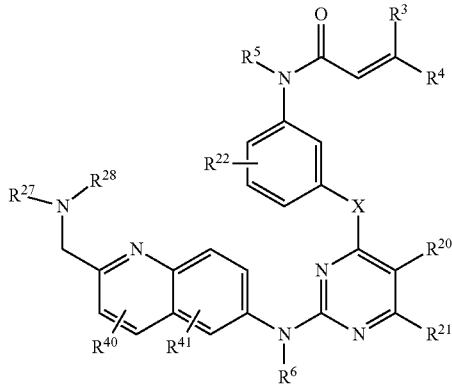

Formula VII wherein

X is $CF_2$, O, $CH_2$ S, or $NR^b$;

$R^b$ is selected from H, substituted or unsubstituted $C_{1-8}$ alkyl, $C_{2-8}$ alkenyl, $C_{2-8}$ alkynyl, aryl, fused aryl, heteroaryl, fused heterocycle, a $C_{3-8}$ carbocyclic ring or a $C_{3-8}$ heterocyclic ring, saturated or unsaturated, wherein each $C_{1-8}$ alkyl, $C_{3-8}$ cyclic alkyl, $C_{2-8}$ alkenyl, $C_{2-8}$ alkynyl can optionally contain a heteroatom selected from N, O and S in place of a carbon atom;

$R^3$ and $R^4$ are independently hydrogen, $C_1$-$C_6$ alkyl, or —$(CH_2)_m N(R^a)_2$, wherein m is one to 6;

$R^5$ is hydrogen or $C_1$-$C_6$ alkyl;

$R^6$ is hydrogen or $C_1$-$C_6$ alkyl;

$R^{20}$ and $R^{21}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, and substituted amino;

$R^{22}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, substituted amino, acylamino, alkoxycarbonylamino, and aminocarbonylamino;

$R^{40}$ and $R^{41}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, substituted amino, acylamino, alkoxycarbonylamino, and aminocarbonylamino;

each $R^a$ is independently hydrogen or $C_1$-$C_6$ alkyl; and $R^{27}$ and $R^{28}$ are independently hydrogen or $C_1$-$C_6$ alkyl; or a pharmaceutically acceptable salt thereof.

Formula VIII

In another embodiment, the compounds have a structure according to Formula VIII:

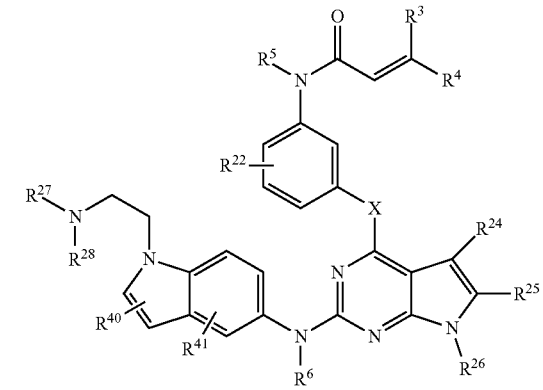

Formula VIII wherein

X is $CF_2$, O, $CH_2$ S, or $NR^b$;

$R^b$ is selected from H, substituted or unsubstituted $C_{1-8}$ alkyl, $C_{2-8}$ alkenyl, $C_{2-8}$ alkynyl, aryl, fused aryl, heteroaryl, fused heterocycle, a $C_{3-8}$ carbocyclic ring or a $C_{3-8}$ heterocyclic ring, saturated or unsaturated, wherein each $C_{1-8}$ alkyl, $C_{3-8}$ cyclic alkyl, $C_{2-8}$ alkenyl, $C_{2-8}$ alkynyl can optionally contain a heteroatom selected from N, O and S in place of a carbon atom;

$R^3$ and $R^4$ are independently hydrogen, $C_1$-$C_6$ alkyl, or —$(CH_2)_m N(R^a)_2$, wherein m is one to 6;

$R^5$ is hydrogen or $C_1$-$C_6$ alkyl;

$R^6$ is hydrogen or $C_1$-$C_6$ alkyl;

$R^{24}$ and $R^{25}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, and substituted amino;

$R^{26}$ is hydrogen, $C_1$-$C_6$ alkyl, or substituted $C_1$-$C_6$ alkyl, wherein $C_1$-$C_6$ alkyl is substituted with halogen, hydroxy, cyano, nitro, sulfonyl, sulfonylamino, aminosulfonyl, amino, or substituted amino;

$R^{22}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, substituted amino, acylamino, alkoxycarbonylamino, and aminocarbonylamino;

$R^{40}$ and $R^{41}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, substituted amino, acylamino, alkoxycarbonylamino, and aminocarbonylamino;

each $R^a$ is independently hydrogen or $C_1$-$C_6$ alkyl; and
$R^{27}$ and $R^{28}$ are independently hydrogen or $C_1$-$C_6$ alkyl; or a pharmaceutically acceptable salt thereof.

Formula IX

In another embodiment, the compounds have a structure according to Formula IX:

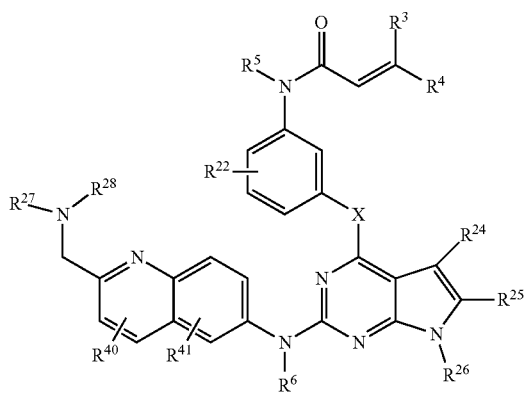

Formula IX wherein
X is $CF_2$, O, $CH_2$, S, or $NR^b$;
$R^b$ is selected from H, substituted or unsubstituted $C_{1-8}$ alkyl, $C_{2-8}$ alkenyl, $C_{2-8}$ alkynyl, aryl, fused aryl, heteroaryl, fused heterocycle, a $C_{3-8}$ carbocyclic ring or a $C_{3-8}$ heterocyclic ring, saturated or unsaturated, wherein each $C_{1-8}$ alkyl, $C_{3-8}$ cyclic alkyl, $C_{2-8}$ alkenyl, $C_{2-8}$ alkynyl can optionally contain a heteroatom selected from N, O and S in place of a carbon atom;

$R^3$ and $R^4$ are independently hydrogen, $C_1$-$C_6$ alkyl, or —(CH$_2$)$_m$N($R^a$)$_2$, wherein m is one to 6;
$R^5$ is hydrogen or $C_1$-$C_6$ alkyl;
$R^6$ is hydrogen or $C_1$-$C_6$ alkyl;
$R^{24}$ and $R^{25}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, and substituted amino;

$R^{26}$ is hydrogen, $C_1$-$C_6$ alkyl, or substituted $C_1$-$C_6$ alkyl, wherein $C_1$-$C_6$ alkyl is substituted with halogen, hydroxy, cyano, nitro, sulfonyl, sulfonylamino, aminosulfonyl, amino, or substituted amino;

$R^{22}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, substituted amino, acylamino, alkoxycarbonylamino, and aminocarbonylamino;

$R^{40}$ and $R^{41}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, substituted amino, acylamino, alkoxycarbonylamino, and aminocarbonylamino;

each $R^a$ is independently hydrogen or $C_1$-$C_6$ alkyl; and
$R^{27}$ and $R^{28}$ are independently hydrogen or $C_1$-$C_6$ alkyl; or a pharmaceutically acceptable salt thereof.

Formula X

In another embodiment, the compounds have a structure according to Formula X:

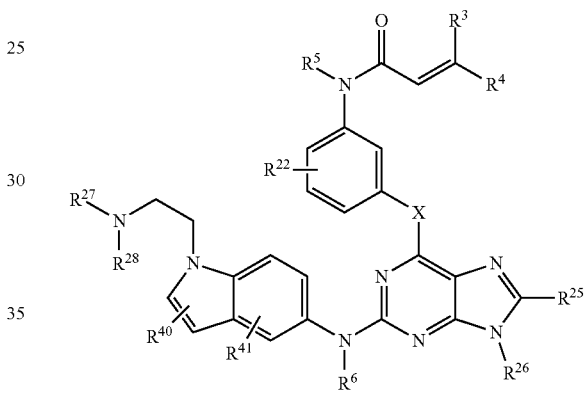

Formula X wherein
X is $CF_2$, O, $CH_2$, S, or $NR^b$;
$R^b$ is selected from H, substituted or unsubstituted $C_{1-8}$ alkyl, $C_{2-8}$ alkenyl, $C_{2-8}$ alkynyl, aryl, fused aryl, heteroaryl, fused heterocycle, a $C_{3-8}$ carbocyclic ring or a $C_{3-8}$ heterocyclic ring, saturated or unsaturated, wherein each $C_{1-8}$ alkyl, $C_{3-8}$ cyclic alkyl, $C_{2-8}$ alkenyl, $C_{2-8}$ alkynyl can optionally contain a heteroatom selected from N, O and S in place of a carbon atom;

$R^3$ and $R^4$ are independently hydrogen, $C_1$-$C_6$ alkyl, or —(CH$_2$)$_m$N($R^a$)$_2$, wherein m is one to 6;
$R^5$ is hydrogen or $C_1$-$C_6$ alkyl;
$R^6$ is hydrogen or $C_1$-$C_6$ alkyl;
$R^{25}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, and substituted amino;

$R^{26}$ is hydrogen, $C_1$-$C_6$ alkyl, or substituted $C_1$-$C_6$ alkyl, wherein $C_1$-$C_6$ alkyl is substituted with halogen, hydroxy, cyano, nitro, sulfonyl, sulfonylamino, aminosulfonyl, amino, or substituted amino;

$R^{22}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, substituted amino, acylamino, alkoxycarbonylamino, and aminocarbonylamino;

$R^{40}$ and $R^{41}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, substituted amino, acylamino, alkoxycarbonylamino, and aminocarbonylamino;

each $R^a$ is independently hydrogen or $C_1$-$C_6$ alkyl; and $R^{27}$ and $R^{28}$ are independently hydrogen or $C_1$-$C_6$ alkyl; or a pharmaceutically acceptable salt thereof.

Formula XI

In another embodiment, the compounds have a structure according to Formula XI:

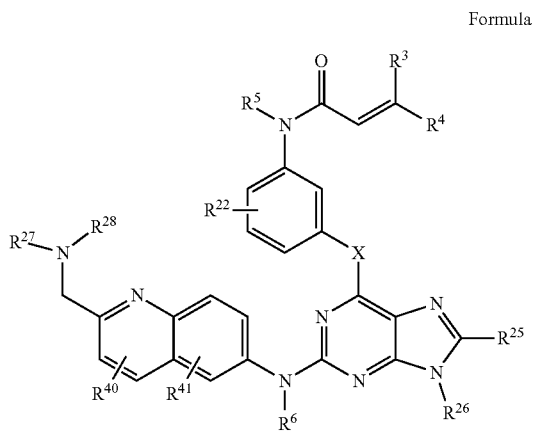

Formula XI wherein

X is CF$_2$, O, CH$_2$ S, or NR$^b$;

$R^b$ is selected from H, substituted or unsubstituted $C_{1-8}$ alkyl, $C_{2-8}$ alkenyl, $C_{2-8}$ alkynyl, aryl, fused aryl, heteroaryl, fused heterocycle, a $C_{3-8}$ carbocyclic ring or a $C_{3-8}$ heterocyclic ring, saturated or unsaturated, wherein each $C_{1-8}$ alkyl, $C_{3-8}$ cyclic alkyl, $C_{2-8}$ alkenyl, $C_{2-8}$ alkynyl can optionally contain a heteroatom selected from N, O and S in place of a carbon atom;

$R^3$ and $R^4$ are independently hydrogen, $C_1$-$C_6$ alkyl, or —(CH$_2$)$_m$N($R^a$)$_2$, wherein m is one to 6;

$R^5$ is hydrogen or $C_1$-$C_6$ alkyl;

$R^6$ is hydrogen or $C_1$-$C_6$ alkyl;

$R^{25}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, and substituted amino;

$R^{26}$ is hydrogen, $C_1$-$C_6$ alkyl, or substituted $C_1$-$C_6$ alkyl, wherein $C_1$-$C_6$ alkyl is substituted with halogen, hydroxy, cyano, nitro, sulfonyl, sulfonylamino, aminosulfonyl, amino, or substituted amino;

$R^{22}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, substituted amino, acylamino, alkoxycarbonylamino, and aminocarbonylamino;

$R^{40}$ and $R^{41}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, substituted amino, acylamino, alkoxycarbonylamino, and aminocarbonylamino;

each $R^a$ is independently hydrogen or $C_1$-$C_6$ alkyl; and $R^{27}$ and $R^{28}$ are independently hydrogen or $C_1$-$C_6$ alkyl; or a pharmaceutically acceptable salt thereof.

In the compounds of Formula VI-XI, X is CH$_2$, CF$_2$, S, O, or NH. In some embodiments of compounds of Formula VI-XI, X is CF$_2$. In some embodiments of compounds of Formula VI-XI, X is S. In some embodiments of compounds of Formula VI-XI, X is NH. In some embodiments of compounds of Formula VI-XI, X is CH$_2$ or O. In some embodiments of compounds of Formula VI-XI, X is NR$^b$. In some embodiments, X is NR$^b$, wherein R$^b$ is hydrogen or $C_1$-$C_6$ alkyl.

In some embodiments of compounds of Formula VI-XI, $R^3$ and $R^4$ are hydrogen. In some embodiments of these compounds, at least one of $R^3$ and $R^4$ is $C_1$-$C_6$ alkyl. In some embodiments, at least one of $R^3$ and $R^4$ is $C_1$-$C_3$ alkyl. In some embodiments, at least one of $R^3$ and $R^4$ is methyl. In some embodiments of these compounds, at least one of $R^3$ and $R^4$ is —(CH$_2$)$_m$N($R^a$)$_2$, wherein m is one to 6. In some embodiments of these compounds, at least one of $R^3$ and $R^4$ is —CH$_2$N(CH$_3$)$_2$.

In some embodiments of compounds of Formula VI-XI, $R^5$ is hydrogen. In some embodiments, $R^5$ is methyl.

In some embodiments of compounds of Formula VI-XI, $R^6$ is hydrogen. In some embodiments, $R^6$ is methyl.

In some embodiments of compounds of Formula VI-XI, $R^{22}$ is hydrogen.

In some embodiments of compounds of Formula VI-XI, $R^{40}$ and $R^{41}$ are hydrogen.

In some embodiments of compounds of Formula VI-XI, $R^{27}$ and $R^{28}$ are $C_1$-$C_6$ alkyl. In some embodiments, $R^{27}$ and $R^{28}$ are $C_1$-$C_3$ alkyl. In some embodiments, $R^{27}$ and $R^{28}$ are methyl.

In some embodiments of compounds of Formula VI-VII, $R^{20}$ is hydrogen, halogen, $C_1$-$C_6$ alkyl, or $C_1$-$C_6$ alkoxy. In some embodiments of these compounds, $R^{20}$ is hydrogen, fluoro, chloro, $C_1$-$C_6$ alkyl, or $C_1$-$C_6$ alkoxy. In some embodiments of these compounds, $R^{20}$ is hydrogen, fluoro, iodo, bromo, $C_1$-$C_6$ alkyl, or $C_1$-$C_6$ alkoxy.

In some embodiments, $R^{20}$ is methoxy, fluoro, chloro, or methyl. In some embodiments, $R^{20}$ is methoxy, ethoxy, propoxy, or isopropoxy. In some embodiments, $R^{20}$ is methoxy. In some embodiments, $R^{20}$ is fluoro or chloro. In some embodiments, $R^{20}$ is fluoro. In some embodiments, $R^{20}$ is chloro. In some embodiments, $R^{20}$ is methyl, ethyl, propyl, isopropyl, or butyl. In some embodiments, $R^{20}$ is methyl.

In some embodiments of compounds of Formula VI-VII, $R^{21}$ is hydrogen.

In some embodiments of compounds of Formula VIII-IX, $R^{24}$ and $R^{25}$ are hydrogen. In some embodiments, $R^{24}$ is hydrogen. In some embodiments, $R^{25}$ is hydrogen.

In some embodiments of compounds of Formula VIII-IX, $R^{26}$ is hydrogen. In some embodiments of these compounds, $R^{26}$ is optionally substituted $C_1$-$C_6$ alkyl, wherein $C_1$-$C_6$ alkyl is substituted with hydroxy.

In some embodiments of compounds of Formula VIII-IX, $R^{24}$, $R^{25}$ and $R^{26}$ are hydrogen.

In some embodiments of compounds of Formula X-XI, $R^{25}$ and $R^{26}$ are hydrogen. In some embodiments, $R^{25}$ is hydrogen. In some embodiments, $R^{26}$ is hydrogen.

In another aspect, the compounds of the present disclosure do not include the following compounds:

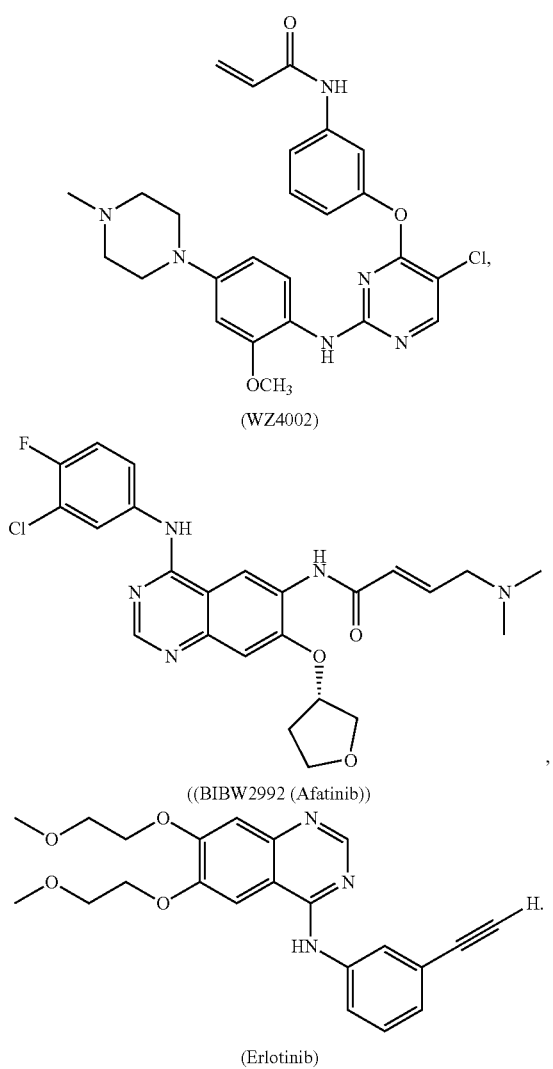

(WZ4002)

((BIBW2992 (Afatinib))

(Erlotinib)

In another aspect, the compounds of the present disclosure do not include compounds disclosed in WO 2010/129053, WO 2011/079231, and WO 2011/140338.

In another aspect, the invention provides a pharmaceutical composition comprising a compound according to any of the foregoing embodiments admixed with at least one pharmaceutically acceptable carrier or excipient. Suitable carriers and excipients are described herein. In some embodiments, this pharmaceutical composition comprises at least one sterile pharmaceutically acceptable carrier or excipient. In some embodiments, the composition comprises at least two pharmaceutically acceptable carriers and/or excipients.

In another aspect, the invention provides a compound according to any one of the foregoing embodiments for use in therapy. In particular embodiments of interest, the compound is for use in therapy to treat cancer, e.g., a cancer selected from leukemia, lymphoma, lung cancer, colon cancer, CNS cancer, melanoma, ovarian cancer, renal cancer, prostate cancer, breast cancer, head and neck cancers, and pancreatic cancer.

In one aspect, the invention provides a method to treat cancer, which comprises administering to a subject in need thereof an effective amount of a compound according to any of the foregoing embodiments, or a pharmaceutical composition comprising one or more of such compounds. In some embodiments, the cancer is selected from leukemia, lymphoma, lung cancer, colon cancer, CNS cancer, melanoma, ovarian cancer, renal cancer, prostate cancer, breast cancer, head and neck cancers, and pancreatic cancer.

Similarly, the invention provides use of a compound according to any one of the foregoing embodiments for the manufacture of a medicament. In some embodiments, the medicament is one for treating cancer, and in some embodiments the cancer is selected from leukemia, lymphoma, lung cancer, colon cancer, CNS cancer, melanoma, ovarian cancer, renal cancer, prostate cancer, breast cancer, head and neck cancers, and pancreatic cancer.

It will be understood that the selections of $W^1$, $W^2$, $W^3$, $W^4$, $W^5$, $W^6$, $W^7$, $W^8$, W and Z, X, Y for any of the above cyclic groups would of course be made by a person of ordinary skill in the art in accordance with well known limitations associated with valence rules and stability. These atoms or bonds would thus be selected to provide only a stable ring or ring system consistent with well-known bonding and valence principles; thus these rings would not be constructed with —O—O— or —S—S— linkages in the rings, for example, or with inappropriate numbers of O or N or S atoms causing instability in aqueous media. Typically each ring of these compounds will be a 5-6 atom ring, whether aromatic or not, and will contain at least one carbon atom, no more than one O or S atom (except for a dioxane ring having two O atoms), and up to four N atoms as ring members. Non-aromatic rings will typically contain no more than two heteroatoms in place of ring carbon atoms, while aromatic rings containing 3-4 heteroatoms—especially N atoms—such as triazines, triazoles, tetrazines and tetrazoles, are included. Likewise, other groups such as R would be selected to avoid compounds generally considered to be too reactive for use as pharmaceuticals, e.g., R would not be Halo in groups such as NHR, NRR, OR, SR, or COOR.

Typical structures of,

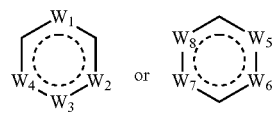

include but are not limited to,

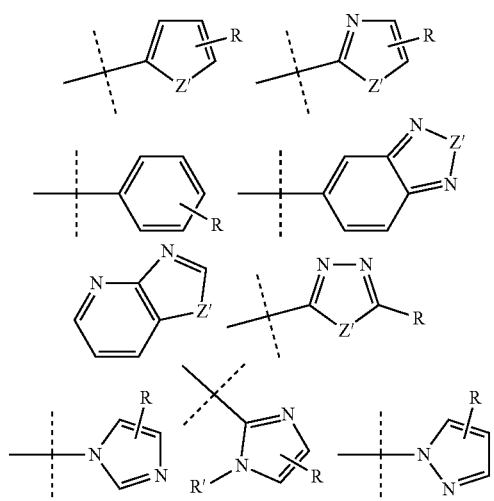

-continued

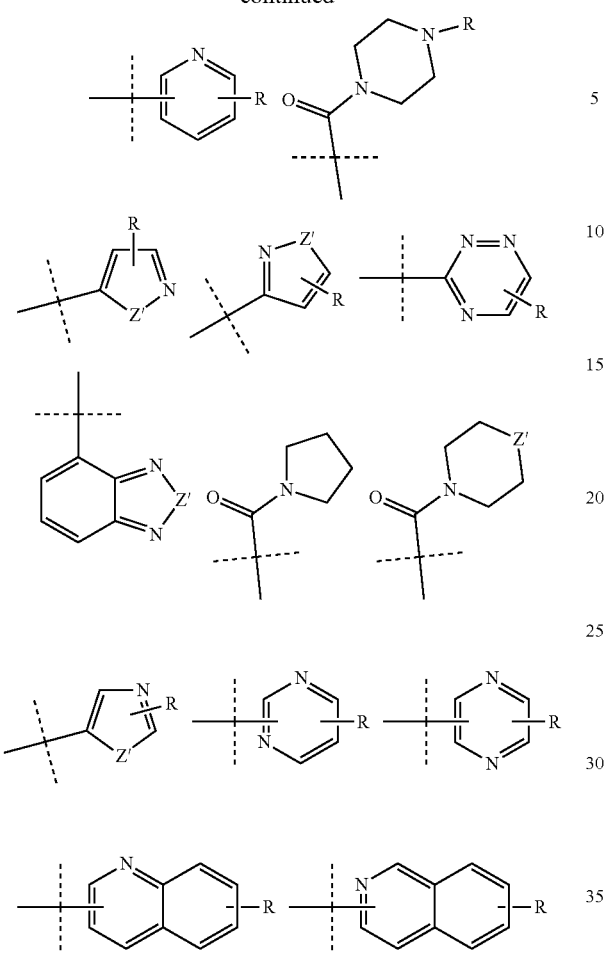

where Z' is selected from the group of O, S, C=O, —NR, SO, SO2, C1-C6 alkyl and C1-C6 haloalkyl.

Suitable dosages, routes of administration, and administration protocols can be selected by a skilled person based on the information herein.

Exemplary Synthesis:

The compounds described above can be synthesized as illustrated in Scheme 1. Some representative compounds are illustrated in Scheme 2 and 3, which depicts some suitable Het groups for use in the compounds described above.

General Procedure for the Synthesis of Substituted Pyrimidine Derivatives (6, Scheme 1):

Scheme 1 General synthetic scheme for substituted pyrimidine derivatives

-continued

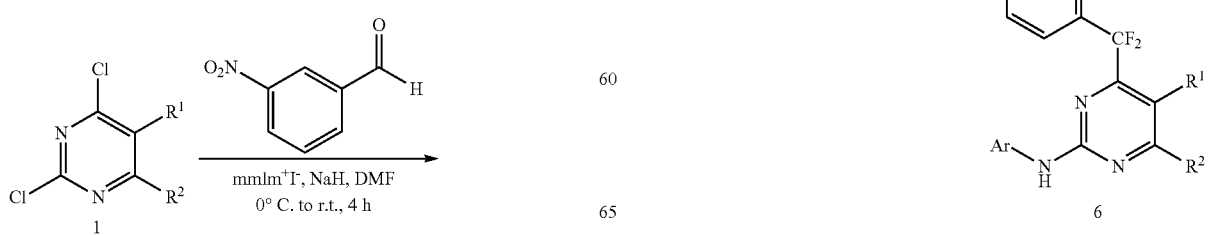

Substituted 2,4-dichloropyrimidine 1 reacted with 3-nitrobenzaldehyde and 1,3-Dimethylimidazolium iodide in DMF for 4 h providing the corresponding substituted (2-chloropyrimidin-4-yl)(3-nitrophenyl)methanone 2. 2 was then further stirred with DAST in DCM at room temperature overnight providing the corresponding 2-chloro-4-(difluoro (3-nitrophenyl)methyl)pyrimidine 3. Pyrimidine 3 was coupled with aryl amine by Buchwald-Hartwig Pd catalyzed aryl C—N formation giving the desired product 4. The nitro group in 4 was then reduced to $NH_2$ followed by amidation with acrylyl chloride to give the final compound 6.

Example 1

Synthesis of N-(3-(difluoro(2-(4-(4-methylpiperazin-1-yl)phenylamino)-9H-purin-6-yl)methyl)phenyl)acrylamide (13a) & N-(3-(difluoro(2-(2-methoxy-4-(4-methylpiperazin-1-yl)phenylamino)-91-1-purin-6-yl)methyl)phenyl)acrylamide (13b)

The synthesis of N-(3-(difluoro(2-(4-(4-methylpiperazin-1- yl)phenylamino)-9H-purin-6-yl)methyl)phenyl)acrylamide 13a and N-(3-(difluoro(2-(2-methoxy-4-(4-methylpiperazin-1-yl)phenylamino)-9H-purin-6-yl)methyl)phenyl) acrylamide 13b were shown in Scheme 2.

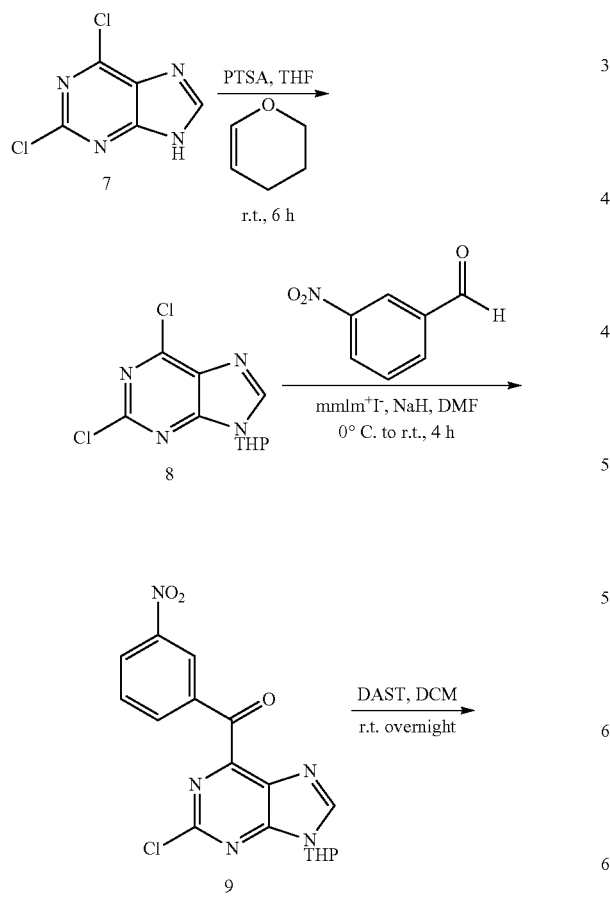

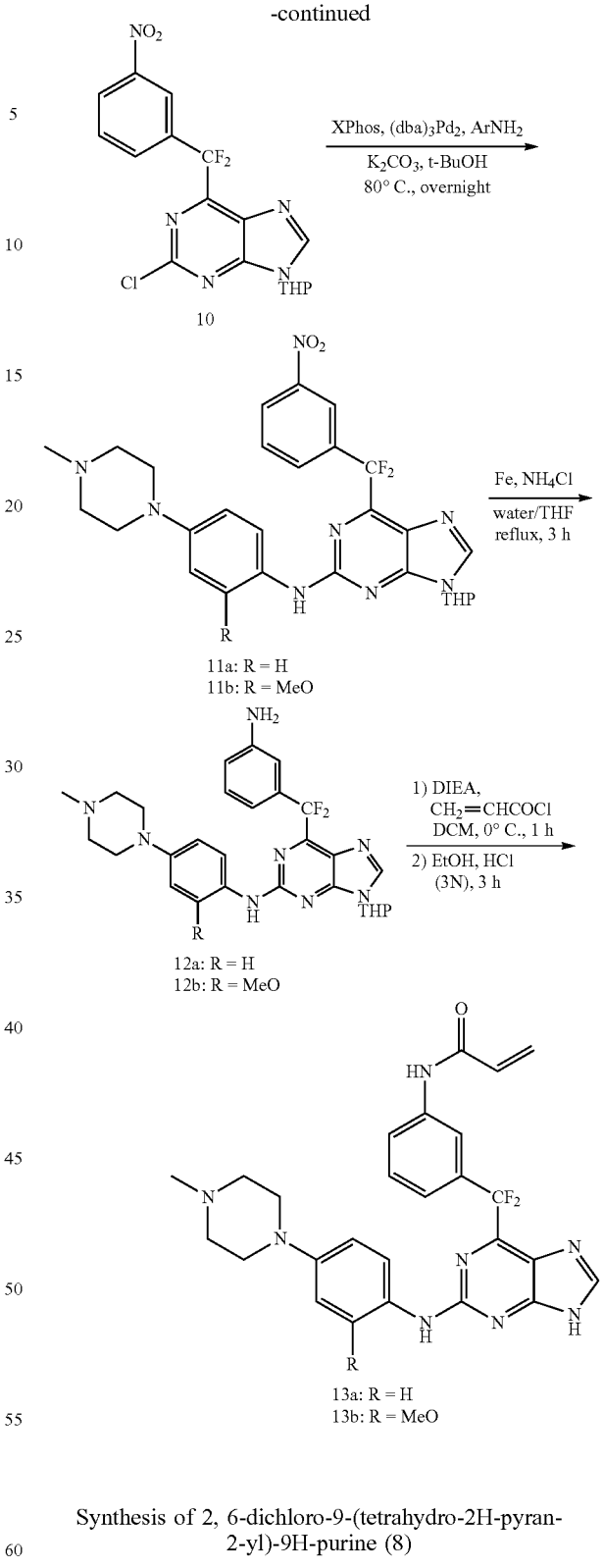

Synthesis of 2, 6-dichloro-9-(tetrahydro-2H-pyran-2-yl)-9H-purine (8)

A mixture of 2,6-dichloropurine 7 (2.4 g, 12.7 mmol), PTSA (222 mg, 1.17 mmol) and 2H-3,4-dihydropyran (1.26 g, 15 mmol) in DCM (30 mL) was stirred at room temperature for 6 h. The mixture was concentrated and purified by column chromatography to give 8 (3.2 g, yield, 94%, $M+H^+=273$) as a pale yellow solid.

Synthesis of (2-chloro-9-(tetrahydro-2H-pyran-2-yl)-9H-purin-6-yl)(3-nitrophenyl)methanone (9)

2, 6-dichloro-9-(tetrahydro-2H-pyran-2-yl)-9H-purine 8 (327 mg, 1.2 mmol) was dissolved in DMF (4 mL) at 0° C. and treated sequentially with 3-nitrobenzaldehyde (220 mg, 1.46 mmol), and 1,3-dimethylimidazolium iodide (109 mg, 0.49 mmol). Sodium hydride (78 mg, 60%, 1.95 mmol) was added slowly and then the mixture was warmed to room temperature. After being stirred for 4 h, the reaction was quenched with water and extracted with EA. The layers were separated. The dried (Na$_2$SO$_4$) organic layer was purified by chromatography on silica gel using hexanes/ethyl acetate 75:25 as eluent. The title compound 9 (230 mg, 50%, M+H$^+$=389) was isolated as a yellow.

Synthesis of 2-chloro-6-(difluoro(3-nitrophenyl)methyl)-9-(tetrahydro-2H-pyran-2-yl)-9H-purine (10)

A round bottom flask equipped with a Teflon-coated magnetic stir bar was charged with 9 (136 mg, 0.35 mmol) in DCM (0.5 mL). The flask was capped with a rubber septum and purged with argon. (Diethylamino)sulfur trifluoride (200 mg, 1.24 mmol) was added by syringe. The mixture was stirred at room temperature overnight. The reaction was carefully poured into ice-water and the resulting mixture was extracted with DCM. The combined organic extracts were washed with brine and dried (Na$_2$SO$_4$). After filtration, removal of the volatiles in vacuo, the crude product was purified by flash chromatography afford the title compound 10 (M+H$^+$=410) as a yellow solid.

Synthesis of 6-(difluoro(3-nitrophenyl)methyl)-N-(4-(4-methylpiperazin-1-yl)phenyl)-9-(tetrahydro-2H-pyran-2-yl)-9H-purin-2-amine (11a)

A mixture of above 10 (135 mg, 0.33 mmol), 4-(4-Methylpiperazino) aniline (100 mg, 0.52 mmol), tris(dibenzylideneacetone)dipalladium (20 mg, 0.022 mmol), dicyclohexyl (2',4',6'-triisopropylbiphenyl-2-yl) phosphine (70 mg, 0.15 mmol) and potassium carbonate (190 mg, 1.37 mmol) in tert-butanol (5 mL) was stirred under argon at 80° C. overnight. After cooling to RT, the reaction mixtures was filtered through Celite, the Celite was washed with methanol and the filtrates were concentrated under reduced pressure. The residue was purified by flash column chromatography (DCM/MeOH=20/1), giving the title compound 11a (190 mg, M+H$^+$=565) as brown oil.

Synthesis of 6-(difluoro(3-nitrophenyl)methyl)-N-(2-methoxy-4-(4-methylpiperazin-1-yl)phenyl)-9-(tetrahydro-2H-pyran-2-yl)-9H-purin-2-amine (11b)

This title compound 11b was prepared according to the synthetic procedure of 11a, using 2-methoxy-4-(4-methylpiperazin-1-yl)aniline instead of 4-(4-Methylpiperazino) aniline.

Synthesis of 6-((3-aminophenyl)difluoromethyl)-N-(4-(4-methylpiperazin-1-yl)phenyl)-9-(tetrahydro-2H-pyran-2-yl)-9H-purin-2-amine (12a)

11a (190 mg, 0.34 mmol) was dissolved in THF (5 mL) and water (5 mL) was added. Iron powder (190 mg, 3.4 mmol) and saturated ammonium chloride aqueous (2.5 mL) were then added, and the resulting mixture was heated to reflux for 3 hours. The reaction mixture was cooled to room temperature and filtered through celite. The THF was removed under reduced pressure, and the resulting residue was basified with sodium bicarbonate and extracted with ethyl acetate. The organic layer was separated and dried using anhydrous sodium sulfate, concentrated, and purified by flash chromatography with 20:1 dichloromethane-methanol to afford the title compound 12a (200 mg, M+H$^+$=535) as yellow solid.

Synthesis of 6-((3-aminophenyl) difluoromethyl)-N-(2-methoxy-4-(4-methylpiperazin-1-yl)phenyl)-9-(tetrahydro-2H-pyran-2-yl)-9H-purin-2-amine (12b)

This title compound 12b was prepared according to the procedure of 12a.

Synthesis of N-(3-(difluoro(2-(4-(4-methylpiperazin-1-yl)phenylamino)-9H-purin-6-yl)methyl)phenyl)acrylamide (13a)

Acryloyl chloride (60 mg, 0.66 mmol) was added dropwise to a solution of 12a (200 mg, 0.37 mmol) and diisopropyethylamine (0.5 mL, 3.1 mmol) in methylene chloride (5 mL) at 0° C. The reaction was stirred for 1 h. And then water was added to quench the reaction. The solvent was removed under reduced pressure and the crude amide was obtained. To this crude amide, THF (3 mL) and HCl (3 mL, 3N) were added. The mixture was stirred at room temperature for 3 h. Then the reaction was quenched and basified with sodium hydrocarbonate and extracted with ethyl acetate. The organic layer was separated and dried using anhydrous sodium sulfate, concentrated, and purified by flash chromatography with 4:1 dichloromethane-methanol to afford the title compound 13a (20 mg, M+H$^+$=505, purity 98.47%) as a yellow powder.

Synthesis of N-(3-(difluoro(2-(2-methoxy-4-(4-methylpiperazin-1-yl)phenylamino)-9H-purin-6-yl)methyl)phenyl)acrylamide (13b)

This title compound 13b was prepared according to the procedure of 13a.

Example 2

Synthesis of N-(3-(difluoro(5-fluoro-2-(4-(4-methylpiperazin-1-yl)phenylamino)pyrimidin-4-yl)methyl)phenyl)acrylamide (19)

Scheme 3 Synthesis of N-(3-(difluoro(5-fluoro-2-(4-(4-methylpiperazin-1-yl)phenylamino)pyrimidin-4-yl)methyl)phenyl)acrylamide (19)

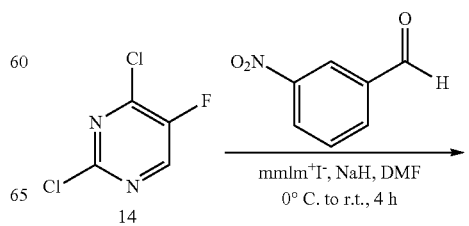

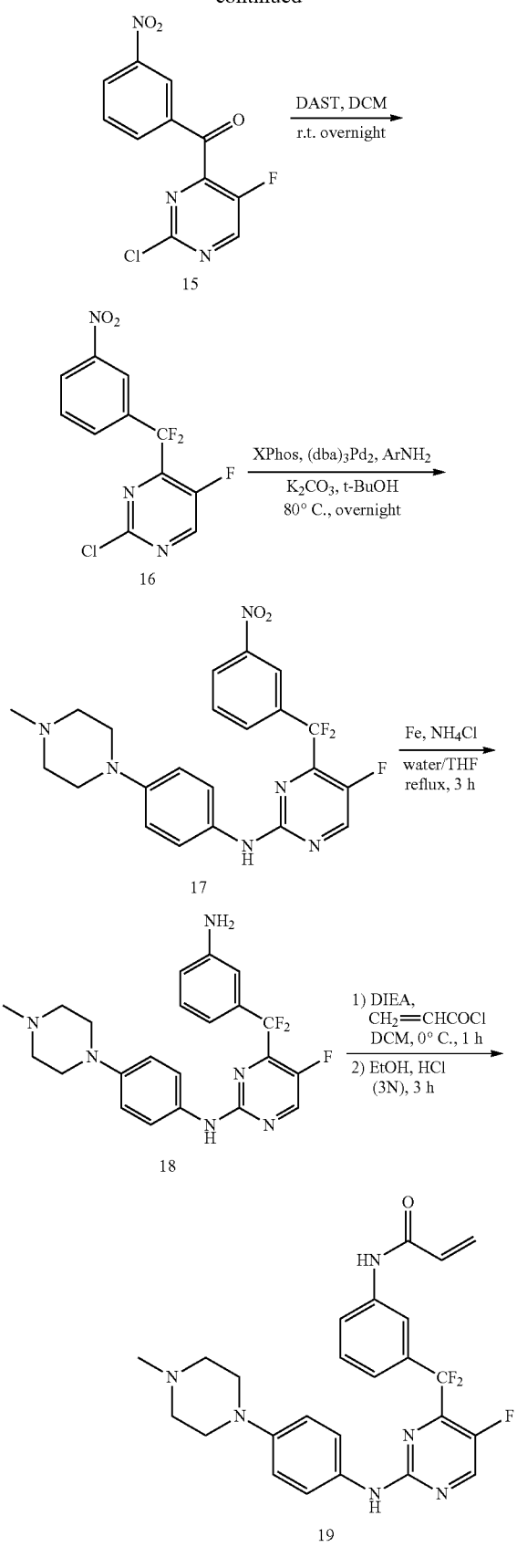

Synthesis of (2-chloro-5-fluoropyrimidin-4-yl)(3-nitrophenyl)methanone (15)

2, 4-dichloro-5-fluoropyrimidine 14 (1002 mg, 6 mmol) was dissolved in DMF (10 mL) at 0° C. and treated sequentially with 3-nitrobenzaldehyde (906 mg, 6 mmol), and 3-ethyl-l-methylimidazolium bromide (300 mg, 1.57 mmol). Sodium hydride (360 mg, 60%, 8.75 mmol) was added slowly. The mixture was stirred at −5-0° C. for 2 h, and then warmed to room temperature with stirring for 8 h. The reaction was then quenched with water and extracted with EA. The layers were separated. The dried ($Na_2SO_4$) organic layer was purified by chromatography on silica gel using hexanes/ethyl acetate 4:1 as an eluant. The title compound 9 (750 mg, 44%, M+H$^+$=282.5) was isolated as white solid.

Synthesis of 2-chloro-4-(difluoro(3-nitrophenyl)methyl)-5-fluoropyrimidine (16)

A round bottom flask equipped with a Teflon-coated magnetic stir bar was charged with 15 (200 mg, 0.71 mmol) in DCM (2 mL). The flask was capped with a rubber septum and purged with argon. (Diethylamino)sulfur trifluoride (0.5 mL) was added by syringe. The mixture was stirred at room temperature overnight. The reaction was carefully poured into ice-water and the resulting mixture was extracted with DCM. The combined organic extracts were washed with brine and dried ($Na_2SO_4$). After filtration and removal of the solvent under reduced pressure, the crude was purified by flash chromatography affording the title compound 16 (186 mg, 61.3%, M+H$^+$=304.5) as white solid.

Synthesis of 4-(difluoro(3-nitrophenyl)methyl)-5-fluoro-N-(4-(4-methylpiperazin-1-yl)phenyl)pyrimidin-2-amine (17)

A mixture of above 16 (60 mg, 0.20 mmol), 4-(4-Methylpiperazino) aniline (45 mg, 0.23 mmol), tris(dibenzylideneacetone)dipalladium (18 mg, 0.02 mmol), dicyclohexyl (2',4',6'- triisopropylbiphenyl-2-yl) phosphine (56 mg, 0.12 mmol) and potassium carbonate (109 mg, 0.78 mmol) in tert-butanol (2.6 mL) was stirred under argon at 80° C. overnight. After cooling to RT, the reaction mixtures was filtered through Celite, the Celite was washed with methanol and the filtrates were concentrated under reduced pressure. The residue was purified by flash column chromatography (DCM/MeOH=20/1) to give the title compound 17 (80 mg, 87%, M+H$^+$=459.5) as brown oil.

Synthesis of 4-((3-aminophenyl)difluoromethyl)-5-fluoro-N-(4-(4-methylpiperazin-1-yl)phenyl)-pyrimidin-2-amine (18)

17 (80 mg, 0.18 mmol) was dissolved in THF (2 mL) and water (2 mL) was added. Iron powder (50 mg, 0.9 mmol) and saturated ammonium chloride aqueous (1.2 mL) were then added, and the resulting mixture was heated to reflux for 4 hours. The reaction mixture was cooled to room temperature and filtered through celite. The THF was removed under reduced pressure, and the resulting residue was basified with sodium bicarbonate and extracted with ethyl acetate. The organic layer was separated and dried using anhydrous sodium sulfate, concentrated, and purified by flash chromatography with 20:1 dichloromethane-methanol to afford the title compound 18 (51 mg, 68%, M+H$^+$= 429.5) as a yellow solid.

Synthesis of N-(3-(difluoro(5-fluoro-2-(4-(4-methylpiperazin-1-yl)phenylamino)pyrimidin-4-yl)methyl)phenyl)acrylamide (19)

Acryloyl chloride (20 mg, 0.20 mmol) was added dropwise to a solution of 18 (51 mg, 0.12 mmol) and diisopropyethylamine (0.17 mL, 1.05 mmol) in methylene chloride (1.5 mL) at 0° C. The reaction was stirred for 3 h. And then water was added to quench the reaction. The solvent was removed under reduced pressure and the crude amide was obtained. To this crude amide, THF (3 mL) and HCl (3 mL, 3N) were added. The mixture was stirred at room temperature for 3 h. Then the reaction was quenched and basified with sodium hydrocarbonate and extracted with ethyl acetate. The organic layer was separated and dried using anhydrous sodium sulfate, concentrated, and purified by flash chromatography with 4:1 dichloromethane-methanol to afford the title compound 19 (53 mg, 92%, M+H⁺=483.5, purity 98.47%) as yellow powder.

Using similar chemistry or synthetic route, the following compounds can also be synthesized:

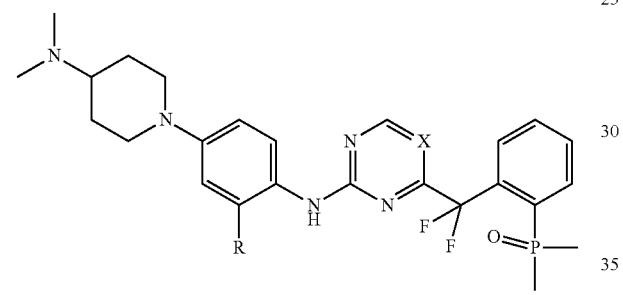

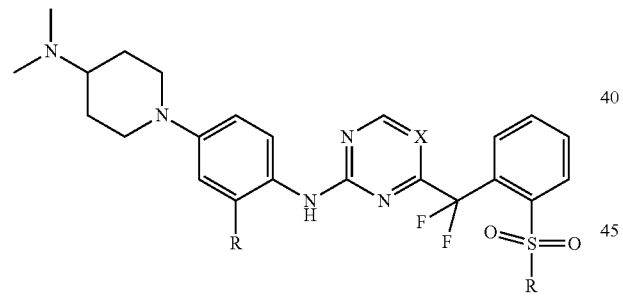

X = CF, CCl, CH, N
R = H, halo, Alkyl, Alkoxy, cycloalkyl, amine, amide, sulfonamide, carboxylic acid General Procedure for the Synthesis of Substituted EGFR Derivatives (28a-d, Scheme 4):

Scheme 4 General Synthetic Scheme for Compounds 28

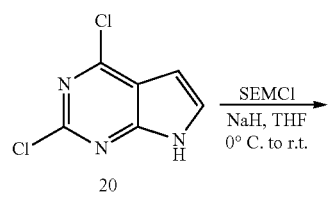

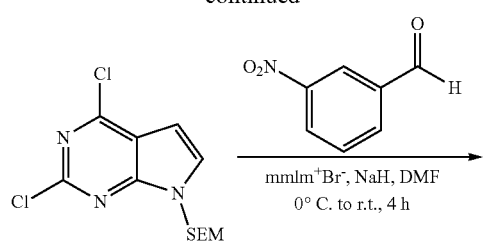

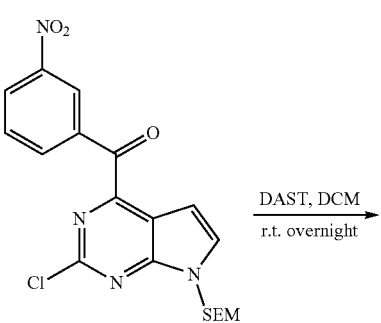

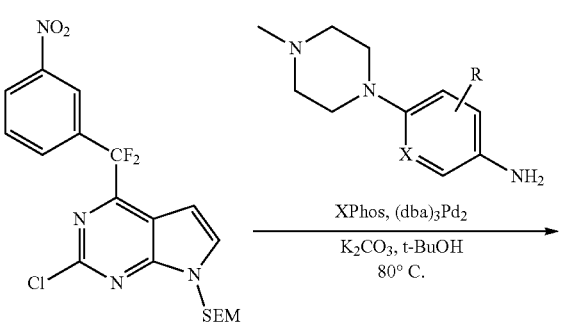

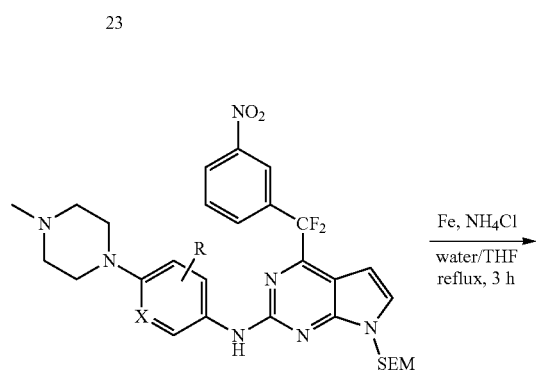

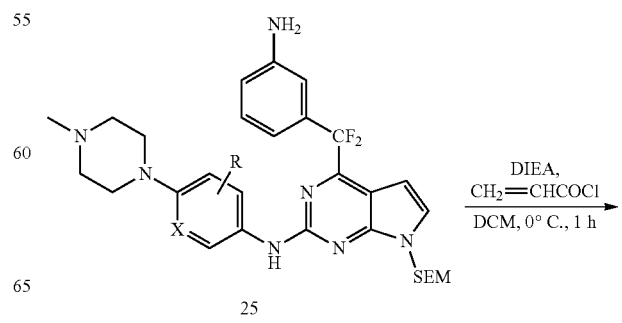

71
-continued
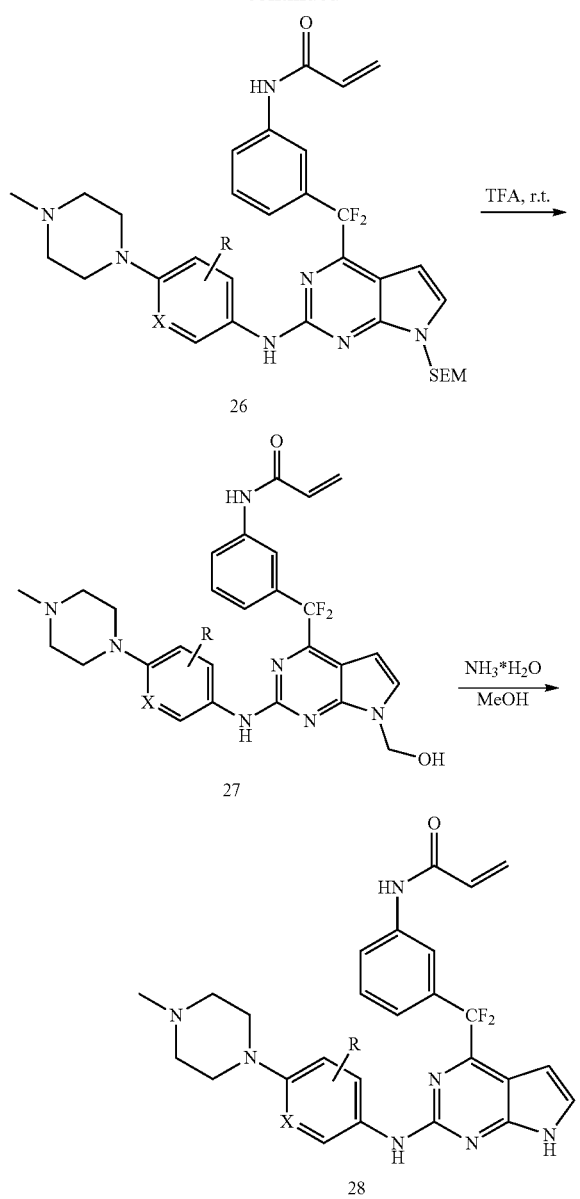
Example 3
N-(3-(difluoro(2-(4-(4-methylpiperazin-1-yl)phe-
nylamino)-7H-pyrrolo[2,3-d]pyrimidin-4-yl)methyl)
phenyl)acrylamide (28a)
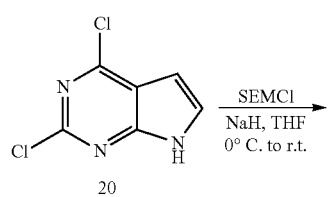
72
-continued
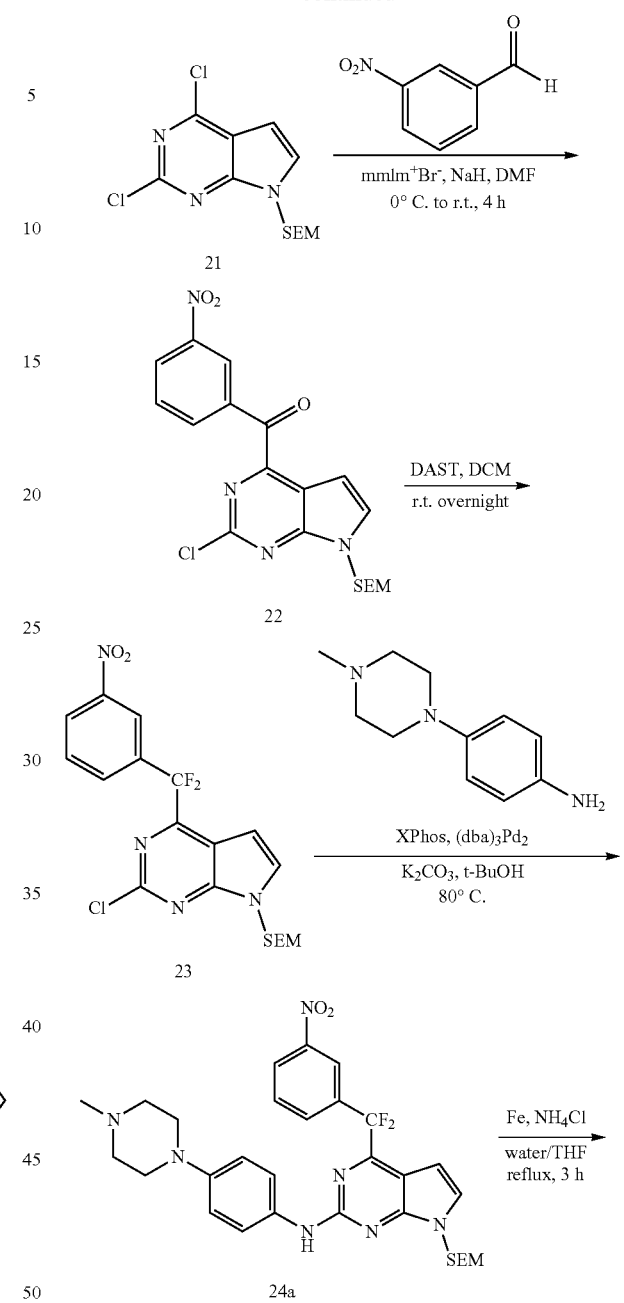
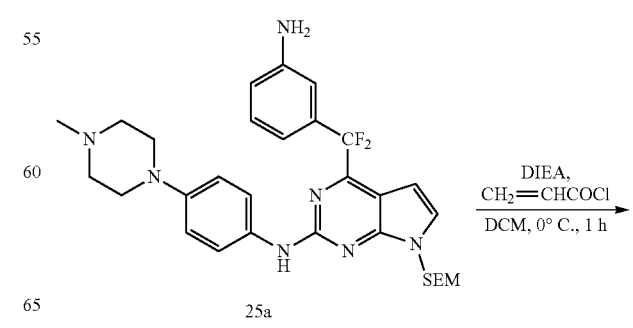

-continued

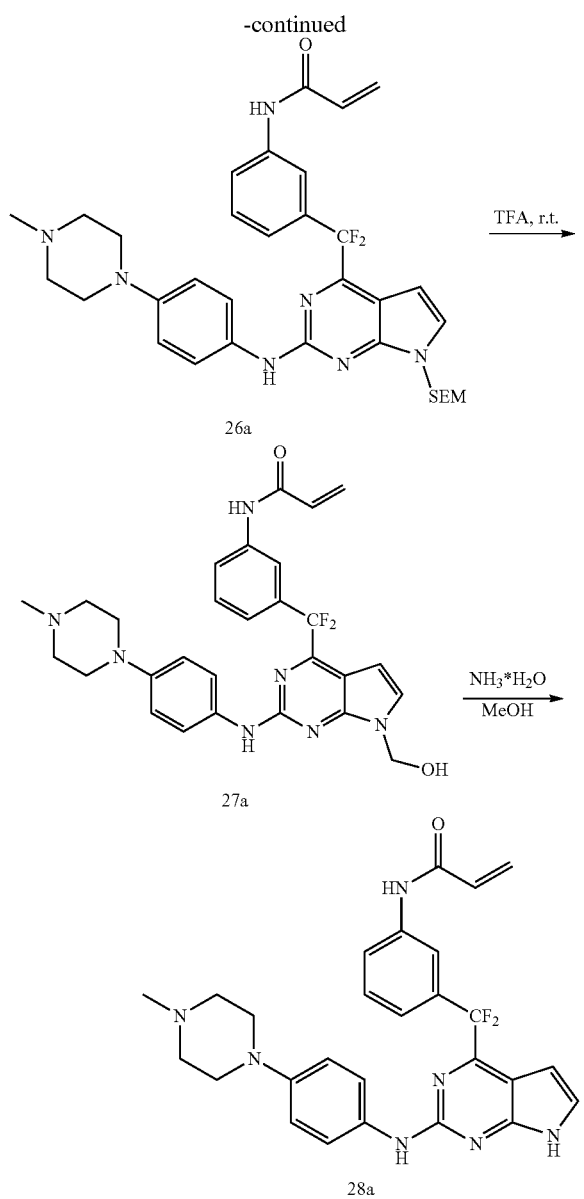

Synthesis of 2,4-dichloro-7-((2-(trimethylsilyl)ethoxy)methyl)-7H-pyrrolo[2,3-d]pyrimidine (2)

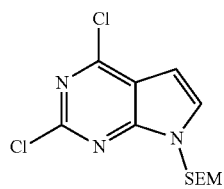

NaH (60%, 46.7 mg, 3.06 mmol) was added to a mixture of 2,4-dichloro-7H-pyrrolo[2,3-d]pyrimidine 1 (575 mg, 3.06 mmol) and SEMCl (561 mg, 3.37 mmol) in THF (5 mL) at 0° C. with stirring. The reaction mixture was allowed to warm to room temperature and stirred for 3 h before quenching with water (5 mL). The mixture was extracted with ethyl acetate (10 mL×3). The organic layers were combined, washed with brine, dried over $Na_2SO_4$ and filtered. The filtrate was concentrated, and the crude was purified by column chromatography (PE/EA=20/1) to give 2 (520 mg, yield 53.4%, M+H$^+$=319.27) as pale yellow solid.

Synthesis of (2-chloro-7-((2-(trimethylsilyl)ethoxy)methyl)-7H-pyrrolo[2,3-d]pyrimidin-4-yl)(3-nitrophenyl)methanone (22)

Compound 21 (517 mg, 1.51 mmol) was dissolved in DMF (3 mL) at 0° C. and treated sequentially with 3-nitrobenzaldehyde (225 mg, 1.5 mmol), and 1, 3-dimethylimidazolium iodide (129 mg, 0.58 mmol). Sodium hydride (100 mg, 60%, 2.5 mmol) was added slowly and then the mixture was warmed to room temperature. After being stirred for 4 h, the reaction was quenched with water and extracted with ethyl acetate. The layers were separated. The organic layer was dried over $Na_2SO_4$, and the solvent was removed under reduced pressure. The crude was purified by chromatography on silica gel using hexanes/ethyl acetate 75:25 as an eluant. The title compound 22 (320 mg, yield 50%, M+H$^+$=433.1) was isolated as yellow solid.

Synthesis of 2-chloro-4-(difluoro(3-nitrophenyl)methyl)-7-((2-(trimethylsilyethoxy)methyl)-7H-pyrrolo[2,3-d]pyrimidine (23)

A round bottom flask equipped with a Teflon-coated magnetic stir bar was charged with 22 (320 mg, 0.74 mmol) in DCM (2 mL). The flask was capped with a rubber septum and purged with argon. (Diethylamino)sulfur trifluoride (600 mg, 3.72 mmol) was added by syringe. The mixture was stirred at room temperature overnight. The reaction was carefully poured into ice-water and the resulting mixture was extracted with DCM. The combined organic layers was washed with brine and dried over Na$_2$SO$_4$. After filtration and removal of solvent under reduced pressure, the crude was purified by flash chromatography to afford the title compound 23 (270 mg, yield 80%, M+H$^+$=455.1) as yellow solid.

Synthesis of 4-(difluoro(3-nitrophenyl)methyl)-N-(4-(4-methylpiperazin-1-yl)phenyl)-7-((2-(trimethylsilyl)ethoxy)methyl)-7H-pyrrolo[2,3-d]pyrimidin-2-amine (24a)

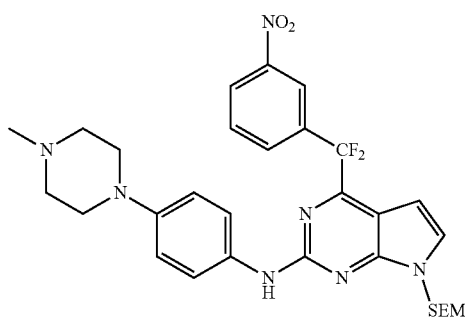

24a

This title compound 24a (yield 76% from 23, M+H$^+$=610.3) was prepared according to the synthetic procedure of 11, but starting from compound 23 and 4-(4-Methylpiperazino) aniline.

Synthesis of 4-((3-aminophenyl)difluoromethyl)-N-(4-(4-methylpiperazin-1-yl)phenyl)-7-((2-(trimethylsilyl)ethoxy)methyl)-7H-pyrrolo[2,3-d]pyrimidin-2-amine (25a)

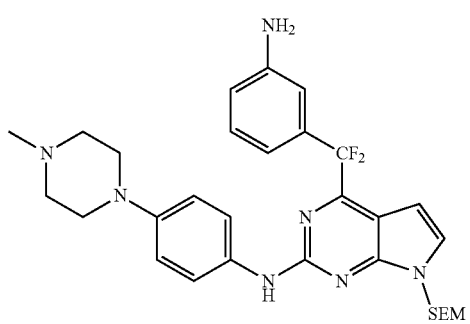

25a 24a (200 mg, 0.33 mmol) was dissolved in THF (5 mL) and water (5 mL) was added. Iron powder (190 mg, 3.4 mmol) and saturated ammonium chloride aqueous (2.5 mL) were then added. The resulting mixture was heated to reflux for 3 hours. The reaction mixture was cooled to room temperature and filtered through celite. The solvent was removed under reduced pressure. The resulting residue was basified with sodium bicarbonate and extracted with ethyl acetate. The organic layer was separated, dried over anhydrous sodium sulfate, concentrated, and purified using flash chromatography with 20:1 dichloromethane-methanol to afford the title compound 25a (179 mg, M+H$^+$=578) as yellow solid.

Synthesis of N-(3-(2-(4-(4-methylpiperazin-1-yl)phenylamino)-7-((2-(trimethylsilypethoxy)methyl)-7H-pyrrolo[2,3-d]pyrimidin-4-yloxy)phenyl)acrylamide (26a)

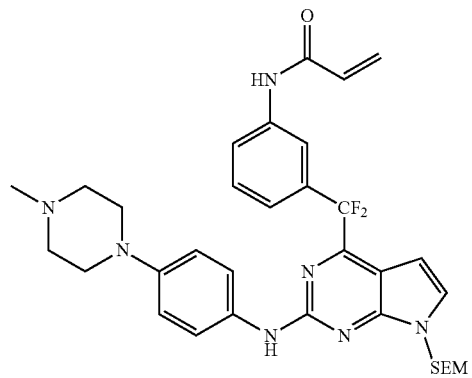

26a

Acryloyl chloride (33.8 mg, 0.374 mmol) was added dropwise to a solution of 25a (180.8 mg, 0.312 mmol) and diisopropylethylamine (55 mg, 0.426 mmol) in methylene chloride (3 mL) at 0° C. The reaction was stirred for 1 h. And then water was added to quench the reaction. The organic layer was washed with water, brine, dried over Na$_2$SO$_4$. After filtration and removal of solvent under reduced pressure, the crude was purified by flash chromatography (DCM/MeOH=20/1) afford the title compound 26a (154 mg, yield 78%, M+H$^+$=634.3) as white solid.

Synthesis of N-(3-(difluoro(7-(hydroxymethyl)-2-(4-(4-methylpiperazin-1-yl)phenylamino)-7H-pyrrolo[2,3-d]pyrimidin-4-yl)methyl)phenyl)acrylamide (27a)

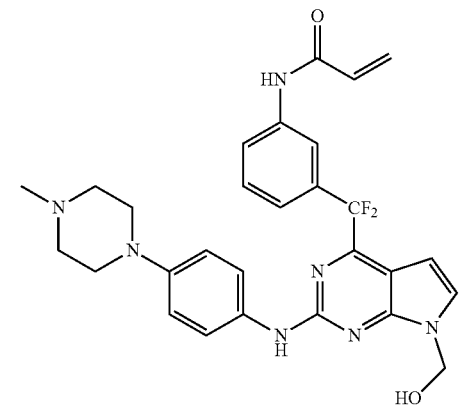

27a

Compound 26a (125 mg, 0.197 mmol) in CH$_2$Cl$_2$ (3 mL) and trifluoroacetic acid (1 mL) was stirred at room temperature for 3 h. TLC indicated all starting material was consumed. Saturated NaHCO$_3$ solution was then added to the mixture at 0° C. to neutralize the excess acid. The mixture was extracted with DCM immediately. The organic layer was separated and washed with water, brine, dried over Na$_2$SO$_4$ and filtered. The filtrate was concentrated, and the crude was purified by column chromatography (DCM/MeOH=20/1) to give 27a (78.8 mg, yield 75%, M+H⁺=534.2) as white solid.

Synthesis of N-(3-(difluoro(2-(4-(4-methylpiperazin-1-yl)phenylamino)-7H-pyrrolo[2,3-d]pyrimidin-4-yl)methyl)phenyl)acrylamide (28a)

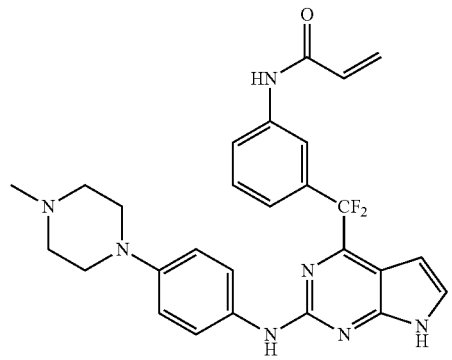

28a

A solution of compound 27a (100 mg, 0.187 mmol) in methanol (2 mL) was saturated with ammonia. The reaction mixture was stirred overnight at room temperature. LC-MS indicated all starting material was consumed. The mixture was concentrated and the crude was purified by column chromatography (DCM/MeOH=20/1) to give 28a (66.8 mg, yield 71%, M+H⁺=504.2) as pale yellow solid.

Example 4

N-(3-(difluoro(2-(6-(4-methylpiperazin-1-yl)pyridin-3-ylamino)-7H-pyrrolo[2,3-d]pyrimidin-4-yl)methyl)phenyl)acrylamide (28b)

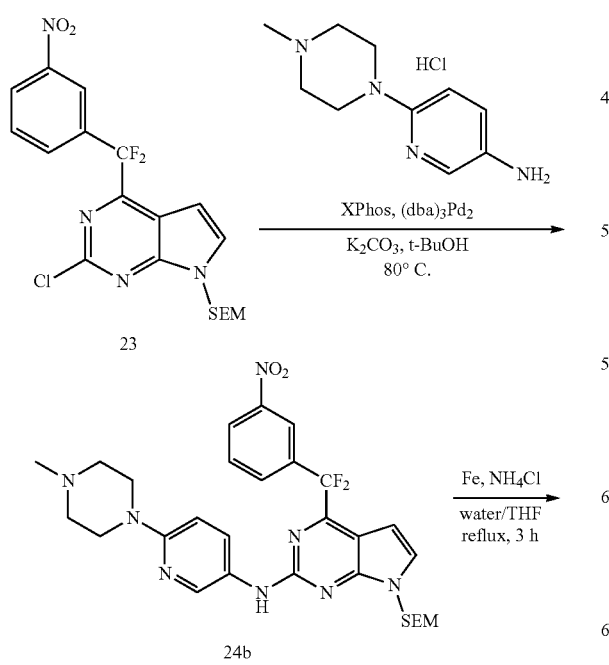

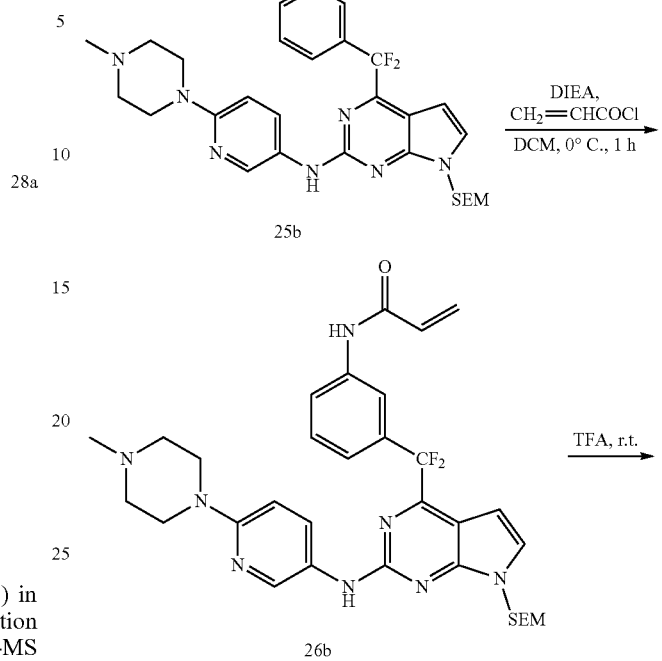

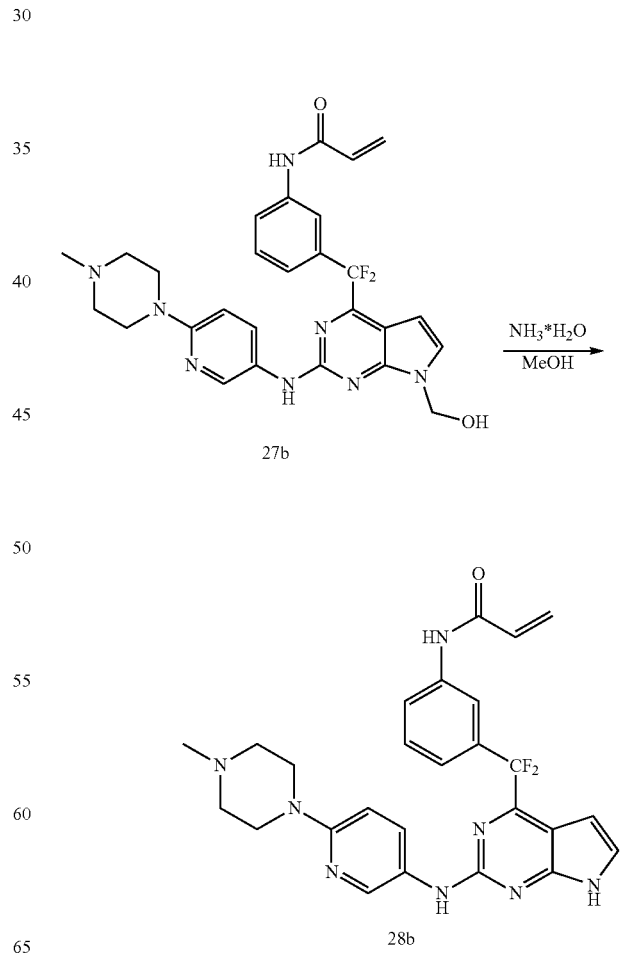

Synthesis of 4-(difluoro(3-nitrophenyl)methyl)-N-(6-(4-methylpiperazin-1-yl)pyridin-3-yl)-7-((2-(trimethylsilyl)ethoxy)methyl)-7H-pyrrolo[2,3d]pyrimidin-2-amine (24b)

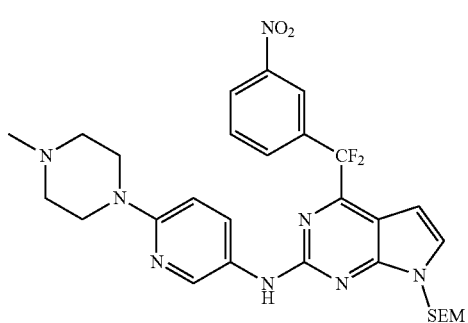

The title compound 24b (yield 76% from 10, M+H⁺= 611.3) was prepared according to the synthetic procedure of 24a, but starting from compound 23 and 3-amino-6-(4-Methyl-1-piperazinyl) pyridine hydrochloride.

Synthesis of 4-((3-aminophenyl)difluoromethyl)-N-(6-(4-methylpiperazin-1-yl)pyridin-3-yl)-7-((2-(trimethylsilyl)ethoxy)methyl)-7H-pyrrolo[2,3d]pyrimidin-2-amine (25b)

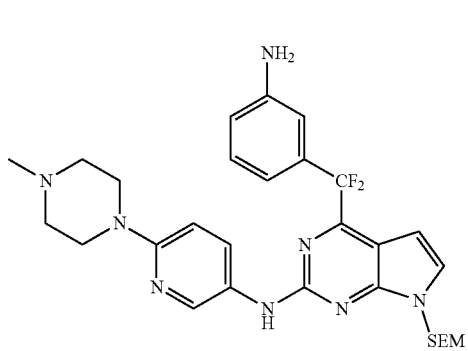

The title compound 25b (yield 71% from 24b, M+H⁺= 581.3) was prepared according to the synthetic procedure of 25a, starting from 24b.

Synthesis of N-(3-(difluoro(2-(6-(4-methylpiperazin-1-yl)pyridin-3-ylamino)-7-((2-(trimethylsilylpethoxy)methyl)-7H-pyrrolo[2,3-d]pyrimidin-4-yl)methyl)phenyl)acrylamide (26b)

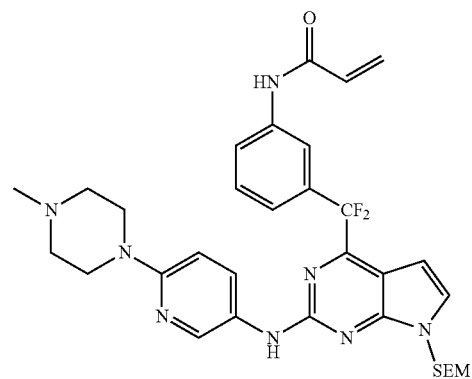

The title compound 26b (yield 75% from 25b, M+H⁺= 635.3) was prepared according to the synthetic procedure of 26a, starting from 25b.

Synthesis of N-(3-(difluoro(7-(hydroxymethyl)-2-(6-(4-methylpiperazin-1-yl)pyridin-3-ylamino)-7H-pyrrolo[2,3-d]pyrimidin-4-yl)methyl)phenyl)acrylamide (27b)

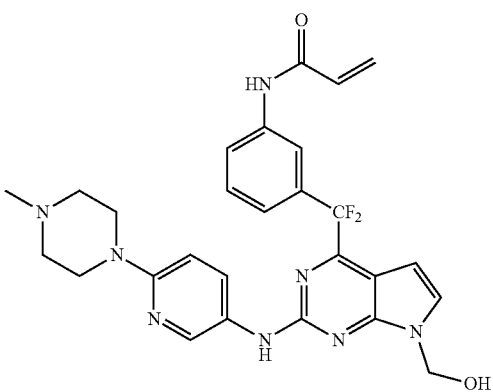

The title compound 27b (yield 70% from 26b, M+H⁺= 535.2) was prepared according to the procedure of 27a, starting from 26b.

81
Synthesis of N-(3-(difluoro(2-(6-(4-methylpiperazin-1-yl)pyridin-3-ylamino)-7H-pyrrolo[2,3-d]pyrimidin-4-yl)methyl)phenyl)acrylamide (28b)
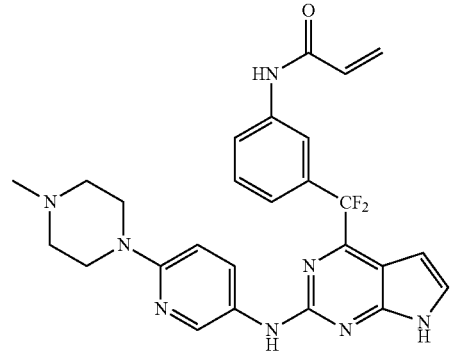
The title compound 28b (yield 75% from 27b, M+H⁺=505.2) was prepared according to the synthetic procedure of 28a, starting from 27b.
Example 5
N-(3-(difluoro(2-(3-fluoro-4-(4-methylpiperazin-1-yl)phenylamino)-7H-pyrrolo[2,3-d]pyrimidin-4-yl)methyl)phenyl)acrylamide (28c)
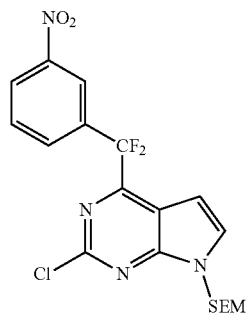 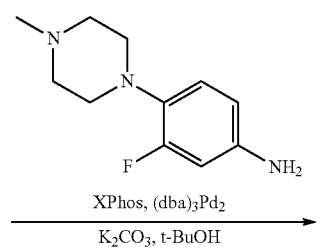
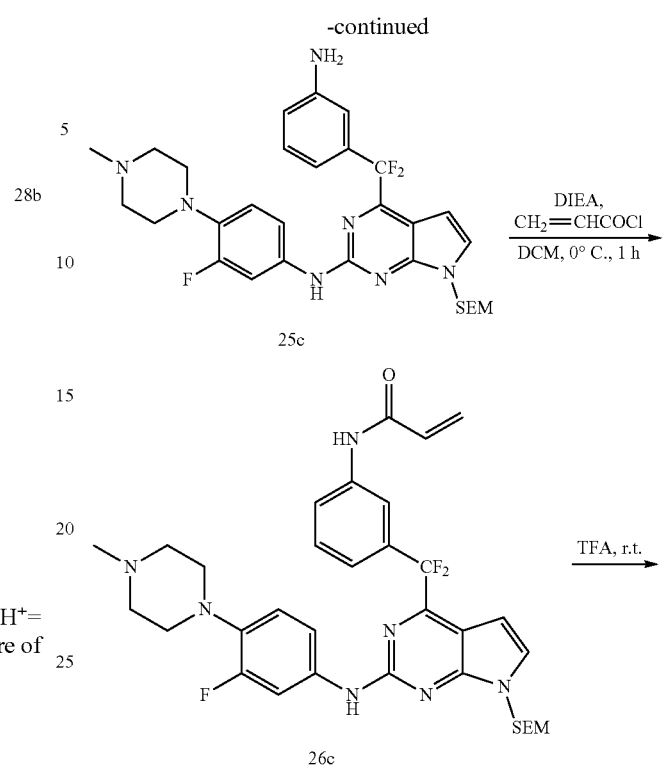
-continued
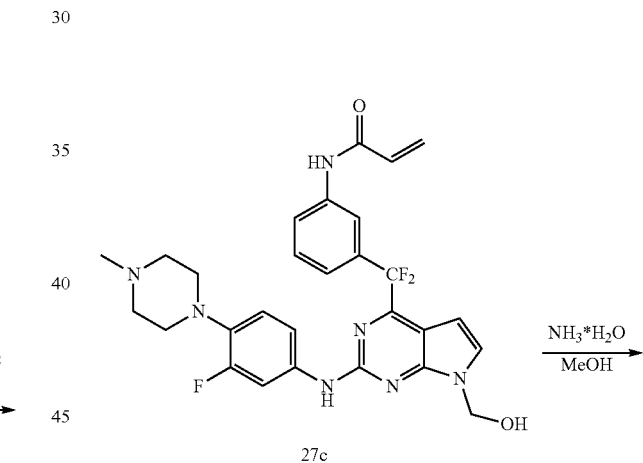
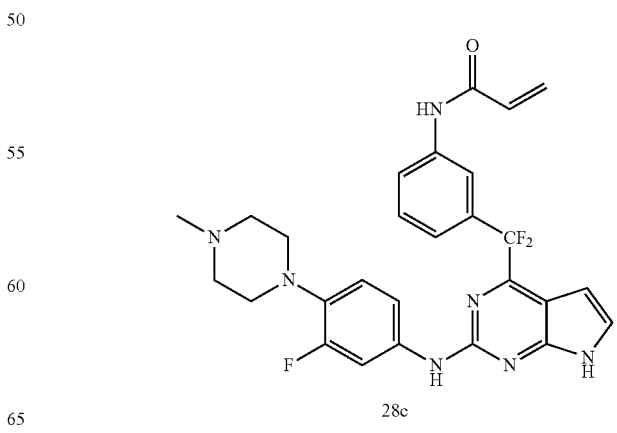

Synthesis of 4-(difluoro(3-nitrophenyl)methyl)-N-(3-fluoro-4-(4-methylpiperazin-1-yl)phenyl)-7-((2-(trimethylsilyl)ethoxy)methyl)-7H-pyrrolo[2,3-d]pyrimidin-2-amine (24c)

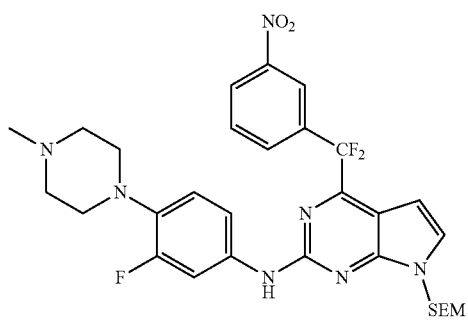

The title compound 24c (yield 75% from 23, M+H$^+$= 628.3) was prepared according to the synthetic procedure of 24a, starting from compound 23 and 3-Fluoro-4-(4-methylpiperazin-1-yl)aniline.

Synthesis of 4-((3-aminophenyl)difluoromethyl)-N-(3-fluoro-4-(4-methylpiperazin-1-yl)phenyl)-7-((2-(trimethylsilyl)ethoxy)methyl)-7H-pyrrolo[2,3-d]pyrimidin-2-amine (25c)

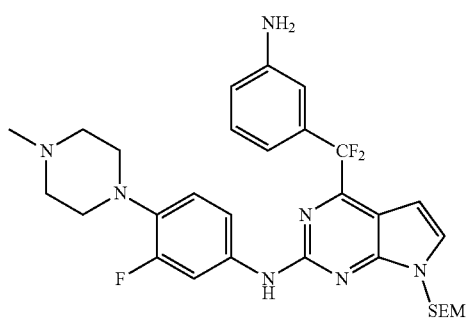

The title compound 25c (yield 78% from 24c, M+H$^+$= 598.3) was prepared according to the synthetic procedure of 25a, starting from 24b.

Synthesis of N-(3-(difluoro(2-(3-fluoro-4-(4-methylpiperazin-1-yl)phenylamino)-7-((2-(trimethylsilyl)ethoxy)methyl)-7H-pyrrolo[2,3d]pyrimidin-4-yl)methyl)phenyl)acrylamide (26c)

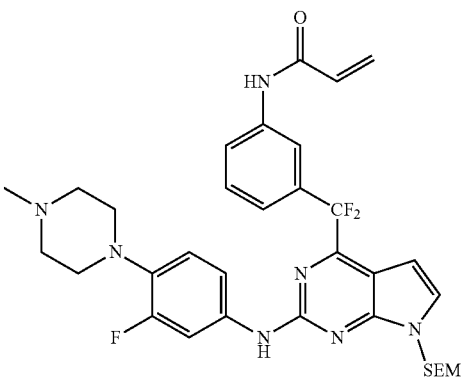

The title compound 26c (yield 76% from 25c, M+H$^+$= 652.3) was prepared according to the synthetic procedure of 26a, starting from 25c.

Synthesis of N-(3-(difluoro(2-(3-fluoro-4-(4-methylpiperazin-1-yl)phenylamino)-7-(hydroxymethyl)-7H-pyrrolo[2,3-d]pyrimidin-4-yl)methyl)phenyl)acrylamide (27c)

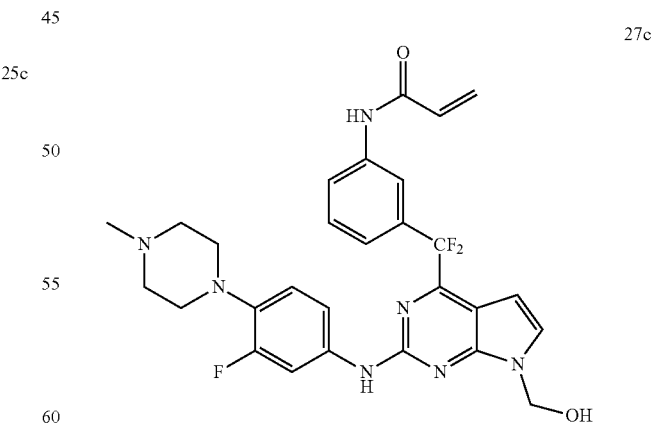

The title compound 27c (yield 78% from 26c, M+H$^+$= 552.2) was prepared according to the synthetic procedure of 27a, staring from 26c.

Synthesis of N-(3-(difluoro(2-(3-fluoro-4-(4-methylpiperazin-1-yl)phenylamino)-7H-pyrrolo[2,3-d]pyrimidin-4-yl)methyl)phenyl)acrylamide (28c)
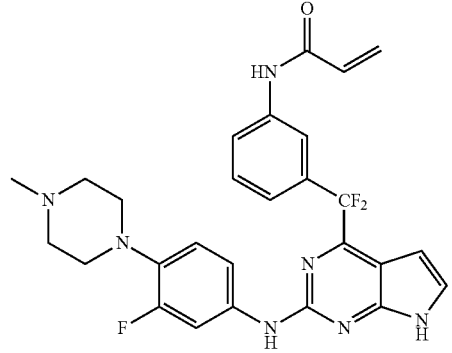
The title compound 28c (yield 65% from 27c, M+H$^+$= 521.2) was prepared according to the synthetic procedure of 28a, starting from 27c.
Example 6
N-(3-(difluoro(2-(2-methoxy-4-(4-methylpiperazin-1-yl)phenylamino)-7H-pyrrolo[2,3-d]pyrimidin-4-yl)methyl)phenyacrylamide (28d)
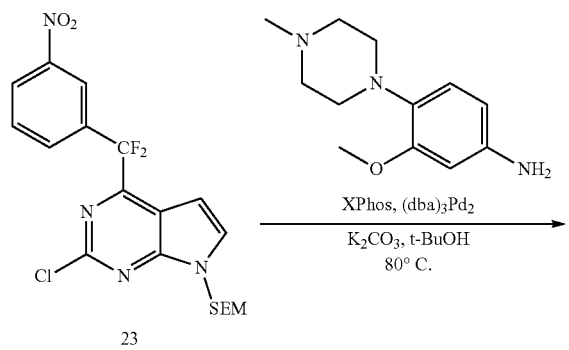
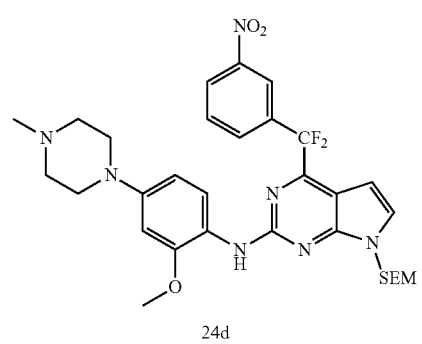
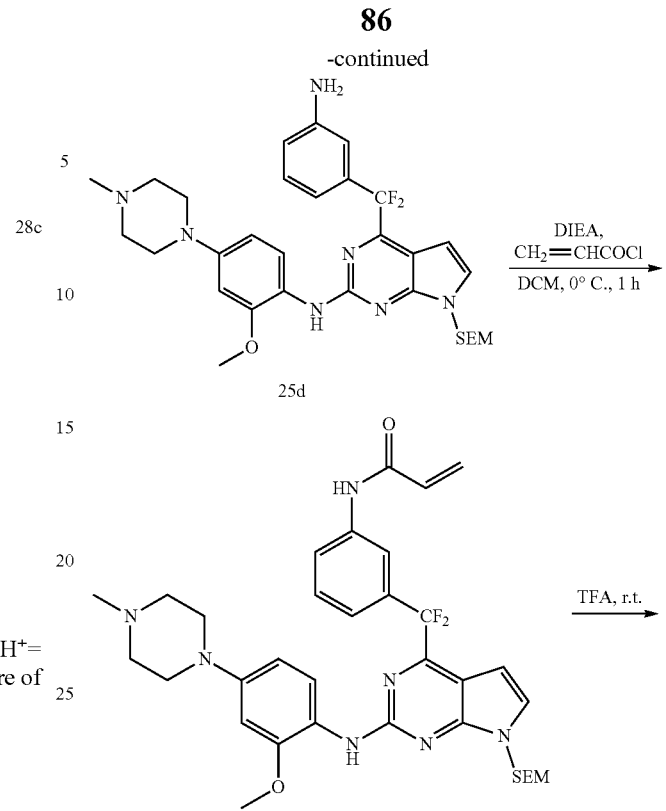
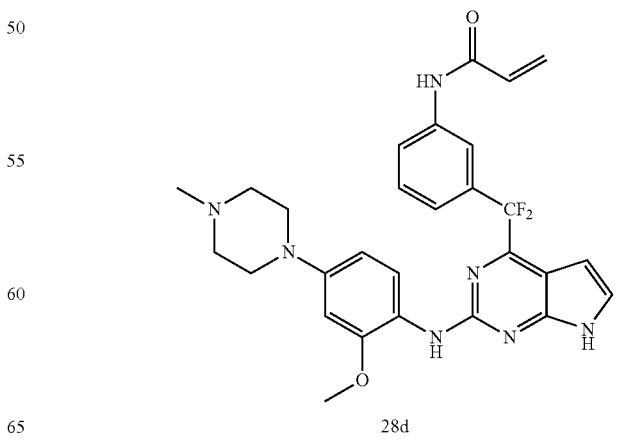

87

Synthesis of 4-(difluoro(3-nitrophenyl)methyl)-N-(2-methoxy-4-(4-methylpiperazin-1-yl)phenyl)-7-((2-(trimethylsilyl)ethoxy)methyl)-7H-pyrrolo[2,3-d]pyrimidin-2-amine (24d)

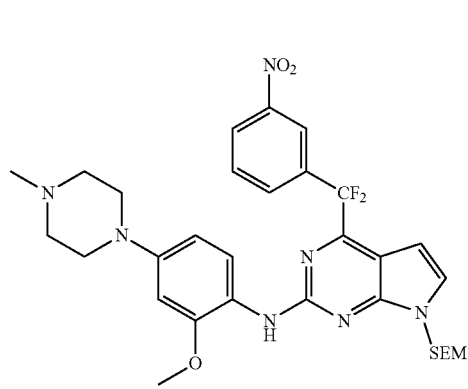

24d

The title compound 24d (yield 81% from 23, M+H$^+$= 640.3) was prepared according to the synthetic procedure of 24a, starting from compound 23 and 3-methoxy-4-(4-methylpiperazin-1-yl) aniline.

Synthesis of 4-((3-aminophenyl)difluoromethyl)-N-(2-methoxy-4-(4-methylpiperazin-1-yl)phenyl)-7-((2-(trimethylsilyl)ethoxy)methyl)-7H-pyrrolo[2,3-d]pyrimidin-2-amine (25d)

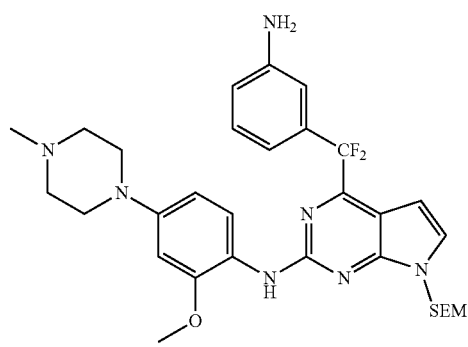

25d

This title compound 25d (yield 75% from 24d, M+H$^+$= 610.3) was prepared according to the synthetic procedure of 25a, starting from 24d.

88

Synthesis of N-(3-(difluoro(2-(2-methoxy-4-(4-methylpiperazin-1-yl)phenylamino)-7-((2-(trimethylsilyl)ethoxy)methyl)-7H-pyrrolo[2,3-d]pyrimidin-4-yl)methyl)phenyl)acrylamide (26d)

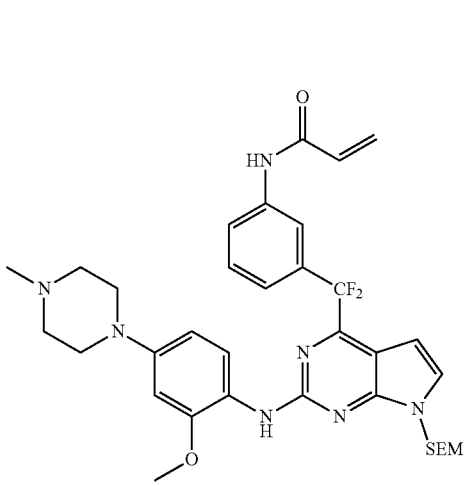

26d

The title compound 26d (yield 78% from 25d, M+H$^+$= 664.3) was prepared according to the synthetic procedure of 26a, starting from 25d.

Synthesis of N-(3-(difluoro(7-(hydroxymethyl)-2-(2-methoxy-4-(4-methylpiperazin-1-yl)phenylamino)-7H-pyrrolo[2,3-d]pyrimidin-4-yl)methyl)phenyl)acrylamide (27d)

27d

The title compound 27d (yield 78% from 26d, M+H$^+$= 564.2) was prepared according to the synthetic procedure of 27a, starting from 26d.

Synthesis of N-(3-(difluoro(2-(2-methoxy-4-(4-methylpiperazin-1-yl)phenylamino)-7H-pyrrolo[2,3-d]pyrimidin-4-yl)methyl)phenyl)acrylamide (28d)
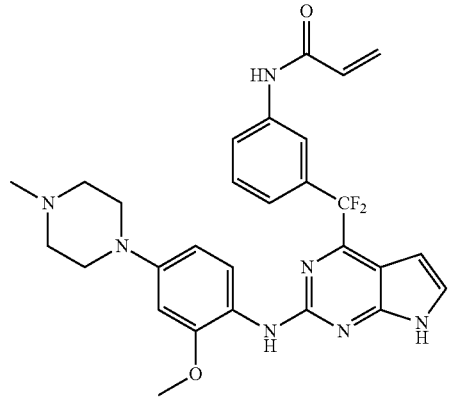
28d
The title compound 28d (yield 75% from 27d, M+H$^+$= 534.2) was prepared according to the synthetic procedure of 28a, starting from 27d.
The present disclosure provides compounds, as shown below.
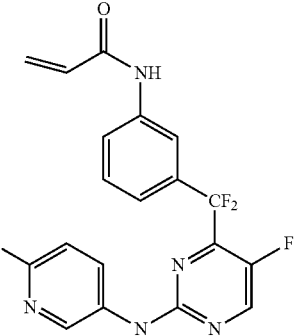
33
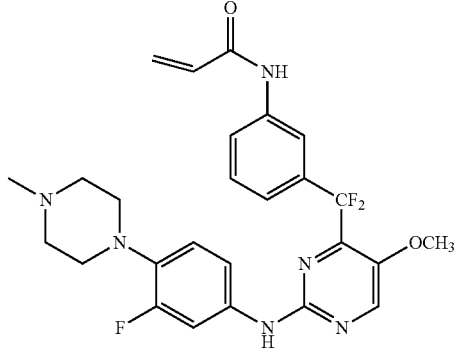
34
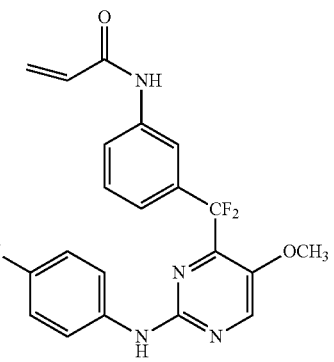
31
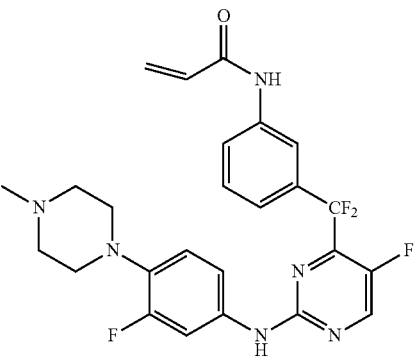
35
32
36

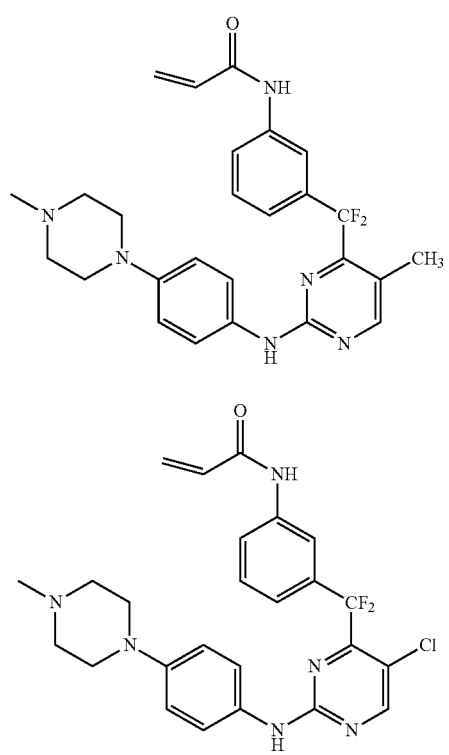
37
38
39
40
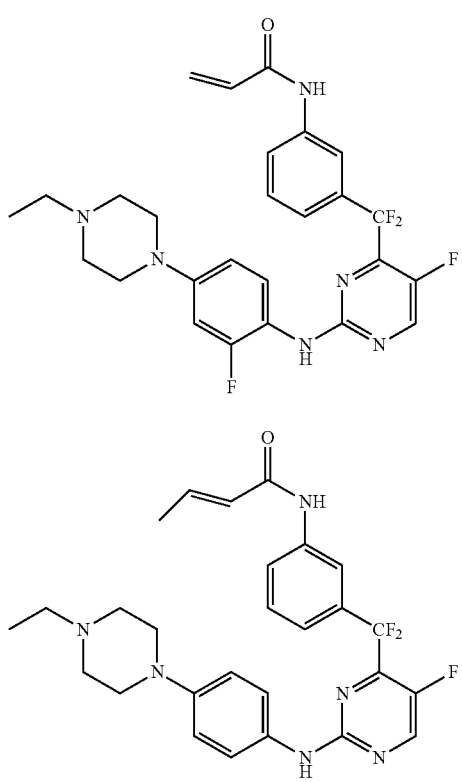
41
42
The present disclosure also provides compounds, as shown below.
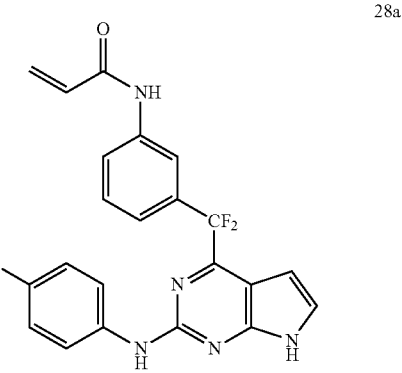
28a
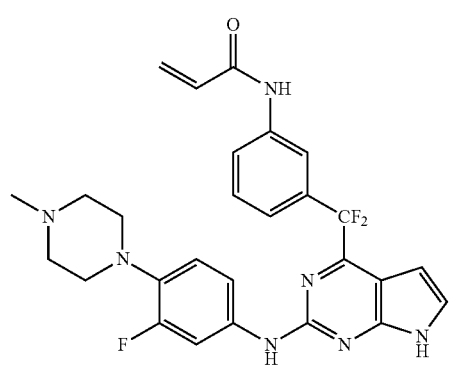
28c

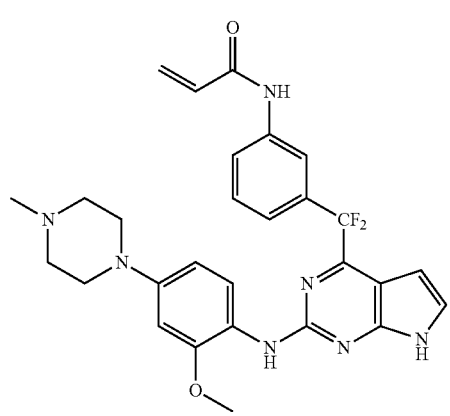
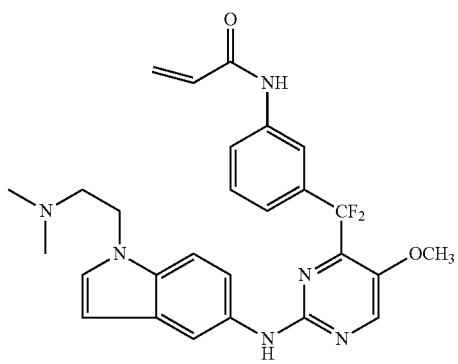
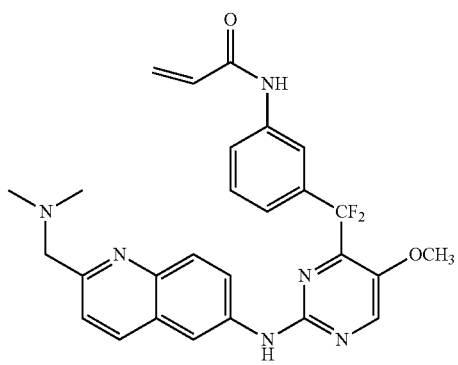
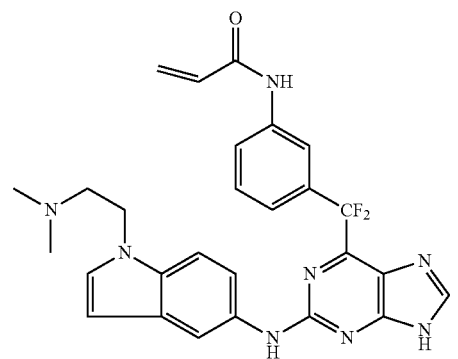
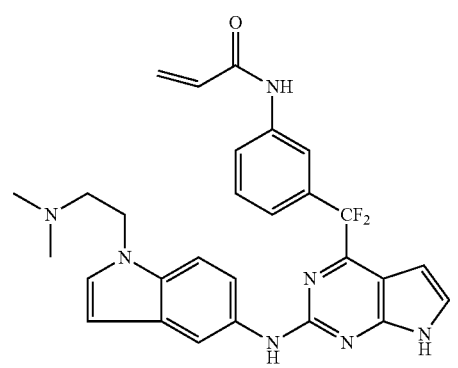
The present disclosure also provides compounds, as shown below.

48
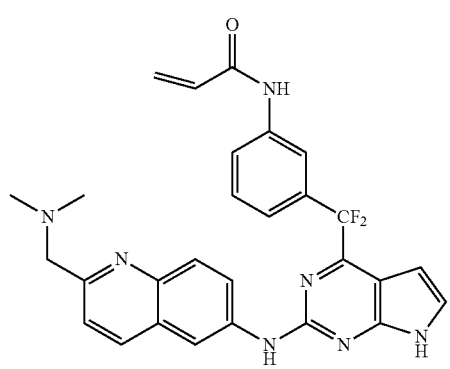
49
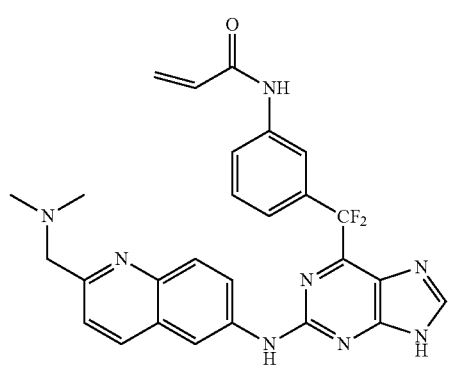
50
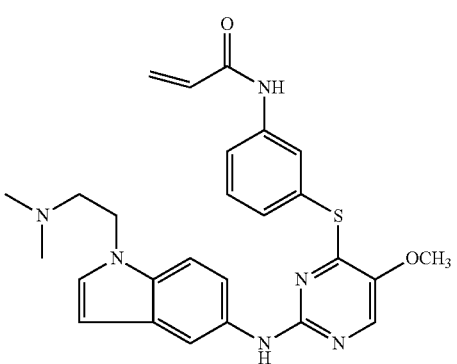
51
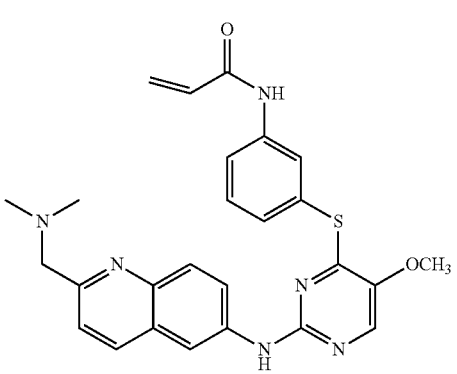
52
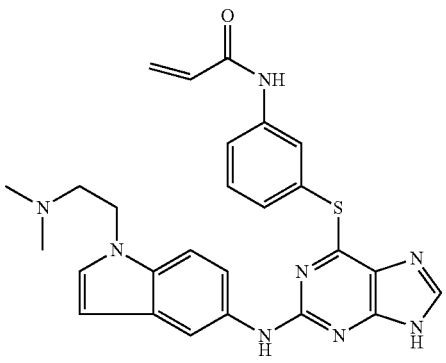
53
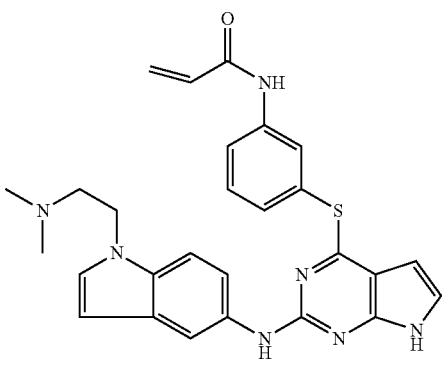
54
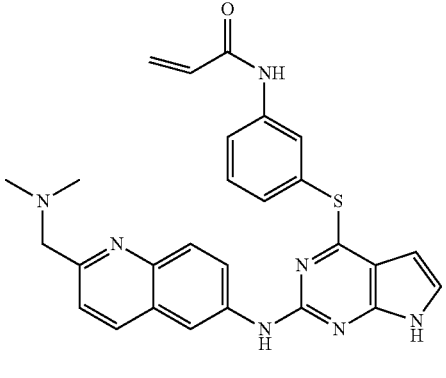
55
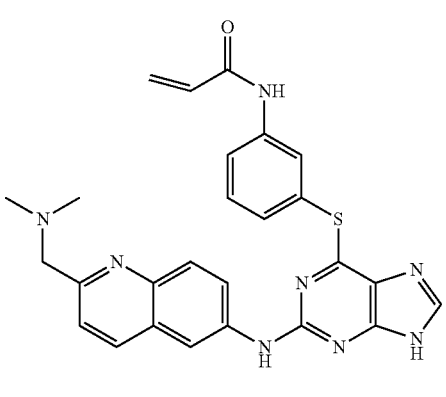
The present disclosure also provides compounds, as shown below.

56
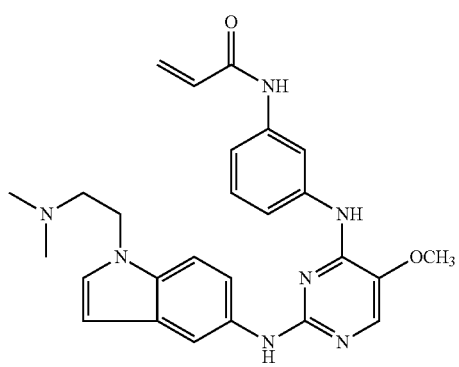
57
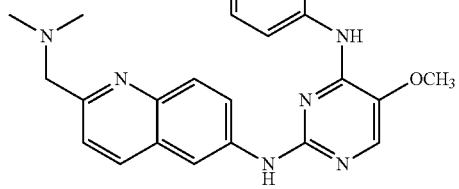
58
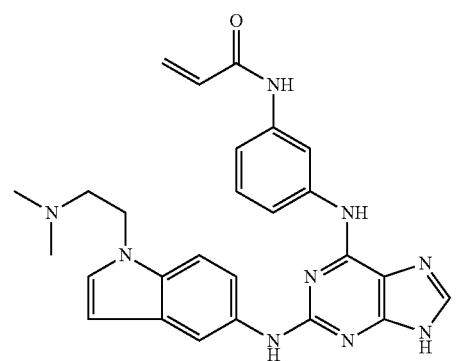
59
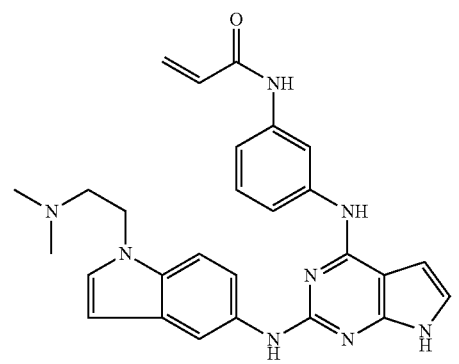
60
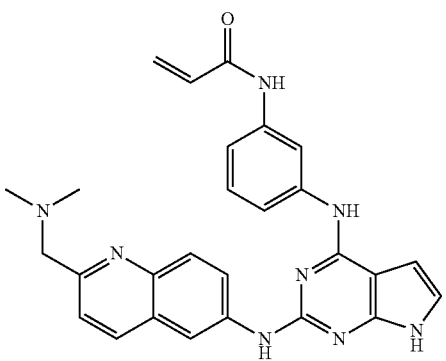
61
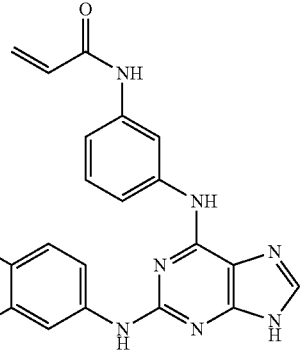
The present disclosure also provides compounds, as shown below.
62
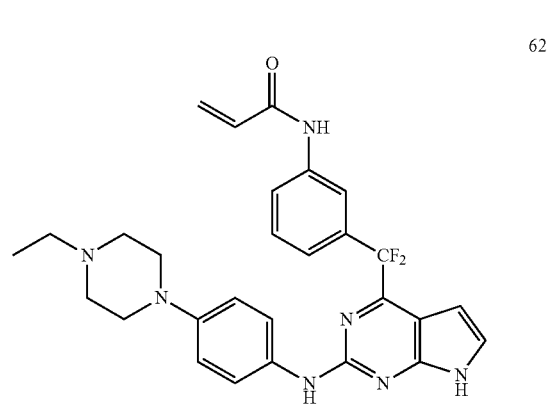

-continued

63

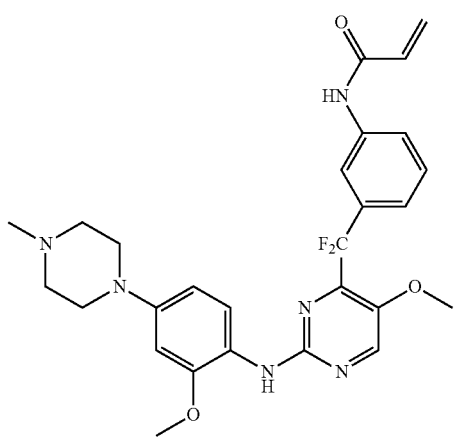

Formulations

Any suitable formulation of the compounds described herein can be prepared. See generally, Remington's Pharmaceutical Sciences, (2000) Hoover, J. E. editor, 20 th edition, Lippincott Williams and Wilkins Publishing Company, Easton, Pa., pages 780-857. A formulation is selected to be suitable for an appropriate route of administration. In cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts. Pharmaceutically acceptable salts are obtained using standard procedures well known in the art, for example, by a sufficiently basic compound such as an amine with a suitable acid, affording a physiologically acceptable anion. Alkali metal (e.g., sodium, potassium or lithium) or alkaline earth metal (e.g., calcium) salts of carboxylic acids also are made.

Where contemplated compounds are administered in a pharmacological composition, it is contemplated that the compounds can be formulated in admixture with a pharmaceutically acceptable excipient and/or carrier. For example, contemplated compounds can be administered orally as neutral compounds or as pharmaceutically acceptable salts, or intravenously in a physiological saline solution. Conventional buffers such as phosphates, bicarbonates or citrates can be used for this purpose. Of course, one of ordinary skill in the art may modify the formulations within the teachings of the specification to provide numerous formulations for a particular route of administration. In particular, contemplated compounds may be modified to render them more soluble in water or other vehicle, which for example, may be easily accomplished with minor modifications (salt formulation, esterification, etc.) that are well within the ordinary skill in the art. It is also well within the ordinary skill of the art to modify the route of administration and dosage regimen of a particular compound in order to manage the pharmacokinetics of the present compounds for maximum beneficial effect in a patient.

The compounds having formula I-II as described herein are generally soluble in organic solvents such as chloroform, dichloromethane, ethyl acetate, ethanol, methanol, isopropanol, acetonitrile, glycerol, N,N-dimethylformamide, N,N-dimetheylaceatmide, dimethylsulfoxide, etc. In one embodiment, the present invention provides formulations prepared by mixing a compound having formula I-II with a pharmaceutically acceptable carrier. In one aspect, the formulation may be prepared using a method comprising: a) dissolving a described compound in a water-soluble organic solvent, a non-ionic solvent, a water-soluble lipid, a cyclodextrin, a vitamin such as tocopherol, a fatty acid, a fatty acid ester, a phospholipid, or a combination thereof, to provide a solution; and b) adding saline or a buffer containing 1-10% carbohydrate solution. In one example, the carbohydrate comprises dextrose. The pharmaceutical compositions obtained using the present methods are stable and useful for animal and clinical applications.

Illustrative examples of water soluble organic solvents for use in the present methods include and are not limited to polyethylene glycol (PEG), alcohols, acetonitrile, N-methyl-2-pyrrolidone, N,N-dimethylformamide, N,N-dimethylacetamide, dimethyl sulfoxide, or a combination thereof. Examples of alcohols include but are not limited to methanol, ethanol, isopropanol, glycerol, or propylene glycol.

Illustrative examples of water soluble non-ionic surfactants for use in the present methods include and are not limited to CREMOPHOR® EL, polyethylene glycol modified CREMOPHOR® (polyoxyethyleneglyceroltriricinoleat 35), hydrogenated CREMOPHOR® RH40, hydrogenated CREMOPHOR® RH60, PEG-succinate, polysorbate 20, polysorbate 80, SOLUTOL® HS (polyethylene glycol 660 12-hydroxystearate), sorbitan monooleate, poloxamer, LABRAFIL® (ethoxylated persic oil), LABRASOL® (capryl-caproyl macrogol-8-glyceride), GELUCIRE® (glycerol ester), SOFTIGEN® (PEG 6 caprylic glyceride), glycerin, glycol-polysorbate, or a combination thereof.

Illustrative examples of water soluble lipids for use in the present methods include but are not limited to vegetable oils, triglycerides, plant oils, or a combination thereof. Examples of lipid oils include but are not limited to castor oil, polyoxyl castor oil, corn oil, olive oil, cottonseed oil, peanut oil, peppermint oil, safflower oil, sesame oil, soybean oil, hydrogenated vegetable oil, hydrogenated soybean oil, a triglyceride of coconut oil, palm seed oil, and hydrogenated forms thereof, or a combination thereof.

Illustrative examples of fatty acids and fatty acid esters for use in the present methods include but are not limited to oleic acid, monoglycerides, diglycerides, a mono- or di-fatty acid ester of PEG, or a combination thereof.

Illustrative examples of cyclodextrins for use in the present methods include but are not limited to alpha-cyclodextrin, beta-cyclodextrin, hydroxypropyl-beta-cyclodextrin, or sulfobutyl ether-beta-cyclodextrin.

Illustrative examples of phospholipids for use in the present methods include but are not limited to soy phosphatidylcholine, or distearoyl phosphatidylglycerol, and hydrogenated forms thereof, or a combination thereof.

One of ordinary skill in the art may modify the formulations within the teachings of the specification to provide numerous formulations for a particular route of administration. In particular, the compounds may be modified to render them more soluble in water or other vehicle. It is also well within the ordinary skill of the art to modify the route of administration and dosage regimen of a particular compound in order to manage the pharmacokinetics of the present compounds for maximum beneficial effect in a patient.

Drug Combinations

The methods of the embodiments comprise administering an effective amount of at least one compound of the embodiments; optionally the compound may be administered in combination with one or more additional therapeutic agents, particularly therapeutic agents known to be useful for treating a proliferative disorder or cancer afflicting the subject.

The additional active ingredients may be administered in a separate pharmaceutical composition from a compound of the embodiments or may be included with a compound of the embodiments in a single pharmaceutical composition. The additional active ingredients may be administered simultaneously with, prior to, or after administration of a compound of the embodiments.

Methods of Using the Invented Compounds and Pharmaceutical Compositions Thereof

The present invention also provides pharmaceutical compositions for the treatment of a cell proliferative disorder, comprising any compound having formula I-XI, To practice the method of the present invention, compounds having formula and pharmaceutical compositions thereof may be administered orally, parenterally, by inhalation, topically, rectally, nasally, buccally, vaginally, via an implanted reservoir, or other drug administration methods. The term "parenteral" as used herein includes subcutaneous, intracutaneous, intravenous, intramuscular, intraarticular, intraarterial, intrasynovial, intrastemal, intrathecal, intralesional and intracranial injection or infusion techniques.

A sterile injectable composition, such as a sterile injectable aqueous or oleaginous suspension, may be formulated according to techniques known in the art using suitable dispersing or wetting agents and suspending agents. The sterile injectable preparation may also be a sterile injectable solution or suspension in a non-toxic parenterally acceptable diluent or solvent. Among the acceptable vehicles and solvents that may be employed include mannitol, water, Ringer's solution and isotonic sodium chloride solution. Suitable carriers and other pharmaceutical composition components are typically sterile.

In addition, sterile, fixed oils are conventionally employed as a solvent or suspending medium (e.g., synthetic mono- or diglycerides). Fatty acids, such as oleic acid and its glyceride derivatives, are useful in the preparation of injectables, as are pharmaceutically acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Various emulsifying agents or bioavailability enhancers which are commonly used in the manufacture of pharmaceutically acceptable solid, liquid, or other dosage forms can also be used for the purpose of formulation.

A composition for oral administration may be any orally acceptable dosage form including, but not limited to, tablets, capsules, emulsions and aqueous suspensions, dispersions and solutions. In the case of tablets for oral use, commonly used carriers include lactose and corn starch. Lubricating agents, such as magnesium stearate, can also be added. For oral administration in a capsule form, useful diluents include lactose and dried corn starch. When aqueous suspensions or emulsions are administered orally, the active ingredient can be suspended or dissolved in an oily phase combined with emulsifying or suspending agents. If needed, certain sweetening, flavoring, or coloring agents can be added. A nasal aerosol or inhalation compositions can be prepared according to techniques well-known in the art of pharmaceutical formulation and can be prepared as solutions in, for example saline, employing suitable preservatives (for example, benzyl alcohol), absorption promoters to enhance bioavailability, and/or other solubilizing or dispersing agents known in the art.

In addition, the compounds having formula I-XI may be administered alone or in combination with other anticancer agents for the treatment of various cancers or conditions. Combination therapies according to the present invention comprise the administration of at least one compound of the present invention or a functional derivative thereof and at least one other pharmaceutically active ingredient. The active ingredient(s) and pharmaceutically active agents may be administered separately or together. The amounts of the active ingredient(s) and pharmaceutically active agent(s) and the relative timings of administration will be selected in order to achieve the desired combined therapeutic effect.

Biological Screening and Anticancer Activity:

Some assays and examples demonstrating the anti-cancer effects of the compounds of the invention are described as below.

In Vitro Cell-based Screening Using Real-time Cell Electronic Sensing (RT-CES) System The heterocyclic compounds in the present invention are developed for the anticancer activities for cancer cells with certain molecular targets, i.e., EGFR (epidermal growth factor receptor). The anticancer efficacy of these heterocyclic compounds and their analogues described above may be preliminarily screened in vitro using a penal of EGFR cancer cell lines by real time electronic cell sensing (RT-CES) system from ACEA Biosciences, Inc. (or xCELLigence system from Roche Applied Sciences/ACEA Biosciences Inc.), which provides dynamic cell response information after exposing to an anticancer agent.

The details of this cell electronic sensing technology, called real-time cell electronic sensing (RT-CES®) and associated devices, systems and methods of use are described in U.S. Pat. Nos. 7,732,127; 7,192,752; 7,459,303; 7,468,255; 7,470,533; 7,560,269; U.S. provisional application No. 60/397,749, filed on Jul. 20, 2002; U.S. provisional application No. 60/435,400, filed on Dec. 20, 2002; U.S. Provisional application 60/469,572, filed on May 9, 2003, PCT application number PCT/US03/22557, filed on Jul. 18, 2003; PCT application number PCT/US03/22537, filed on Jul. 18, 2003; PCT application number PCT/US04/37696, filed on Nov. 12, 2004; PCT application number PCT/US05/04481, filed on Feb. 9, 2005; U.S. patent application Ser. No. 10/705,447, filed on Nov. 10, 2003; U.S. patent application Ser. No. 10/705,615, filed on Nov. 10, 2003; U.S. patent application Ser. No. 10/987,732, filed on Nov. 12, 2004; U.S. patent application Ser. No. 11/055,639, filed on Feb. 9, 2005, each of which is incorporated by reference. Additional details of RT-CES technology is further disclosed in U.S. provisional application No. 60/519,567, filed on Nov. 12, 2003, and U.S. provisional application No. 60/542,927, filed on Feb. 9, 2004, U.S. provisional application No. 60/548,713, filed on Feb. 27, 2004, U.S. provisional application No. 60/598,608, filed on Aug. 4, 2004; U.S. provisional application No. 60/598,609, filed on Aug. 4, 2004; U.S. provisional application No. 60/613,749, filed on Sep. 27, 2004; U.S. provisional application No. 60/613,872, filed on Sep. 27, 2004; U.S. provisional application No. 60/614,601, filed on Sep. 29, 2004; U.S. provisional application No. 60/630,071, filed on Nov. 22, 2004; U.S. provisional application No. 60/630,131, filed on Nov. 22, 2004, each of which is incorporated herein by reference.

For measurement of cell-substrate or cell-electrode impedance using RT-CES technology, microelectrodes having appropriate geometries are fabricated onto the bottom surfaces of microtiter plate or similar device, facing into the wells. Cells are introduced into the wells of the devices, and make contact to and attach to the electrode surfaces. The presence, absence or change of properties of cells affects the electronic and ionic passage on the electrode sensor surfaces. Measuring the impedance between or among electrodes provides important information about biological status of cells present on the sensors. When there are changes to the biological status of the cells analogue, electronic readout signals are measured automatically and in real time, and are converted to digital signals for processing and analysis.

In a RT-CES system, a cell index is automatically derived and provided based on measured electrode impedance values. The cell index obtained for a given well reflects: 1) how many cells are attached to the electrode surfaces in this well; 2) how well cells are attached to the electrode surfaces in this well. Thus, the more the cells of same type in similar physiological conditions attach the electrode surfaces, the larger the cell index. And, the better the cells attach to the electrode surfaces (e.g., the cells spread-out more to have larger contact areas, or the cells attach tighter to electrode surfaces), the larger the cell index. We have found that the cMet-addictive cell lines would produce a transient impedance response profile when treated with positive-control EGFR (epidermal growth factor receptor) inhibitors.

Through the use of the RT-CES system, the heterocyclic compounds described in the examples above have been shown to produce a similar cell response impedance profile on RT-CES system to that generated by positive control inhibitors. In addition, these compounds have been shown to inhibit EGFR (epidermal growth factor receptor)-induced cell migration in several cell lines. In addition, these compounds have shown no or negligible effects when they were used to treat non-cMet addictive cancer cell lines.

The RT-CES system (or xCELLigence RTCA system) comprises three components, an electronic sensor analyzer, a device station and 16× or 96× microtiter plate devices (i.e. E-Plate 16 or E-Plate 96). Microelectrode sensor array was fabricated on glass slides with lithographical microfabrication methods and the electrode-containing slides are assembled to plastic trays to form electrode-containing wells. Each 16× (or 96×) microtiter plate device used in RT-CES system comprises up to 16 (or 96) such electrode-containing wells. The device station receives the 16× or 96× microtiter plate devices and is capable of electronically switching any one of the wells to the sensor analyzer for impedance measurement. In operation, the devices with cells cultured in the wells are placed into a device station (xCELLigence RTCA SP station or RT-CES SP station) that is located inside an incubator. Electrical cables connect the device station to the sensor analyzer (xCELLigence RTCA analyzer or RT-CES analyzer). Under the RT-CES or xCELLigence RTCA software control, the sensor analyzer can automatically select wells to be measured and continuously conduct impedance measurements. The impedance data from the analyzer is transferred to a computer, analyzed and processed by the integrated software.

Impedance measured between electrodes in an individual well depends on electrode geometry, ionic concentration in the well and whether there are cells attached to the electrodes. In the absence of the cells, electrode impedance is mainly determined by the ion environment both at the electrode/solution interface and in the bulk solution. In the presence of the cells, cells attached to the electrode sensor surfaces will alter the local ionic environment at the electrode/solution interface, leading to an increase in the impedance. The more cells there are on the electrodes, the larger the increase in cell-electrode impedance. Furthermore, the impedance change also depends on cell morphology and the extent to which cells attach to the electrodes.

To quantify cell status based on the measured cell-electrode impedance, a parameter termed Cell Index is derived, according to $$CI = \max_{i=1,\ldots,N}\left(\frac{R_{cell}(f_i)}{R_b(f_i)} - 1\right)$$

where $R_b(f)$ and $R_{cell}(f)$ are the frequency dependent electrode resistances (a component of impedance) without cells or with cell present, respectively. N is the number of the frequency points at which the impedance is measured. Thus, Cell Index is a quantitative measure of the status of the cells in an electrode-containing well. Under the same physiological conditions, more cells attached on to the electrodes leads to larger $R_{cell}(f)$ value, leading to a larger value for Cell Index. Furthermore, for the same number of cells present in the well, a change in the cell status such as morphology will lead to a change in the Cell Index. For example, an increase in cell adhesion or cell spreading leads to larger cell-electrode contact area which will lead to an increase in $R_{cell}(f)$ and thus a larger value for Cell Index. The Cell Index may also be calculated using a formula different from the one described here. Other methods for calculating the Cell Index based on impedance measurement can be found in U.S. Pat. Nos. 7,732,127; 7,192,752; 7,459,303; 7,468,255; 7,470,533; 7,560,269; PCT application number PCT/US04/37696, fined on Nov. 12, 2004, PCT application number PCT/US05/04481, filed on Feb. 9, 2005, U.S. patent application Ser. No. 10/987,732, filed on Nov. 12, 2004, and U.S. patent application Ser. No. 11/055,639, filed on Feb. 9, 2005.

Control Compounds for Testing

The following compounds can be used as comparison compounds for testing the compounds in the present disclosure.

WZ4002 is an irreversible inhibitor against EGFR T790M. (Nature 2009 Dec. 24; 462(7276): 1070-1074) The structure of WZ4002 is shown below:

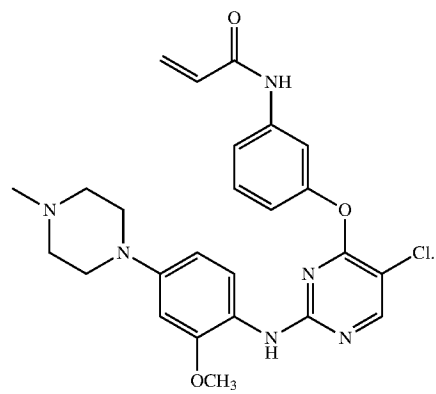 [SMILES: C=CC(=O)Nc1cccc(Oc2nc(Nc3ccc(N4CCN(C)CC4)cc3OC)ncc2Cl)c1]

BIBW2992 (Afatinib) is an irreversible EGFR/HER2 inhibitor. (Oncogene 2008; 27:4702-4711) The structure of BIBW2992 is shown below:

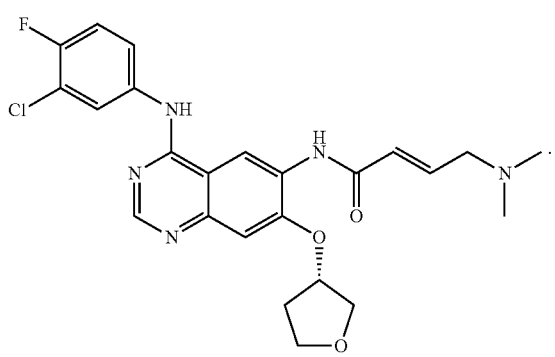 [SMILES: CN(C)C/C=C/C(=O)Nc1cc2c(Nc3ccc(F)c(Cl)c3)ncnc2cc1O[C@H]1CCOC1]

Erlotinib is a reversible tyrosine kinase inhibitor which acts on EGFR. (Drugs 2000, 60 Suppl 1: 15-23; discussion 41-2.) The structure of erlotinib is shown below:

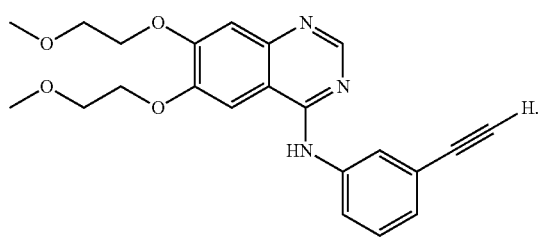

Bioactivity of Heterocyclic Compounds on EGFR Mutated Cell Lines as Determined using Real-time Cell Electronic Sensing (RT-CES) System Material and Methods Cell Culture and Reagents All cell lines were obtained from the American Type Culture Collection and were maintained at 37° C. with 5% CO2, in media supplemented with 10% fetal bovine serum and 1% L-glutamine-penicillin-streptomycin. H1975, HCC827 and A549 cells were cultured with RPMI 1640 media. A431 and Hela cells were maintained in Dulbecco's Modification of Eagle's Medium. EGF (R&D), EGF inhibitors were resuspended and stored according to the manufacturers' instructions.

EGF Stimulation Assay

Impedance measurements were taken using the xCelligence RTCA system (Roche Applied Science) instrument using the E-plates 96-well device from the same company. Cells were trypsinized and seeded on a 96-well E-plate at a density of 15000 cells per well in a volume of 0.1 ml. Cells were allowed to attach and proliferate overnight. Prior to compound treatment, H1975 cells were serum starved in RPMI-1640 for a total of 4 h. Following serum starvation, the cells were pretreated with compounds or vehicle for 40 min and then stimulated with EGF at 30 ng/mL. Throughout the experimental process, the cells were continually monitored, and the changes in impedance were acquired with the xCelligence RTCA system. After EGF treatment, data acquisition was done every minute for up to 2 h. For each cell type the optimal cell concentration was chosen based on their respective proliferation pattern.

Cytotoxicity Assays

Cells were seeded in 96-well E-Plate devices, and attachment, spreading, and proliferation were monitored using the xCelligence RTCA system. After 20 h of RTCA profiling, the cells were treated with the indicated compounds prediluted in growth media to a final maximal DMSO concentration of 0.1%, and the responses were measured at 30-min intervals for 3 days. For each cell type the optimal cell concentration was chosen based on their respective proliferation pattern.

Results

Figure 2:
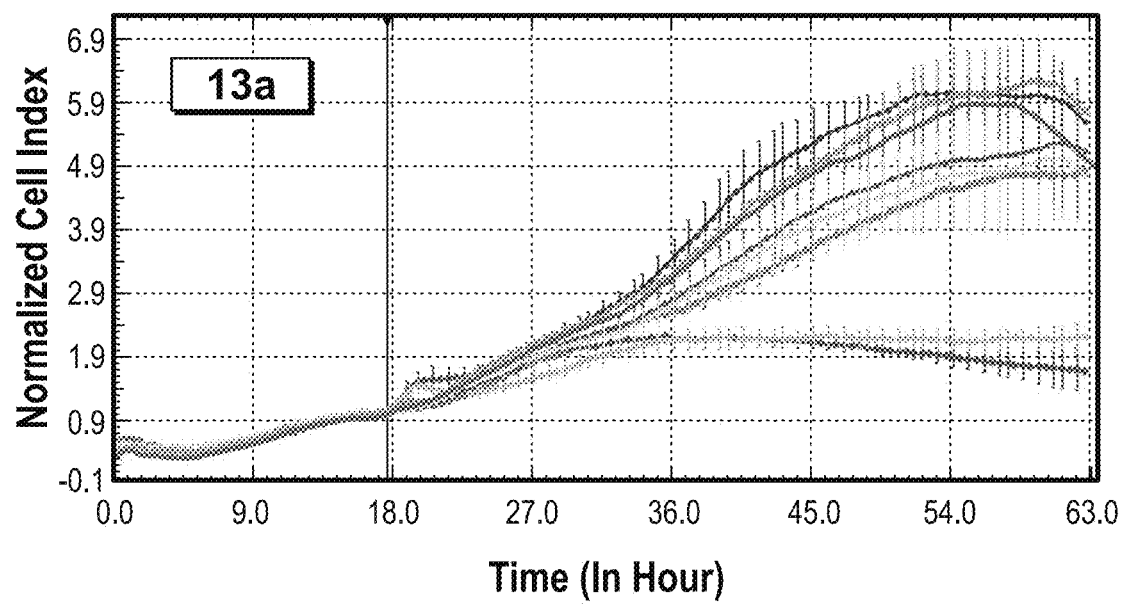
FIG. 2 shows detailed assay plots of HeLa cell viability assay for Compounds 13a, 13b, 19 and WZ4002.
Figure 2:
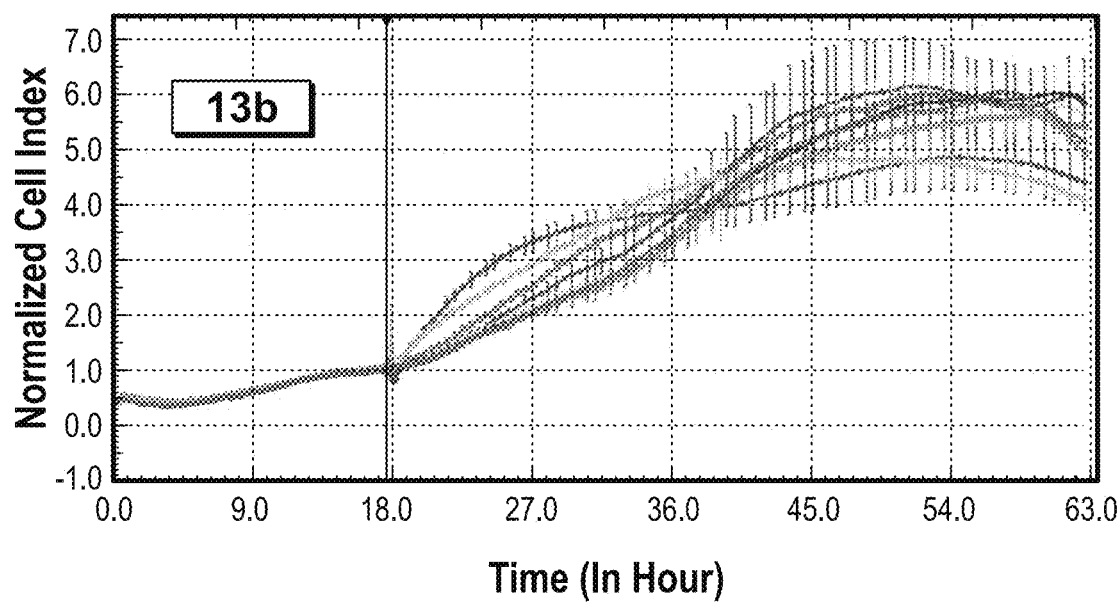
Figure 2:
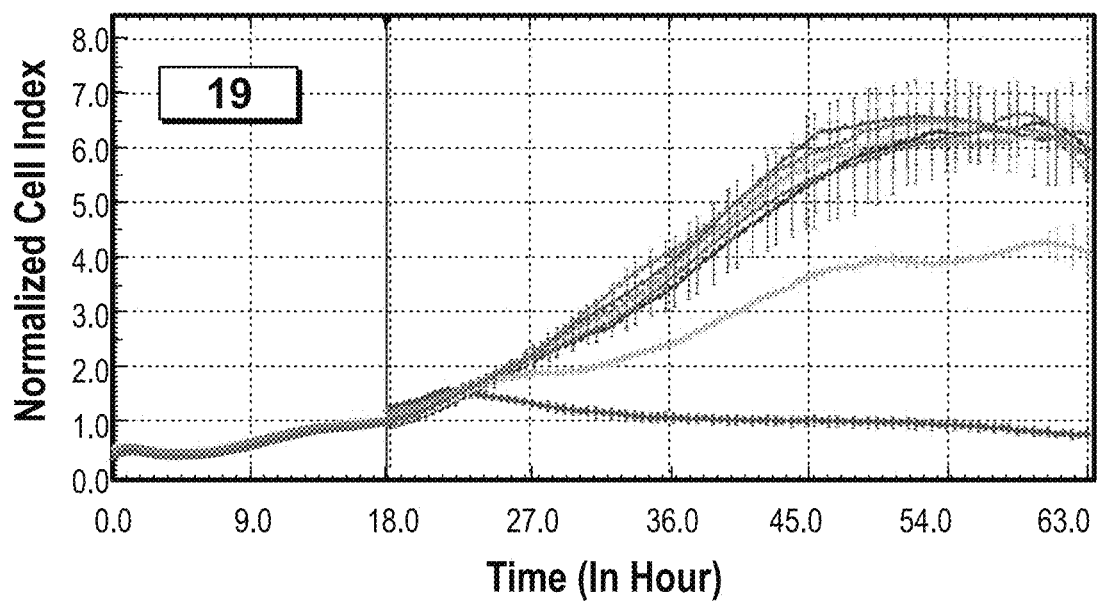
Figure 2:
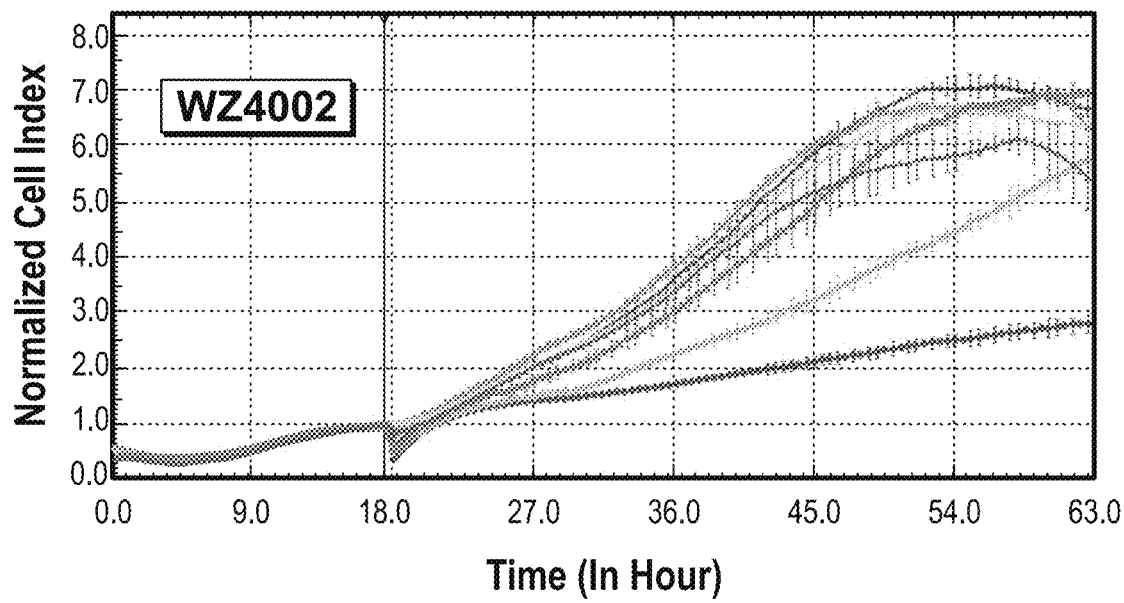
Figure 3:
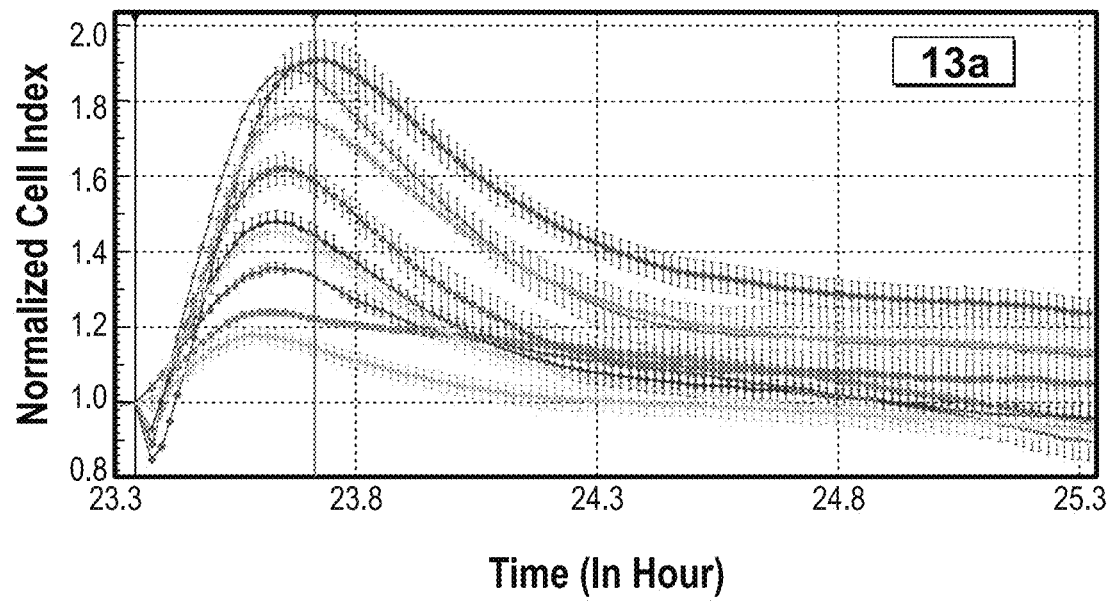
FIG. 3 shows detailed assay plots of H1975 EGF stimulation assay for Compounds 13a, 13b, 19 and WZ4002.
Figure 3:
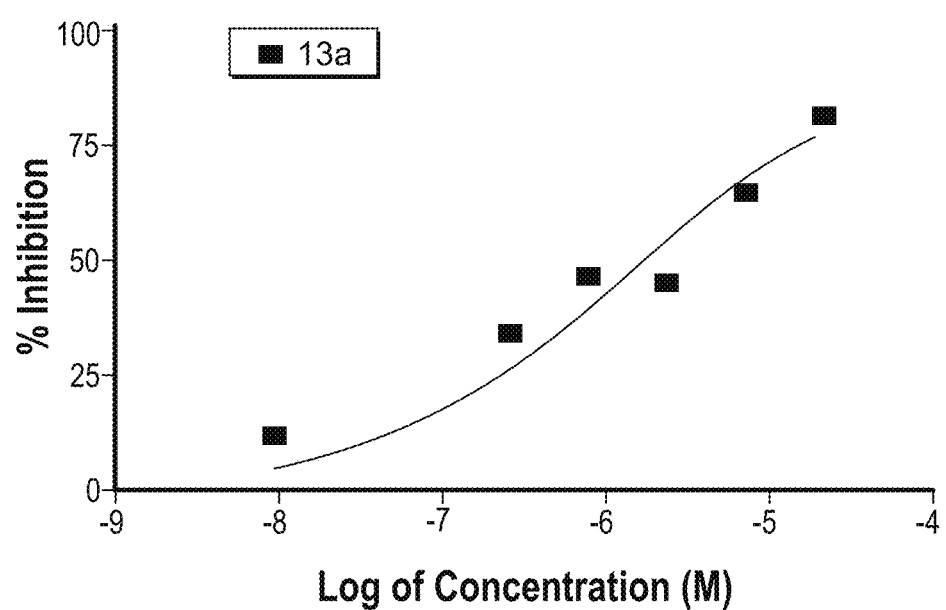
Figure 3:
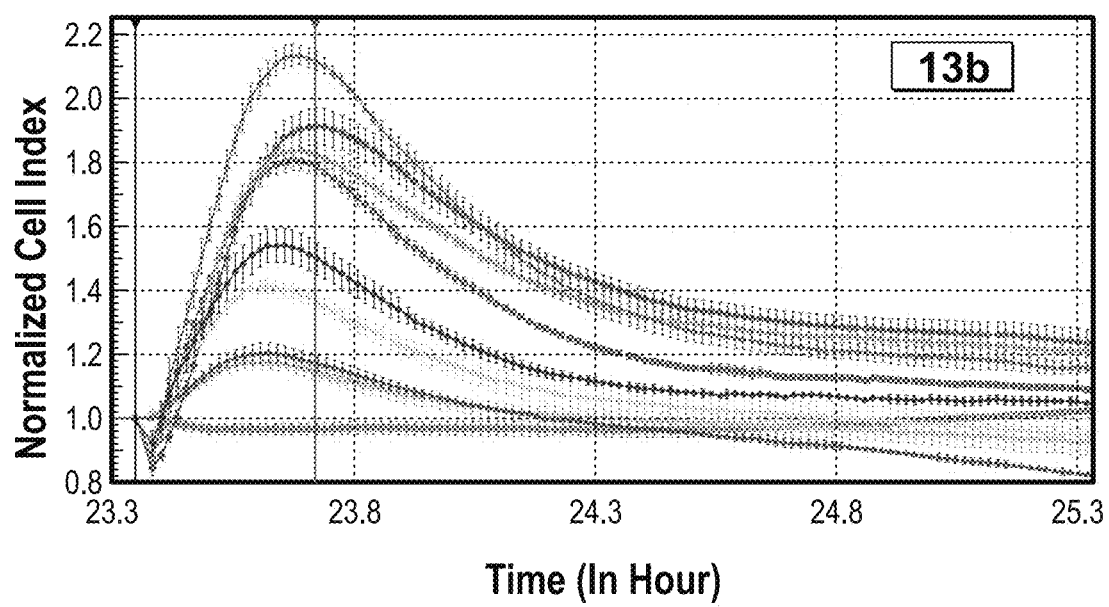
Figure 3:
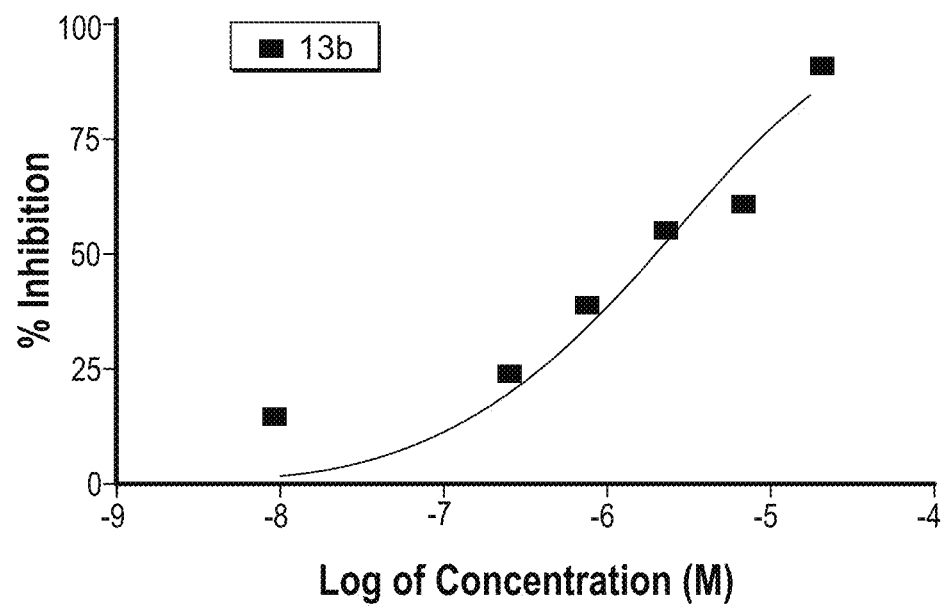
Figure 3:
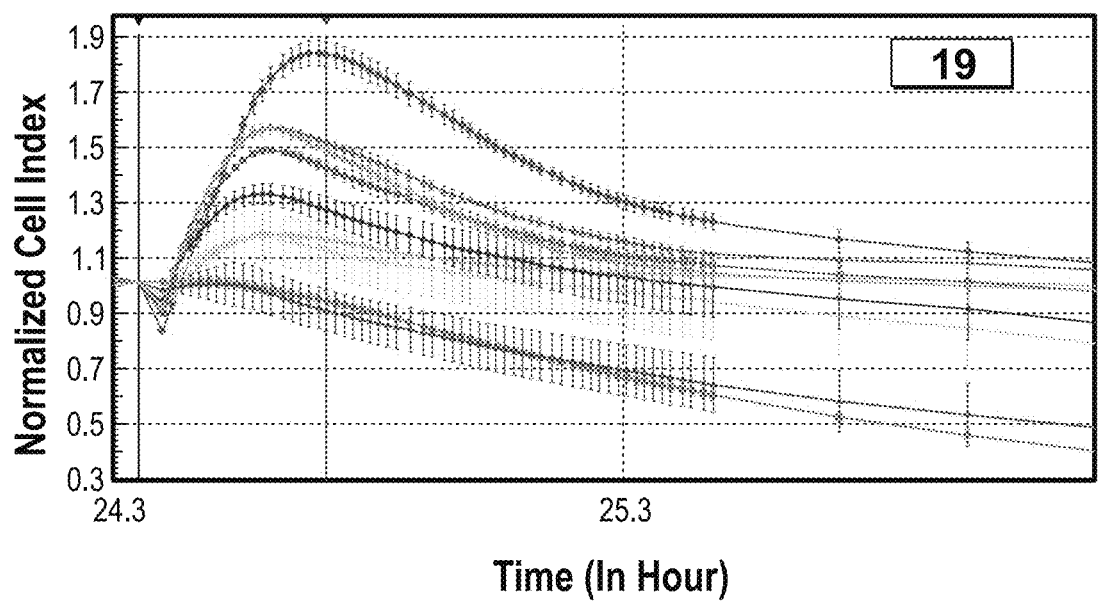
Figure 3:
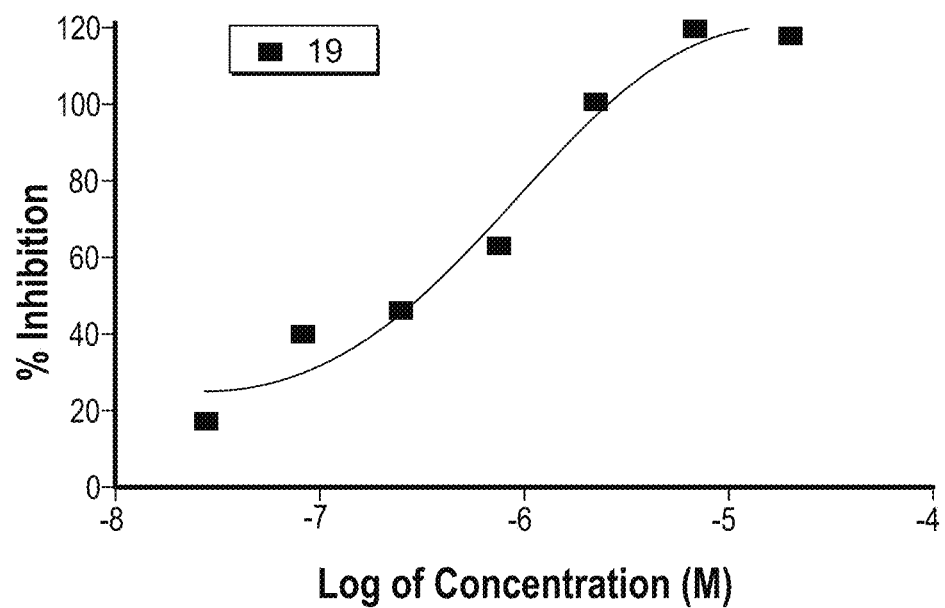
Figure 3:
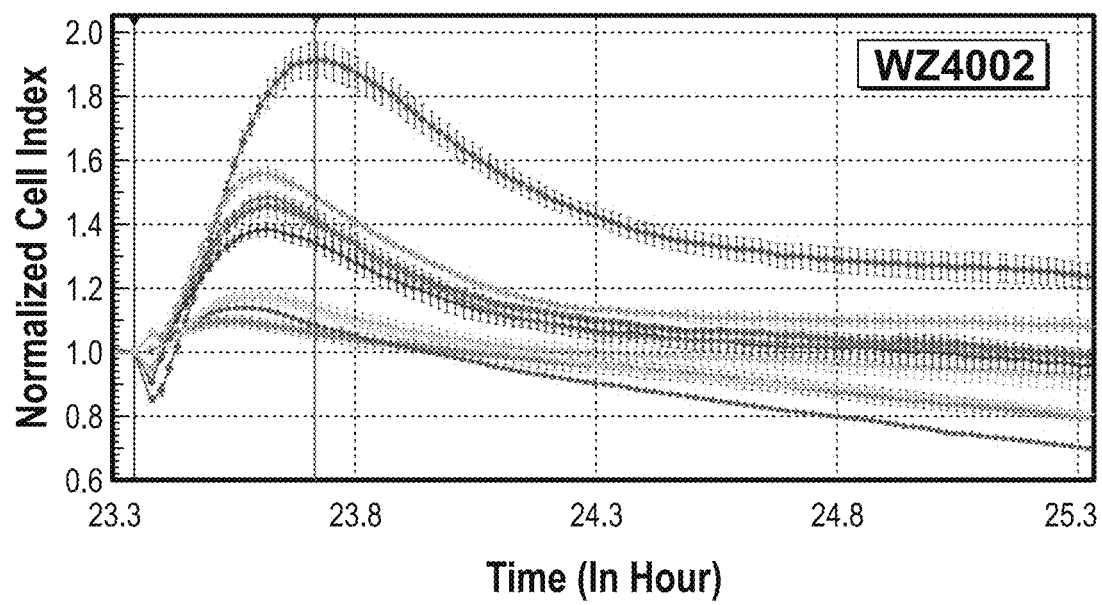
Figure 3:
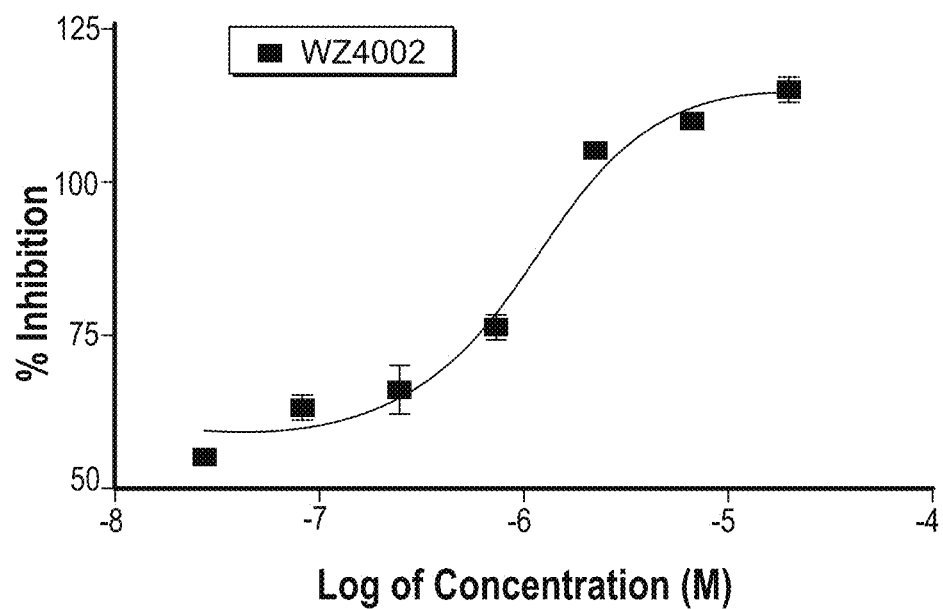
Figure 4:
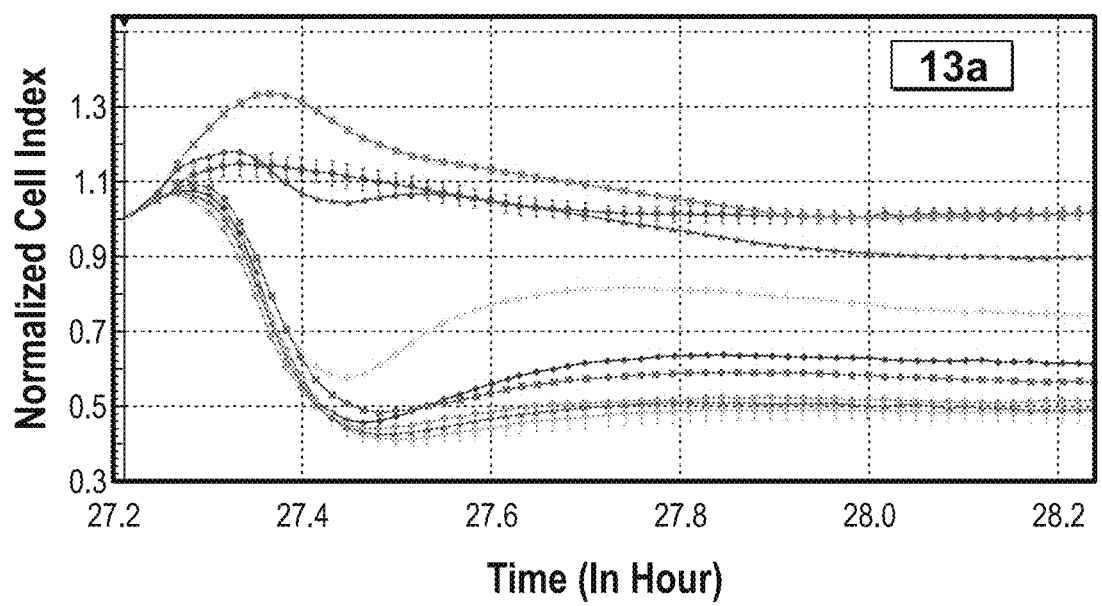
FIG. 4 shows detailed assay plots of A431 EGF stimulation assay for Compounds 13a, 13b, 19 and WZ4002.
Figure 4:
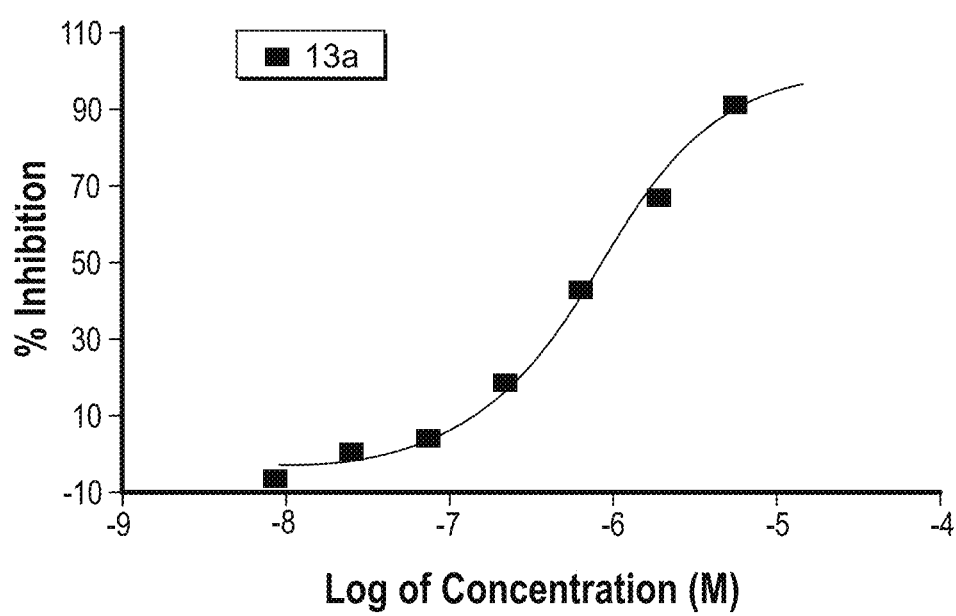
Figure 4:
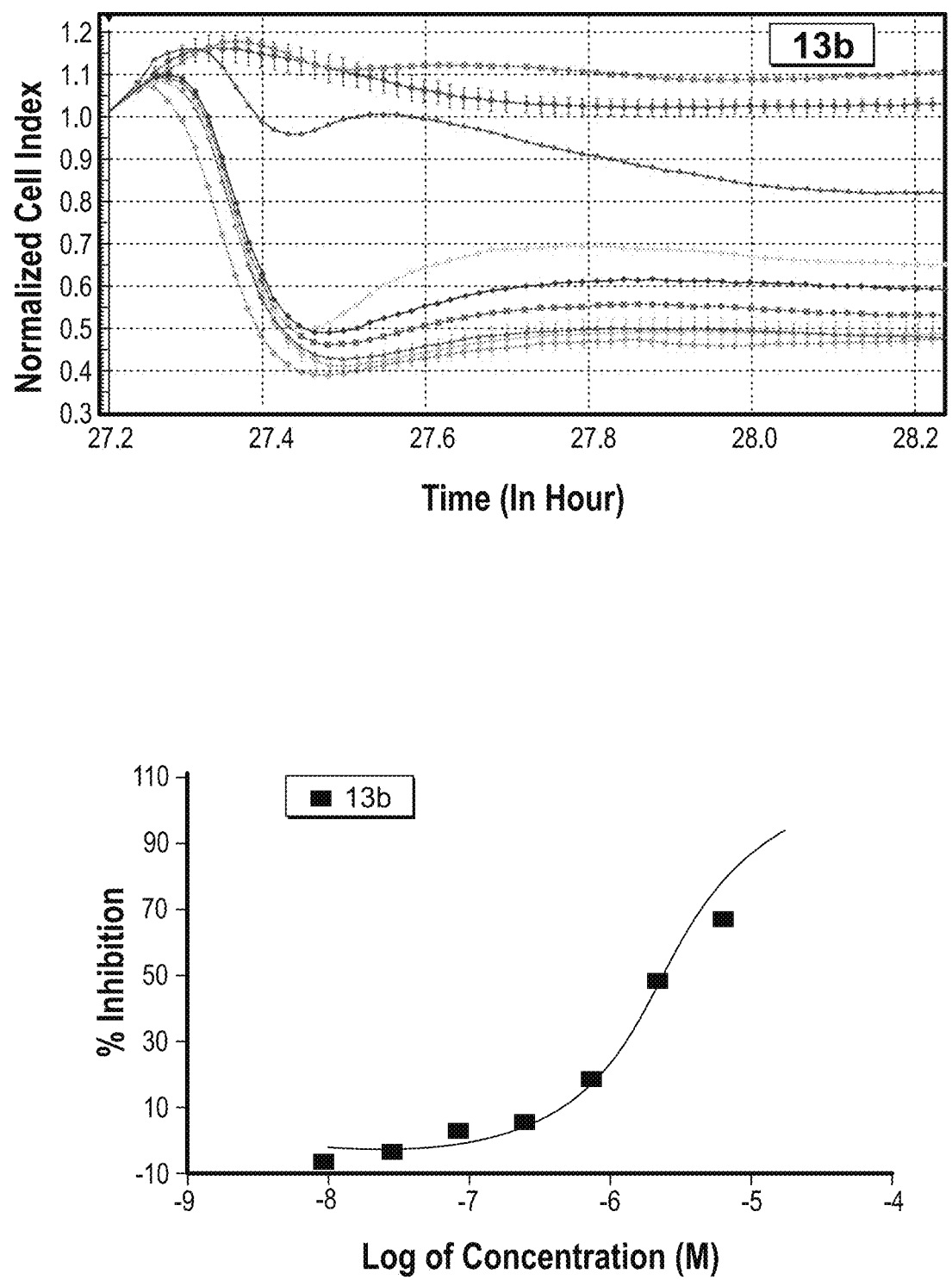
Figure 4:
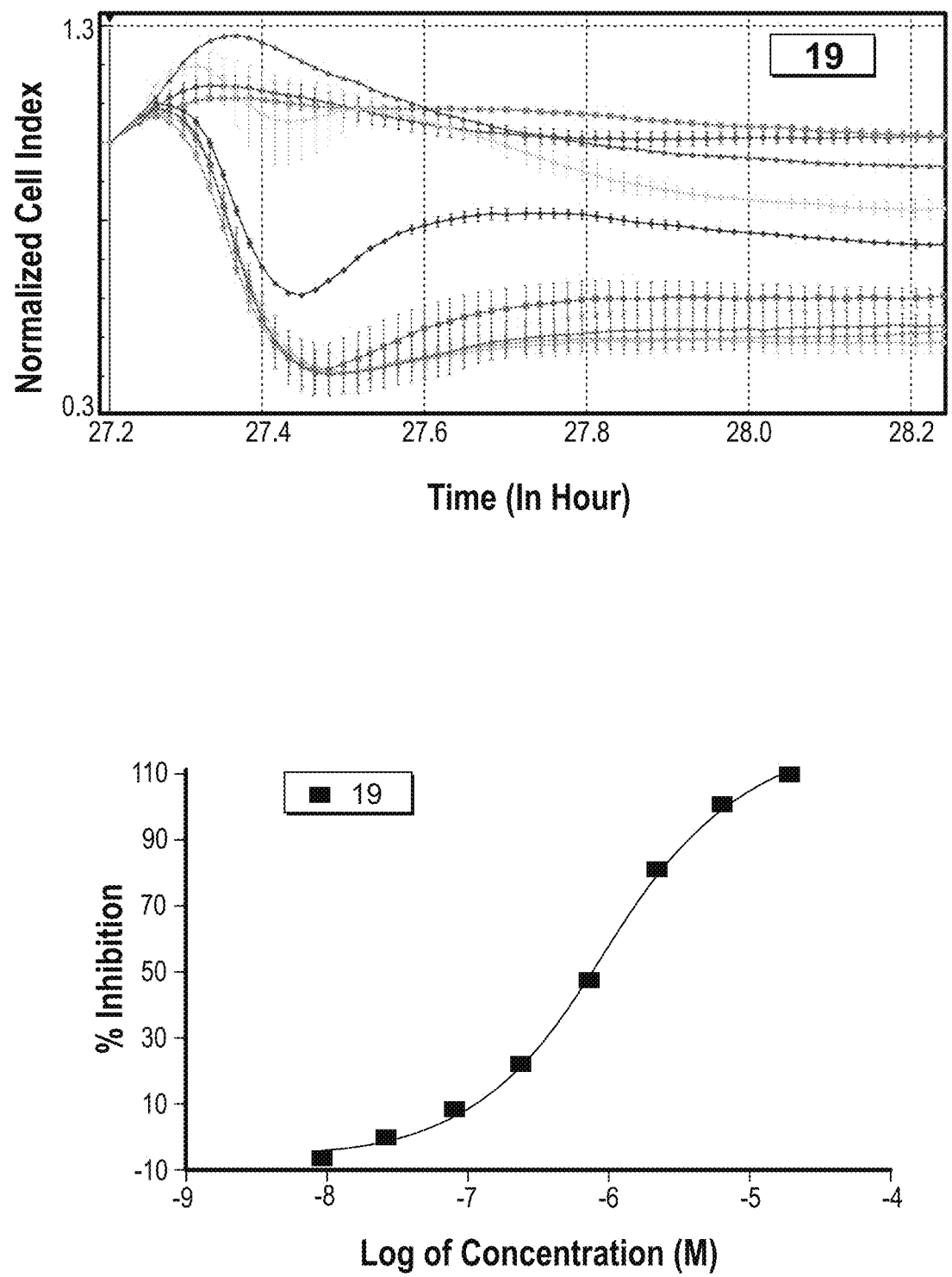
Figure 4:
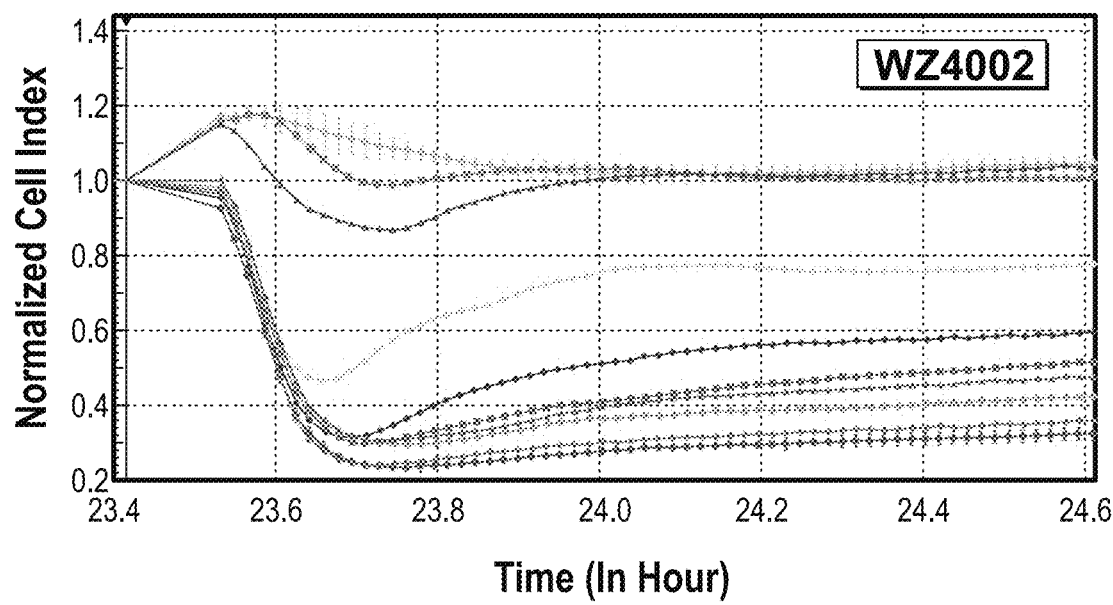
Figure 4:
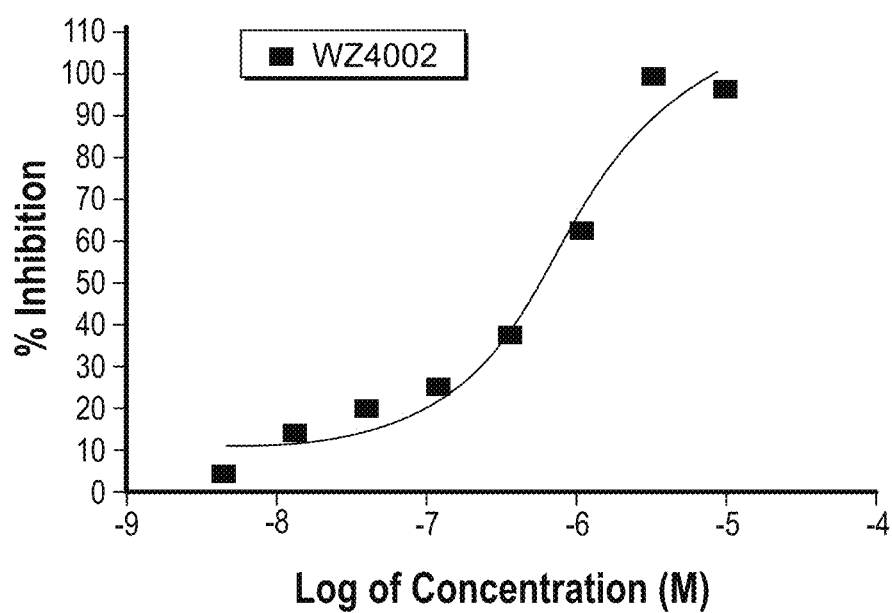
Figure 5:
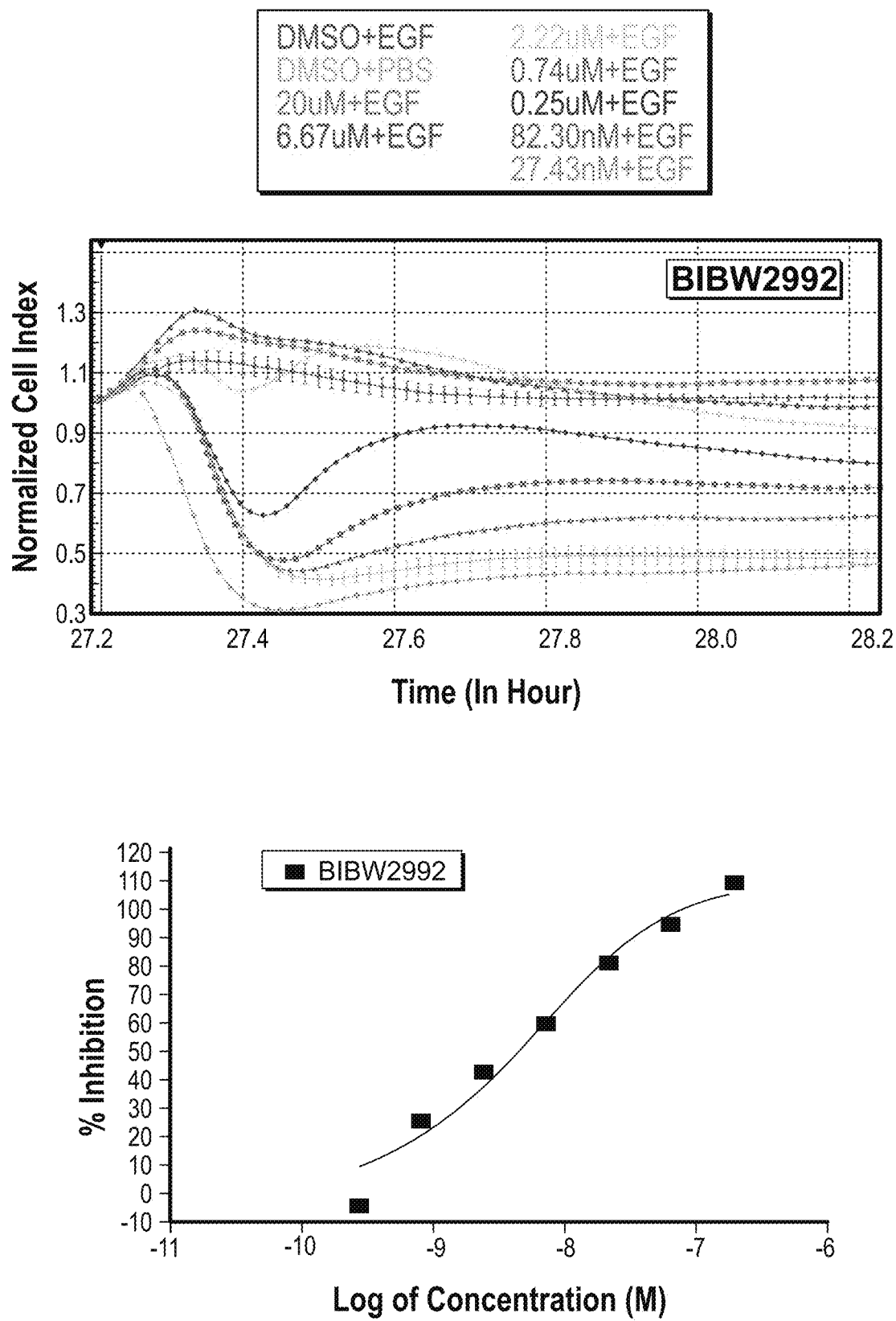
FIG. 5 shows detailed assay plots of A431 EGF stimulation assay for BIBW2992 and erlotinib.
Figure 5:
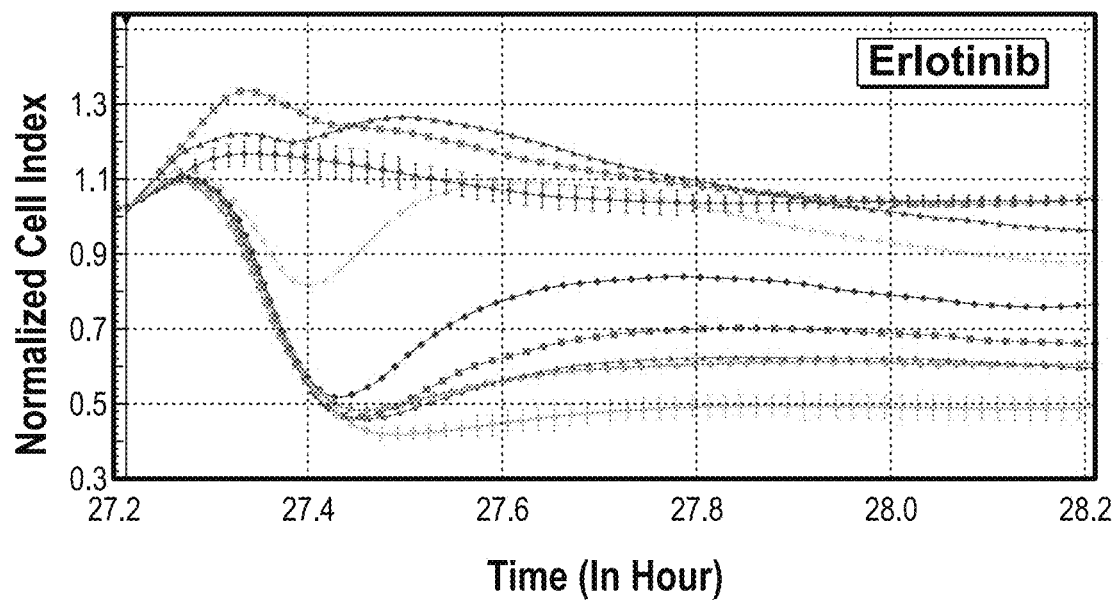
Figure 5:
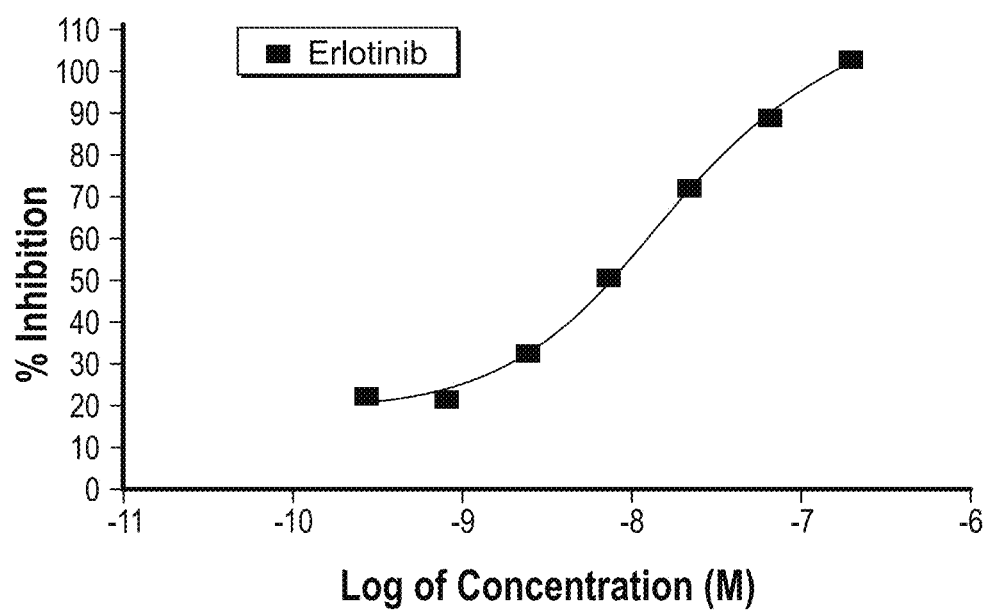

The results are shown in Table 1 below and in FIGS. 1-5.

Assay Results Summary

TABLE 1

| | $IC_{50}$ (uM) | | | | | |
|---|---|---|---|---|---|---|
| | 13a | 13b | 19 | WZ4002 | BIBW2992 | Erlotinib |
| H1975 cell viability assay | Active | Weak activity | Active | Active | | |
| A549 cell viability assay | >20 | >20 | >6.7 | >20 | | |
| HeLa cell viability assay | >2.2 | >20 | >6.7 | >6.7 | | |
| H1975 EGF stimulation assay | 1.7 | 1.9 | 1.1 | 1.1 | | |
| A431 stimulation assay | 2.4 | 4.1 | 0.97 | 0.817 | 0.006 | 0.015 |

ELISA assay

H1975 and A431 cells were seeded onto each well of a 96-well plate at a density of $4 \times 10^4$ cells per well. After 24 hours of growth in serum-containing media, cells were treated with test compound in serum-free medium for 2 hours. A431 cells were stimulated with 30 ng/mL EGF during the last 15 minutes of compound treatment. Cells were washed with ice cold PBS before extraction with 100 μl per well cell lysis buffer. Phosphorylation of EGFR was measured using a sandwich ELISA assay with the pair of phospho-specific EGFR (pY1068) and total EGFR antibodies. The results are shown in Table 2 below.

Results

TABLE 2

| Compound # | $IC_{50}$ (μM) H1975 cell (T790M/L858R) | $IC_{50}$ (μM) A431 cell (WT) | Selectivity (WT/T790M) |
|---|---|---|---|
| 13a | 0.170 | 13.7 | 82 |
| 13b | 0.340 | 10.8 | 32 |

TABLE 2-continued

| Compound # | IC$_{50}$ (μM) H1975 cell (T790M/L858R) | IC$_{50}$ (μM) A431 cell (WT) | Selectivity (WT/T790M) |
|---|---|---|---|
| 19 | 0.029 | 2.46 | 85 |
| 31 | 0.030 | >20 | >657 |
| 63 | 0.030 | 28.8 | 974 |
| 27a | 0.058 | 23.4 | 403 |
| 28a | 0.026 | 2.73 | 107 |
| 28b | 0.026 | 12 | 466 |
| 28c | 0.080 | 8.05 | 100 |
| 28d | 0.158 | >20 | >127 |
| 29 | 1.560 | >20 | >12.8 |
| 32 | 1.300 | >20 | >15.4 |
| 33 | 0.099 | 7.17 | 72.6 |
| 34 | 0.038 | 4.37 | 113 |
| 35 | 0.062 | 3.61 | 58.4 |
| 36 | 0.093 | 2.17 | 23.3 |
| 37 | 0.106 | 11.1 | 105 |
| 38 | 0.341 | 3.81 | 11.2 |
| 39 | 0.041 | 0.71 | 17.3 |
| 40 | 1.740 | 25.3 | 14.6 |
| 42 | 1.630 | 11.8 | 7.2 |

Embodiments

The present disclosure provides for the following embodiments.

Embodiment A1. A compound of Formula I:

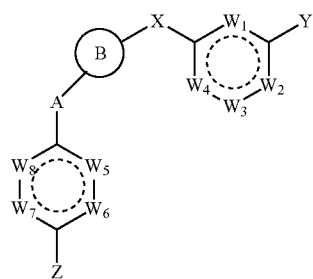

Formula I where

in a ring indicates the ring is an aromatic or heteroaromatic ring;

X is O, S, C=O, —NR, SO, SO$_2$, C1-C6 alkyl or C1-C6 haloalkyl;

W$_1$, W$_2$, W$_3$, W$_4$, W$_5$, W$_6$, W$_7$ and W$_8$ are each independently absent, N, NH, NR$^1$, O, S, CH, or CR$^2$;

not more than one of them is absent;

R$^1$ and R$^2$ is independently selected from H, OH, Halo, NHR, NRR, OR, SR, COOR, C(=O)R, CN, CF$_3$, OCF$_3$, NO$_2$, OC(O)R, SO$_3$R, PO$_3$R$_2$, or CR(COOR)$_2$;

Y is H, OH, Halo, NHR, NRR, NHC(=O)R, OR, SR, COOR, C(=O)R, CN, CF$_3$, OCF$_3$, NO$_2$, OC(O)R, SO$_3$R, PO$_3$R$_2$, or CR(COOR)$_2$;

Z is H, OH, Halo, NHR, NRR, OR, SR, COOR, C(=O)R, CN, CF$_3$, OCF$_3$, NO$_2$, OC(O)R, SO$_3$R, PO$_3$R$_2$, CR(COOR)$_2$, or

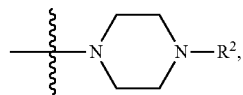

A is NH, S, SO, SO$_2$, SO$_2$NH, SO$_2$NR$^3$, NHSO$_2$, NR$^1$, CR$^1$R$^2$, NR$^1$, or O;

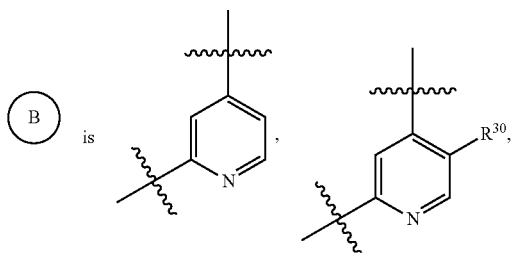

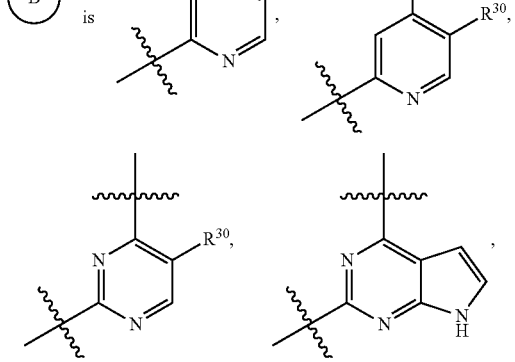

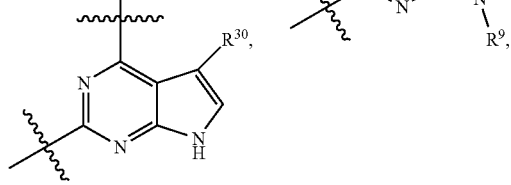

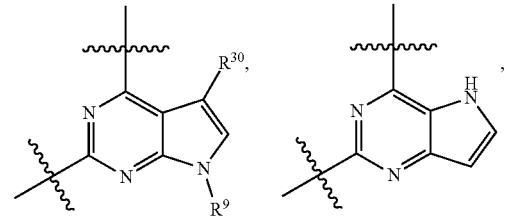

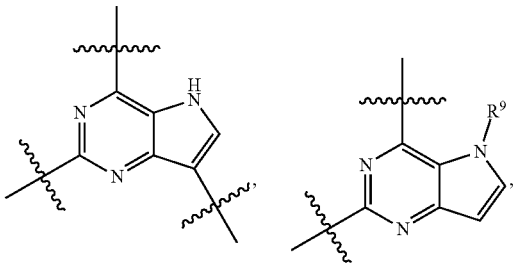

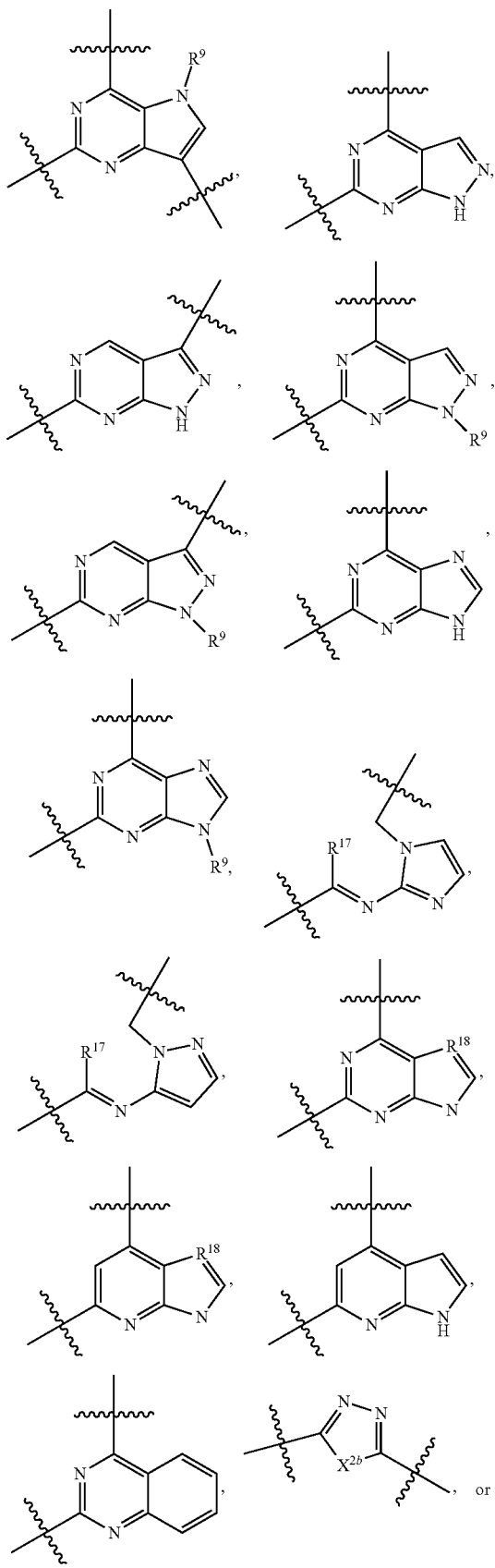

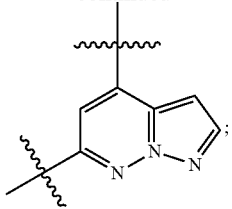

$R^{17}$ is N, CH, or $CR^{30}$;
$R^{18}$ is O or S;
$R^{11}$ is halogen or $C_1$-$C_6$ alkyl; and
each R—$^{11}$ is independently hydrogen, $C_1$-$C_3$ alkyl, $C_1$—$C_3$ alkoxy, $C_1$—$C_3$ haloalkyl, or $C_1$-$C_3$ haloalkoxy;
$R^{12}$ is $CH_2$ or C(O);
$X^{2b}$ is O, S, NH, or NR;
each R is selected from H, substituted or unsubstituted $C_{1-8}$ alkyl, $C_{2-8}$ alkenyl, $C_{2-8}$ alkynyl, aryl, fused aryl, heteroaryl, fused heterocycle, a $C_{3-8}$ carbocyclic ring or a $C_{3-8}$ heterocyclic ring, saturated or unsaturated, wherein each $C_{1-8}$ alkyl, $C_{3-8}$ cyclic alkyl, $C_{2-8}$ alkenyl, $C_{2-8}$ alkynyl can optionally contain a heteroatom selected from N, O and S in place of a carbon atom;
or a pharmaceutically acceptable salt thereof.

Embodiment A2. The compound of embodiment A1, wherein X is C1-C6 haloalkyl.

Embodiment A3. The compound of embodiment A2, wherein $CF_2$, CHF, $CHCF_3$ or $C(CF_3)_2$.

Embodiment A4. A pharmaceutical composition comprising a compound of any one of the embodiments A1-A3 admixed with at least one pharmaceutically acceptable carrier or excipient.

Embodiment A5. The pharmaceutical composition of embodiment A4, which comprises at least one sterile pharmaceutically acceptable carrier or excipient.

Embodiment A6. The pharmaceutical composition of embodiment A4, which comprises at least two pharmaceutically acceptable carriers and/or excipients.

Embodiment A7. A compound according to any one of embodiments A1-A6 for use in therapy.

Embodiment A8. The compound of embodiment A7, wherein the use in therapy is a use to treat cancer.

Embodiment A9. The compound of embodiment A8, wherein the cancer is selected from leukemia, lymphoma, lung cancer, colon cancer, CNS cancer, melanoma, ovarian cancer, renal cancer, prostate cancer, breast cancer, head and neck cancers, and pancreatic cancer.

Embodiment A10. A method to treat cancer, which comprises administering to a subject in need thereof an effective amount of a compound according to any one of embodiments A1-A6.

Embodiment A11. The method of embodiment A10, wherein the cancer is selected from leukemia, lymphoma, lung cancer, colon cancer, CNS cancer, melanoma, ovarian cancer, renal cancer, prostate cancer, breast cancer, head and neck cancers, and pancreatic cancer.

Embodiment A12. Use of a compound according to any one of embodiments A1-A6 for the manufacture of a medicament.

Embodiment A13. The use of embodiment A12, wherein the cancer is selected from leukemia, lymphoma, lung cancer, colon cancer, CNS cancer, melanoma, ovarian cancer, renal cancer, prostate cancer, breast cancer, head and neck cancers, and pancreatic cancer.

The present disclosure also provides for the following embodiments.

Embodiment B1. A compound of Formula Ia:

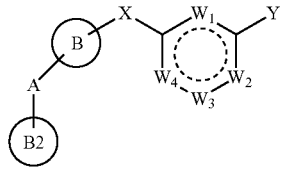

where

in a ring indicates the ring is an aromatic or heteroaromatic ring;

X is O, S, C=O, —NR, SO, SO$_2$, C$_1$-C$_6$ alkyl or C$_1$-C$_6$ haloalkyl;

W$_1$, W$_2$, W$_3$, W$_4$, W$_5$, W$_6$, W$_7$ and W$_8$ are each independently absent, N, NH, NR$^1$, O, S, CH, or CR$^2$;

not more than one of them is absent;

R$^1$ and R$^2$ are each independently selected from H, C$_1$-C$_6$ alkyl, OH, halogen, NHR, NRR, OR, SR, COOR, C(=O)R, CN, CF$_3$, OCF$_3$, NO$_2$, OC(O)R, SO$_3$R, SO$_2$R, PO$_3$R$_2$, —POR$_2$, CR(COOR)$_2$, C$_1$-C$_6$ haloalkyl, C$_1$-C$_6$ alkoxy, C$_1$-C$_6$ haloalkoxy, C$_1$-C$_6$ alkenyl, C$_1$-C$_6$ alkynyl, —C(O)NR$_2$, sulfonyl, sulfonylamino, aminosulfonyl, acylamino, alkoxycarbonylamino, and aminocarbonylamino;

Y is H, OH, halogen, NHR, NRR, NHC(=O)R, OR, SR, COOR, C(=O)R, CN, CF$_3$, OCF$_3$, NO$_2$, OC(O)R, SO$_3$R, PO$_3$R$_2$, or CR(COOR)$_2$;

A is NH, S, SO, SO$_2$, SO$_2$NH, SO$_2$NR$^3$, NHSO$_2$, NR$^1$, CR$^1$R$^2$, NR$^1$, or O;

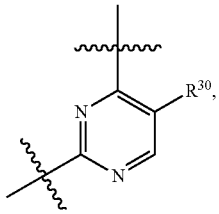

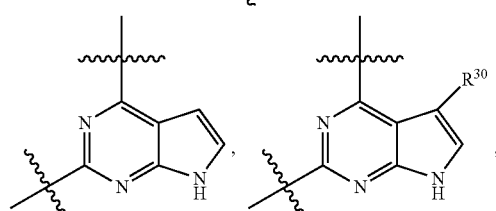

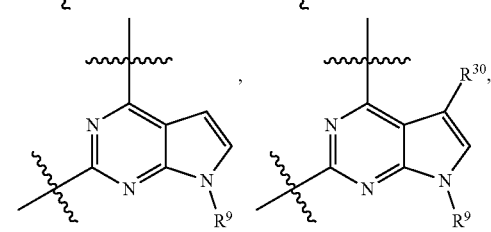

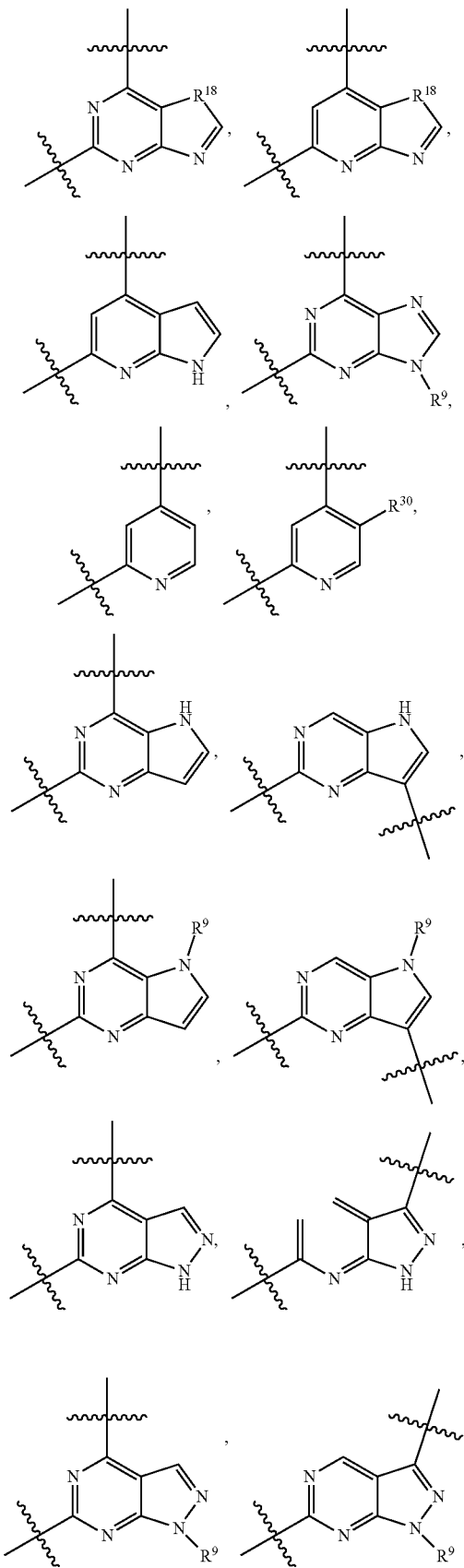

113

-continued

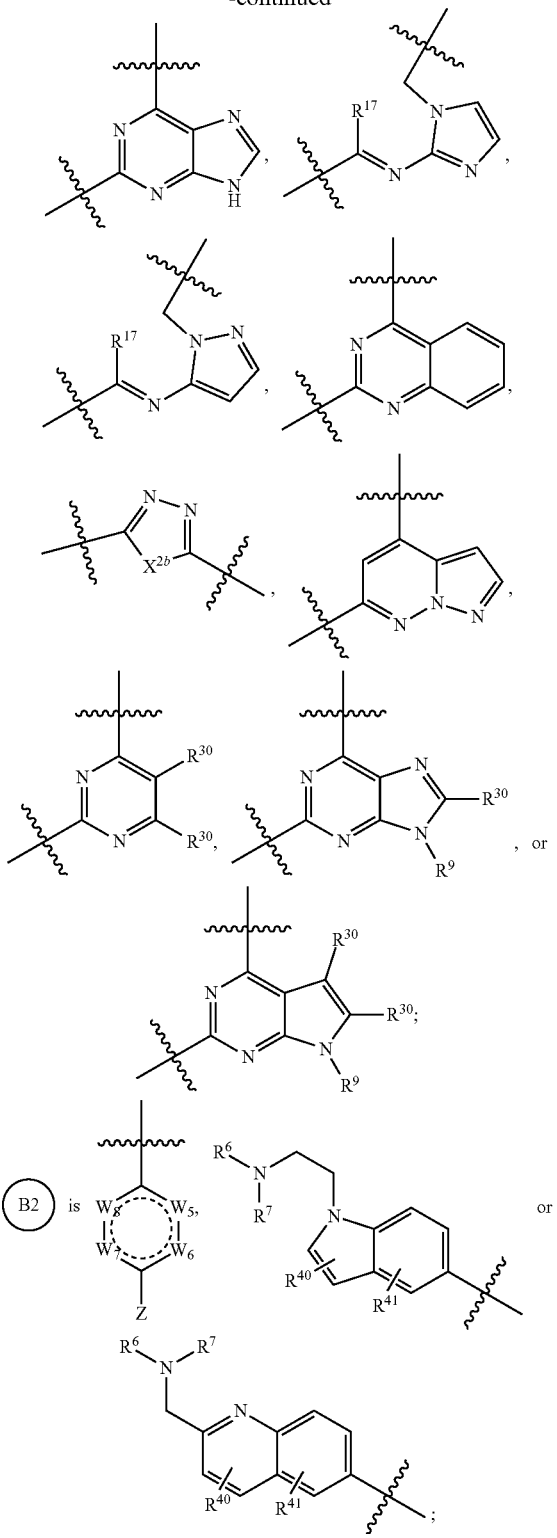

$R^{17}$ is N, CH, or $CR^{30}$;

$R^{18}$ is O or S;

$R^9$ is hydrogen, $C_1$-$C_6$ alkyl, or substituted $C_1$-$C_6$ alkyl, wherein $C_1$-$C_6$ alkyl is substituted with halogen, hydroxy, cyano, nitro, sulfonyl, sulfonylamino, aminosulfonyl, amino, or substituted amino;

114 each $R^{30}$ is independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, and substituted amino;

$X^{2b}$ is O, S, NH, or NR;

Z is H, OH, halogen, NHR, NRR, OR, SR, COOR, C(=O)R, CN, $CF_3$, $OCF_3$, $NO_2$, OC(O)R, $SO_3$R, $PO_3R_2$, $CR(COOR)_2$, or

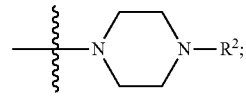

$R^6$ is hydrogen or $C_1$-$C_6$ alkyl;

$R^7$ is hydrogen or $C_1$-$C_6$ alkyl;

$R^{40}$ and $R^{41}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, substituted amino, acylamino, alkoxycarbonylamino, and aminocarbonylamino; and each R is selected from H, substituted or unsubstituted $C_{1-8}$ alkyl, $C_{2-20}$ alkenyl, $C_{2-8}$ alkynyl, aryl, fused aryl, heteroaryl, fused heterocycle, a $C_{3-8}$ carbocyclic ring or a $C_{3-8}$ heterocyclic ring, saturated or unsaturated, wherein each $C_{1-8}$ alkyl, $C_{3-8}$ cyclic alkyl, $C_{2-8}$ alkenyl, $C_{2-8}$ alkynyl can optionally contain a heteroatom selected from N, O and S in place of a carbon atom;

or a pharmaceutically acceptable salt thereof.

Embodiment B2. The compound of embodiment B1, wherein the compound is Formula Ib:

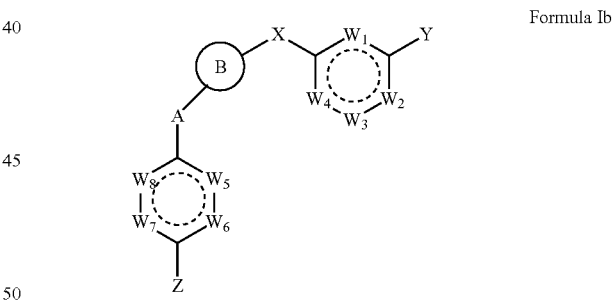

Formula Ib where

in a ring indicates the ring is an aromatic or heteroaromatic ring;

X is O, S, C=O, —NR, SO, $SO_2$, $C_1$-$C_6$ alkyl or $C_1$-$C_6$ haloalkyl;

$W_1$, $W_2$, $W_3$, $W_4$, $W_5$, $W_6$, $W_7$ and $W_8$ are each independently absent, N, NH, $NR^1$, O, S, CH, or $CR^2$;

not more than one of them is absent;

$R^1$ and $R^2$ are each independently selected from H, $C_1$-$C_6$ alkyl, OH, halogen, NHR, NRR, OR, SR, COOR, C(=O)R, CN, CF$_3$, OCF$_3$, NO$_2$, OC(O)R, SO$_3$R, SO$_2$R, PO$_3$R$_2$,—POR$_2$, CR(COOR)$_2$, C$_1$-C$_6$ haloalkyl, C$_1$-C$_6$ alkoxy, C$_1$-C$_6$ haloalkoxy, C$_1$-C$_6$ alkenyl, C$_1$-C$_6$ alkynyl, —C(O)NR$_2$, sulfonyl, sulfonylamino, aminosulfonyl, acylamino, alkoxycarbonylamino, and aminocarbonylamino;

Y is H, OH, halogen, NHR, NRR, NHC(=O)R, OR, SR, COOR, C(=O)R, CN, CF$_3$, OCF$_3$, NO$_2$, OC(O)R, SO$_3$R, PO$_3$R$_2$, or CR(COOR)$_2$;

Z is H, OH, halogen, NHR, NRR, OR, SR, COOR, C(=O)R, CN, CF$_3$, OCF$_3$, NO$_2$, OC(O)R, SO$_3$R, PO$_3$R$_2$, CR(COOR)$_2$, or

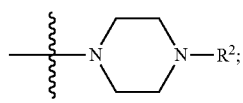

A is NH, S, SO, SO$_2$, SO$_2$NH, SO$_2$NR$^3$, NHSO$_2$, NR$^1$, CR$^1$R$^2$, NR$^1$, or O;

B is

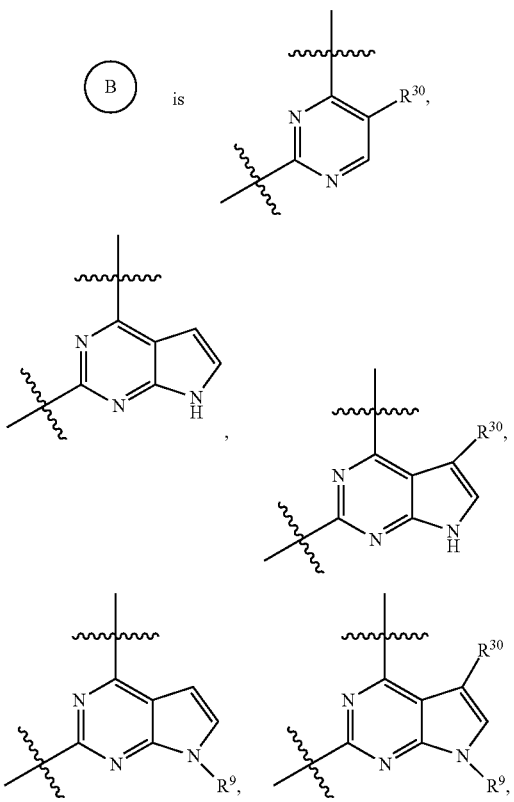

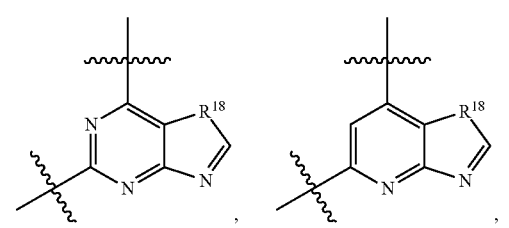

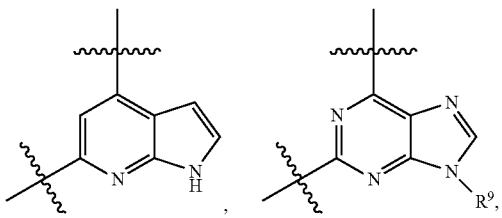

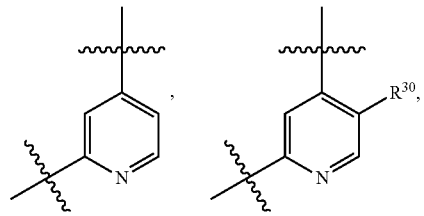

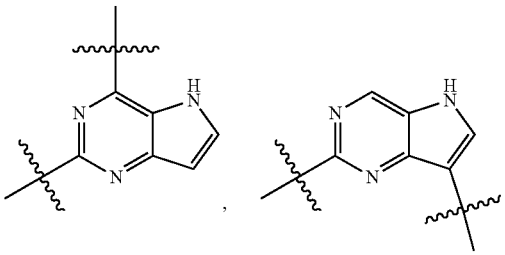

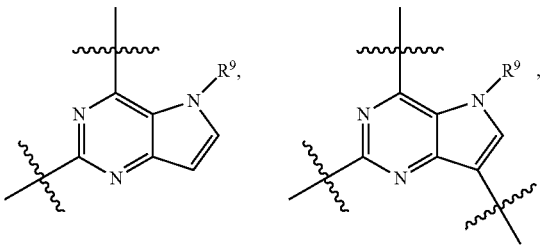

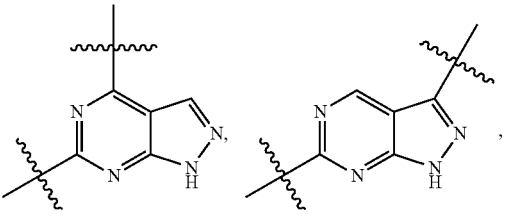

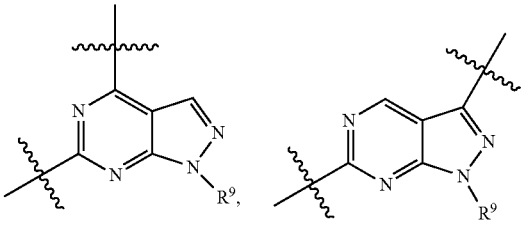

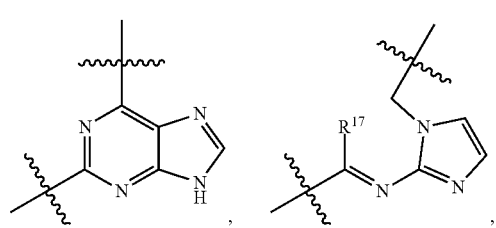

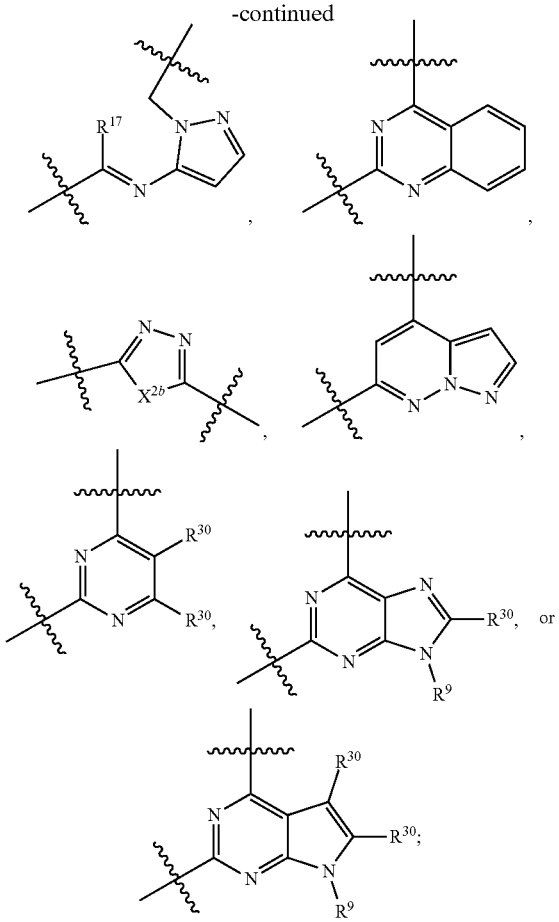

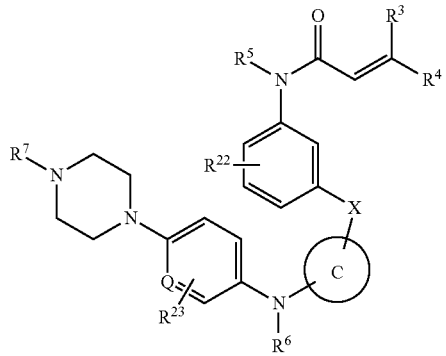

Formula Ic wherein

X is CF$_2$, O, CH$_2$ S, or NR$^b$;

R$^b$ is selected from H, substituted or unsubstituted C$_{1-8}$ alkyl, C$_{2-8}$ alkenyl, C$_{2-8}$ alkynyl, aryl, fused aryl, heteroaryl, fused heterocycle, a C$_{3-8}$ carbocyclic ring or a C$_{3-8}$ heterocyclic ring, saturated or unsaturated, wherein each C$_{1-8}$ alkyl, C$_{3-8}$ cyclic alkyl, C$_{2-8}$ alkenyl, C$_{2-8}$ alkynyl can optionally contain a heteroatom selected from N, O and S in place of a carbon atom;

R$^3$ and R$^4$ are independently hydrogen, C$_1$-C$_6$ alkyl, or —(CH$_2$)$_m$N(R$^a$)$_2$, wherein m is one to 6;

R$^5$ is hydrogen or C$_1$-C$_6$ alkyl;

R$^6$ is hydrogen or C$_1$-C$_6$ alkyl;

R$^7$ is hydrogen or C$_1$-C$_6$ alkyl;

R$^{17}$ is N, CH, or CR$^{30}$;

R$^{18}$ is O or S;

R$^9$ is hydrogen, C$_1$-C$_6$ alkyl, or substituted C$_1$-C$_6$ alkyl, wherein C$_1$-C$_6$ alkyl is substituted with halogen, hydroxy, cyano, nitro, sulfonyl, sulfonylamino, aminosulfonyl, amino, or substituted amino;

each R$^{30}$ is independently selected from hydrogen, halogen, C$_1$-C$_6$ alkyl, C$_1$-C$_6$ haloalkyl, C$_1$-C$_6$ alkoxy, C$_1$-C$_6$ haloalkoxy, C$_1$-C$_6$ alkenyl, C$_1$-C$_6$ alkynyl, hydroxy, cyano, nitro, —C(O)R$^a$, —OC(O)R$^a$, —C(O)OR$^a$, —C(O)N(R$^a$)$_2$, sulfonyl, sulfonylamino, aminosulfonyl, amino, and substituted amino; and X$^{2b}$ is O, S, NH, or NR;

each R is selected from H, substituted or unsubstituted C$_{1-8}$ alkyl, C$_{2-20}$ alkenyl, C$_{2-8}$ alkynyl, aryl, fused aryl, heteroaryl, fused heterocycle, a C$_{3-8}$ carbocyclic ring or a C$_{3-8}$ heterocyclic ring, saturated or unsaturated, wherein each C$_{1-8}$ alkyl, C$_{3-8}$ cyclic alkyl, C$_{2-8}$ alkenyl, C$_{2-8}$ alkynyl can optionally contain a heteroatom selected from N, O and S in place of a carbon atom;

or a pharmaceutically acceptable salt thereof.

Embodiment B3. The compound of embodiment B2, wherein X is C$_1$-C$_6$ haloalkyl.

Embodiment B4. The compound of embodiment B3, wherein X is selected from CF$_2$, CHF, CHCF$_3$ or C(CF$_3$)$_2$.

Embodiment B5. The compound of embodiment B1, wherein the compound is Formula Ic:

C is

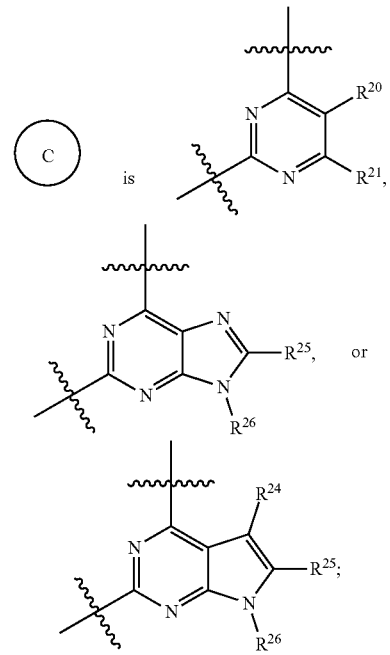

R$^{20}$ and R$^{21}$ are independently selected from hydrogen, halogen, C$_1$-C$_6$ alkyl, C$_1$-C$_6$ haloalkyl, C$_1$-C$_6$ alkoxy, C$_1$-C$_6$ haloalkoxy, C$_1$-C$_6$ alkenyl, C$_1$-C$_6$ alkynyl, hydroxy, cyano, nitro, —C(O)R$^a$, —OC(O)R$^a$, —C(O)OR$^a$, —C(O)N(R$^a$)$_2$, sulfonyl, sulfonylamino, aminosulfonyl, amino, and substituted amino;

R$^{24}$ and R$^{25}$ are independently selected from hydrogen, halogen, C$_1$-C$_6$ alkyl, C$_1$-C$_6$ haloalkyl, C$_1$-C$_6$ alkoxy, C$_1$-C$_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, and substituted amino;

$R^{26}$ is hydrogen, $C_1$-$C_6$ alkyl, or substituted $C_1$-$C_6$ alkyl, wherein $C_1$-$C_6$ alkyl is substituted with halogen, hydroxy, cyano, nitro, sulfonyl, sulfonylamino, aminosulfonyl, amino, or substituted amino;

$R^{22}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, thiol, —C(O)$R^a$, —OC(O)$R^a$, —C(O)O$R^a$, —C(O)N($R^a$)$_2$, sulfonyl, sulfonylamino, aminosulfonyl, amino, substituted amino, acylamino, alkoxycarbonylamino, and aminocarbonylamino;

$R^{23}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, substituted amino, acylamino, alkoxycarbonylamino, and aminocarbonylamino;

each $R^a$ is independently hydrogen or $C_1$-$C_6$ alkyl; and

Q is CH, C$R^{23}$, or N;

or a pharmaceutically acceptable salt thereof.

Embodiment B6. The compound of embodiment B5, wherein the compound is Formula IIa

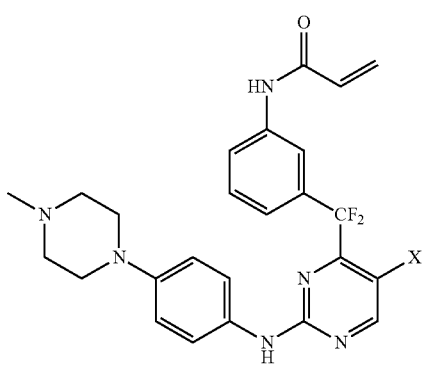

Formula IIa where X is $C_1$-$C_6$ alkyl, $C_1$-$C_6$ alkoxy, or halo, wherein the halo is Cl, F, I, or Br.

Embodiment B7. The compound of embodiment B6, wherein halo is F, I, or Br.

Embodiment B8. The compound of embodiment B5, wherein the compound is Formula III:

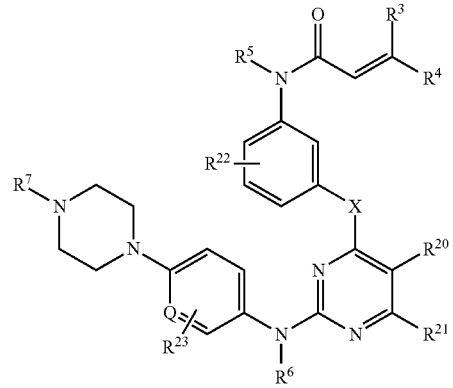

Formula III wherein

X is CF$_2$, O, CH$_2$ S, or N$R^b$;

$R^b$ is selected from H, substituted or unsubstituted $C_{1-8}$ alkyl, $C_{2-8}$ alkenyl, $C_{2-8}$ alkynyl, aryl, fused aryl, heteroaryl, fused heterocycle, a $C_{3-8}$ carbocyclic ring or a $C_{3-8}$ heterocyclic ring, saturated or unsaturated, wherein each $C_{1-8}$ alkyl, $C_{3-8}$ cyclic alkyl, $C_{2-8}$ alkenyl, $C_{2-8}$ alkynyl can optionally contain a heteroatom selected from N, O and S in place of a carbon atom;

$R^3$ and $R^4$ are independently hydrogen, $C_1$-$C_6$ alkyl, or —(CH$_2$)$_m$N($R^a$)$_2$, wherein m is one to 6;

$R^5$ is hydrogen or $C_1$-$C_6$ alkyl;

$R^6$ is hydrogen or $C_1$-$C_6$ alkyl;

$R^7$ is hydrogen or $C_1$-$C_6$ alkyl;

$R^{20}$ and $R^{21}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, and substituted amino;

$R^{22}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, thiol, —C(O)$R^a$, —OC(O)$R^a$, —C(O)O$R^a$, —C(O)N($R^a$)$_2$, sulfonyl, sulfonylamino, aminosulfonyl, amino, substituted amino, acylamino, alkoxycarbonylamino, and aminocarbonylamino;

$R^{23}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, substituted amino, acylamino, alkoxycarbonylamino, and aminocarbonylamino;

each $R^a$ is independently hydrogen or $C_1$-$C_6$ alkyl; and

Q is CH, C$R^{23}$, or N;

or a pharmaceutically acceptable salt thereof.

Embodiment B9. The compound of embodiment B8, wherein $R^{20}$ is hydrogen, halogen, $C_1$-$C_6$ alkyl, or $C_1$-$C_6$ alkoxy.

Embodiment B10. The compound of embodiment B8, wherein $R^{20}$ is hydrogen, fluoro, chloro, $C_1$-$C_6$ alkyl, or $C_1$-$C_6$ alkoxy.

Embodiment B11. The compound of embodiment B8, wherein $R^{20}$ is hydrogen, fluoro, iodo, bromo, $C_1$-$C_6$ alkyl, or $C_1$-$C_6$ alkoxy.

Embodiment B12. The compound of embodiment B8, wherein $R^{21}$ is hydrogen.

Embodiment B13. The compound of embodiment B8, wherein $R^{23}$ is hydrogen, halogen, or $C_1$-$C_6$ alkoxy.

Embodiment B14. The compound of embodiment B8, wherein $R^7$ is $C_1$-$C_3$ alkyl.

Embodiment B15. The compound of embodiment B8, wherein $R^3$ and $R^4$ are hydrogen.

Embodiment B16. The compound of embodiment B8, wherein at least one of $R^3$ and $R^4$ is $C_1$-$C_6$ alkyl.

Embodiment B17. The compound of embodiment B8, wherein Q is CH or $CR^{23}$.

Embodiment B18. The compound of embodiment B8, wherein Q is N.

Embodiment B19. The compound of embodiment B5, wherein the compound is Formula IV:

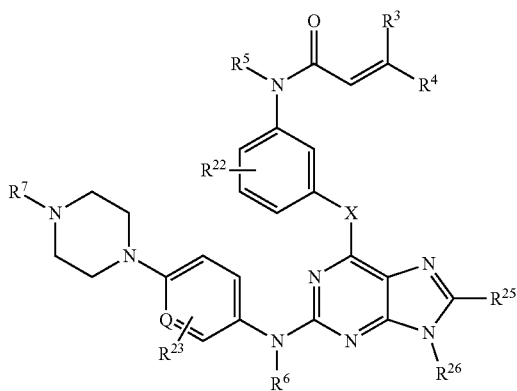

Formula IV wherein

X is $CF_2$, O, $CH_2$ S, or $NR^b$;

$R^b$ is selected from H, substituted or unsubstituted $C_{1-8}$ alkyl, $C_{2-8}$ alkenyl, $C_{2-8}$ alkynyl, aryl, fused aryl, heteroaryl, fused heterocycle, a $C_{3-8}$ carbocyclic ring or a $C_{3-8}$ heterocyclic ring, saturated or unsaturated, wherein each $C_{1-8}$ alkyl, $C_{3-8}$ cyclic alkyl, $C_{2-8}$ alkenyl, $C_{2-8}$ alkynyl can optionally contain a heteroatom selected from N, O and S in place of a carbon atom;

$R^3$ and $R^4$ are independently hydrogen, $C_1$-$C_6$ alkyl, or —$(CH_2)_m N(R^a)_2$, wherein m is one to 6;

$R^5$ is hydrogen or $C_1$-$C_6$ alkyl;

$R^6$ is hydrogen or $C_1$-$C_6$ alkyl;

$R^7$ is hydrogen or $C_1$-$C_6$ alkyl;

$R^{25}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, and substituted amino;

$R^{26}$ is hydrogen, $C_1$-$C_6$ alkyl, or substituted $C_1$-$C_6$ alkyl, wherein $C_1$-$C_6$ alkyl is substituted with halogen, hydroxy, cyano, nitro, sulfonyl, sulfonylamino, aminosulfonyl, amino, or substituted amino;

$R^{22}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, substituted amino, acylamino, alkoxycarbonylamino, and aminocarbonylamino;

$R^{23}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, substituted amino, acylamino, alkoxycarbonylamino, and aminocarbonylamino;

each $R^a$ is independently hydrogen or $C_1$-$C_6$ alkyl; and

Q is CH, $CR^{23}$, or N;

or a pharmaceutically acceptable salt thereof.

Embodiment B20. The compound of embodiment B19, wherein $R^{25}$ and $R^{26}$ are hydrogen.

Embodiment B21. The compound of embodiment B19, wherein $R^{23}$ is hydrogen, halogen, or $C_1$-$C_6$ alkoxy.

Embodiment B22. The compound of embodiment B19, wherein Q is CH.

Embodiment B23. The compound of embodiment B19, wherein $R^7$ is $C_1$-$C_3$ alkyl.

Embodiment B24. The compound of embodiment B19, wherein $R^3$ and $R^4$ are hydrogen.

Embodiment B25. The compound of embodiment B5, wherein the compound is Formula V:

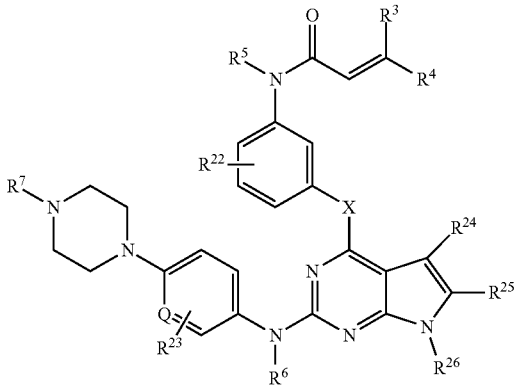

Formula V wherein

X is $CF_2$, O, $CH_2$ S, or $NR^b$;

$R^b$ is selected from H, substituted or unsubstituted $C_{1-8}$ alkyl, $C_{2-8}$ alkenyl, $C_{2-8}$ alkynyl, aryl, fused aryl, heteroaryl, fused heterocycle, a $C_{3-8}$ carbocyclic ring or a $C_{3-8}$ heterocyclic ring, saturated or unsaturated, wherein each $C_{1-8}$ alkyl, $C_{3-8}$ cyclic alkyl, $C_{2-8}$ alkenyl, $C_{2-8}$ alkynyl can optionally contain a heteroatom selected from N, O and S in place of a carbon atom;

$R^3$ and $R^4$ are independently hydrogen, $C_1$-$C_6$ alkyl, or —$(CH_2)_m N(R^a)_2$, wherein m is one to 6;

$R^5$ is hydrogen or $C_1$-$C_6$ alkyl;

$R^6$ is hydrogen or $C_1$-$C_6$ alkyl;

$R^7$ is hydrogen or $C_1$-$C_6$ alkyl;

$R^{24}$ and $R^{25}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, and substituted amino;

$R^{26}$ is hydrogen, $C_1$-$C_6$ alkyl, or substituted $C_1$-$C_6$ alkyl, wherein $C_1$-$C_6$ alkyl is substituted with halogen, hydroxy, cyano, nitro, sulfonyl, sulfonylamino, aminosulfonyl, amino, or substituted amino;

$R^{22}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, substituted amino acylamino, alkoxycarbonylamino, and aminocarbonylamino;

$R^{23}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)R$^a$, —OC(O)R$^a$, —C(O)OR$^a$, —C(O)N(R$^a$)$_2$, sulfonyl, sulfonylamino, aminosulfonyl, amino, substituted amino acylamino, alkoxycarbonylamino, and aminocarbonylamino;

each R$^a$ is independently hydrogen or $C_1$-$C_6$ alkyl; and

Q is CH, CR$^{23}$, or N;

or a pharmaceutically acceptable salt thereof.

Embodiment B26. The compound of embodiment B25, wherein R$^{24}$ and R$^{25}$ are hydrogen.

Embodiment B27. The compound of embodiment B25, wherein R$^{26}$ is hydrogen.

Embodiment B28. The compound of embodiment B25, wherein R$^{26}$ is substituted $C_1$-$C_6$ alkyl, wherein $C_1$-$C_6$ alkyl is substituted with hydroxy.

Embodiment B29. The compound of embodiment B25, wherein R$^{24}$, R$^{25}$ and R$^{26}$ are hydrogen.

Embodiment B30. The compound of embodiment B25, wherein R$^{23}$ is hydrogen, halogen, or $C_1$-$C_6$ alkoxy.

Embodiment B31. The compound of embodiment B25, wherein Q is CH or CR$^{23}$.

Embodiment B32. The compound of embodiment B25, wherein Q is N.

Embodiment B33. The compound of embodiment B25, wherein R$^7$ is $C_1$-$C_3$ alkyl.

Embodiment B34. The compound of embodiment B25, wherein R$^3$ and R$^4$ are hydrogen.

Embodiment B35. The compound of embodiment B25, wherein at least one of R$^3$ and R$^4$ is $C_1$-$C_6$ alkyl.

Embodiment B36. The compound of embodiment B1, wherein the compound is Formula Id:

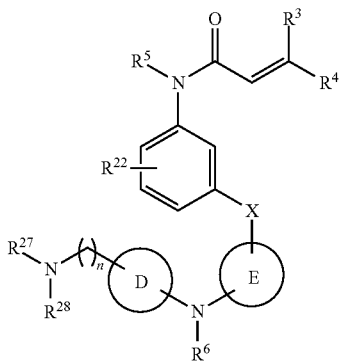

Formula Id wherein

X is CF$_2$, O, CH$_2$ S, or NR$^b$;

R$^b$ is selected from H, substituted or unsubstituted $C_{1-8}$ alkyl, $C_{2-8}$ alkenyl, $C_{2-8}$ alkynyl, aryl, fused aryl, heteroaryl, fused heterocycle, a $C_{3-8}$ carbocyclic ring or a $C_{3-8}$ heterocyclic ring, saturated or unsaturated, wherein each $C_{1-8}$ alkyl, $C_{3-8}$ cyclic alkyl, $C_{2-8}$ alkenyl, $C_{2-8}$ alkynyl can optionally contain a heteroatom selected from N, O and S in place of a carbon atom;

R$^3$ and R$^4$ are independently hydrogen, $C_1$-$C_6$ alkyl, or —(CH$_2$)$_m$N(R$^a$)$_2$, wherein m is one to 6;

R$^5$ is hydrogen or $C_1$-$C_6$ alkyl;

R$^6$ is hydrogen or $C_1$-$C_6$ alkyl;

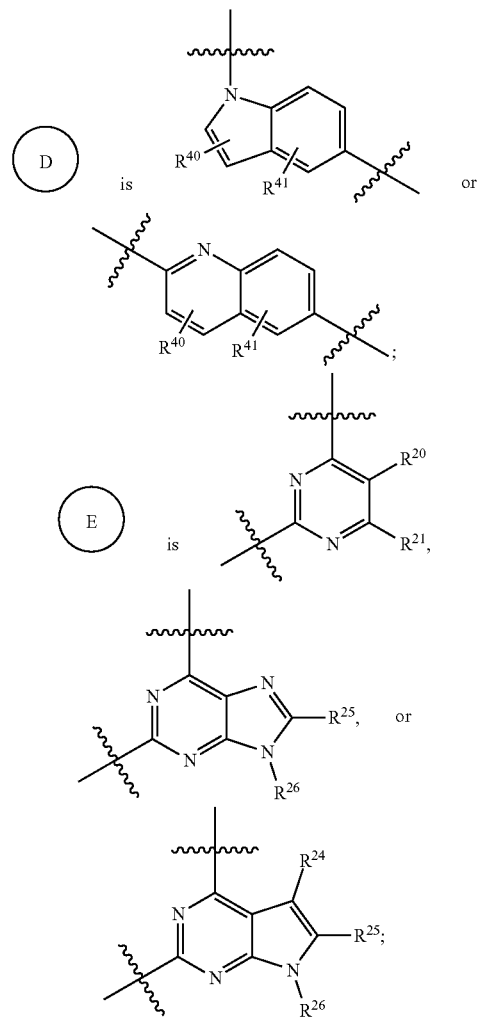

R$^{20}$ and R$^{21}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)R$^a$, —OC(O)R$^a$, —C(O)OR$^a$, —C(O)N(R$^a$)$_2$, sulfonyl, sulfonylamino, aminosulfonyl, amino, and substituted amino;

R$^{24}$ and R$^{25}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)R$^a$, —OC(O)R$^a$, —C(O)OR$^a$, —C(O)N(R$^a$)$_2$, sulfonyl, sulfonylamino, aminosulfonyl, amino, and substituted amino;

R$^{26}$ is hydrogen, $C_1$-$C_6$ alkyl, or substituted $C_1$-$C_6$ alkyl, wherein $C_1$-$C_6$ alkyl is substituted with halogen, hydroxy, cyano, nitro, sulfonyl, sulfonylamino, aminosulfonyl, amino, or substituted amino;

R$^{40}$ and R$^{41}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)R$^a$, —OC(O)R$^a$, —C(O)OR$^a$, —C(O)N(R$^a$)$_2$, sulfonyl, sulfonylamino, aminosulfonyl, amino, substituted amino, acylamino, alkoxycarbonylamino, and aminocarbonylamino;

R$^{22}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, thiol, —C(O)

$R^a$, —OC(O)$R^a$, —C(O)O$R^a$, —C(O)N($R^a$)$_2$, sulfonyl, sulfonylamino, aminosulfonyl, amino, substituted amino, acylamino, alkoxycarbonylamino, and aminocarbonylamino;

each $R^a$ is independently hydrogen or $C_1$-$C_6$ alkyl;

$R^{27}$ and $R^{28}$ are independently hydrogen or $C_1$-$C_6$ alkyl; and n is one or two;

or a pharmaceutically acceptable salt thereof.

Embodiment B37. The compound of embodiment B36, wherein the compound is Formula VI:

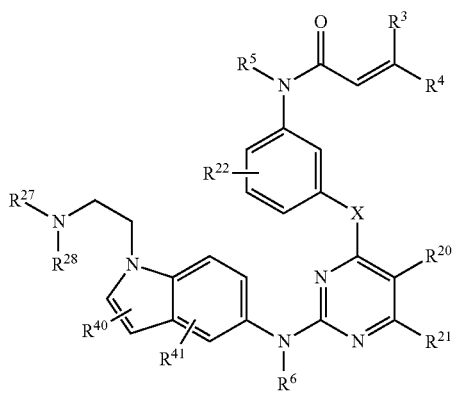

Formula VI wherein

X is $CF_2$, O, $CH_2$ S, or $NR^b$;

$R^b$ is selected from H, substituted or unsubstituted $C_{1-8}$ alkyl, $C_{2-8}$ alkenyl, $C_{2-8}$ alkynyl, aryl, fused aryl, heteroaryl, fused heterocycle, a $C_{3-8}$ carbocyclic ring or a $C_{3-8}$ heterocyclic ring, saturated or unsaturated, wherein each $C_{1-8}$ alkyl, $C_{3-8}$ cyclic alkyl, $C_{2-8}$ alkenyl, $C_{2-8}$ alkynyl can optionally contain a heteroatom selected from N, O and S in place of a carbon atom;

$R^3$ and $R^4$ are independently hydrogen, $C_1$-$C_6$ alkyl, or —(CH$_2$)$_{11}$N($R^a$)$_2$, wherein m is one to 6;

$R^5$ is hydrogen or $C_1$-$C_6$ alkyl;

$R^6$ is hydrogen or $C_1$-$C_6$ alkyl;

$R^{20}$ and $R^{21}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, and substituted amino;

$R^{22}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, substituted amino, acylamino, alkoxycarbonylamino, and aminocarbonylamino;

$R^{40}$ and $R^{41}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, substituted amino, acylamino, alkoxycarbonylamino, and aminocarbonylamino;

each $R^a$ is independently hydrogen or $C_1$-$C_6$ alkyl; and $R^{27}$ and $R^{28}$ are independently hydrogen or $C_1$-$C_6$ alkyl;

or a pharmaceutically acceptable salt thereof.

Embodiment B38. The compound of embodiment B36, wherein the compound is Formula VII:

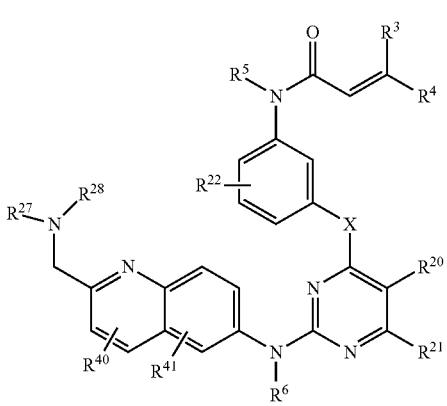

Formula VII wherein

X is $CF_2$, O, $CH_2$ S, or $NR^b$;

$R^b$ is selected from H, substituted or unsubstituted $C_{1-8}$ alkyl, $C_{2-8}$ alkenyl, $C_{2-8}$ alkynyl, aryl, fused aryl, heteroaryl, fused heterocycle, a $C_{3-8}$ carbocyclic ring or a $C_{3-8}$ heterocyclic ring, saturated or unsaturated, wherein each $C_{1-8}$ alkyl, $C_{3-8}$ cyclic alkyl, $C_{2-8}$ alkenyl, $C_{2-8}$ alkynyl can optionally contain a heteroatom selected from N, O and S in place of a carbon atom;

$R^3$ and $R^4$ are independently hydrogen, $C_1$-$C_6$ alkyl, or —(CH$_2$)$_m$N($R^a$)$_2$, wherein m is one to 6;

$R^5$ is hydrogen or $C_1$-$C_6$ alkyl;

$R^6$ is hydrogen or $C_1$-$C_6$ alkyl;

$R^{20}$ and $R^{21}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, and substituted amino;

$R^{22}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, substituted amino, acylamino, alkoxycarbonylamino, and aminocarbonylamino;

$R^{40}$ and $R^{41}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —C(O)$R^a$, —OC(O)$R^a$, —C(O)O$R^a$, —C(O)N($R^a$)$_2$, sulfonyl, sulfonylamino, aminosulfonyl, amino, substituted amino, acylamino, alkoxycarbonylamino, and aminocarbonylamino;

each $R^a$ is independently hydrogen or $C_1$-$C_6$ alkyl; and $R^{27}$ and $R^{28}$ are independently hydrogen or $C_1$-$C_6$ alkyl;

or a pharmaceutically acceptable salt thereof.

Embodiment B39. The compound of embodiment B36, wherein the compound is Formula VIII:

Formula VIII

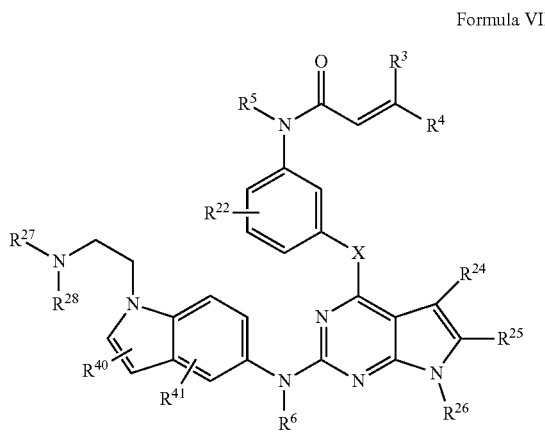

Formula IX

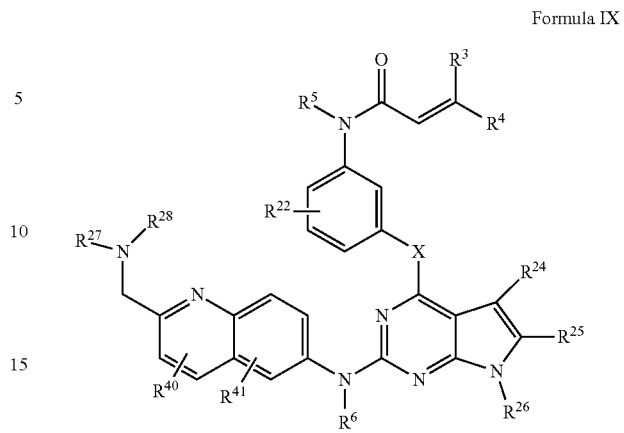

wherein

X is $CF_2$, O, $CH_2$ S, or $NR^b$;

$R^b$ is selected from H, substituted or unsubstituted $C_{1-8}$ alkyl, $C_{2-8}$ alkenyl, $C_{2-8}$ alkynyl, aryl, fused aryl, heteroaryl, fused heterocycle, a $C_{3-8}$ carbocyclic ring or a $C_{3-8}$ heterocyclic ring, saturated or unsaturated, wherein each $C_{1-8}$ alkyl, $C_{3-8}$ cyclic alkyl, $C_{2-8}$ alkenyl, $C_{2-8}$ alkynyl can optionally contain a heteroatom selected from N, O and S in place of a carbon atom;

$R^3$ and $R^4$ are independently hydrogen, $C_1$-$C_6$ alkyl, or —$(CH_2)_m N(R^a)_2$, wherein m is one to 6;

$R^5$ is hydrogen or $C_1$-$C_6$ alkyl;

$R^6$ is hydrogen or $C_1$-$C_6$ alkyl;

$R^{24}$ and $R^{25}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, and substituted amino;

$R^{26}$ is hydrogen, $C_1$-$C_6$ alkyl, or substituted $C_1$-$C_6$ alkyl, wherein $C_1$-$C_6$ alkyl is substituted with halogen, hydroxy, cyano, nitro, sulfonyl, sulfonylamino, aminosulfonyl, amino, or substituted amino;

$R^{22}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, substituted amino, acylamino, alkoxycarbonylamino, and aminocarbonylamino;

$R^{40}$ and $R^{41}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, substituted amino, acylamino, alkoxycarbonylamino, and aminocarbonylamino;

each $R^a$ is independently hydrogen or $C_1$-$C_6$ alkyl; and $R^{27}$ and $R^{28}$ are independently hydrogen or $C_1$-$C_6$ alkyl;

or a pharmaceutically acceptable salt thereof.

Embodiment B40. The compound of embodiment B36, wherein the compound is Formula IX:

wherein

X is $CF_2$, O, $CH_2$ S, or $NR^b$;

$R^b$ is selected from H, substituted or unsubstituted $C_{1-8}$ alkyl, $C_{2-8}$ alkenyl, $C_{2-8}$ alkynyl, aryl, fused aryl, heteroaryl, fused heterocycle, a $C_{3-8}$ carbocyclic ring or a $C_{3-8}$ heterocyclic ring, saturated or unsaturated, wherein each $C_{1-8}$ alkyl, $C_{3-8}$ cyclic alkyl, $C_{2-8}$ alkenyl, $C_{2-8}$ alkynyl can optionally contain a heteroatom selected from N, O and S in place of a carbon atom;

$R^3$ and $R^4$ are independently hydrogen, $C_1$-$C_6$ alkyl, or —$(CH_2)_m N(R^a)_2$, wherein m is one to 6;

$R^5$ is hydrogen or $C_1$-$C_6$ alkyl;

$R^6$ is hydrogen or $C_1$-$C_6$ alkyl;

$R^{24}$ and $R^{25}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, and substituted amino;

$R^{26}$ is hydrogen, $C_1$-$C_6$ alkyl, or substituted $C_1$-$C_6$ alkyl, wherein $C_1$-$C_6$ alkyl is substituted with halogen, hydroxy, cyano, nitro, sulfonyl, sulfonylamino, aminosulfonyl, amino, or substituted amino;

$R^{22}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, substituted amino, acylamino, alkoxycarbonylamino, and aminocarbonylamino;

$R^{40}$ and $R^{41}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, substituted amino, acylamino, alkoxycarbonylamino, and aminocarbonylamino;

each $R^a$ is independently hydrogen or $C_1$-$C_6$ alkyl; and $R^{27}$ and $R^{28}$ are independently hydrogen or $C_1$-$C_6$ alkyl;

or a pharmaceutically acceptable salt thereof.

Embodiment B41. The compound of embodiment B36, wherein the compound is Formula X:

Formula X

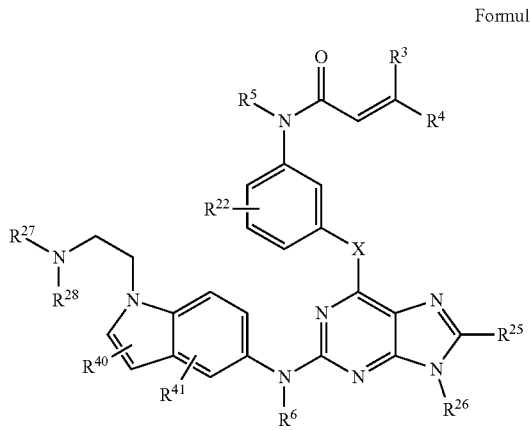

wherein

X is $CF_2$, O, $CH_2$ S, or $NR^b$;

$R^b$ is selected from H, substituted or unsubstituted $C_{1-8}$ alkyl, $C_{2-8}$ alkenyl, $C_{2-8}$ alkynyl, aryl, fused aryl, heteroaryl, fused heterocycle, a $C_{3-8}$ carbocyclic ring or a $C_{3-8}$ heterocyclic ring, saturated or unsaturated, wherein each $C_{1-8}$ alkyl, $C_{3-8}$ cyclic alkyl, $C_{2-8}$ alkenyl, $C_{2-8}$ alkynyl can optionally contain a heteroatom selected from N, O and S in place of a carbon atom;

$R^3$ and $R^4$ are independently hydrogen, $C_1$-$C_6$ alkyl, or —$(CH_2)_m N(R^a)_2$, wherein m is one to 6;

$R^5$ is hydrogen or $C_1$-$C_6$ alkyl;

$R^6$ is hydrogen or $C_1$-$C_6$ alkyl;

$R^{25}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, and substituted amino;

$R^{26}$ is hydrogen, $C_1$-$C_6$ alkyl, or substituted $C_1$-$C_6$ alkyl, wherein $C_1$-$C_6$ alkyl is substituted with halogen, hydroxy, cyano, nitro, sulfonyl, sulfonylamino, aminosulfonyl, amino, or substituted amino;

$R^{22}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, substituted amino, acylamino, alkoxycarbonylamino, and aminocarbonylamino;

$R^{40}$ and $R^{41}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, substituted amino, acylamino, alkoxycarbonylamino, and aminocarbonylamino;

each $R^a$ is independently hydrogen or $C_1$-$C_6$ alkyl; and $R^{27}$ and $R^{28}$ are independently hydrogen or $C_1$-$C_6$ alkyl;

or a pharmaceutically acceptable salt thereof.

Embodiment B42. The compound of embodiment B36, wherein the compound is Formula XI:

Formula XI

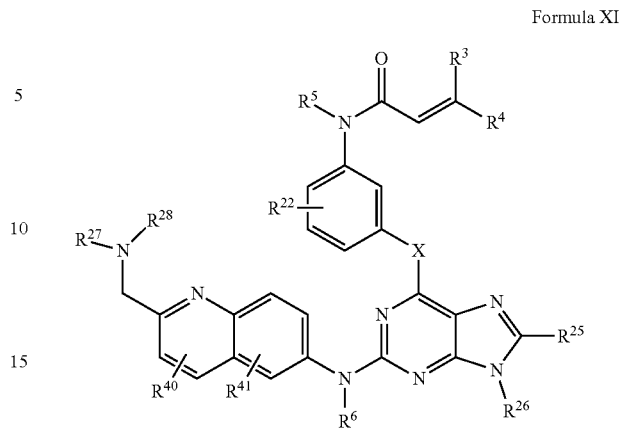

wherein

X is $CF_2$, O, $CH_2$ S, or $NR^b$;

$R^b$ is selected from H, substituted or unsubstituted $C_{1-8}$ alkyl, $C_{2-8}$ alkenyl, $C_{2-8}$ alkynyl, aryl, fused aryl, heteroaryl, fused heterocycle, a $C_{3-8}$ carbocyclic ring or a $C_{3-8}$ heterocyclic ring, saturated or unsaturated, wherein each $C_{1-8}$ alkyl, $C_{3-8}$ cyclic alkyl, $C_{2-8}$ alkenyl, $C_{2-8}$ alkynyl can optionally contain a heteroatom selected from N, O and S in place of a carbon atom;

$R^3$ and $R^4$ are independently hydrogen, $C_1$-$C_6$ alkyl, or —$(CH_2)_m N(R^a)_2$, wherein m is one to 6;

$R^5$ is hydrogen or $C_1$-$C_6$ alkyl;

$R^6$ is hydrogen or $C_1$-$C_6$ alkyl;

$R^{25}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, and substituted amino;

$R^{26}$ is hydrogen, $C_1$-$C_6$ alkyl, or substituted $C_1$-$C_6$ alkyl, wherein $C_1$-$C_6$ alkyl is substituted with halogen, hydroxy, cyano, nitro, sulfonyl, sulfonylamino, aminosulfonyl, amino, or substituted amino;

$R^{22}$ is selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, substituted amino, acylamino, alkoxycarbonylamino, and aminocarbonylamino;

$R^{40}$ and $R^{41}$ are independently selected from hydrogen, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, $C_1$-$C_6$ alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, substituted amino, acylamino, alkoxycarbonylamino, and aminocarbonylamino;

each $R^a$ is independently hydrogen or $C_1$-$C_6$ alkyl; and $R^{27}$ and $R^{28}$ are independently hydrogen or $C_1$-$C_6$ alkyl;

or a pharmaceutically acceptable salt thereof.

Embodiment B43. A pharmaceutical composition comprising a compound of any one of the embodiment B1-B42 admixed with at least one pharmaceutically acceptable carrier or excipient.

Embodiment B44. The pharmaceutical composition of embodiment B43, which comprises at least one sterile pharmaceutically acceptable carrier or excipient.

Embodiment B45. The pharmaceutical composition of embodiment B43, which comprises at least two pharmaceutically acceptable carriers and/or excipients.

Embodiment B46. A compound according to any one of embodiment B1-B42 for use in therapy.

Embodiment B47. The compound of embodiment B46, wherein the use in therapy is a use to treat cancer.

Embodiment B48. The compound of embodiment B47, wherein the cancer is selected from leukemia, lymphoma, lung cancer, colon cancer, CNS cancer, melanoma, ovarian cancer, renal cancer, prostate cancer, breast cancer, head and neck cancers, and pancreatic cancer.

Embodiment B49. A method to treat cancer, which comprises administering to a subject in need thereof an effective amount of a compound according to any one of embodiment B1-B42.

Embodiment B50. The method of embodiment B49, wherein the cancer is selected from leukemia, lymphoma, lung cancer, colon cancer, CNS cancer, melanoma, ovarian cancer, renal cancer, prostate cancer, breast cancer, head and neck cancers, and pancreatic cancer.

Embodiment B51. Use of a compound according to any one of embodiment B1-B42 for the manufacture of a medicament.

Embodiment B52. The use of embodiment B51, wherein the cancer is selected from leukemia, lymphoma, lung cancer, colon cancer, CNS cancer, melanoma, ovarian cancer, renal cancer, prostate cancer, breast cancer, head and neck cancers, and pancreatic cancer.

Embodiment B53. A combination for treating and/or preventing cancer in a subject, which combination comprises an effective amount of a compound of any of embodiment B1-B42, or a pharmaceutically acceptable salt thereof, and an effective amount of a second prophylactic or therapeutic agent for treating and/or preventing cancer in a subject.

Embodiment B54. A method for treating and/or preventing cancer in a subject, which methods comprises administering to a subject in need thereof an effective amount of the combination of embodiment B53.

The invention claimed is:
1. A compound of Formula V:

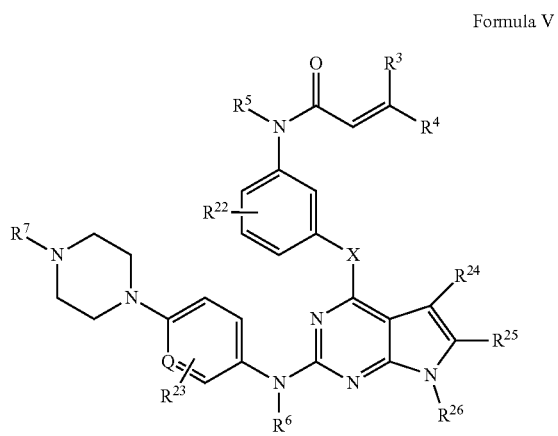

Formula V wherein
X is $CF_2$;
$R^3$ and $R^4$ are independently hydrogen, C1-C6 alkyl, or —$(CH_2)_m N(R^a)_2$, wherein m is one to 6;
$R^5$ is hydrogen or C1-C6 alkyl;
$R^6$ is hydrogen or C1-C6 alkyl;
$R^7$ is hydrogen or C1-C6 alkyl;

$R^{24}$ and $R^{25}$ are independently selected from hydrogen, halogen, C1-C6 alkyl, C1-C6 haloalkyl, C1-C6 alkoxy, C1-C6 haloalkoxy, C1-C6 alkenyl, C1-C6 alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, and substituted amino;

$R^{26}$ is hydrogen, C1-C6 alkyl, or substituted C1-C6 alkyl, wherein C1-C6 alkyl is substituted with halogen, hydroxy, cyano, nitro, sulfonyl, sulfonylamino, aminosulfonyl, amino, or substituted amino;

$R^{22}$ is selected from hydrogen, halogen, C1-C6 alkyl, C1-C6 haloalkyl, C1-C6 alkoxy, C1-C6 haloalkoxy, C1-C6 alkenyl, C1-C6 alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, substituted amino acylamino, alkoxycarbonylamino, and aminocarbonylamino;

$R^{23}$ is selected from hydrogen, halogen, C1-C6 alkyl, C1-C6 haloalkyl, C1-C6 alkoxy, C1-C6 haloalkoxy, C1-C6 alkenyl, C1-C6 alkynyl, hydroxy, cyano, nitro, —$C(O)R^a$, —$OC(O)R^a$, —$C(O)OR^a$, —$C(O)N(R^a)_2$, sulfonyl, sulfonylamino, aminosulfonyl, amino, substituted amino acylamino, alkoxycarbonylamino, and aminocarbonylamino;

each $R^a$ is independently hydrogen or C1-C6 alkyl; and
Q is CH, $CR^{23}$, or N;
or a pharmaceutically acceptable salt thereof.

2. The compound of claim 1, wherein $R^{24}$ and $R^{25}$ are hydrogen.

3. The compound of claim 1, wherein $R^{26}$ is hydrogen.

4. A pharmaceutical composition comprising a compound of claim 1 admixed with at least one pharmaceutically acceptable carrier or excipient.

5. A method to treat cancer, which comprises administering to a subject in need thereof an effective amount of a compound according to claim 1.

6. A combination for treating cancer in a subject, which combination comprises an effective amount of a compound of claim 1, or a pharmaceutically acceptable salt thereof, and an effective amount of a second prophylactic or therapeutic agent for treating and/or preventing cancer in a subject.

7. A method for treating cancer in a subject, which method comprises administering to a subject in need thereof an effective amount of the combination of claim 6.

8. The compound according to claim 1, wherein $R^3$ and $R^4$ are hydrogen.

9. The compound according to claim 1, wherein $R^5$, $R^6$ and $R^{22}$ are hydrogen.

10. The compound according to claim 1, wherein $R^7$ is C1-3 alkyl.

11. The compound according to claim 1, wherein $R^7$ is methyl.

12. The compound according to claim 1, wherein $R^{23}$ is hydrogen.

13. The compound of claim 1, wherein $R^{26}$ is C1-6 alkyl substituted with hydroxy.

14. The compound according to claim 1, wherein Q is CH.

15. The compound according to claim 1, wherein Q is CF.

16. The compound according to claim 1, wherein Q is N.

17. A compound chosen from:
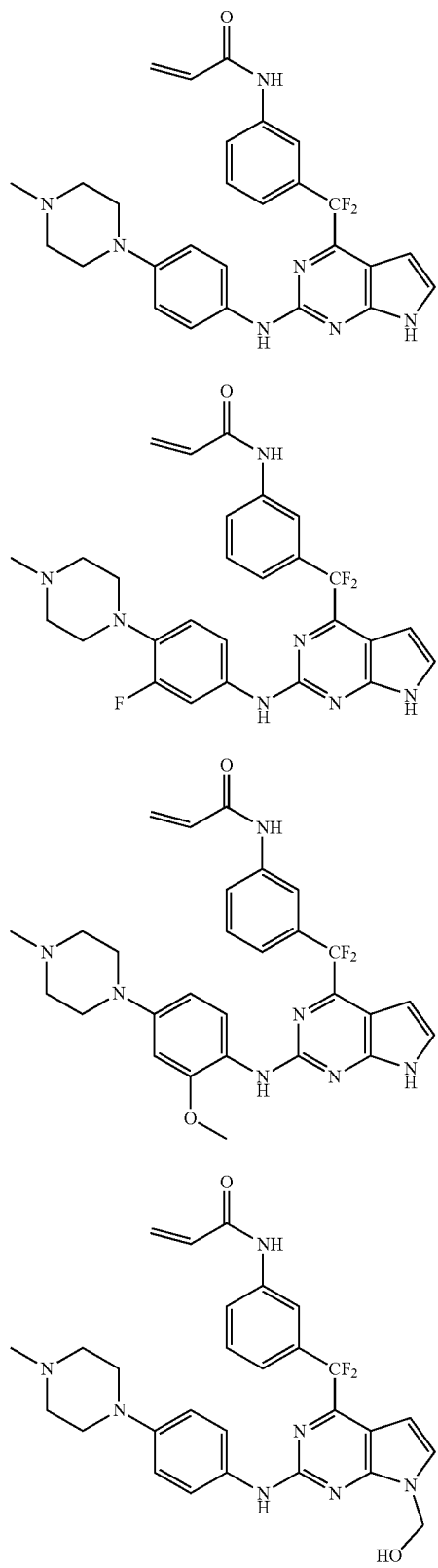
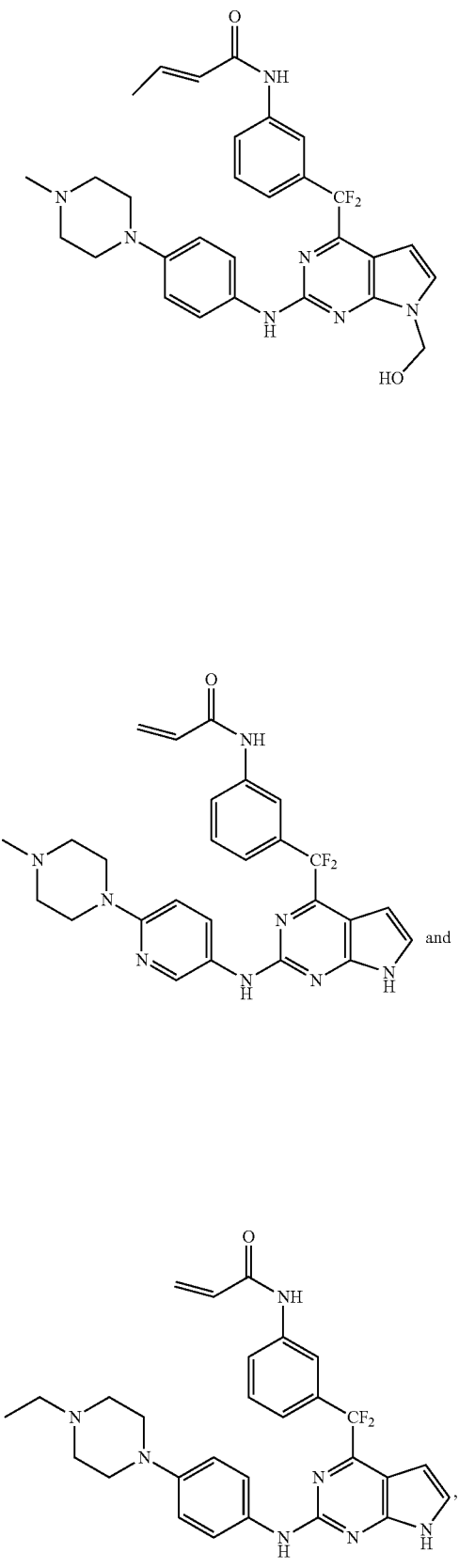
or a pharmaceutically acceptable salt thereof.

18. The compound according to claim 17, wherein the compound is:
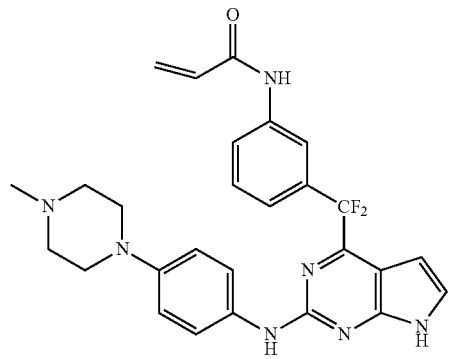
28a
or a pharmaceutically acceptable salt thereof.
19. The compound according to claim 17, wherein the compound is:
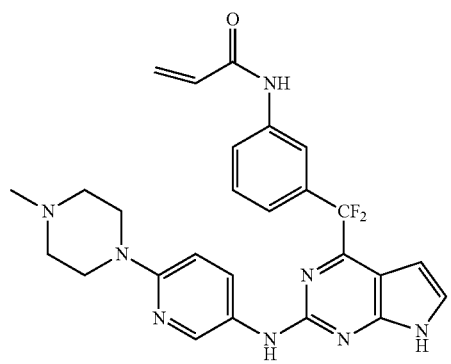
28b
or a pharmaceutically acceptable salt thereof.
20. The compound according to claim 17, wherein the compound is:
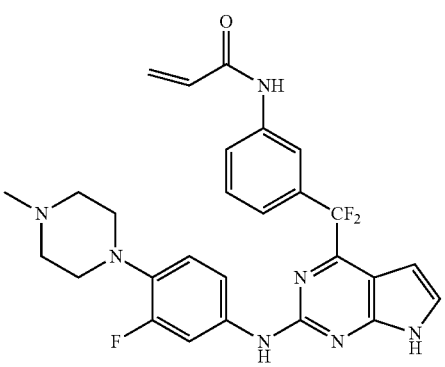
28c
or a pharmaceutically acceptable salt thereof.
* * * * *